United States Patent
Fong et al.

(10) Patent No.: US 10,273,446 B2
(45) Date of Patent: Apr. 30, 2019

(54) COMPOSITIONS AND METHODS FOR RECOVERY OF STRANDED GAS AND OIL

(71) Applicant: CALYSTA, INC., Menlo Park, CA (US)

(72) Inventors: Howard Lam Ho Fong, Sugar Land, TX (US); John H Grate, Los Altos, CA (US); Luan Nguyen, San Ramon, CA (US); Joshua A. Silverman, Los Altos Hills, CA (US); Lisa Marie Newman, San Jose, CA (US); Lorraine Joan Giver, Sunnyvale, CA (US); Drew D. Regitsky, San Francisco, CA (US)

(73) Assignee: Calysta, Inc., Menlo Park, CA (US)

( * ) Notice: Subject to any disclaimer, the term of this patent is extended or adjusted under 35 U.S.C. 154(b) by 5 days.

(21) Appl. No.: 15/111,723

(22) PCT Filed: Jan. 16, 2015

(86) PCT No.: PCT/US2015/011806
§ 371 (c)(1),
(2) Date: Jul. 14, 2016

(87) PCT Pub. No.: WO2015/109221
PCT Pub. Date: Jul. 23, 2015

(65) Prior Publication Data
US 2016/0333307 A1    Nov. 17, 2016

Related U.S. Application Data

(60) Provisional application No. 61/928,349, filed on Jan. 16, 2014.

(51) Int. Cl.
| | |
|---|---|
| C12N 1/20 | (2006.01) |
| B01D 53/85 | (2006.01) |
| C10L 3/10 | (2006.01) |
| A23K 10/10 | (2016.01) |
| A23N 17/00 | (2006.01) |
| C10G 3/00 | (2006.01) |
| C10L 1/04 | (2006.01) |
| C10L 1/06 | (2006.01) |
| C10L 1/08 | (2006.01) |
| C12N 15/74 | (2006.01) |
| C12R 1/01 | (2006.01) |
| C12N 9/02 | (2006.01) |
| C12P 7/64 | (2006.01) |

(52) U.S. Cl.
CPC ............... *C12N 1/20* (2013.01); *A23K 10/10* (2016.05); *A23N 17/00* (2013.01); *B01D 53/85* (2013.01); *C10G 3/00* (2013.01); *C10L 1/04* (2013.01); *C10L 1/06* (2013.01); *C10L 1/08* (2013.01); *C10L 3/102* (2013.01); *C12N 9/0051* (2013.01); *C12N 9/0069* (2013.01); *C12N 15/74* (2013.01); *C12P 7/6463* (2013.01); *C12R 1/01* (2013.01); *B01D 2251/95* (2013.01); *B01D 2256/24* (2013.01); *B01D 2256/245* (2013.01); *B01D 2257/304* (2013.01); *B01D 2258/05* (2013.01); *C10G 2300/1025* (2013.01); *C10G 2300/202* (2013.01); *C10G 2400/02* (2013.01); *C10G 2400/04* (2013.01); *C10G 2400/08* (2013.01); *C10L 2290/544* (2013.01); *Y02A 50/2359* (2018.01); *Y02P 30/20* (2015.11)

(58) Field of Classification Search
None
See application file for complete search history.

(56) References Cited

U.S. PATENT DOCUMENTS

| | | | |
|---|---|---|---|
| H1430 H | 4/1995 | Apel et al. | |
| 6,689,601 B2 | 2/2004 | Koffas et al. | |
| 6,756,022 B2 * | 6/2004 | Sakai | C10G 27/00 208/226 |
| 6,818,424 B2 | 11/2004 | DiCosimo et al. | |
| 7,098,005 B2 | 8/2006 | DiCosimo et al. | |
| 2002/0028505 A1 | 3/2002 | Sakai et al. | |
| 2003/0003528 A1 | 1/2003 | Brzostowicz et al. | |
| 2003/0032170 A1 | 2/2003 | Ito et al. | |
| 2003/0203456 A1 | 10/2003 | Clark et al. | |
| 2004/0126848 A1 | 7/2004 | Dicosimo et al. | |
| 2005/0176121 A1 | 8/2005 | Takeshita et al. | |
| 2006/0057726 A1 * | 3/2006 | Sharpe | C12N 9/00 435/471 |
| 2008/0026005 A1 | 1/2008 | Miguez et al. | |

(Continued)

FOREIGN PATENT DOCUMENTS

| | | |
|---|---|---|
| EP | 1 932 910 A1 | 6/2008 |
| WO | 02/18617 A2 | 3/2002 |

(Continued)

OTHER PUBLICATIONS

Gassner et al., "Component Interactions in the Soluble Methane Monooxygenase System from *Methylococcus capsulatus* (Bath)," *Biochemistry* 38: 12768-12785, 1999.

(Continued)

*Primary Examiner* — Nancy A Treptow

(74) *Attorney, Agent, or Firm* — Seed IP Law Group LLP

(57) ABSTRACT

The present disclosure provides compositions and methods for using recombinant C1 metabolizing microorganisms capable of metabolizing sulfur containing compounds and other contaminants to biologically convert sour or acidic natural gas into high-value molecules, and to allow recovery of stranded oil.

28 Claims, No Drawings
Specification includes a Sequence Listing.

(56) References Cited

U.S. PATENT DOCUMENTS

| | | |
|---|---|---|
| 2008/0057554 A1 | 3/2008 | Huhnke et al. |
| 2010/0199548 A1 | 8/2010 | del Cardayre et al. |
| 2010/0221813 A1 | 9/2010 | Miguez et al. |
| 2012/0064622 A1 | 3/2012 | Fischer et al. |
| 2013/0323809 A1 | 12/2013 | Yang et al. |

FOREIGN PATENT DOCUMENTS

| | | |
|---|---|---|
| WO | 03/027301 A1 | 4/2003 |
| WO | 2014/062703 A1 | 4/2014 |
| WO | 2014/066670 A1 | 5/2014 |
| WO | 2014/089436 A1 | 6/2014 |

OTHER PUBLICATIONS

Strøm et al., "The Carbon Assimilation Pathways of *Methylococcus capsulatus, Pseudomonas methanica* and *Methylosinus trichosporium* (OB3B) during Growth on Methane," *Biochem. J.* 144:465-476, 1974.

Ali et al., "Duplication of the mmoX gene in Methylosinus sporium: cloning, sequencing and mutational analysis," *Microbiology* 152:2931-2942, 2006.

Ali et al., "Development and validation of promoter-probe vectors for the study of methane monooxygenase gene expression in Methylococcus capsulatus Bath,"*Microbiology* 155:761-771, 2009.

Anthony et al., "The Microbial Oxidation of Methanol," *Biochem. J.* 96:808-812, 1965.

Bodrossy et al., "A novel thermophilic methane-oxidising γ-Proteobacterium," *FEMS Microbiology Letters* 170:335-341, 1999.

Bodrossy et al., "Heat-Tolerant Methanotrophic Bacteria from the Hot Water Effluent of a Natural Gas Field," *Applied Environ. Microbiol.* 61(10):3549-3555, 1995.

Cardy et al., "Molecular analysis of the methane monooxygenase (MMO) gene cluster of Methylosinus trichosporium OB3b," *Molecular Microbiology* 5(2):335-342,1991.

Cardy et al., "The methane monooxygenase gene cluster of Methylosinus trichosporium: cloning and sequencing of the mmoC gene," *Archives of Microbiology* 156:477-483, 1991.

Colby et al., "The Soluble Methane Mono-oxygenase of Methylococcus capsulatus (Bath)—Its Ability to Oxygenate n-alkanes, n-alkenes, Ethers, and Alicyclic, Aromatic and Heterocyclic Compounds," *Biochem. J.* 165:395-402, 1977.

Cornish et al., "In vivo $^{13}$C NMR Investigations of Methanol Oxidation by the Obligate Methanotroph *Methylosinus trichosporium* OB3b," *J. Gen. Microbiol.* 130:2565-2575, 1984.

Coufal et al., "Sequencing and analysis of the Methylococcus capsulatus (Bath) soluble methane monooxygenase genes," *Eur. J. Biochem.* 267:2174-2185, 2000.

Fennell et al., "Methanotrophic Attached-Film Reactor Development and Biofilm Characteristics," *Biotechnology and Bioengineering* 40:1218-1232, 1992.

Föllner et al., "Expression of polyhydroxyalkanoic-acid-biosynthesis genes in methylotrophic bacteria relying on the ribulose monophosphate pathway," *Appl. Microbiol. Biotechnol.* 40:284-291, 1993.

Friedrich, "Physiology and Genetics of Sulfur-oxidizing Bacteria," *Advances in Microbial Physiology* 39:235-289, 1998.

Funhoff et al., "CYP153A6, a Soluble P450 Oxygenase Catalyzing Terminal-Alkane Hydroxylation," *Journal of Bacteriology* 188(14):5220-5227, 2006.

Gilbert et al., "Molecular Analysis of the pmo (Particulate Methane Monooxygenase) Operons from Two Type II Methanotrophs," *Applied and Environmental Microbiology* 66(3):966-975, 2000.

Griesbeck et al., "Biological Sulfide Oxidation: Sulfide-Quinone Reductase (SQR), the Primary Reaction," *Recent Res. Dev. Microbiol.* 4:179-203, 2000. (26 pages).

Hou et al., "Complete genome sequence of the extremely acidophilic methanotroph isolate V4, Methylacidiphilum infernorum, a representative of the bacterial phylum Verrucomicrobia," *Biology Direct* 3(26), 2008. (25 pages).

Hyman et al., "Interaction of Ammonia Monooxygenase from Nitrosomonas europaea with Alkanes, Alkenes, and Alkynes," *Applied and Environmental Microbiology* 54(12):3187-3190, 1988.

Jiang et al, "Methanotrophs: Multifunctional bacteria with promising applications in environmental bioengineering," *Biochemical Engineering Journal* 49:277-288, 2010.

Kelly et al., "Oxidative metabolism of inorganic sulfur compounds by bacteria," *Antonie van Leeuwenhoek* 71:95-107, 1997.

Kim et al., "Creating auxotrophic mutants in Methylophilus methylotrophus AS1 by combining electroporation and chemical mutagenesis," *Applied Microbiology and Biotechnology* 48(1):105-108, 1997.

Kopriva et al., "The Presence of an Iron-Sulfur Cluster in Adenosine 5'-Phosphosulfate Reductase Separates Organisms Utilizing Adenosine 5'-Phosphosulfate and Phosphoadenosine 5'- Phosphosulfate for Sulfate Assimilation," *The Journal of Biological Chemistry* 277(24):21786-21791, 2002.

Kubota et al., "Isolation and Functional Analysis of Cytochrome P450 CYP153A Genes from Various Environments,"*Biosci. Biotechnol. Biochem.* 69(12):2421-2430, 2005.

Lillig et al., "Molecular and Catalytic Properties of *Arabidopsis thaliana* Adenylyl Sulfate (APS)-Kinase," *Archives of Biochemistry and Biophysics* 392(2):303-310, 2001.

Lin et al., "Analysis of Methane Monooxygenase Genes in Mono Lake Suggests That Increased Methane Oxidation Activity May Correlate with a Change in Methanotroph Community Structure," *Applied and Environmental Microbiology* 71(10):6458-6462, 2005.

Lloyd et al., "Heterologous expression of soluble methane monooxygenase genes in methanotrophs containing only particulate methane monooxygenase," *Arch Microbiol* 171:364-370, 1999.

Lu et al., "Biosynthesis of Monomers for Plastics from Renewable Oils," *J. Am. Chem. Soc.* 132(43):15451-15455, 2010.

McTavish et al., "Sequence of the Gene Coding for Ammonia Monooxygenase in *Nitrosomonas europaea,*" *Journal of Bacteriology* 175(8):2436-2444, 1993.

Motoyama et al., "Effects of the amplification of the genes coding for the L-threonine biosynthetic enzymes on the L-threonine production from methanol by a gram-negative obligate methylotroph, Methylobacillus glycogenes,"*Appl Microbiol Biotechnol* 42:67-72, 1994.

Nelson et al., "P450 superfamily: update on new sequences, gene mapping, accession numbers and nomenclature," *Pharacogenetics* 6:1-42, 1996.

Norton et al., "Diversity of ammonia monooxygenase operon in autotrophic ammonia-oxidizing bacteria," *Arch Microbiol* 177:139-149, 2002.

Park et al., "Batch Cultivation of *Methylosinus trichosporium* OB3b. I: Production of Soluble Methane Monooxygenase," *Biotechnology and Bioengineering* 38:423-433, 1991.

Pfluger et al., "Selection of Type I and Type II methanotrophic proteobacteria in a fluidized bed reactor under non-sterile conditions," *Bioresource Technology* 102:9919-9926, 2011.

Ruggeri et al., "Determination of Optimal Biofilm Activity in a Biological Fluidized Bed (BFB) Reactor," *Wat. Sci. Tech.* 29(10-11):347-351, 1994.

Semrau et al., "Particulate Methane Monooxygenase Genes in Methanotrophs," *Journal of Bacteriology* 177(11):3071-3079, 1995.

Shiemke et al., "Detergent Solubilization of Membrane-Bound Methane Monooxygenase Requires Plastoquinol Analogs as Electron Donors," *Archives of Biochemistry and Biophysics* 321(2):421-428, 1995.

Springer et al., "Sequence and characterization of mxaB, a response regulator involved in regulation of methanol oxidation, and of mxaW, a methanol-regulated gene in Methylobacterium extorquens AM1," *FEMS Microbiology Letters* 160:119-124, 1998.

Stainthorpe et al., "Molecular analysis of methane monooxygenase from Methylococcus capsulatus (Bath)," *Archives of Microbiology* 152:154-159, 1989.

Stainthorpe et al., "The methane monooxygenase gene cluster of Methylococcus capsulatus (Bath)," *Gene* 91:27-34, 1990.

Stetter, "Hyperthermophilic procaryotes," *FEMS Microbiology Reviews* 18:149-158, 1996.

(56) References Cited

OTHER PUBLICATIONS

Stolyar et al., "Role of multiple gene copies in particulate methane monooxygenase activity in the methane-oxidizing bacterium Methylococcus capsulatus Bath," *Microbiology* 145:1235-1244, 1999.
Stolyar et al., "Search for Systems of Genetic Exchange in Methane-Oxidizing Bacteria," *Microbiology* 64(5):584-588, 1995. (Translated from Mikrobiologiya 64(5):686-691, 1995).
Toyama et al., "Construction of insertion and deletion mxa mutants of Methylobacterium extorquens AM1 by electroporation," *FEMS Microbiology Letters* 166:1-7, 1998.
Toyama et al., "pqqA is not required for biosynthesis of pyrroloquinoline quinone in Methylobacterium extorquens AM1," *Microbiology* 144:183-191, 1998.
Toyama et al., "Sequence analysis of pqq genes required for biosynthesis of pyrroloquinoline quinone in Methylobacterium extorquens AM1 and the purification of a biosynthetic intermediate," *Microbiology* 143:595-602, 1997.
Van Dien et al., "Reconstruction of C3 and C4 metabolism in Methylobacterium extorquens AM1 using transposon mutagenesis," *Microbiology* 149:601-609, 2003.
Yoshida et al., "Improved conditions for the transformation by electroporation of the extracellular polysaccharide-producing methylotroph *Methylobacillus* sp.," *Biotechnology Letters* 23:787-791, 2001.

\* cited by examiner

SEQUENCE LISTING

<160> NUMBER OF SEQ ID NOS: 108

<210> SEQ ID NO 1
<211> LENGTH: 1635
<212> TYPE: DNA
<213> ORGANISM: Artificial Sequence
<220> FEATURE:
<223> OTHER INFORMATION: Codon optimized Gordonia sp. propane
      monooxygenase hydroxylase large subunit sequence

<400> SEQUENCE: 1

```
atgagccgcc agtcccttac caaagcccat gccaagatca ccgaactgtc ctgggagccg      60
acgttcgcaa cgcccgcgac tcgcttcggc accgactaca ccttcgaaaa ggccccgaag     120
aaagaccccc tgaaacagat aatgcgctcc tacttcccga tggaggaaga aaaggacaat     180
cgcgtgtacg gcgcgatgga cggcgctatc cggggtaata tgttccgcca ggtgcaagag     240
cgctggctgg agtggcagaa actcttcctt tcgattatcc cgttccctga gatctcggcg     300
gcacgggcca tgcccatggc catcgacgcc gtgccgaatc ccgagatcca taatggcctc     360
gcggtccaga tgatcgatga ggtccgccat agcacgattc agatgaatct gaagaagctg     420
tatatgaaca actacatcga tccggccggt ttcgatatca ccgagaaggc cttcgcgaat     480
aactatgccg ggaccatcgg caggcaattc ggtgagggct tcatcaccgg ggacgcgatc     540
accgcggcca atatctacct gaccgtggtg gcggaaacgg ccttcaccaa tactctcttt     600
gtcgccatgc ccgacgaagc ggcagcgaat ggcgactacc tcctgccgac cgtgttccac     660
agcgtccagt cggatgagtc gcggcatatc agcaacggct attcgatcct cctcatggcc     720
ctggcggacg agcggaatcg gccgctcttg gagcgggatc tccgctacgc gtggtggaac     780
aaccattgcg tggtggacgc tgccattggc acgttcatcg agtatggcac caaggatcgg     840
cgcaaggacc gcgagagtta cgccgagatg tggcggcgct ggatatacga cgactattat     900
cgctcctatc tgctgcctct ggagaagtat ggcctcacca tcccgcacga cctcgtcgag     960
gaggcctgga acaggatcgt cgataagcat tacgtgcatg aagtggcgcg gttcttcgcc    1020
acgggctggc cggtcaacta ctggcgcatc gacgcgatga ccgacaccga cttcgagtgg    1080
ttcgaagaga gtatcccgg ctggtacaac aagttcggca gtggtggga aactacaat      1140 cgccttgcgt atccggggaa gaacaagccg atcgcgttcg aggacgttga ctacgagtat    1200
ccgcaccggt gctggacctg tatggtccca tgcctgatcc gcgaggacat ggttaccgat    1260
aaagtcgacg gccagtggcg cacctattgc tcggaaacgt gcgcttggac ggacaaagtc    1320
gcatttcggc cggagtatga gggcaggccc acgcccaaca tgggacggct caccggattc    1380
cgcgagtggg agactctgca tcacggcaaa gacttggctg atatcatcac ggacctcggt    1440
```

| | |
|---|---:|
| tacgtccgcg acgacggcaa gaccctgatt ccgcaacccc atctcgacct ggacccaag | 1500 |
| aaaatgtgga ccctcgacga tgtgcgcggc atcccgtttg gctcgccgaa cgtcgcgctg | 1560 |
| aatgaaatgt ccgacgatga gcgcgaggcg cacatcgccg cgtacatggc gaacaaaaac | 1620 |
| ggtgccgtca cggtc | 1635 |

<210> SEQ ID NO 2
<211> LENGTH: 1104
<212> TYPE: DNA
<213> ORGANISM: Artificial Sequence
<220> FEATURE:
<223> OTHER INFORMATION: Codon optimized Gordonia sp. propane
      monooxygenase hydroxylase small subunit sequence

<400> SEQUENCE: 2

| | |
|---|---:|
| atgagtgccc agcccaacc ccgcgaacgc agtttcccct ccattgagtt caccgacgca | 60 |
| gaagccgacg cccgcgagtt cccgtcgtcg cgctcccgca agtataacta ctatcagccg | 120 |
| agtaagaaac gggccacgat ctatgaagat gtgacggtcg acgtccagcc tgatccggag | 180 |
| cgccatctca cccagggctg gatctacggc ttcgcgacg gcccgggcgg ctaccccaaa | 240 |
| gagtggactt cggcccagag ctcgaactgg catcagtttc tcgatccgaa cgaggagtgg | 300 |
| gagcagagca tctaccgcaa taactcggca gtcgtgcacc aagtcgatct ctgcctgcag | 360 |
| aacgcgaagc gcgcgagggc ctatgacggc tggaatagcg cgtggctcaa gttcatcgag | 420 |
| aggaatctgg gcgcgtggat gcacgccgag tcgggtatgg gcctccacgt gttcacctcc | 480 |
| atccagcggt ccgcgccgac gaatatgatc aataatgccg tctgcgtcaa tgccgcgcat | 540 |
| aagctgcggt tcgcccaaga cctcgcgctg ttcaaccttg acttgtccga ggccgaggaa | 600 |
| gcgttcgacg gttccgcgca taagaggtg tggcagtccg caccggagtg gcagccgacc | 660 |
| cgcgaggccg tcgagcgcct gaccgcgatc ggcgactggg ctgagctgct gttctgctcg | 720 |
| aacatcgttt tcgagcaact ggtcggcagc ctcttccgca gcgagcttgt gatgcaagtg | 780 |
| gctgccccgga acggcgatta tatcacgccg accatcgtcg gcaccggtga gtatgactac | 840 |
| gatcgggacc tgaactactc ccgggctctg ttccagatgc ttgcgcgcga cgagaaacat | 900 |
| gggatagaca atcgcaagct gttctcgcgc tggatgagcg agtggtttcc cggagcgagc | 960 |
| acgcgggctc gggggctcca gccgatctgg tcccagccgg cagacaagag cgtgaccttc | 1020 |
| tcgtcgtcgc tggagcatgc caagaccaag ttcgccgacg tgctcgcggc gattgacgtg | 1080 |
| gacatccccg aagaactgaa caag | 1104 |

<210> SEQ ID NO 3
<211> LENGTH: 1038
<212> TYPE: DNA
<213> ORGANISM: Artificial Sequence
<220> FEATURE:
<223> OTHER INFORMATION: Codon optimized Gordonia sp. propane
      monooxygenase reductase sequence

<400> SEQUENCE: 3

| | |
|---|---:|
| atggcagaca cccacaagat tagcttcgag ccagtggata tagagatgga agttggcgaa | 60 |
| gatgaaacga ttctcgatgc ggcgttccgg caagagtcca cgtcgtgcac cgctgccgcc | 120 |
| cggccgctgt tcggttgcaa gtcgtacatg cttgagggcg acgtgcagat ggacgactac | 180 |
| tcgaccttcg cgtgcaacga cgccgaggaa gccgagggct acgtgcttct ctgccgcacc | 240 |
| tatgcctaca gcgactgcga gatcgagctg ctcaatttcg acgaggacga gctcctgggc | 300 |

```
ggagcccga tccaagatgt gacgaccaaa gtcgcggcca tcgagcccat gaccccggac      360
atcgtgtcgc tcaagctcga cgtcgtggag ccggagtccg tcgagtttaa gtccggccag      420
tacttcgacc tgttcatccc gggcaccgag acaagcgca gcttctccat cgcgacgacc      480
cccgctaccc cggaccggct cgaattcctc atcaaaaagt acccggggg actgttcgcg      540 ggcatgttga ctgatggcct gagtgtcggg caagaaatca agctgaatgg gccctatggt      600
agttgcaccc tccgcaatgg ccatgtgctg ccgatcgtcg ccatcggtgg cggcgccggc      660 atggcccgt tgctcagcct cctgaggcat atctcggaaa ccggcctcaa tcgcccggtc      720
cgcttctatt atggtgcgcg gaccgcagcc gacctgttcc tgctggatga gatcgcgacg      780
ctgggcgaga aaattgatga cttctcgttc accgcctgcc tgtccgagtc cacggacaac      840
gcgcctgagg cgtcaccgt gatcggcggc aacgtgacgg acatcgtcaa cgataacgaa      900
gcggaccttg cccgcaccga ggtgtacttt tgtgccccgc cccgatggt cgacgcggca      960 ctggcgctgg cggagcagca tagcgtcccc cacgaccaga tcttctatga caagttcacg     1020
tcgcccgctt tcgacagc                                                  1038

<210> SEQ ID NO 4
<211> LENGTH: 333
<212> TYPE: DNA
<213> ORGANISM: Artificial Sequence
<220> FEATURE:
<223> OTHER INFORMATION: Codon optimized Gordonia sp. propane
      monooxygenase coupling protein sequence

<400> SEQUENCE: 4
atgcagtttg gagcggatac ggaatttagt aacatgtgcg gtgtgaccct gatgaatacc       60
cctataggcc gggttgtcgc cgacgtcatg ggcgctaaag acggcgtgga actcaccgag      120
tatccgtcga tgatccgcgt ggacggcgtc aaccgccttg atttcgacta cgacgagctg      180
accgacgcgc tcggtcaaga cttcgacggg tccattttcg aggagatcag cagcacgcac      240
tacggccgca tggtccatct ggacgataag accatcctct cgcctcgcc cgaggatgcg      300 gcagagttca tcggcttcga cctgacggcc tcc                                  333

<210> SEQ ID NO 5
<211> LENGTH: 1704
<212> TYPE: DNA
<213> ORGANISM: Artificial Sequence
<220> FEATURE:
<223> OTHER INFORMATION: Codon optimized Thauera butanivorans BmoG
      sequence

<400> SEQUENCE: 5
atgatctccc tgaactgcaa gaaaacgacc actggcctca ccgccatct cgccctcgtc       60 cgcggcatga aagccctcgc cgagctcgtc ggcaccacgc tgggcccgca gggtcgccat      120
gtgatgctcg cgcatcgcgc aggcttggca ccgcacgtgt cgaaagacg cgttgaggtc      180 gctcgccatt tgtccctgcc cgactccgag gaagaactcg gcgttcggct gctccgcaat      240
gctgccgtgg ccgtgagtga gtcgttcggc gacggcacca gtaccgcgac ggtgtttacc      300
gccgacctcg ccgtgcgcgc tctgaagctg attggtgccg ggccgacac gcttgaagtc      360 cgcagggttc tgggcctcgc ggcgtatgcc cgctggtcg cgctgaacga catggcgagg      420
cgcgcagacc gggcatgct caccgccgtc gcgcaaaccg cggcaaatgg cgatcggcgg      480
gtcgccgatc tcctcgtcga ggccttcgag gcgcgtggga gcggaaggcac gatcgaggtc      540 gagatgggca actccgtcga ggatgtcctc gaagttgcgc agggctcgta cttcgacacg      600
```

```
gttccgctcg tgaccgcgct gctgccgccg acgggccagg tcgagtttgc gaggcctctg      660
atcctgttcc attgcgacgc catcgagact gcggacgaga tattgccggc gcttgagctc      720
gcgcgctcct cgcggcgccc gctgctgatc ttggcggaca cgtcggcat cgatgtggaa       780 acgctgctcg tgcgcaatca gaacgagggc accctcgcgg tcgcagtggt gcgggcaccc      840
atgtatggcg atacgcggcg cgaggccctc ctggacctca cctccaagtt cggcgggacg      900
gcgttcggac gcgagggctt cgtcgagttc gcgctgcgca gcctgggctc cctgtccgag      960
ggcgacctcg gccaggccga cgaagcgatc cttgaggccg acggtgtcac ccttcgcggt     1020
gcgggcaaca ccccagcgc gcttgaggat aggatcgcgc tggtgcgcgc cgagctggac      1080
cggggtgacg tgagcgtggg cgactcgccg agcgccaagc tcgactacat tgaaaagcgc     1140
aaggagcgcc tgaagctgtt ggctgcgggc agcgccaaac tccacatcgg cggaccgacc     1200
gacgtcgaga tcaagacccg cctgccgctg gcggagaatg cccaccgggc tctgctggcc     1260
gcagcgaaat ccggcgtgct gcccggtggc ggcgtcgcga tgattcgcgc ggcggagaag     1320
gtccaacagg agatgggacg gcttgagggt gacgtcgcct cggggcttc catcttcctg      1380 cagtcgctgg acacgccgat ccggtggatc gcccggaatg ccgggctgag gccagacgag     1440
gtcctcgcgc gcaccctggc gaacgagtcg gacttctacg gcttgaacgc gatgaccgga     1500
cggtacggtg acctcgccga agatggcgtc ctggacgccc tcgacatggt caccgatgtg     1560
atccgcgtgg cagtctcggt cgtggggagc atgctcggcg tcggtgccct ggtgacccgc     1620
gctagcccga agcccgcacc cgagcgcttc aagggcaccg agcgcgtgca tgacaagctc     1680
atgcgcgagg gcggcttcga tgag                                             1704

<210> SEQ ID NO 6
<211> LENGTH: 1092
<212> TYPE: DNA
<213> ORGANISM: Artificial Sequence
<220> FEATURE:
<223> OTHER INFORMATION: Codon optimized Thauera butanivorans butane
      monooxygenase reductase sequence

<400> SEQUENCE: 6
atgttgatgc agcagtataa gatagtggca aggtttgagg atggcgtgac ttacgagtac       60
gattgtgggg aagatgagaa tctgctggca gcggcgctcc ggcaaaatgt ccggctgctc      120
tgccagtgcc gcaaagcgtt ctgcgggtcc tgcaaggccc tgtgctccga gggtgactac      180
gaattgggcg accacatcaa cgtccaggtc cttccccggg acgaggagga ggacggcgtc      240
gttgtgacgt gcgacacgtt cccgcggtcc gacctcgtgc tcgaattccc ctataccagc      300
gatcggctcg gcacggtgac ggccaccgag gccaagacct ccgtcgtgtc ggtggagcgc      360
ctgagcagca ccgtgtatcg cctggtgctg caggccctgg acgccgaggg catgcccgca      420
cgcttcgact tcgtcccggg acaatatgtc gagatttcga ccgccgacag cctggaaacc      480 cggggcgttca gtctcgcgaa cctcccgaat gacgccggct gcttgagtt cctgatccgg      540 ctggtgccgg cggctacta cgctgcgtac ctggagcagc gggctgcggc tggccagacc      600
atcaacgtga aggtccgtt tggcgagttc gtcctgcgcg agcatgagct cgtcgaagat      660 ttcaccctc cggcggacag cccggcgcgc ggtggcacga tcgccttcct ggcgggctcg      720
accggcctcg ccctctcgc gtcgatgctc cgcgagcttg gccgccgcgg attcaatggc      780
gagtgccatc tcttcttcgg catgcaagac accgccacca tgttctatga aaagaactc      840 cgcgacatca agcgcacgct ccccggtctg accctgcatc tcgccctgat ggttcccagt      900
```

```
gcggagtggg agggctaccg gggcaatgcc gtcgcggcct tcaaggagca cttcgcggcc    960
tcctcgcaga ttcccgagaa cgtctatctg tgccggcccgg gcccaatgat cgcagcggcc   1020
ctgggggcgt gccgcgagct gggtatcccg gacaacaggg tccatcgcga agagttcgtg   1080
gcgtccggtg gc                                                        1092

<210> SEQ ID NO 7
<211> LENGTH: 504
<212> TYPE: DNA
<213> ORGANISM: Artificial Sequence
<220> FEATURE:
<223> OTHER INFORMATION: Codon optimized Thauera butanivorans butane
      monooxygenase hydroxylase BMOH gamma sequence

<400> SEQUENCE: 7
atgagcaaac aagtttggta taacacgccc gtgcgcgatg agtggattga aaaataacg     60 gctatcagga ctgcccgcga gggcaccgac atgctggcgc gcttccgggc tgagcacacg   120
ggtccggacc gcaccaccta tgacctcaag aaagaataca attggatcga gtcccggatc   180
gagatgcgcg tgtcgcagct gcatgccgag gcgacggcct cggatgagga cctcctgacc   240
aagaccatcg acggccgctg cgcgaaggaa gtcgccgcag agtggctcaa aaaagccgcg   300
gacatcgatt gccattacga aatgaacgg ttgtgcgtgg ccttccgcaa ggcctgcaag   360
ccgccgatga tgccgatcaa cttcttcgca ccggcggaga agaacttgt cgcgaagctc   420 atgaagctgc gggcgcccac ctacctcacg acctccctgg acgagctgcg cgaggcgcgg   480
ggcgtgacca tgatcagcgt ccag                                           504

<210> SEQ ID NO 8
<211> LENGTH: 261
<212> TYPE: DNA
<213> ORGANISM: Artificial Sequence
<220> FEATURE:
<223> OTHER INFORMATION: Codon optimized Thauera butanivorans butane
      monooxygenase hypothetical assembly protein
      sequence

<400> SEQUENCE: 8
atgaaagaag cccccgccat ccctgatctg cccggactcc cagaaaccgt cggtgagccc    60
acccttgtcc tcgaagagga cggcttccgg gtgttcgcga ccgagctgac gattatgtgg   120
cgctgggaca tctacaacgg cgacgcccat gtgcacaccg gctgcgcaca gcatccggag   180
tcgtgcgttg tggcggctcg gtccaagatc cgcttcctgc gcaggccgac ggtcgcgatg   240
ctcctggggg gcgagggcca a                                              261

<210> SEQ ID NO 9
<211> LENGTH: 411
<212> TYPE: DNA
<213> ORGANISM: Artificial Sequence
<220> FEATURE:
<223> OTHER INFORMATION: Codon optimized Thauera butanivorans butane
      monooxygenase regulatory protein sequence

<400> SEQUENCE: 9
atgagcaatg ttaacgcata ccatgctgga accaatggga agagggcca agatttcatc    60 gacgacttcc tgagcgaaga gaactccgcg ctcccgacgt cggaagccgt ggtgctggcg   120
ctcatgaaaa ccgaagagat cgacgccgtg gtggacgaaa tgatcaagcc gcagatggag   180 gacaaccccca ccatagcggt cgaggaccgg ggtggctact ggtggatcaa ggccaacggc   240
```

| | |
|---|---|
| aagatcgtca tcgattgcga tgaagccacc gagctgctcg gcaaaaagta caccgtctat | 300 |
| gacctcctgg tcaatgtgtc gacgacggtc ggtcgcgcga tgaccctggg caatcagttc | 360 |
| attatcacca acgagttgct tggcctggag actaaggtcg agtccgtgta t | 411 |

<210> SEQ ID NO 10
<211> LENGTH: 1173
<212> TYPE: DNA
<213> ORGANISM: Artificial Sequence
<220> FEATURE:
<223> OTHER INFORMATION: Codon optimized Thauera butanivorans butane
monooxygenase hydroxylase BMOH beta subunit
sequence

<400> SEQUENCE: 10

| | |
|---|---|
| atgtccacca acattttac ccgcggaatg gtcgatccag aaaggcaagc gtgcatccaa | 60 |
| gaagtcgtcc cgaaagcgcc cctcgaaacc aagcgcgatc acatcccctt cgccaagcgc | 120 |
| ggctggcgca ggctcaccga gtatgaggcc gtgatgctgc acgcgcagaa ttcgctcgac | 180 |
| gccgtcccgg gctcccaaga ggtcggcgag gtcgtgcaga gtggccgggg tggacgcccg | 240 |
| aactatggcg tcgagagtac cgctgccctg agctccaatt ggttccattt ccgcgatccc | 300 |
| agcaaacgct ggttcatgcc gtatgtgaag caaaagaacg aggagggcca gacggccgag | 360 |
| cgggccatga agtcgtgggc cgagggtggc gacgcagaga tgatgaacgc cgcctggcgc | 420 |
| gaacacatcc tcgctcggca ttatggcgcg ttcgtgtaca atgaatatgg cctgttctcg | 480 |
| gcgcatagca ccaccgtgta tggcggcctt tcggacctga tcaagacctg gatcgccgaa | 540 |
| gcggcgttcg ataagaatga cgctggccag atgatccaga tgcaacgggt gctgctctcc | 600 |
| aaagtgttcc ggggtttga cgcggacttg gccgaggcga acaggcgtg gaccgaggat | 660 |
| aagtcgtgga agcctgcacg cgagttcgtc gagcacatct gggccgaaac gtacgactgg | 720 |
| gtcgagcaac tgtgggcgat ccatgccgtg tacgaccata tcttcggcca gtttgtcagg | 780 |
| cgcgagttct tccagcgcct gggcggcatc catggggaca ctctcacccc gttcatccag | 840 |
| aatcaggccc tgacctacca tcttcaggca cgcgacggtg tgacggccct ctgcttcaag | 900 |
| ttcctgatcg aggacgagcc cgtttacgcc cagcacaacc gccgctacct ccgggcgtgg | 960 |
| acgggtcggt atctgcccca ggtcgggcgg gcgctgaagg ccttcctcgc gatctacaaa | 1020 |
| gaggtcccgg tcaagatcga cggcgtgacg tgccgcgagg gcgtgcgcgc gagcgtggag | 1080 |
| cgcgtggtcg acgactgggc agcgcggttc gcggagccga ttaatttcaa gttcaaccgg | 1140 |
| gctgcgttca tagacgacgt tctgtccggc tac | 1173 |

<210> SEQ ID NO 11
<211> LENGTH: 1590
<212> TYPE: DNA
<213> ORGANISM: Artificial Sequence
<220> FEATURE:
<223> OTHER INFORMATION: Codon optimized Thauera butanivorans butane
monooxygenase hydroxylase BMOH alpha subunit
sequence

<400> SEQUENCE: 11

| | |
|---|---|
| atgtccgcca atatggccgt gaaacaagcc ctgaaagcaa atcccgtccc gagctccgtc | 60 |
| gatccccaag aggtgcataa gtggctgcaa gacttcacct gggacttcaa gggcaagacc | 120 |
| gcgaagtatc ccacgaaata tgaaatggac gtcaatacgc gggagcaatt caagcttacc | 180 |
| gccaaagagt atgcgcgcat ggaatccatc aagaggaac ggcagtacgg gaccctcctg | 240 |
| gacggcctgg accgcctgga cgcgggcaac aaagtccatc gaagtgggg cgaagtgatg | 300 |

```
aagctcgtgt cgaacttcct ggagactgga gagtacggcg caatcgccgg cagcgcgctc    360
ctctgggata cggctcagag tccggagcag cgcaacggct atctggccca ggtcatcgac    420
gaaattcgcc acgtcaacca gaccgcgtat gtcaactact actatggtaa gcattactat    480
gacccggctg ccacaccaa catgcgccag ctccgcgcaa ttaacccact ctatccgggc     540
gtgaagcgcg cctttggcga gggcttcttg gcgggtgacg ccgtggagtc gagcatcaat    600
ctccagctcg tcggtgaggc ctgcttcacg aaccccctca tcgtgagcct caccgagtgg    660
gccgctgcca acggcgatga gatcacgccc acggttttcc tgtcgatcga gactgacgag    720
ctgcggcaca tggcgaacgg gtaccagacc atcgtgagca tcatgaataa tcccgaaacc    780
atgaagtatc tccagaccga tctggacaat gcgttctgga cccaacataa gttcctcacg    840
ccgttcgtgg gcgtggccct ggagtacggc tccaagtaca agtcgagcc ttgggcgaag     900 tcgtggaacc ggtgggtcta cgaagattgg gcgggaatct ggctgggtcg cttgcaacag    960
tttggcgtca agacgcccaa gtgcctgccg gacgcgaaga agacgccgt gtgggcgcat     1020 catgacctcg cgctcctcgc gcttgcgctt tggccgctca ccggcatccg catggaactg    1080
ccggactcgc tggcgatgga gtggttcgag gcgaattacc ccggttggta taaccactac    1140
ggcaagatct acgaagagtg gcgggccgca ggctttgagg accctaagtc cggcttctgc    1200
ggtgcgctgt ggctcatgga gaggggccac ggcattttcg tcgatcatgc ctcgggattg    1260
ccgttctgcc cctccctggc gaaatccagc ataaagccgc ggttcaccga gtacaacggt    1320
aagcgctacg cgttcgccga ccgtatggc gagcgccagt ggctcctgga gccggagcgg      1380
tatgaattcc agaatttctt cgagcaattc gagggctggg aactgtcgga cctggttaaa    1440
gccgctgggg gcgtgcgcag tgacggtaag accctcatcg cgcagccgca tctcagggac    1500
accgacatgt ggacgctgga cgatctgaag cgcatcaacc tcaccatccc ggacccgatg    1560
aagatcctga attggcagcc agtcgcccag                                     1590

<210> SEQ ID NO 12
<211> LENGTH: 765
<212> TYPE: DNA
<213> ORGANISM: Artificial Sequence
<220> FEATURE:
<223> OTHER INFORMATION: Codon optimized Nocardioides sp. pariculate
      butane monooxygenase subunit A sequence

<400> SEQUENCE: 12
atgaccgttg ccaccgaatc cgtcgagact ccccaacatc cacccccgac ccgcatgata     60
ggccgccgct gggatatcct gctcgtcgcc agtgcgctcc tcctggtcgc cggtgcggcc    120
catctgaaca atatgctgtt cgtgggtgat tggtccttct gggtcgactg gaaagaccgc    180
cagtggtggc cgctgctcac gcccgcgctt agcatcatcg tgcccgcggc gctgcagtac    240
atcacctgga cccaactgcg gctcccgttc ggcgccacgc tgggagccgt ggcgctggtc    300
ctcgccgaat gggtgtcgcg ctatttcagc ttcgagtggt gggcgaatat cccgctgaac    360
ttcacctggc cggaaaccct ggttctggct gccgtcgtgc tcgacgtgat cctcctcatc    420
acccggtcgt tcttcctcac gtcgctgttc ggcggcttga tgtggggctt tgtgttctgg    480
ttcttcaact ggccggcact ggcgccgttc atgcagcctg tcgagttcca cggctacatc    540
gtcaccgtgg ccgacgtgat gtccttcaac atcgtccgca cgcagacgcc ggagtatctc    600
cgcattatcg aggagggcag gcttcgggcg ctggtcgaga atatcaccat ggtcgtgtcc    660
ttcttcgcgg gcatgttgag cgcagcggtc tactggtttg gcctcgccat tggtaagttc    720
```

```
cttgccgtgg ctccggcagg gcgcttcttc cggctgggct cggac         765
```

<210> SEQ ID NO 13
<211> LENGTH: 1254
<212> TYPE: DNA
<213> ORGANISM: Artificial Sequence
<220> FEATURE:
<223> OTHER INFORMATION: Codon optimized Nocardioides sp. particulate
      butane monooxygenase subunit B sequence

<400> SEQUENCE: 13

```
atgcgcctta tgagaatctc gatgaatcct gagtccaccg gtcacctcct ccgccgcctg    60
ttccgccttg ccgtcggggt tctggctctc ctggtgctcc ccgtgagtcc ggcctccgcc   120
catggcgagg agtcgcagca agcgttccag cgcacgagca ccgtggtgtt ctatgacgtc   180
aagttcagcg atgatacggt cgacgtgggc gagtccgtca ccatcaccgg catggtccgg   240
gtgatgaaat cctggccgga ccatactctg gagccgccag agatgggcta cttgacggtg   300
tcgacgcccg gccggtgtt ctacgtccaa gagcgcgaga tgtcgggcga gttcaccccg   360
cagagcgtcc gcatcgaaaa gggtgcgacc tacccgttca agctcgtgat taaggccagg   420
cagccgggca cttggcacgt ccatccgggc ttcggggtcg agggcgcagg caccctggtg   480
ggagcgggca agatatcac ggtcaacgac accggggttt tcgagaacac ggtgacgctt   540
gctaacggca ccaccgtgga cctggaaacc ttcggcctcg gtcgcgtcgt gacctggcat   600
ctgatatcgc tcgtggtggg cctggcgtgg ctcctgttct ggctgcggcg gcccatcctc   660
gacagggcga tggccatttc cgagggtcgc ggtgccacgc tcatcacgcg ctcggaccgc   720
cggatcggaa tcggcttcgc ggttgtggcg ctggtcgtcg gcacgggcgg atatgcgtat   780
gccgagatga cgcagtccag ttcggtgccg ctgcaagtcg tcaggaccac cccggtcccg   840
ctcgctgagg aagaggttag cggtgccgtc gcacccgaga tcgagagcat ccggttcaat   900
gccgaagcgg acactctgac catgaagctg gcgtggaga ataccggtgc agcggccgtg   960
cgcctgcagc gcgtccagtt tggcgatgtc gagttcgtca gccctcgtt cgcctccgca  1020
gcggaccccg acgcccaggc catgacggtg accccgacc aggccatcga gcccggggc  1080
tcggccacct tcaccgtcga gattcagtcc gaggacctga tcgtgcggag cctcgtcccg  1140
gttaacgaag cggaactccg cgtcaccggc ctcctgtttt cgaggacga aaccggcgag  1200
caagtcgtgt ccgaggtcaa tgaactgacc tcggcgatct tgcaggattt ccac        1254
```

<210> SEQ ID NO 14
<211> LENGTH: 741
<212> TYPE: DNA
<213> ORGANISM: Artificial Sequence
<220> FEATURE:
<223> OTHER INFORMATION: Codon optimized Nocardioides sp. particulate
      butane monooxygenase subunit C  sequence

<400> SEQUENCE: 14

```
atgctcctct ggcgctggta tcaacaagca ttcgcattca ctaaaggact ggataggacc    60
ctccccgaat tcaatcagtt ctggggcacc atgtttctcg tcaacatgac cgtgttgccg   120
cttctggcag gggcctggta cgtgtacctg tggtccagct cgcggaagct tgcgcctccg   180
gccaatggtg ccgaggaggc cggtcgcatt tggcgcctct ggctgctggt cgcgggcttc   240
accgccgccg tctactgggg cggctcctac ttcgccgagc aagacgcgtc ctggcatcag   300
gtgaccatgc gggacagcgc gttcacccc agccacgcga tcctgttcta cggcgtgttc   360
```

```
ccactcatga tctatatggc gacgggtacc tatttgtatg cgcgcacccg cctgccgcat      420
ctgtacgggg gcaaggccat cccggtgtcc ttcgcgctca tgatcggcgg ctcgtcgctg      480
ctggtgttcc aggtcgccat gaacgagttt ggccattcgt tctgggaagc cgaggaactc      540
ttcagtgcct cgctgcactg gccgttcgtc atcttcggct atctcctggc ggccacgttc      600
tcggtttggt tcgaaaccac cccgcggctg ttcgcgatag cgcgccaaga gcgcgacgcc      660
ctcgtcgcgg cggagcaaca gatgaccccc gctgctcccg ctggcgagag caacacggcg      720
acgacccagc cgacgagcat c                                                741

<210> SEQ ID NO 15
<211> LENGTH: 1491
<212> TYPE: DNA
<213> ORGANISM: Artificial Sequence
<220> FEATURE:
<223> OTHER INFORMATION: Codon optimized Xanthobacter autotrophicus
      oxygenase alpha subunit XamoA sequence

<400> SEQUENCE: 15
atggcgctct tgaatcggga tgattggtat gacatagcac gcgacgttga ttggacccct      60
agctacgtgg ataggccgt ggctttccct gaggagtgga agggcgagaa agacatctgc       120
ggcacggcgt gggatgactg gacgagccg ttccgcgtga gcttccgcga atatgtcatg       180
gtccagaggg ataaagaggc ctccgtgggc gcgatccgcg aggccatggt ccgcgccaag      240
gcctatgaga agctcgacga cgggcataag gccacgagcc atctgcacat gggcaccatc      300
accatggtcg agcacatggc tgtgacgatg cagtcccggt tcgtgcgctt cgctccgagt      360
gcgcggtggc gctccctcgg cgcgttcggt atgctcgacg agactcgcca cacccagctc      420
gacctccggt tctcgcatga tctgctgaat gacagcccat cgttcgactg gtcgcagagg      480
gcattccata ccgacgagtg ggcagtcctg gccacccgca acctcttcga cgacatcatg      540
ctgaacgccg actgcgtcga ggccgcactg gccacctcct tgacgctgga gcacggcttc      600
acgaacatcc aatttgtcgc gctggcgagc gacgcgatgg aggccggtga cgtgaacttc      660
agcaatctcc tttcctccat tcagaccgac gaagcgcgcc acgcgcagct cggcttcccg      720
accctcgacg tcatgatgaa gcatgacccg aagcgcgctc aacagatcct ggatgtcgcc      780
ttctggcgca gttatcgcat cttccaagcc gtcaccggcg tgtcgatgga ctattacacc      840
cccgtcgcta agcgccagat gtcgttcaaa gagttttatgc tcgaatggat cgtgaagcat      900
cacgagcgga tcctgcggga ctacggactc cagaagccgt ggtactggga caccttcgag      960
aaaacgctcg accacggcca tcatgcgctg catatcggta cctggttctg cgcgcccgacc    1020 ttgttctggg acccgaatgg cggggtcagc cgcgaggaac ggcgctggct gaatcagaag     1080
tatccgaatt gggaagagtc gtggggcgtc ctgtgggatg aaatcatttc gaacatcaac     1140
gccggcaaca tcgagaaaac cctgccggaa accctgccga tgctctgcaa tgttaccaac     1200
ctccccatcg gctcgcattg gatcgctttt cacctcaagc ccgagcaact tgtgtacaag     1260
ggtcgcctgt ataccttcga ctccgacgtg tcgaagtgga tcttcgagct ggaccccgag     1320
cggtacgcgg tcataccaa cgtcgtcgac cggtttatcg ggggacagat ccagccgatg     1380
acgatcgaag gcgtgctgaa ttggatgggc ctgacgcccg aggtcatggg caaagacgtg     1440
ttcaactacc gctgggcggg tgactacgcg gagaaccgga ttgccgccga g              1491

<210> SEQ ID NO 16
<211> LENGTH: 264
<212> TYPE: DNA
```

<213> ORGANISM: Artificial Sequence
<220> FEATURE:
<223> OTHER INFORMATION: Codon optimized Xanthobacter autotrophicus
      oxygenase gamma subunit XamoB sequence

<400> SEQUENCE: 16

```
atgagcctgt tccccattgt cggtcgcttt gttggagact tcgtccctca cctcgtcgct    60
gttgatactt ccgatacgat cgaccagatc gcagagaaag tcgccgtgca taccgtgggc   120
cgccggttgc cgccggaccc gaccgcgacg ggctacgaag tgctgctgga cggcgaaacc   180
ctcgacggcg gggcgaccct gaggccatc atgaccaagc gcgagatgct ccccctgcaa    240
tggttcgacg tgcggttcaa gaag                                          264
```

<210> SEQ ID NO 17
<211> LENGTH: 366
<212> TYPE: DNA
<213> ORGANISM: Artificial Sequence
<220> FEATURE:
<223> OTHER INFORMATION: Codon optimized Xanthobacter autotrophicus
      ferredoxin XamoC sequence

<400> SEQUENCE: 17

```
atgaatttgc acgcccccaa tgctgaacaa gatgacatcg aatatgttga cgtctgcgca    60
gtcgacgacc tctgggatgg cgagatggac gtgttcgatg tgggcgagca cgaagtgctc   120
ctcgtcaagc atgagggtcg cttccatgcg tacgacggga tttgcccgca ccagtccgtg   180
agcctggtcg agggccatct gaccgaggac ggcgtgctta tctgcaaggc ccatgagtgg   240
cagttctcgg tcgagggcgg acagggcatc aacccggcga acgtgtgcct gcagtcgttc   300
ccgctcaaag tcgagggtgg ccgggtcctg atcggcacgg aaccctgcc gaaagagggc    360 gaggcg                                                              366
```

<210> SEQ ID NO 18
<211> LENGTH: 303
<212> TYPE: DNA
<213> ORGANISM: Artificial Sequence
<220> FEATURE:
<223> OTHER INFORMATION: Codon optimized Xanthobacter autotrophicus
      coupling/effector protein XamoD sequence

<400> SEQUENCE: 18

```
atgagtaacg cgacggtgga tgatatggac gagaatttgg tgggaccggt gattagggca    60
ggcgatctgg cagacgccgt gatcgacgcc gtcatcgcgg acaaccccgg caaagaggtt   120
cacgtcatcg agcggggtga ctacgtccgg atccataccg accgcgactg ccggctgacc   180
cgcgcttcga tcgagcaagc gctcgggcgc agcttcgtcc tcgcggccat cgaagccgaa   240
atgtccagct tcaagggccg catgtcgtcg tccgactccg agatgcgctg gtactataag   300
agc                                                                 303
```

<210> SEQ ID NO 19
<211> LENGTH: 1023
<212> TYPE: DNA
<213> ORGANISM: Artificial Sequence
<220> FEATURE:
<223> OTHER INFORMATION: Codon optimized Xanthobacter autotrophicus
      oxygenase beta subunit XamoE sequence

<400> SEQUENCE: 19

```
atgactcaac aacgccccac ccggacccgc gaacgcaaaa agacctggac tgcatttgga    60
aaccttggcc gcaagccgac cgactacgaa gttgtcaccc acaacatgaa tcacacgatg   120
```

-continued

```
cgcggcacgc cgctcgaact ctcgcccacc gtgcatgcca acgtctggct gaagaaaaat      180
cgcgacgaga tcgcgctgaa agtcgattcg tgggacctgt tccgcgaccc tgatcgcacc      240
acgtacgaca cctatgtgaa gatgcaagat gaccaggaaa cctacgtcga caatctgctc      300
ctcagctaca ccggcgaggg ccgctatgac gaggagctgc gtcccgctc cctcgacttg       360 ctgagtgccg gccttacccc gacgcgctat ctgggacatg gtctgcagat gttggccgct      420
tatatccagc aactcgcccc gtcggcgtac gtcggcaatt gcccgtgtt ccagaccagc       480 gacgcgctca ggcgcgtcca gcgcgtggcg tatcggaccc gccagctcgc ggatgcccac      540
ccagctcggg gtttcggctc cggggaccgg gctgtctggg agaagtcgcc ggactggcag      600
ccgatccgga aggccatcga ggagcttctg gtgacgttcg agtgggacaa agcgctggcc      660
ggcacgaact tcgttgtcaa gccgattctg acgagctgt cctcaaccca tctggcacgg       720
ctgctgcatg tcgagggcga cgagctggac agcctggtgc tgcggaatct ccacggggac      780
gcgcagcggc acgcccgctg gacggccgca ctgggtcgct tcgcggtcga gcagaacgtg     840
aacaacagga ccgtgcttcg cgacgcgatc gccggctggc atgaaaccgg cgaggcagtg      900
ctcgccgcgg cgctggcat gctcgcgagc cgggcgccct ccgccgatgc ggcgaagatc       960
gcggatgagg tccgcgccac cctcgcgcag ctccatgcga atgccggtct gggccatgac     1020
gcc                                                                   1023
```

<210> SEQ ID NO 20
<211> LENGTH: 981
<212> TYPE: DNA
<213> ORGANISM: Artificial Sequence
<220> FEATURE:
<223> OTHER INFORMATION: Codon optimized Xanthobacter autotrophicus
      reductase XamoF sequence

<400> SEQUENCE: 20

```
atgcgcttga atgatggccg ctccttctcc tgccgctccg accagactgt tctccatgcc       60
gcccttgctg ccggtatcga catgccgtac gagtgcgcgt cgggcagctg cggttcctgt      120
cggtgccgcc tctcgcacgg cagcgtcagt ctgctgtggc ccgaggcccc gggcctgagc      180
gcgagggacc gccaaaaggg tgaccgcatc ctcgcgtgcc aatcgacgcc cagctcggac      240
cttgagataa acgtccgcgc cggcgacgcg ctcctggagc ccctccacg ccgccatgcg       300 gcacgcgtga ccgtgaaaga aacgctgtgc gcgagtgtga tccgcctggt gctcaatgtc      360
ggcggaccga tccatttcct tccgggccag ttcttcatcc tcgatctgcc gggtgcgggc     420
cggcgcgcct attcggtcgc gaacctggag aacgccgcgg gtggcatcga gctcctgatt      480
aagcggaaga ttggcggagc cggcaccgct gcgttgttcg atcagtgcgc cccgggtatg     540
ggcctggtga tcgaagggcc gtacgggcgg gcgtatctcc gggcggactc ggccaggggc      600
atcgttgcgg tcgcgggggg cagcggcctc gcgccgatgc tgtccatctt gcgcggtgcg      660
ctcgcacggg gcttcggcgg cccgatggac ctctatttcg gcgtgaacac cgccgaggaa      720
ctgttctgcg tgcccgagct gtccgccctg caggccgccg gggcacgggt ccatctggcc      780
ctgcgggatg gtgccccgg cccgcgggc ctgcaccgcc aggctggcct catcggcgac       840
gccctcgtcg cgggagagcc ggacctcaag gcaaaagacc tgtacgtcgc cggcccggcg      900
ccgatgaccg atgacatcct ggcccggacc gtgcgccagg aagccatccc cgctgaccgc     960
gtgttcttcg acaggttcgt c                                              981
```

<210> SEQ ID NO 21
<211> LENGTH: 1710
<212> TYPE: DNA
<213> ORGANISM: Artificial Sequence
<220> FEATURE:
<223> OTHER INFORMATION: Codon optimized Escherichia coli sulfite reductase (NADPH) hemoprotein alpha subunit sequence

<400> SEQUENCE: 21

| | | | |
|---|---|---|---|
| atgtccgaga agcaccccgg tccccttgtt gttgaaggca aactcactga cgccgaacgc | 60 |
| atgaagcatg agtccaacta tctgcgcggt accattgcgg aagatctcaa tgacggcctg | 120 |
| acgggcggat ttaagggcga taacttcctg ctcattcggt ttcatggtat gtatcagcaa | 180 |
| gacgacaggg acattcgggc ggagagggcc gagcaaaagc tcgaacctcg ccacgccatg | 240 |
| ctcctgcgct gccggttgcc gggcggggtc atcaccacga gcaatggca ggccatcgac | 300 |
| aagttcgcgg gtgagaacac catctacggc tccatccgcc tgaccaatcg ccaaaccttc | 360 |
| cagttccatg gcatcctcaa gaaaaacgtc aagcccgtgc atcagatgct ccattcggtc | 420 |
| ggtctggatg ccctcgcgac ggcgaacgac atgaatcgaa cgtgctctg caccagcaat | 480 |
| ccctacgaga gtcagctcca cgctgaggcg tatgagtggg cgaaaaagat cagcgagcac | 540 |
| ttgctcccgc gcacgcgcgc gtacgccgag atctggctcg atcaggaaaa agtcgccacc | 600 |
| accgatgagg agccgatcct tggccagacc tatctgcccc gcaagttcaa gaccaccgtg | 660 |
| gtgatcccac gcagaatga catcgatctc cacgccaatg acatgaactt cgtggcgatc | 720 |
| gccgagaatg gtaagctcgt cggcttcaac ctcctcgtcg gcgggggct gtcgatagag | 780 |
| catggcaaca gaaaaacgta cgcccgcacc gcgtccgagt tcggttatct gccctggaa | 840 |
| cataccctgg ccgtcgctga ggcagtcgtc acgacgcagc gggactgggg caaccgcacc | 900 |
| gaccgcaaaa acgccaagac gaaatacacc ctggagcgcg tcggcgtgga gactttcaaa | 960 |
| gccgaggtcg agaggcgcgc tgggatcaag ttcgagccga tccggccgta cgagttcacg | 1020 |
| ggtcggggcg atcggatcgg ctgggtgaaa ggcatcgacg acaattggca cctgacgctg | 1080 |
| ttcatcgaaa atggccgcat cttggactat ccggcacggc cgctcaagac cggactgctt | 1140 |
| gagatcgcca agatccataa gggcgatttc cgcatcaccg cgaatcagaa cctgatcatt | 1200 |
| gcgggcgtgc cagagtcgga gaaagcgaag atcgaaaaga ttgcaaaaga atcgggcctg | 1260 |
| atgaacgccg tcaccccgca gcgcgagaat tccatggcgt gcgtgagctt cccgacgtgc | 1320 |
| ccgctcgcga tggccgaggc cgagcggttc ctcccgtcgt tcatcgacaa catcgacaat | 1380 |
| ctcatggcga agcacggcgt gtcggacgag catatcgtca tgcgcgtgac cggttgccct | 1440 |
| aatggctgtg gtcgcgctat gctggctgag gtcggccttg tcggcaaggc cccgggccgg | 1500 |
| tacaacttgc atctgggcgg caaccgcatt gggacccgca tcccgcgcat gtacaaggag | 1560 |
| aacatcaccg agcccgagat cctggccagc ctggacgaac tgatcggccg gtgggccaag | 1620 |
| gaacgcgagg ccggagaggg cttcggcgac ttcaccgtcc gggcgggcat aatccgcccg | 1680 |
| gtcctggacc cggcgaggga cctctgggac | 1710 |

<210> SEQ ID NO 22
<211> LENGTH: 1797
<212> TYPE: DNA
<213> ORGANISM: Artificial Sequence
<220> FEATURE:
<223> OTHER INFORMATION: Codon optimized Escherichia coli sulfite reductase (NADPH) flavoprotein beta subunit sequence

<400> SEQUENCE: 22

| | |
|---|---|
| atgaccacgc aagtcccgcc ctccgccctc ctgcccctga accccgagca actcgcacgc | 60 |
| ctccaagccg cgaccaccga cctgacgccg acgcagctcg cgtgggtgag cggctacttc | 120 |
| tggggagtgc tcaatcagca gccggcagct ctggcggcga ccccggcacc cgcagccgag | 180 |
| atgccgggca tcaccattat ctcggcgtcg cagacgggta atgccaggcg cgtcgccgag | 240 |
| gccctccggg acgacctcct cgccgccaaa ctgaatgtga agctcgtcaa cgctggggac | 300 |
| tataagttca acagatcgc gtccgagaag cttctcatcg tggtcacctc gacccagggc | 360 |
| gagggcgagc cgcctgaaga ggctgttgcg ctgcacaagt tcctcttctc gaagaaagcc | 420 |
| cccaaactgg aaaacaccgc ttttgcggtg ttctccctgg gggattcgag ctatgagttc | 480 |
| ttttgccaga gcggcaaaga ctttgatagc aagcttgccg agctgggtgg ggagcgcctg | 540 |
| ctggaccgcg tcgatgccga cgtggagtac aagccgcgg cgagtgagtg gcgcgccagg | 600 |
| gtcgtcgacg ccctgaagtc gcgggctccg gtcgcggcgc cgtcccagtc cgtggcgacg | 660 |
| ggcgcagtga atgaaatcca caccagcccg tatagcaagg acgcgcctct ggtcgcgtcc | 720 |
| ttgagcgtta accaaaagat caccggccgg aactccgaga aagatgtccg gcacattgag | 780 |
| atcgacctcg cgactcggg catgcgctac cagccgggtg atgccctggg cgtctggtac | 840 |
| cagaacgacc ccgcgttggt caaggaactg gtcgagctcc tgtggctcaa gggcgatgag | 900 |
| cccgtgaccg tcgagggcaa gaccctcccc ctcaacgagg ccctgcagtg gcatttcgag | 960 |
| ctgacggtga acactgcgaa cattgtggag aattacgcga ccctcacccg cagcgagact | 1020 |
| ctcctgccgc tggtcggtga caaggccaag ctccagcatt acgcggcgac gaccccgatc | 1080 |
| gtggacatgg tcccgcttcag tcccgcccaa ctcgatgccg aggcgctgat caatttgctt | 1140 |
| cggcccctca ccccacgcct gtactcgata gcgagctcgc aggcagaggt tgagaacgaa | 1200 |
| gtgcatgtga cggtcggagt cgtccggtac gacgtcgagg gtagggctcg cgctggcgga | 1260 |
| gcgagttcct tcctggctga ccgggtggaa gaggagggcg aggtgcgcgt gttcatcgag | 1320 |
| cacaatgaca atttccggct cccggcgaac ccggaaaccc cggtgatcat gatcggccca | 1380 |
| ggcacgggca tcgccccgtt ccgcgccttc atgcaacaac gggcagcgga cgaagcgccg | 1440 |
| ggcaagaact ggctgttctt cggcaatccg catttcaccg aagatttcct gtaccaagtg | 1500 |
| gagtggcagc ggtatgtcaa ggacggcgtg ctgacccgca tcgatctggc gtggtcgcgg | 1560 |
| gaccagaaaag aaaaagtcta tgtccaggac aaactgcgcg agcagggtgc cgagctttgg | 1620 |
| cgctggatca acgacggtgc ccatatctat gtttgcgggg acgccaatcg catggccaag | 1680 |
| gacgtggaac aggcccttcct tgaggtcatc gccgagttcg gcggcatgga caccgaagcc | 1740 |
| gcggacgagt tcctgagcga gttgcgcgtg gagcgccgct atcagcgcga cgtctat | 1797 |

<210> SEQ ID NO 23
<211> LENGTH: 1659
<212> TYPE: DNA
<213> ORGANISM: Artificial Sequence
<220> FEATURE:
<223> OTHER INFORMATION: Codon optimized Rhodobacter capsulatus sulfite reductase (NADPH) hemoprotein subunit beta sequence

<400> SEQUENCE: 23

| | |
|---|---|
| atgtatgagt atagcgattt cgatgaagct tttgttagga atagggttgc acagtttagg | 60 |
| gaccaagtgg cgaggcgcct cgacggctcg ctcaccgagg aagagttccg gcctctccgc | 120 |
| ctcatgaacg gcctctatct ccagctgcat ggctacatgc tccgcgtcgc catccctac | 180 |
| ggcacgctga gctccaacca gatgcgcgcc cttgccgacg tggcggaccg cttcgaccgc | 240 |

```
gggtacggtc atttcacgac ccggcagaac atccagttca attggatcaa gctgaccgac    300
accccggata tcctggagcg gctggcggac gatggcctcc atgcgatcca gaccagcggc    360
aactgcattc gcaacgtcac gaccgacgcg ttcgcgggtg cggcggcgga cgagatcgag    420
gacccacgcc gtacgccga gctcatccgg cagtggtcgt cggatcacgc agagttccaa    480
ttcctcccgc gcaagttcaa gatcgcaatc acgggctcgc ccgaggaccg ggcagcgatc    540
cgggcccacg acgtcggcct gcagttgatc cagcgcggtg gagagactgg cttccgcgtg    600
cttgtgggtg gcggcctggg ccggaccccg atgctcgctc ccgagcttcg cgacttcctc    660
ccgaaagccg acctcctccc gtatctggaa gcgatcctcg ccgcgtataa cttgattggg    720
cggcgggaca ataagtacaa agcgcgcatc aagattaccg tgttcgaaac cggcatcgag    780
ccgttccgcg acctggtgga gcaagagttc gagcggatac gccctcagtt caccggcgcg    840
gaccaggccc tgcttgccga gatcacgccc cacttcgcgc tccccgacct ggtcgcgaaa    900
gatcccgcgc cgttcgctgc ggcccaggtg accgacccgg cattcgccgc gtgggtcaag    960
cactccgtga ccgaccataa acggccggat cacgccgtcg tgaccatttc cgtcaagacc   1020
ccgggagagg aaccgggcga cgtgagtgcc gcgcaaatgc gcgcagtggc cgacctggcc   1080
gatctgcatg ggtacggcga gctgcggatc agccacatgc agaacatcgt cctgccccat   1140
gtcgctcgcg ccgacctccc ggctctccac gccgctctgc gcaaggttgg cctgccgct   1200 gcgaacgtcg gtctgatctc ggatatgatc gcgtgtcccg gcatggacta ctgcgcgctt   1260
gcgaccgcca ggtcgatccc gctcgcgcaa gagatcgccc agcatttcga accctgggc   1320 ctggtcgaaa cgataggccc gctgcccttg aagatctccg gctgcatcaa tgcctgcggc   1380
catcatcatc tgggcgcgat cgggattctg ggcctggatc gcgcggggc cgagaattac   1440 cagatcaccc tgggtggcgc cgagggccca gaggcagcga tcggagagaa aatgggtccg   1500
ggcttcgctt atgacgccgt ggtcccggcc atcgagcgcc tggtccgggc gtacctcacg   1560
ctgcggctgt ccgagggcga gactttcctc gcggccttgc atcggctcgg tcgcgagccg   1620
tttcgcgcag ccctgtatga cgaagcgcaa gacgccgcc                         1659
```

<210> SEQ ID NO 24
<211> LENGTH: 2205
<212> TYPE: DNA
<213> ORGANISM: Artificial Sequence
<220> FEATURE:
<223> OTHER INFORMATION: Codon optimized Rhodobacter capsulatus sulfite
      reductase (NADPH) flavoprotein subunit alpha
      sequence

<400> SEQUENCE: 24

```
atgctccgct tccttcaccg ctggcctggc ctcctcgctg ccctcctcgt ccttgtcctc     60
gcgttgtccg gttccgccct gagcctgtat ccggccctgg agcggctcgc ggtgccgcag    120
gcagagtcga cccttactgt ggccgacctc gccgctcgcg tggcctcggc gcatcccggc    180
ctggagcaaa tccgcagggc accgagtgga cgcgtcgtcg cgtggtggtt cgagggtggc    240
cggccggggg cggccgtcat agaccccgcc accggcgcgg accttggcag cccggacccg    300
cttccgggca gccgcttcct gacggatctc caccgcgagc tgttcgcggg cgatacgggt    360
cgcctggtgg cagcggctgg agccgccctg atgctggcgc tcgccatctc gggtgcctgg    420
ctggttgctc ggcgcatggg cggtggagt cgctggttcg gccgcacccg gggtccgttc    480
gccggtcgcc tgcatgtcga gctcgcccgc tttgcggtcg gcggcttgat cctctcgtcc    540
```

```
ctgaccgcgc tctggatgac cgcgtccatg ttctccctgc tccccgacgg tgccgccgag    600
cccgctcccg ccctggcgac ggcgacccctc ccgcggttgc cgtacgacca gattccggcg   660
ctggcgaaca ctccggcagc ggccctgcgc gagctgtccc tgccgagccc ggacgatccc    720
accgacacgt tcaagctcgt taccgagggt ggcgcagccc tgatcgaccc cggcaccgga    780
gccatgctgt cgagtgccac gccgggattc ttcgagaaag cgaccgagat catggtgatg    840
ctgcacaccg gcagggcgc gtcggccctg ggcctgctgc tcggcctcat gtcgctgtcc     900
gtgccagcgc ttgcgctcac cggtgcccag cattggtggg cgggcctgcg gtcgaatcgg    960
cggattcggc gcaacgccag ggcgcagctg gcggaaaccg tggtcctggt ggcctccgag   1020
ggtgggacca cgtgggctt cgcgcgcacg ctgcacgacg gcctgactgc cgctgggcaa    1080
aaagtccata ccgcgcctct ggcgagcttc gaccccgcca ggtatgccag gcacgccgc    1140 ttcctcattc tggccgccac gtatggcgag ggcgaggcgc cgacggcagc gaaagccgtc   1200
ctcgaccgca ttgcggcgct cacctcggca ccggctgccc cgctggccat actgggcttt   1260
ggggatcgca ccttcccgca attctgcggc ttcgcggagt ccctgcgcgc cgcagccgca   1320
gccatcggct gggagagcct catgccgatg ccaccgtcg accgccagag cgcccaagac    1380
ttcgcgcgct ggtcgaggga tctgggtgcc gtcctcggcc tcccgctgga tctcacgcat   1440
ctccccgaac gcccaaagac cacggctctt accctcatca gtcggcggga ccatggcgcc    1500
gaggtccagg cgcccacctc gatcctgcgc ttcgaggttc gcaggcgac gctctggcag    1560 cgcctgaccg gccagggctt tgcgcggttt gaagcgggcg acctcatcgg catcctgccc    1620
aagggctcgg accttccgcg cttctactcg ctggcgagca cgctctcgcga tggcttcctg   1680 gaaatctgcg tgcgcaggca cccgggtggc ctgtgctccg gccagctcac cgacctcacc   1740
ccaggcgcca cggtcgcggg cttcgtgcgc cgcaaccccg ccttccggcc tcaaaagggt   1800
cggaaaccgg tcatcctcat cggagccggc accggggtgg ggcccctggc aggcttcctc   1860
cgcgcgaatc ggcgccaccg gccgatgcat ttgtatttcg cgcccgcgc accgcagtcg   1920 gacttgctgt acgaagccga gctgcgggat tggcaggccg cggggcaact cagccgcttg   1980
accaccgcgt tctcccggca tggccccaag acctatgtgc aagacgcgct ccgcgcagac   2040
gcgcccgagc tggcacggct gatcggtgct ggcgcccaga tcatggtgtg tggcggacgc   2100
gacatggccg ctgcggtgcg ggacgcgctg gccgaaatcc tcgtcccgat cggccagacc   2160
ccagcctccc tgaaggccga gggccgctac gctgaggacg tgtac                   2205
```

<210> SEQ ID NO 25
<211> LENGTH: 1695
<212> TYPE: DNA
<213> ORGANISM: Artificial Sequence
<220> FEATURE:
<223> OTHER INFORMATION: Codon optimized Shewanella putrefaciens sulfite reductase (NADPH) beta subunit sequence

<400> SEQUENCE: 25

```
atgagtgagc aaaaactggc cctgaatgaa tatcttaaaa ccgacagcga ctatctgagg    60
ggtaccatca aggaaggcct ggacagctcg tcaccgggt ccttctccga tggcgaccaa    120
cagctgatca agttccacgg cttctaccag caagacgatc gcgacctccg caacgagcgg   180
aaggagcaga aattggagcc gctctactcc ttcatgctgc gcgctcgcgt ccccggcggc    240
atctgctcgc cgcagcagtg gctcggcgtc gacaaaatcg cgagtacgct tacgtcgtcg    300
aactcgatcc ggctcacgac ccggcagacc ttccagtatc atggtatccc caagcgcaac   360
```

```
ctcaagacca tcattcaaga tctcgaccgc caagcgctgg acagcatcgc ggcctgcggc      420
gacgtcaatc gcaatgtgat gtgtaacccg aacccggtcg agtcgaagct gcacgagcaa      480
gcctacgcag tggcgaaaaa gctctccgac catctcctgc cgcatacccg cgcttacgcg      540
gaaatctggc tggatgagga gaagctcctg accaccgagg acgaaacggt cgagcccgtg      600
tacggcaaga cctatcttcc gcgcaagttt aagatggccg tggcagtgcc acccgacaac      660
gacgtcgatg tgtataccaa cgacctcggc ttcatcgccg tggccgagaa cggtgaactc      720
gtgggcttca acctgaccgc gggtggcggc atgggatcca ctcacggcga ggttgaaacg      780
ttccctcggc tcgcggatga ctttgggttc atcaagaccg aggacgtcat gaaattcgcc      840
gaggctgtca tgaccgtgca gcgcgactgg ggcaaccggt ccaatcggaa gcgcagccgc      900
cttaagtaca ccatagtcga ccatggctac gagaagttta aggcagaggt cgaggcgcgc      960
gcaggcgtga agttcgagcc gaagcgcgag gtcgtgatcg gcgacagggg tgaccgctac     1020
ggctgggttg agggcgtgga cggcaagtgg cacctgacgc tgttcattga gtccgggcgg     1080
atcaaagatc tgccgggaca gacgctgcag acgggcctgc gcgagatcgc gaagatccat     1140
aagggcgact ccgcatgac ctccaatcag aacatgatca tcgcgggtgt ggccgccgag     1200
gataaggcca cgatcgaagg gctcgccagg aaacacggct tgctcggtca ggttctgacc     1260
caaacccgcg acatagcat cgcgtgcgtc gcgctgccca cgtgcccct ggcgatggcc     1320 gaggccgagc ggtacttccc cgagttcatc gaccatatcg acgcgctcca ggcgaaacat     1380
ggcatcagcg agcaagccat tgtggtccgg atgaccgggt gcccgaacgg ctgcgctcgg     1440
ccattcgccg cagagatcgg cctcgtgggc aaggcccccgg acggtataa tctgtatctt     1500 ggtgcgtcgt tcgagggtac ccgcctgaat aagatgcatc gcgagaacat acaggaagcc     1560
gacatcctcg cggaactcga taccttgttc ggccgctacg ccgtggagcg cgacgcgggc     1620
gaaaccttcg gcaatttcac cgtccgggtc ggcgtcgtca agccgtcat tgacgccgcc     1680 aaagacttcc acggc                                                      1695

<210> SEQ ID NO 26
<211> LENGTH: 1797
<212> TYPE: DNA
<213> ORGANISM: Artificial Sequence
<220> FEATURE:
<223> OTHER INFORMATION: Codon optimized Shewanella putrefaciens sulfite
      reductase (NADPH) alpha subunit sequence

<400> SEQUENCE: 26
atgctcctga agaacttag ctccctcgcc tccccgctgt cccaaggcca agtcgaaaag       60
ctcaaacagc tcaccagcga gctgagcgcc gtgcagctcg cctgggtgag cggctaccctc     120 gccgctaccg cgaatgccgg tcagctgccc ccgtcgcgc aggcgcagac ggcgcagacc      180
gtgaccatcc tctatggtag ccagacgggc aatggccggg gtgtggccaa ggcactggcg      240
gacaaggccc aagcgcaggg ttatgccgtg aacctggcct ccatgggcga gtacaatgtg      300
cggcagttga agcaagaggc cgtcctgctg ctcgtcgtga gcacgcatgg cgagggtgag      360
gctccggacg acgcaatcga gcttcataag ttcctggcgt cgaagcgcgc gcctaagctt      420
gacaatctcc actattcggt gctggccctg ggggatagcc cctacgagtt cttctgccag      480
accggcaaag acttcgacac ccggctggcg gcccttgggg cgaagagtct cctgccgctc      540
atcgagtgcg acgtggacta tgaagctgcg cagggcagtg gcatgccga tgtgctggaa      600 gctgtcaagc cgctgatcga aacgtcctcc gcctcggtcg tgtcgatcgg cacggcgaaa      660
```

| | |
|---|---|
| gcgatcggcg agagtgagtt caccaagcaa aaccccctatt cggccgaggt cctcgtttcg | 720 |
| cagaagatca ccgggcgggg cagtgatcgc gacgtccgcc atgtcgagat tgacctgggc | 780 |
| gactcgggac tgacctacca ggctggcgac gccctgggcg tgtggttttc gaataacgaa | 840 |
| gctctggtcg aggaaatcct gacggcgctg tcgctgtcgg gcgatgagca agtcgtcgtg | 900 |
| gagaaagagt cgttgaccct gaagcaggcc ctcgtggaca gaaagagct cacccagctg | 960 |
| tatcccgggt tggtcaaggc ctgggcgag ctgtccggca gcgcagagct cctgccctg | 1020 |
| tccgaggaca aggaacaagt taggcacttc atcctcaagc atcagttcgc ggacctcgtc | 1080 |
| acccagtatc cgctgtcgaa taacagcgtg acgctcaatg ccgcgaagtt gcttgagctg | 1140 |
| ctcaggccac tcacgcctcg cctctacagc atagcgagct cccaatccga ggtcgaaacc | 1200 |
| gaggtgcatc tcaccgttgc cctggtggaa gatgagcgcc atggcgctgc gcgcttcggg | 1260 |
| ggagcgagcc acttcctcgc gtccgcgcag gaaggcaccc aggtcaaggt ctacgtggag | 1320 |
| cccaacaagc acttccggct gccggagaac ccggagactc cggtcattat gatcggtccc | 1380 |
| ggcacgggcg tcgcgccgtt ccgcgccttc atgaagagc gcgtggccca gggaatccag | 1440 |
| ggtgactcct ggttgttctt cggcaatccg catttcgagc aagactttct gtaccagacc | 1500 |
| gagtggcaac agtacctgaa aaacggcgac ctgtcgcgga tcgacgtggc cttctcgcgc | 1560 |
| gatcaggcgc ataagattta cgtccagcac cgcatcaagg accagggcca ggccctgtgg | 1620 |
| cagtggctcc aaaacggcgc ccacatctac atctgcggcg acgcagagcg gatggcaaaa | 1680 |
| gacgtgcacc aggcactgat cgaggtcgcg gttgaggttg gcggcctgaa caccgaagcg | 1740 |
| gccgaggcgt acttcgagac tctccgctcc gataagcgct accagaaaga tgtctat | 1797 |

<210> SEQ ID NO 27
<211> LENGTH: 1815
<212> TYPE: DNA
<213> ORGANISM: Artificial Sequence
<220> FEATURE:
<223> OTHER INFORMATION: Codon optimized Bacillus subtilis sulfite
       reductase [NADPH] flavoprotein, alpha-component
       sequence

<400> SEQUENCE: 27

| | |
|---|---|
| atgcagctcc aagtgatgaa ctccccttc aaccaagaac aagccgagct cctgaatagg | 60 |
| ctcctcccga cccttaccga gagccagaaa atctggctgt ccggctatct gtcggcgcag | 120 |
| agcgtgagtg cgcaagaggc cgcgggcacg cccgcggcgg ccgtgagcgc cgaggcaccc | 180 |
| gctcccgccg tgtcgaagga agtcactgtc ctttacggct cgcaaaccgg caacgcacaa | 240 |
| gggctggcag agaacgccgg aaagcagctt gagcagtccg gtttccaggt caccgtttcg | 300 |
| tccatgagcg acttcaagcc caaccagctg aaaaaagtca ccaatttgct gatcgtcgtg | 360 |
| tcgacccacg gtgagggcga gccgcctgac aatgccctct ccttccatga gttcctgcat | 420 |
| ggtcgcaggg ctccgaaact ggaagatctc cggttctccg tcctggcgct cggagactcg | 480 |
| tcctatgagt tcttttgcca aaccggcaaa gagttcgacc agaggcttga ggagctgggc | 540 |
| ggcaagcgca ttagtccgcg ggtggattgc gacctcgact atgacgagcc ggcggcggag | 600 |
| tggctggaag gcgtcctgaa gggcctgaat gaggccggtg ggggctccgc cgctcccgcg | 660 |
| ccggccgcgg ccagccagac cggcgagtcc agctatagtc gcacgaaccc gtttcgggcc | 720 |
| gaggtcctgg agaacctcaa cttgaatggg cgcggcagca ataagaaac gcgccatgtc | 780 |
| gagctctccc tcgaaggctc gggcctgacc tatgagcctg cgactcgtt gggcgtctat | 840 |
| cccgagaacg acccagagct cgttgagctc ctgctgaagg agatgaactg ggatccggaa | 900 |

| | | |
|---|---|---|
| gagatcgtga ccctgaataa acagggcgat gtccgcccct tgaaagaggc actcatctcc | 960 | |
| cattacgaga tcaccgtgct taccaagccg ctcctggagc aagcggcgca gctcacgggc | 1020 | |
| aacgacgaac tccgcgagct cctcgcccca ggcaatgagg aaaacgtgaa ggcctacatc | 1080 | |
| gagggtcgcg atctcctgga cctcgtgcgg gactacggcc cgttctcggt ttcggcgcaa | 1140 | |
| gaattcgtgt cgatcctccg gaagatgccg gcccgcctgt actcgatcgc gagcagcctc | 1200 | |
| tcggcgaacc ccgatgaggt ccacctgacc attggagcgg tccgctatga cgcccatggc | 1260 | |
| cgggagcgca agggcgtgtg ctccatcctg tgcgctgagc gcctccagcc gggtgatacg | 1320 | |
| ctgccggtct acgtgcagca taatcagaat ttcaagctgc cgaaggaccc ggaaacgccg | 1380 | |
| ataatcatgg tcggcccggg caccggtgtg gcgccgttcc gctcgttcat gcaagagcgc | 1440 | |
| gaggaaacgg gcgctgaggg taaggcctgg atgttcttcg gcgaccagca cttcgtcacc | 1500 | |
| gacttcctgt accagaccga gtggcagaac tggctcaagg acggcgtgct gactaaaatg | 1560 | |
| gacgtcgcct tcagccgcga caccgaagaa aaagtctacg tccagcatcg gatgctggag | 1620 | |
| cacagcgcgg aactgttcga gtggttgcag gagggcgccg cggtgtacat ctgtggtgac | 1680 | |
| gagaagcaca tggcccatga tgttcacaac acgctccttg agatcatcga aaagagggc | 1740 | |
| aatatgtcgc gcgaggaggc cgaggcgtat ctggcagata tgcagcagca gaaacggtac | 1800 | |
| cagcgcgacg tgtac | 1815 | |

<210> SEQ ID NO 28
<211> LENGTH: 1713
<212> TYPE: DNA
<213> ORGANISM: Artificial Sequence
<220> FEATURE:
<223> OTHER INFORMATION: Codon optimized Bacillus subtilis sulfite
      reductase (NADPH) hemoprotein, beta-component
      sequence

<400> SEQUENCE: 28

| | | |
|---|---|---|
| atggtgacca aaattctcaa agctcccgat ggctccccct ccgacgttga acgcatcaaa | 60 | |
| aaagaatcgg attatctgcg gggtacgctc aaagaggtga tgctcgaccg catcagtgcc | 120 | |
| ggcattccgg acgacgacaa ccgcctgatg aagcatcacg atcgtacttg caggacgac | 180 | |
| cgcgacctcc gcaacgagcg ccagaagcaa aagcttgagc cggcgtatca gttcatgctg | 240 | |
| cgcgtgcgga tgcctggcgg ggtgtcgacc ccggagcagt ggctcgtcat ggacgatctc | 300 | |
| agccagaaat acgggaatgg cactctgaag ctgaccaccc gggagacttt ccagatgcac | 360 | |
| ggcatcctga gtggaatat gaaaaagacc attcagacca tccactcggc actgctcgac | 420 | |
| accatcgcgg cgtgcggcga cgtcaaccgc aacgtgatgt gtgcgtccaa ccctatcag | 480 | |
| agtgagatcc attccgaggt gtacgagtgg agcaaaaagc ttagcgacga cctcctcccg | 540 | |
| cgcacccggg cgtatcacga aatctggctc gacgaggagc gcgtggcagg caccccggaa | 600 | |
| gaagaggtga gcccatgta cggcccgctg tatctccccc gcaagttcaa gattggcatc | 660 | |
| gccgtcccgc cgtccaacga catcgacgtg ttcagccaag acctgggctt catcgcgatc | 720 | |
| gtcgaggatg caagctgat cggcttcaat gtcgcgatcg gtggcggcat gggcatgacg | 780 | |
| catggcgaca cggcgacgta tccgcagctg gccaaggtta tcggttctg caggccagag | 840 | |
| caaatgtacg atgtcgcgga aaagaccatc accatccaac gcgactatgg aaatcgcagc | 900 | |
| gtgcggaaga acgcgcgctt caagtatacg gtcgatcggc tcggcttgga gaatgtcaag | 960 | |
| gaagaattgg agaacaggct gggctggtcg cttgaggaag ccaagccgta ccatttcgac | 1020 | |

| cataatggcg atcgctacgg gtgggtcgag ggcatagagg acaaatggca tttcacgctg | 1080 |
| ttcgtcgagg gtggccggat cacggattac gatgactaca agctgatgac gggtctgcgc | 1140 |
| gagatcgcca aggtccatac cggcgagttc cggctgaccg cgaaccagaa cctcatgatt | 1200 |
| gcgaatgtgt cctcggacaa gaaagaagag atcagcgccc tgatcgagca gtatgggctc | 1260 |
| accgatggca agcactattc cgccctccgc cggtccagca tggcatgcgt cgcgctcccg | 1320 |
| acgtgcggcc tggcgatggc cgaggccgag cggtacctcc ccacgctgct cgacaagatc | 1380 |
| gaagagatca tcgacgagaa cggcctgcgc gaccaagaga tcaccattcg catgaccggg | 1440 |
| tgcccgaacg gctgcgccag gcatgccctg gagagatcg gctttatcgg caaggctccg | 1500 |
| ggcaagtaca atatgtatct cggagcagcg ttcgacggct cgcgcctgtc gaaaatgtac | 1560 |
| cgggagaaca taggtgaggc cgacatcctg tccgagctcc gcatccttct gtcgcgggtac | 1620 |
| gcgaaggagc gcgaggaggg cgagcatttc ggcgacttcg tcatccgggc tggtatcatt | 1680 |
| aaagccacca ccgatgggac caattttcat gac | 1713 |

<210> SEQ ID NO 29
<211> LENGTH: 1764
<212> TYPE: DNA
<213> ORGANISM: Artificial Sequence
<220> FEATURE:
<223> OTHER INFORMATION: Codon optimized Acidithiobacillus ferrooxidans
      sulfite reductase (NADPH) flavoprotein subunit
      alpha sequence

<400> SEQUENCE: 29

| atggaactca ttcgccaatc cgactttctc ctggacccac gcaaacaaga agatctccgc | 60 |
| cgctttgccg agggcatgac gcgcgagcaa cttctctggt ccagcggcta cctcaccggc | 120 |
| ttcggggagt ccgctccggc gtccaagatc caggaggaca taggcgagaa atcaccatc | 180 |
| ctgttcggca cggaaacggg aaatgcgaag cgcctggccg agctgctcgc ggcgcgggcg | 240 |
| caggccatgg gcgtgcagac cagcatccaa gacatgctca cctacggccg ggcgcagctg | 300 |
| aggcgcgacc gcgtcatcgt gcttatcgtg agcacccacg cgacggcga ccaccggac | 360 |
| agcgcccgga tgctgctggc gagcctgacc gatggccccg tccccgacct ccatggctcc | 420 |
| cggttcgcca tcctcgcgct gggcgacgcg tcctacccga agttctgcca ggccggcaaa | 480 |
| gcgttcgaca tcgcccttgc gtcggctggc gccgagcggc tgttgcctcg ggtggactgc | 540 |
| gacgtcgact atgagcgcga cgccatgtat tggatggagc aagtcctcgg tgcactgacg | 600 |
| accggcaagt cgtccctgc cgtccccttc ccgctccgg tgcccaaaca gggttacagc | 660 |
| agccacgcga cctttccgc ggtcctgttg ggtaaggtca acctgagtgg acgcggcagt | 720 |
| gaccgcgagg tgtggcatct ggaactggat ctcgacggct cgggcctcca ctatgctccg | 780 |
| ggggacatag tttccgtggc cccctcgaat ccgccgcaac tggtcgaaga actcctggat | 840 |
| cgcctggagc tcgatcacaa ggcatcggtt cgcacccgcc agggcgagat gccgctggtc | 900 |
| gaggccctgg ctgcgcatta cgagattact cgcattacgt ggccgttcct ggaaaggtac | 960 |
| gcacggctga cgacgccaa ggcactgcag agcgccatcg cgggccgcga cgttaacggc | 1020 |
| ctggacacct ggactgacgg gcgcgaagtg atcgacattg tgggccagta cccggtgaag | 1080 |
| ggcctcagtg cgcagtcgtt cgcggactgc cttcggccgc tcccgccccg ccgctattcg | 1140 |
| atcgcatcgt cgctcctcgc cgtcccggga gaggtccatc tcaccgtcgc ggccatccgc | 1200 |
| tattcctccc atgccgcgga gcggctgggc gtggcctcga cgttcctcgc agaccgcgtc | 1260 |
| gccatcggca ggcccgtccc gatcttcatc gagcccaacg ccgagttccg gctcccggaa | 1320 |

```
gatagcggac aggccatgat catgatcggt gcgggcaccg gggtcgcgcc gttccggtcg    1380
ttcctgcaag agcgcgaggc actcggggca gctggcaaca attggctgtt cttcggcgac    1440
cggcatttca gcaccgattt cctctaccag cgcgagtggc tgcggtggct gcgcgatggc    1500
aggctgacgc gcctcgatgt ggcgttctcg cgggaccaag agcggaagat ctacgtgcag    1560
gatcgcctgc gggagagggc cggcgacgtg ttcgcctggc ttgaggaggg tgcggccgtt    1620
tacgtctgcg gtgccgaggc catgggtcgc gcggtccatc agtccctggt ggacatcgtc    1680
cagtccgcgg gtcgcaccca ggtccaagcc gaggaataca tcctggagtt gaaacagacg    1740
ggccggtatc accgcgacgt gtat                                           1764
```

<210> SEQ ID NO 30
<211> LENGTH: 1689
<212> TYPE: DNA
<213> ORGANISM: Artificial Sequence
<220> FEATURE:
<223> OTHER INFORMATION: Codon optimized Acidithiobacillus ferrooxidans
      sulfite reductase (NADPH) hemoprotein subunit beta
      sequence

<400> SEQUENCE: 30

```
atgagcataa acgacaaggc acttagcgat gtggagagga taaaagcgga aagtcaagga      60
ttgcggggca ccctgcgcga gtcgctccac aacccggtca cgggtgccct ggccgaagat     120
gacgtccagg tcatcaagtt ccatggcatc tatcaacagg actatcgcga cctccgggcg     180
gagcgccacc aacagaaact ggagcccctc taccagttca tggcccggct ccgcctgccg     240
ggtggcgtcc tgagcggagc gcagtggctg gcgttgggcg atatcgcgcg cacctatgga     300
aatgcctccc ttcggatcac ctcgcggcag agcatccagt tccacggcct gctgaaaccg     360
catctccggc cggtgctgca ggccctcgac cgcgctctcc tcgacaccgt gtccgcctgc     420
ggcgacgtca ccggaatgt catcgcgtcg tccgcacccc agatcagtgc cttccacgcc     480
gaggcgtatg gctgggccca aaagatcgca gagcatctgc tgccgcagag ccatgcatac    540
catgagatct ggctcggcgg ccaacagatt accgcgcctg aggaagatct tctgtacggc    600
tcgacctatc tgccgcgcaa attcaagatc gcgatcgccg ttcccccgca caatgacgtc    660
gacgtcctga cccaggacct cggcttcatt gcgatccacg aagagggtcg cctcgccggc    720
ttcaatgtct gcgtcggcgg cggcctcggc cgctcccata caagcctga cacctattcg    780 cgcctggccg atgtgtgcgg gttctgtgcg ccgggtcaag tgctggcgat cgccgaggct    840
gtgctgatca cgcagcgcga ccacggcgac cgcagcaacc gctcccatgc gaggctcaag    900
tataccgtgg accggatggg actcgaccgc ttcatggaag aggtgcagca gcgcacgggc    960
ttctcgctgg cgccgccacg ccccttccat tttgaaacct ccggcgaccg cttcggctgg   1020
ctggagaacg atgacggcac cgcgtgcctc accctgttca ttccgggggg gcgggtggcg   1080
gacggcgata tcccgctgct ctcggtctct gacgcgctcg cgaggctgca tcatggcgag   1140
atccgcctca cgtgcaacca gaatctgctt atcgcgggca tctccccagc cgagaggccc   1200
gtggttgaga ctgtcctggc cgagtacggc ctcaaccggc tcctgaacct cgcgcccgtg   1260
cgcgcccatg cgatggcctg cgtcgccctc ccgacgtgcc cctcgcgat ggcagaggcc    1320 gagcgctact tgccggtgtt tctcgaccgg attgaagccc tcctcgccga ggtcggcctt   1380
gagggcgagg ccctgaccgt gcggatgacg ggttgcccga atggctgcgc tcgcccgtac   1440
ctggccgaga tcgggctcgt gggcaaggct cccggcctgt acgacctgta cctgggtggc   1500
```

```
gaccgcaccg gcatgcgcct gaacgcgctc taccgcgagg cacttgacga agaggccctg    1560
ctggatgcgc tgcggccctt gttgaagcgc ttcgcagggc agcggtgggc gggtgaaacc    1620
ttcggcgact tcgtcaggcg ccaagacctc ctgcccccgg acccgggtct gccgcacacg    1680
ggtcgccgg                                                             1689
```

<210> SEQ ID NO 31
<211> LENGTH: 2037
<212> TYPE: DNA
<213> ORGANISM: Artificial Sequence
<220> FEATURE:
<223> OTHER INFORMATION: Codon optimized Cyanidioschyzon merolae sulfite reductase, ferredoxin dependent sequence

<400> SEQUENCE: 31

```
atgatgtttg ttacctacgc taaaccactt gtcggagccc ccgcggact tgcacctacc     60 ggaagcgctg cccccggcgt gtaccccctc accgaagtgc tgctgcgcga taggctccgg   120
cggcagcgcc agtgccgcac cgcccgccgc aacatcatcg cgaatcttag cagtgagcag   180
agccgcaaga acataccgt cgtgccgatt accacccgga agcatatcga agaggccatc    240
cgcgacggca ccttggacca actgaagctt aaccccctacg agctgcccaa gctgaactcg   300
gactatctcc gccacccgct gatggaagaa ctgggcaacg accaaatctt catttccgac   360
gactgcatcg gcctgatcaa gttccacggc ggctatctgc aagacaatcg cgaccagcgg   420
gtccgcggtg agcttaaaaa gtatcagttc atgctgaggc tgaaaatgcc cgcaggcgag   480
tgccctccgt cgctctatac gaccctcgac gacatctcgg agacttatgg caataagacg   540
ctgcgcctca ccacccgctc gtcgttccaa attcatggca tccacaagag caacctcaag   600
accgtcgtgc agtccatcgt gcgggccggg ggcggcctct acggcgcgtc cggcgactgc   660
tcgcgcaatg tcattgcgcc cccggctccg ttcgtcgacg ccgcatacgc ccaggccagg   720
catgtcgcgc ggatggtggc cgagctgttc gccatccaga gccatgcctt cgctgacctc   780
tggctggacg gtgagctggc ggcctccatc gagtactgga agaaagagtt ggatatggac   840
gaggttcgcc ggctgatgac cgaggacaat ggtcgcggcc aggtcctgca agactcggtg   900
gagccgctgt acggcaagct ctatttgccg cgcaagttca aggttggcgt cacggtgccg   960
ggcgacaact cgatagacat atacacgcac gacatcggca tcgtcgtgtt ctgcgacgcc   1020
cagggccagc tcgaaggcgc gaatatcctc gtcgggggcg gcatgggccg gacgcacaac   1080
aaagaggaga ctttcgcgcg ggcggcggac ccgctgggct atgtgccggc ggcggccctg   1140
tatgataccc tgaaggccat cctcgctgcc cagcgcgacc acgggaaccg gcggtccgg    1200 accaacgccc gcatgaagta tctcgtccat cgcctgggca tcgaccgctt cgcgaactc    1260 gtgaagtcgt acatggtcgg cggcggctcg gccctggaga cattcggtc catgccgccg   1320 tggaccttcc aggactacct cggctggcgc gagcagggcg atgggcgctg gttcttcggc   1380
ctctatgtcc agaatggcag gattaaagac gagctcaaaa aagcgctgcg cgcgttgacc   1440
gaccggttca acttcccgct ggtgtgcacg ccccagcaga atctgctgat acccaggtg    1500 cccgcaaccg ctcgcccgga tgtggaaacg ctcctggcct cgtttggtgt ggaaacggcc   1560
gccagcgcgc tcgatccgtt gatgcgcgac gcgatggcct gccgctct cccgctgtgt    1620 ccgccagcaa tcaccgaggc agagcgcgtc atgccccggt atgtgcagcg cgtgcgggag   1680
ctcctctcca aggtcggcat cagtccgcat gcgtccttcg tcatgcggat gaccgggtgc   1740
ccaaatggtt gcacccgccc gtacatggcc gaactgggct tcgtgggcag tggcccgaat   1800
```

-continued

| | |
|---|---|
| tgcacgtacc aagtctggct gggtgggtcg cctatgcaga cgcgcctcgc gtggccgtac | 1860 |
| atcgataggg tcaccgatga tcaagtggag cgcgtccttg agcccgtttt cgtgttctgg | 1920 |
| aaaagcgcgc gcgagccgga cgagtcgttc ggcgacttct gcgaccgggt gggaaaggcc | 1980 |
| cagcttgagg cgtatgcgca acggtattgg gatggtgtcc ccgctgcgcc tgtgtcg | 2037 |

<210> SEQ ID NO 32
<211> LENGTH: 1986
<212> TYPE: DNA
<213> ORGANISM: Artificial Sequence
<220> FEATURE:
<223> OTHER INFORMATION: Codon optimized Oscillatoria nigro-viridis
       sulfite reductase (ferredoxin) sequence

<400> SEQUENCE: 32

| | |
|---|---|
| atgatcacct cctccactag cacccccggtt gcccgcaaac ccagcaaaag cgaaggcctg | 60 |
| aaagagcgct ccaactacct ccgggagcca gtcgccaccg agtcctgca agaaaccacg | 120 |
| cacttcaccg aggacggcat ccagatcctg aagttccatg gctcctacca gcaagacaac | 180 |
| cgggacaatc gcgtgaaggg ccaagagaaa gactaccagt tcatgctgcg gacccgcaat | 240 |
| ccgggcggat tcacgccgcc tcagctgtat ctggccctgg ataagctgtc cgaggaatat | 300 |
| ggtaaccaca ccatccgcgt gaccaccgc cagggcttcc agctccatgg cgtgctgaaa | 360 |
| aagaacttga aggccgtgtt cagttcgatc atcaagaaca tgggctcgac gcttggggcg | 420 |
| tgcggcgacc tgaaccggaa cgtcatggcg ccgccggctc cctacaagaa taggcccgag | 480 |
| tacaaatacg cactgcagta tgcgaataat gtcgcggact tgctgacgcc caaacgggga | 540 |
| gcgtattacg agatctggct ggatggcgag aaagccatca gcgcagagga ggacccagca | 600 |
| gtgaaagctg cgcgccagaa gaatggcaat gggaccatct tttcggataa agaggagccg | 660 |
| atctacggca gccattacat gccccgcaag ttcaagtgct cggtgaccgt cccgggagac | 720 |
| aacagcatcg acctgtacag tcaagacctc tcgttggtcg tgattaccaa caaagctggc | 780 |
| gagctccagg gttttgacgt gttcgcgggt ggcggcctcg gtcgcaccca aataaagag | 840 |
| gaaacctttg cgcgcgtggc cgatgaaatt tgctacgtcg cgaaggatga cgtttacgac | 900 |
| ctcgtgaagg ccatcgtggc gacgcagcgg gactatggtg accgcacgga ccgcaggcat | 960 |
| gctcgcctca gtacctgat caacgacaag ggcgtgcagt ggttccgcga gaaagtcgcg | 1020 |
| gagtatttcg gcaagccact cgaagcgttc aagcccctgc cggagtggaa gtatttcgac | 1080 |
| ttccttggct ggcatgacca gggtgatgga aagctgttcg tcggtatctc ggtggataat | 1140 |
| ggccggatta aggacgaggg ctccttccag ctgaaaaccg cgctccgcga gatcgtgcag | 1200 |
| aagtataacc tcccggtgct cgccaccccg catcaaaacg tcctcattta cgatatttcc | 1260 |
| ccggacctca gcaagagat ccagggcatc ctcgaccgct gcggtatcca gcgcgaaacc | 1320 |
| gccatcgacc cgctcgtgcg ctatgccatg gcgtgtccgg ccatgcccac gtgcggcctc | 1380 |
| gccataaccg agtccgagcg cgtcatccct tcgatcctgg agcgcatccg ggctctcctg | 1440 |
| accaaggtcg gccttgaaga tgagcatctg gtcgtccgga tgaccgggtg cccgaacggc | 1500 |
| tgcgcgaggc cctatatggc cgagctgggc ttcgtcgggt ccagcccgga gtcgtatcag | 1560 |
| atatggctgg gcggcagccc ggaccagacg cggctggcga gccgatcga ggaaaagctc | 1620 |
| cacgtcaaga atttcgaggc cttcctggag cccatcttcg tctacttcaa gcaaaagcgc | 1680 |
| caactgagcg agagcttcgg gaatttctgc gaccgggtgg gcttggagtc catccgccag | 1740 |
| ttcgtgacga actaccaatc ggccgacagc atgaccaccg agattaacga acttgaggtc | 1800 |

```
acgtcgtcga acggcgaaga gaacgaaacc gcgactgcgg gcggcggcaa ggtccggcgc    1860
aggatcagcg ttcgggacga gatctataac gagctcaagg aagaggccgc acgccagggc    1920
aagcccatca cccagctggc caccgaggcc atctcgacgt atctgaagaa aatcaaagag    1980
gaggcg                                                              1986

<210> SEQ ID NO 33
<211> LENGTH: 2007
<212> TYPE: DNA
<213> ORGANISM: Artificial Sequence
<220> FEATURE:
<223> OTHER INFORMATION: Codon optimized Pseudomonas putida sulfite
      reductase (ferredoxin) sequence

<400> SEQUENCE: 33
atgaatgatt gtcacttgat atgcgcgaat aggttggatg atggagcagt ggtgtggttg      60
gatgcgggac atgaatgggt ggagactctc cagcaggccg caccttcga cgcccaggca     120 ctggtgagcg cgacgctggc ggcagaggct gcggtcctgg cgaaccaagt ggtcgcgccg    180
accccgtgcg aggcatggct cgtggacggt cgccccgagc ccaagtccct gcgcgagcgg    240
cttcgggccc ggggtcccag cgtccggtcg gaccttggga acaagcggc tggcacccca    300 ccgtcgtcca ttgcccgcat gcgcccagtc ctccccgtcg aggccggtca ggctggcgtg    360
taccgctacg accgcttcga gagggaattc ctgaaagacc gggctcgcca gttcgagcag    420
caagtggcgc gccgcctctc cggcgagctg gacgaggaag cgttcaaggt ctaccggctt    480
atgaacggcc tgtatctgca gctgcatggc tacatgctgc gcgtggcgat cccgtacggc    540
accctgagtg cgctccaact gcggcagctc gcgtacgtgg cgcacaccta tgacaagggc    600
tacggccatc tgaccacccg ccagaatatt cagttcaact ggccgaggct ggcggacacg    660
cccgagatcc tcagcgtgct ggcggacgct gacttgcatt gcatccagac cagcggtaac    720
tgcatccgca atgtcacgac cgaccatttc gccggggcgg ccgaggacga ggtcctggat    780
ccgcgcgtcc atgcggaaat cctccgccaa tggtcgactg agcacccgga gtttacgtat    840
ctcccgcgca aattcaagat tgcgataccc ggctccccga agatcgggc gccgtccgc    900 ttccatgaca ttggcatcct cgcgcagcgc aatgcgcagg gcgaggtcgg cttccaggtg    960
tatgccggtg gcgggctggg ccgcaccccc atcgttggca cccgcgtgcg ggagtggctg   1020
ccggagcgcg agctcctgcg ctatgtggaa gcgatcctcc gcgtgtacaa tgcgctgggt   1080
cgccgcgaca acctgtacaa ggccaggatc aagatcctcg ttcgggagct taagcctggc   1140
cgcttcatcg agatgatcga agaagagttc gcctcgctgc ccgcggatca ccaatatctc   1200
gaaccggcca tcgtccaagg gatccatgcc cgcttcgtcc agccggcgtt cgaggcgctg   1260
ccgggcctct gcgacagctt tctgagggca cgggccgatg acaacgcgtt cgcgagttgg   1320
gtgcgcacga atacgcatcc ccacaaaaag cgcgggtata tctgcgcggt gatttccctc   1380
aagccgcctg gcggcatacc gggcgacatc agcgccgagg aaatgctggc gcttgcagat   1440
ctcgccgagg cctactcgct gaacgagatc cgcgtgtccc atgagcaaaa cgtcgtcctg   1500
ccgcacattc ggctcgtcga tctctactcg gtgtggcagg ccctccggca ggccggactg   1560
gcgacgtcga atatcgggct gctgtcggac acgatcgcct gccaggcat ggactattgc   1620 tcgcttgcca ccgctaggtc cgtgcccgtc gcgcagcgga tcgcccagcg gttcgacgcg   1680
gctcggcagc aagacatcgg cgagctcaag ctcaacgtca gcggttgcat caacgcatgc   1740
gcccaccacc atgtcgccca tatcggcatc ctgggcctgg acaaggccgg ccatgagaac   1800
```

```
taccaaatca ccctgggcgg cagcgcagag gaggacgccg ctgtcgggac cattctcggc      1860
cggtccgtcc cgttcgaaga ggttccggac atcgtcgagg ccatcgtggc tatctatctc      1920
cagctgcgcg aggacgatga gcgctttctc gacacctatc gccgcgtcgg tatcgagccg      1980
ttcaaagaag tcctccgcga cgcgcgg                                         2007
```

<210> SEQ ID NO 34
<211> LENGTH: 1911
<212> TYPE: DNA
<213> ORGANISM: Artificial Sequence
<220> FEATURE:
<223> OTHER INFORMATION: Codon optimized Anabaena cylindrica sulfite
      reductase (ferredoxin) sequence

<400> SEQUENCE: 34

```
atggttaact ccgcacccte ccccgtcagc aatcgcaaac cgtccaaagt cgaaggcatc        60
aaagagaaca gcaacttcct gcgggagccc gtggccactg agatactcca ggacaccacg       120
cacttttccg aggacgcgat ccagatcctg aagttccatg gttcgtacca acaggacaat       180
cgggacaaca gggcgaaggg ccaggaaaaa gactaccagt tcatgttgcg gacgaagaac       240
cccggtggcc tggtgcctcc gcagctgtac ttggcccttg ataagctcgc cgacgagtat       300
ggtaatcaca cgctccgggc gaccacccgc cagggcttcc aagtgcacgg catcctgaag       360
aaaaacctga aagcgccat cgccacgatc gtccagaacc tgggctcgac cctcggagcc       420
tgcggggaca tcaaccgcaa cgtcatggct ccgccagcgc cgctcaagaa tcggccggag       480
tacgagtatg cttgggagta tgctcagaac attgccgatc tgctctcccc gcagactggc       540
gcatactatg agatctggct ggacggcgag aaggccatct cggtcgagga catcccgac        600 gtcaaagccg cacgccagtc gaatggtaac gggacgattg tccatgacag cgtggagccg       660
atctacggca cccattacat gccgcgcaag ttcaagatct gcgtgaccgt gcccggtgat       720
aactcggtcg atctgtattc ccaagacttg acgcttgtgg tgatcaccaa taagaagggc       780
gagctgcagg gcttcgacgt gttcgccggt ggcggactgg caggaccca taacaaagag        840 gaaacgttcg gcgggtggc ggacccgatc tgctacgtcg gaaggacga cgtgtacaat        900 ttcgtgaagg ccgtcgtcgc cacccagcgg gattacggcg accggaccga tcgccggcac       960
gctcgcctga gtacttgat caacgactgg ggcgtcgaca gttccgcac ccaggtcgag       1020 gagtatttcg gcaaaagtgt cgagcctttc agccccctcc gaagtttaa gtatcaagac      1080 ttcctgggct ggaatgaaca gggcgatggg aaactgttcc tcggaatcag catcgagaat      1140
ggcagggtca aggacgaggg cgcgttccag ctcaagaccg cgctgcgcga gatcgttgaa      1200
aagttcaacc tcccgatacg cctcaccggc aaccagaatc tgctttttcta tgaaatcgac      1260 cccgaggaca aggccgcgat tcaagaaatc ctggaccgct cggcgttgt cgcggatccg      1320 tcccaaattg ctgccctcac ccgcttcgcg atggcgtgcc cagcgctgcc gacgtgcggc       1380
ctcgcgatca ccgagtcgga gcgcgcgatc ccgggcatcc tggatcggat cagggcgctc      1440
ctcgacaagc tcggcctgca aaaggaccat ttcgtggtgc ggatgacggg ctgccctaat      1500
ggttgtgcac gcccgtacat ggccgagctg ggttttgtgg ggagtgcgcc ggagtcctat      1560
caagtctggc tgggcggcag cccggatcag acccgcctcg cccagcccat catcgagaag      1620
ctccacgaca acgatatcga gagcttcctt gagccgatct tcatctattt caagaaattc      1680
cgcaagggca agagagcttt cggcgacttc tgcgaccgca tgggctttga cgccattcgc      1740
gagttctcgg cgacctacac gcccggtgag ccgacctcgt cgggcaaatc gcgccatcgc      1800
```

```
gtgtcccttc gcgacgacgt ctatctgcat ctgaaggaaa ccgccgagaa gcaaaaccgg      1860
cccatgaccg atctcgtcca cgacgcgctc gacaagtact tccagaatct c              1911
```

<210> SEQ ID NO 35
<211> LENGTH: 2001
<212> TYPE: DNA
<213> ORGANISM: Artificial Sequence
<220> FEATURE:
<223> OTHER INFORMATION: Codon optimized Halothece sp. sulfite reductase
      (ferredoxin) sequence

<400> SEQUENCE: 35

```
atgatggaac tgataaccgt tataccctcc gaattgtccg ttatccagaa gtgcgctgcc       60
attgagcaaa aagctgtgat ggtcgcgagc aaggccaaaa aggcatcgaa gccgagcaag      120
ctcgaaggca tcaaggagaa cagcaacttc ctgcgcgagc ccctggccac cgagctcctg      180
gaagatacca cgcacttctc ccaggacgcc gtgcagatcc tcaaattcca tggctcgtat      240
caacaggata accgggataa tcgccaaaag ggccaagaga agactacca gttcatgctg       300 aggactcgca atccgggtgg cttcatcccg ccagagctgt atctcaccct ggacgatctg      360
tccagtgagt atggcaatga aaccctccgg gtgaccaccc gccagggatt ccagctccat      420
ggcatcctga agaaaaatct gaaagaaacg atcaaccgga tcgttcgcaa cctcgggtcg      480
accctgggcg cgtgcggtga cctgaaccgc aatgtcatgg cgccaccggc accgttcaag      540
gaccggaaag aatatcaata cgcctggcaa tatgcggaca atatcgcgga ccttctccgc      600
ccgcagaccg aggcgtatta tgagatctgg ctcgacggcg agaaattcct ctccgtcgag      660
gaagcgcccg aggtccaagc tgcccgcgag aggaacggga acggcacgat tttccacgag      720
ggtgaggagc ccatctacgg caagtactac atgccgcgca agttcaagtg ctgcgtcacc      780
gtcccgggcg acaactcgat cgacgtgtac acgcacgacg tgtccctgat cgtgatcacc      840
gacgaccagg gcgagctcaa gggcttcaat gtccttgcgg ggggcggcat gggtcggacc      900
cataacaaag aagagacttt cgcccggatg agtgatccga tctgctacgt ggacaaggca      960
gatgtctacg atttgctcaa ggccattgtg gcaacccagc gcgactacgg cgaccgggtc     1020
caacgccgcc atgcccgcat gaaatacttg ctgtacgact ggggcgtcga agagtttcag     1080
tcgaagcttg aagagtacta tggcaaaccg ctgcagccgt atcaggacct cccgcctttt     1140
gagtataaag acttccttgg gtggcatgag cagggcgatg gtaagctgtt cttcggactc     1200
tcggtggaaa atggccgggt gaaagacgag ggtaagttcc gcctcaagac cgccttgcgg     1260
aagatcgtgg agcagtacca ggtccccatg cgcctcacgg ctaaccacga cgtgatcctg     1320
tacgagatta gcctgaggga ccagtcggcg atcgagaaaa tccttacgga ccatggcctg     1380
atcacggacc cgaataatct ggatcatctg ctgcgctata gcatggcgtg ccccgcgctc     1440
ccgacgtgtg gcctcgccat caccgagagc gagcgcgccc tgccctcgat cctcgacagg     1500
gtccgcaatg tcctcaagaa gctcggcatg gctgagcaag acctcgtggt ccgcatgacg     1560
ggctgcccca acggctgcgc ccggccgtat atggccgagc tcgggttcgt cggctcggcg     1620
cccaaggcct atcagctctg gctgggtggc accccgaacc agaccgcgct ggctcgcccg     1680
tatatggagc ggatgccgat cgacgaactg gagtcctaca tcgagcccat gctggcgttt     1740
tacaaggaga gcgccaaaa ggacgagagc ttcggcgagt tctgcaaccg ggtcggattc      1800
gaggccatcg aaacgtatgt caagtcgtat gagttcaagc ccaccaagac cccgagcgcg     1860
ggtggcaagg gtcggcgcca tcgcatctcg gtgtacgagg gcctgcacga gcggctcaaa     1920
```

```
gccgcagccg agaagcgcgg cacctccatg acccagctcg tgtccgaggc cctggagcag    1980
tacctggacg acagccagag g                                              2001
```

<210> SEQ ID NO 36
<211> LENGTH: 1281
<212> TYPE: DNA
<213> ORGANISM: Artificial Sequence
<220> FEATURE:
<223> OTHER INFORMATION: Codon optimized Rhodobacter capsulatus
      sulfide:quinone oxidoreductase  sequence

<400> SEQUENCE: 36

```
atggcacata tagtggtgtt gggggcgggt ttgggtggag caattatggc gtatgaactg     60
agggagcaag ttaggaaaga ggataaggtc accgtcatca cgaaagaccc gatgtaccat    120
ttcgtcccgt ccaaccccctg gtggctgtt ggctggcgcg accggaagga gatcaccgtg    180
gacctggctc cgaccatggc acgcaagaat atcgacttta tcccggtcgc agccaagcgc    240
ctccatccgg cggagaaccg cgtcgagctg gagaacggcc aaagtgtgtc gtacgaccag    300
atcgtcatcg cgacgggacc cgagctggcg ttcgacgaaa ttgagggatt cggtcccgag    360
ggccataccc agtcgatctg ccatatcgac catgccgagg aagcccggct ggccttcgat    420
cgcttctgcg agaacccggg tccgatcctc atcggtgcgg cgcagggcgc ctcgtgcttt    480
ggtccggcgt acgagttcac cttcatcctt gataccgcgc tccgcaagcg gaagattcgc    540
gacaaggttc cgatgacctt cgtgacgagc gagccctacg tcggccacct gggtctggat    600
ggcgtcggcg acaccaaagg gctgcttgag ggcaatctcc gcgacaagca catcaagtgg    660
atgacttcca cgcggatcaa gcgcgtcgag aagggcaaga tggtcgtgga gaggtcacc    720 gaggacggga ccgtgaagcc cgagaaagag ctcccgttcg gctatgcgat gatgctgcct    780
gcgttccggg gcatcaaggc cctcatgggt atcgaagggc tggtcaatcc acggggcttc    840
gtgatcgtcg accagcatca gcagaacccg acgttcaaaa acgtgttcgc cgtcggcgtg    900
tgcgtcgcca taccgcccat ggcccgacc ccgtgccgt gcggcgtgcc gaaaaccggc     960
ttcatgatcg agagcatggt cacgccacg gcccacaaca tcggccggat cgtccgcggc    1020
ttcgaggccg acgaggtcgg ctcctggaat gctgtgtgtc tcgcggactt cggcgaccaa    1080
ggcatcgcct tcgtggccca gccccagatc ccgcctcgca acgtcaattg gtcgtcccag    1140
ggcaagtggg tgcactgggc gaaggaaggc tttgagcggg atttcatgca caagctgcgc    1200
cgcggcacca gcgaaacctt ctacgagaaa gccgccatga aattcctcgg tatcgataag    1260
ctcaaggctg tgaaaaaggg c                                             1281
```

<210> SEQ ID NO 37
<211> LENGTH: 1308
<212> TYPE: DNA
<213> ORGANISM: Artificial Sequence
<220> FEATURE:
<223> OTHER INFORMATION: Codon optimized Oscillatoria limnetica str.
      sulfide quinone reductase  sequence

<400> SEQUENCE: 37

```
atggcacatg ttgcagttat tggagcagga ctcgcaggac ttcccaccgc atacgaactc     60
aggcatatac ttccacggca gcatcgggtg accctgatca gcgacaaacc gaactttacc    120
tttaccccgt ccctgccgtg ggtggcgttc gacctgacgc ccttggagcg cgtgcaactc    180
gacgtgggta agctcctcaa gggtcgcaac attgactgga tccacggtaa ggtcaaccat    240
atcgaccctg agaacaagac tctggtcgcc ggcgagcaga cctggagta tgactacgtc    300
```

| | | |
|---|---|---|
| gtcgtcgcga ccggtccgga gctggccacc gacgcgatag cgggcctggg gcctgaaaac | 360 |
| ggctacaccc agagtgtctg caatccccat catgcgctga tggcgaaaga ggcgtggcag | 420 |
| aaattcctgc aagacccggg tccsctcgtg gtgggtgccg ttccgggcgc ctcgtgcttc | 480 |
| ggccccgcct atgaattcgc cctcctcgct gactatgtcc tccgccggaa aggcatgcgc | 540 |
| gaccgggtcc cgatcacctt cgtgacgccg gagccgtatg tcggccatct gggcatcggc | 600 |
| ggcatggcga attcggccga gctcgtgacc gatctcctgg agaacaaggg tattcgcgtg | 660 |
| ctgccgaaca ccgcggttaa ggagatccac cccgagcaca tggatctgga tagcggcgag | 720 |
| cagctgccat tcaaatacgc gatgctcctg ccgccgttcc gcgggccggc attcctgcgc | 780 |
| gaggcgcccg agctcaccaa tccgaagggc ttcgtgcccg tgaccaatac gtaccaacac | 840 |
| cccaaatacg aaagcgtcta tcggccgga gtcatcgtcg agatcaatcc gccggagaaa | 900 |
| acgccgttgc cggtcggcgt gccgaaaacc gggcagatga ctgaggccat gggtatggct | 960 |
| gcggcccata atatcgcgat caagcttggc gtcagcaagg ctaagcccgt gcagccgacg | 1020 |
| ctcgaagcga tctgcatcgc cgacttcggc gacacgggca tcgtgttcgt ggctgacccg | 1080 |
| gtcctgccgg accccaagac gggcactcgg cgcagggcca tcacgaagcg cggcaaatgg | 1140 |
| gtttcctggt ccaagaccgc gttcgaaacc ttctttctca gcaagatgcg cttcgggctg | 1200 |
| gccgtcccat ggttcgagcg tgggggcctc cggttcatgg gcctctcgct ggtcgagccg | 1260 |
| ctcgacacca cccgcgaaac gggcaatcag gccttcgcgt ccaagtcg | 1308 |

<210> SEQ ID NO 38
<211> LENGTH: 1125
<212> TYPE: DNA
<213> ORGANISM: Artificial Sequence
<220> FEATURE:
<223> OTHER INFORMATION: Codon optimized Acidithiobacillus ferrooxidans
      sulfide quinone reductase sequence

<400> SEQUENCE: 38

| | | |
|---|---|---|
| atgactcaag tgacgataat aggggcagga tttggaggac ttacggcggt taggcatctt | 60 |
| cggcggcgca tgccagatgc tgagatcacc gtgatcgcgc ccgcgccga gttcgtctac | 120 |
| tacccgtcgc tgatctggat cccaacgggc ctccggcaag gtgagaatct caggatccct | 180 |
| ctggaccgct tcttccaacg ccgccgcgtc cagttccatc agggccgcgt caccggcctg | 240 |
| cgcgacggtg gccgcacggt gattaccgac cagggtgagg tccgcaacga cgcgctgatc | 300 |
| atcgcgtccg gcgccgcgg catccggaag ctgccgggca tagaacatag cttcgccatc | 360 |
| tgcgacggta tcgatgcagc agagaatatt cgggaccggc tcgcgctcat ggataagggc | 420 |
| accatcgcgt ttggcttcgc gggcaatccc ctggaaccga cggccgtgcg cggtggcccg | 480 |
| gtgttcgagc tgttgttcgg catcgacacc tacctccgcc aaatcgacaa gcgcgggcag | 540 |
| atcgagctcg tcttttcaa ccccatgact gaaccgggca accggctggg accgaaagcc | 600 |
| gtcgagggcc tgctggcgga atgcagcgc cgggacatcc gcacccatct tggccacaag | 660 |
| atcagcggct tctccgtcaa caaagtcatg accgagggcg gcgacattgc gccgatctc | 720 |
| atcctcttca tgccgggcat gacgggtccc gactggcgg ccgactcggg cctgcccctg | 780 |
| agtgctggcg gcttcttcca gtccgatctg cactgcaccg tgccggacca ccccggtgtg | 840 |
| ttcgtgattg gggacggtgg ctcgtacgcg ggcagcccgg attggctgcc caaacagggc | 900 |
| cacatggcca atctgcaggc cgggaccgcg gtccataacc tcctgctcca tctgcagggc | 960 |
| aaggccgctg ataacaccct ccgcagcgag ctcatctgca tcgtcgacac cctcgactcc | 1020 |

```
ggcatcatgg tgtatcggtc cccgaatcac gcgagcatcc tgccgaattc gctctggcat   1080
gccgctaaag tcgccttcga gtggcgctat ttgctccatt accgg                   1125

<210> SEQ ID NO 39
<211> LENGTH: 1290
<212> TYPE: DNA
<213> ORGANISM: Artificial Sequence
<220> FEATURE:
<223> OTHER INFORMATION: Codon optimized Aquifex aeolicus sulfide-
      quinone reductase  sequence

<400> SEQUENCE: 39
atggcgaaac atgtggtggt gattggtggg ggagtggggg ggatagcaac ggcgtacaat     60
ttgcggaatc tgatgccgga cctcaagatc accctcatct cggatcgccc gtatttcggc    120 ttcaccoctg cattcccgca cctggcgatg ggctggcgca agttcgaaga tatttcggtc    180
ccgctggcac cgctcctgcc caagtttaac attgagttta tcaatgaaaa ggccgagtcc    240
atcgacccgg acgcgaacac ggtgaccacg cagtcgggca agaaaattga gtacgactac    300
ctcgtgatcg ccaccggccc aaagctcgtg ttcggtgccg agggccaaga agagaatagc    360
acctccatct gcacggccga gcatgcgctg gagactcaga agaagctgca agagctctac    420
gctaatccgg gaccggtcgt catcggcgcc atcccgggcg tgtcgtgctt cggtccggct    480
tatgagttcg cgctgatgct tcactatgag ctgaagaaac ggggcatccg ctacaaagtc    540
ccgatgacct ttatcacgag tgagccgtat ctcggccatt tcggcgtggg cgggatcggc    600
gcctccaagc gcctggtcga ggacctcttc gcggagcgga atatcgactg gatcgccaac    660
gttgccgtca aggccatcga gccggacaaa gtgatctacg aagatttgaa cggcaatacc    720
catgaggtgc cagcgaagtt caccatgttc atgcccagct tccagggacc cgaagtcgtg    780
gcgtcggcgg gtgacaaagt tgccaatccc gcgaacaaaa tggtgatcgt gaaccgctgc    840
ttccagaatc cgacctataa gaacattttc ggcgtcggtg tcgtcaccgc gataccgccc    900
atcgagaaaa cgccgatccc gaccggcgtg cccaagaccg gtatgatgat cgaacagatg    960
gcgatggccg tcgcacataa catcgtcaac gacatccgca caacccccga caagtatgca   1020
ccccgcctga gcgcgatctg catcgccgac ttcggcgagg atgcgggctt ttcttcgcc    1080 gacccggtca tccctccgcg ggagcgcgtc atcacgaaga tgggcaaatg gcccactac    1140 ttcaagaccg ccttcgagaa gtatttcctc tggaaagtca ggaacggcaa catcgcgccg   1200
tccttcgagg aaaaggtcct tgagatcttc ctcaaggtcc acccgatcga gctgtgcaag   1260
gactgcgagg gcgctcccgg cagccgctgt                                    1290

<210> SEQ ID NO 40
<211> LENGTH: 1320
<212> TYPE: DNA
<213> ORGANISM: Artificial Sequence
<220> FEATURE:
<223> OTHER INFORMATION: Codon optimized Halothece sp. sulfide-quinone
      oxidoreductase sequence

<400> SEQUENCE: 40
atggcacata tagttattgt tggtggggga tttgggggat tgagtgcggc gtatgaattg     60
aaacaccttc ttcatggcaa gcacaagatc acgctgatct cggacgaaac caccttcacg    120
ttcatcccga gcctgccgtg ggtcgcgttc aatctgaggc gcctcgaaga tgtgcaactg    180
ccgctggccc cactgctggc tcggcagggc atcaactggc agcatggccg cgtgaccggc    240
```

```
ctggacccta atcagaaacg ggtgagcgtg ggcgaggaca tcaccttcga ctacgactac      300
ctcgtcatca ccacgggcgc ttccctggcg tatcatctca tgtccggcct cggccccgag      360
gaggggtata cccagagcgt ctgcaacgcc catcatgccg agatggcacg ggacgcgtgg      420
gatgagttcc ttgagaatcc ggggccgctg ttggtgggtg ccgtgcctgg cgcttcgtgt      480
atgggccccg cctatgagtt cgccctcctg gcggactatg ccctgcggca ggagggcaag      540
cgcgaccaag tgccgatcac gttcatttcg ccggagccgt acctgggcca cctcggcatc      600
ggcggcatgg ccaactccgg gaagctcgtc acggaactga tgaagcagcg caatatcgac      660
tgggtggaga cgcagagat agccgagatc aaagaggatc acgtcaagct taccgatggc      720
cgcgagttcc cgttcaacta ctccatgttc ctcccgccgt tccgcggtgc gcagttcctc      780
aaagaggtcc cgggtctgac cgacgaaaag ggctttctcc cggtcctcga cacgtaccag      840
catcccgact accctcgat ctatagcgcg ggagtcatca cccaactcgc tgcccccgag      900
gaaaccgagg tgcccctggg agcgccaaag actggccaaa tgaccgagtc gatggcgatg      960
gccgtcgcgc acaatatcgc ccgcgagctg ggcgagatca atgcgcgccc cgtgaagccg     1020
agcctggaag cgatttgcat ggccgatttc ggcgacaccg gtatcatctt catcgcagcc     1080
cccgtcgtcc cggatccctc cgtcggccat cggcgccacg cgaccgccct caggggcctg     1140
tgggtgaact gggccaaaaa cgcgttcgag tggtatttcc tcgcgaagat gcgctggggc     1200
accgccgtgc cgtggttcga aaagctcggt ctgtacctcc tgcggctcac gctggtcacg     1260
ccgatttccg agactccgac ccagcagaaa gacctcacct cgatcaaggg tttctgctgc     1320
```

<210> SEQ ID NO 41
<211> LENGTH: 1293
<212> TYPE: DNA
<213> ORGANISM: Artificial Sequence
<220> FEATURE:
<223> OTHER INFORMATION: Codon optimized Allochromatium vinosum
flavocytochrome c flavoprotein subunit precursor
sequence

<400> SEQUENCE: 41

```
atgactttga ataggcgcga ttttatcaag acgagcgggg cagcggtggc agcggtgggt       60
atacttggat tcccccatct ggccttcggc gcgggccgca aggtcgtggt cgtgggtggc      120
ggcaccggtg gggccacggc agcgaagtat atcaagctcg ccgatccgtc catcgaagtg      180
accctcatcg agccgaacac cgactactac acgtgctatc tgtcgaacga ggtcattggg      240
ggcgacagga aactggagtc gatcaaacat ggctatgatg gactccgggc gcatggcatc      300
caggtcgtgc acgactccgc gaccggcatc gaccccgata agaaactcgt gaaaaccgcc      360 ggcgcgccg agttcggcta cgaccgctgc gtggtggccc ccggcatcga gctcatttac      420
gacaagatcg agggctattc ggaagaggct gcggcgaagc tgccgcatgc gtggaaggcc      480
ggtgagcaga cggcgatcct ccggaaacag cttgaggaca tggcagacgg cggcaccgtg      540
gtgatcgccc accggcggc tccgttccgc tgccgcctg ccccctacga gcgggcgtcc      600
caggtcgcct attacctgaa ggcccacaag ccgaaatcga agtcatcat cctggatagc      660 tcgcaaaccct tcagtaagca agtcagttc agcaagggct gggagcgcct gtatggcttc      720
ggcaccgaga atgcgatgat agagtggcac cccggtccgg atagcgccgt cgtcaaggtc      780
gatggcggag agatgatggt tgaaacggca tcggtgacg aattcaaggc cgacgtgatc      840
aacctgatcc caccccaacg ggctggtaag atcgcccaga tcgctggact gaccaacgac      900
gccggctggt gtccggtcga catcaagacc ttcgagagct cgatccataa gggtatccat      960
```

```
gtcatcggcg acgcctgcat cgcgaacccc atgccgaaat ccggctactc cgcgaattcg    1020
caaggtaaag tcgcggcggc ggccgtggtt gcgctcctca agggcgagga acccggcacg    1080
ccgtcgtatc tcaatacgtg ctactcgatc ctggcaccgg cgtatggcat ttccgtcgcc    1140
gccatttacc gccccaacgc cgacggcagc gcgatcgagt ccgtgccgga ctccggcggc    1200
gtcaccccgg tcgacgctcc ggactgggtg ctggagcgcg aggtccagta tgcctactcc    1260
tggtacaata acatcgtcca tgacaccttc ggc                                 1293
```

<210> SEQ ID NO 42
<211> LENGTH: 597
<212> TYPE: DNA
<213> ORGANISM: Artificial Sequence
<220> FEATURE:
<223> OTHER INFORMATION: Codon optimized Allochromatium vinosum
      flavocytochrome c heme subunit  sequence

<400> SEQUENCE: 42

```
atgacccagt ccactcctcg cctcatgctc gccgcctccg tcctcgctct tggcctcgcc      60
tccaatgccg gtgcagagcc gacggccgag atgctgacga ataactgcgc gggttgccac     120
ggcacccatg gcaactcggt gggacccgcg agcccgtcga ttgcgcagat ggacccgatg     180
gtgttcgttg aggtcatgga gggcttcaag agtggcgaga tcgccagcac catcatgggt     240
cgcatcgcca agggctattc gaccgccgat ttcgagaaaa tggccggcta ctttaaacag     300
caaacctacc agccggcgaa gcaatcgttc gacaccgcgc tggcggacac gggcgcaaag     360
ctgcatgaca gtactgcga gaagtgccac gtcgagggcg ggaagcccct ggcggacgag      420
gaggattatc atatcctggc agggcagtgg accccctact tgcaatatgc gatgtccgac     480
ttccgggaag aacggcgccc gatggaaaag aaaatggcga gcaagctgcg cgagctgctc     540
aaagctgagg gcgatgcggg cctggacgcc ctcttcgcct tctatgcgag ccagcag         597
```

<210> SEQ ID NO 43
<211> LENGTH: 1290
<212> TYPE: DNA
<213> ORGANISM: Artificial Sequence
<220> FEATURE:
<223> OTHER INFORMATION: Codon optimized  Chlorobium limicola
      Flavocytochrome c sulphide dehydrogenase
      flavin-binding sequence

<400> SEQUENCE: 43

```
atgagtcaaa agttcagtcg gcgggatttt aacaagttgt tggttagtgg ggttgcggga      60
agcgcgttcg ggatcttcgg cgcagtcagg ccggcttacg ctgcgcagaa ccggatcgtg     120
gtcattggtg gcgggttcgg cggagcgtcg cggcaaagt acctccgcaa actggacccg      180
agcctgtccg tcaccctcgt cgagccgaag gccacgttct acacgtgccc gtttagcaat     240
tgggtgctcg gcggactgaa gaacatggaa gatatcgcgc agacctacac cgtgctgaag     300
aacaagtatg gcgtgaatgt catcgccgac tatgcctcct ccatcgacgc agcgaagggc     360
accgtcacgc tgaagtccgg caaagtcctg aactatgacc gccttattgt gagccccggt     420
atcgacttca gtggaacac gatcgaaggc tattcggagt ccgtgtcgaa tacgaagatg      480
ccccatgcgt acgaggccgg tccgcagact gtgctgctgc ataagcaact cctcgcgatg     540
aatgacggcg gcaccgtgct catttgccct ccgccaacc ccttccgctg tccgccaggg      600
ccctatgagc gcgcctccct ggtggctcac tacctcaaag aaaagaaacc gaagtcgaag     660
attatcatcc tcgatccgaa ggacaagttc tcgaagcaag gcctgttcaa aaagggttgg     720
```

```
gagaaactct accccggcat gatcgagtgg cgctccgtgg ccaccggtgg gaaaatctcg      780
aaagttgatg cggccaccat gaccgtgacc accgacttcg cgtcgagaa aggcgacgtg       840 atcaatatca taccgccgca acaggctggt aagatcgcgg tcgatgcggg cctgaccgac      900
gcctcgggct ggtgcccggt caacccgatc accttcgagt cgaccatcca tcctggcatc     960
cacgtgatcg cgacgcctg cattgctggc ccatgccga agtccggctt cgccgcgagc      1020
tcgcagggta aagtcgtggc ggcctccatc atccgcctct gccagggcaa ggtccccgcg    1080
ccgcccagcc tggtcaatac gtgctatagc ctgataggtc cgggctatgg cgtgagcgtc    1140
gccggagtct acaagctgac ctcggcaggc atcgtcgaga tcccgggctc gggtggcctc    1200
acgccaatgg acgcggacga tgaccatctt aacgaagagg cgaccttcgc ccggggctgg    1260
tacaacaata tcgtccaaga catctggggc                                     1290
```

<210> SEQ ID NO 44
<211> LENGTH: 369
<212> TYPE: DNA
<213> ORGANISM: Artificial Sequence
<220> FEATURE:
<223> OTHER INFORMATION: Codon optimized Chlorobium limicola cytochrome
      c subunit of flavocytochrome c sulfide dehydrogenase sequence

<400> SEQUENCE: 44

```
atgctcggtc ttgttttcac tgtcgtcccc ctcttccacg ctggctccac cgtcatggcc      60
gctgacgccc ccgccccggc aaccgtggcg gcccctgcgc cgaccccggc aatggatccg     120
gccaagatgc gcgagcgcgg gcagatcctg gccctgagtt gctcgggctg ccatggcacc     180
gacggcaaat cgtcgtcgat tatgccgtcc atctacggca agacgaccgg ctatatcgag     240
agcgcgctgc tggacttcaa gagcggagcg cggatgagca ccgtgatggg tcgccatgcg     300
aagggctata cgcccgagga aatccacctc atcgcggagt acttcggcaa tttgtccaag     360
aaaaagaac                                                            369
```

<210> SEQ ID NO 45
<211> LENGTH: 1290
<212> TYPE: DNA
<213> ORGANISM: Artificial Sequence
<220> FEATURE:
<223> OTHER INFORMATION: Codon optimized Chlorobium tepidum sulfide
      dehydrogenase, flavoprotein subunit sequence

<400> SEQUENCE: 45

```
atgggaaata ctattagtcg ccgcaccttc aatcgcctcc tgatctccgg acttgctggt      60
tcctcgctgc ttatgtcggg cggaccctc atggccagcg ccccaaaggc ccatgtcgtg      120
gtcatcggcg gcgggttcgg tggcgcgacc gtcgcccgct acctccggca gctggacccg     180
tcgatcagcg tcaccctcgt ggagccgaag aaagttttcc acacgtgtcc gatgagcaat     240
tgggtcatcg gtggcctctt ctccatgcag aacacggcgc atacgtatca cgccctgcgg    300
tcccggtacg gtgtcgaggt tgtccaggaa atggccaccg gcattgaccc cgtcaagaaa    360
accgtgaagc tcaagggcgg ccggatgctc tcgtatgata ggctcgtcgt gtcgcccggt   420
gtggacttca tctgggacgc gattgagggc tacagccgcg atgtcgccga gagctccatg   480
ccctatgcgt gggaggctgg cccgcagacg ctgctcctgc gcaggcagct gttggggatg    540
aaagacggcg agaacgtcat aatctgcgca ccgaagaatc cattccgctg cccgggcggcg  600 ccttacgagc gcgcctcgct catcgcctac tatctcaaaa agtcgaagcc caagagtaag    660
```

```
gtcatcatcc tggacgacaa ggaagtgttc acgaaacaag acctgtttat gcttggctgg    720
gatcggctct atcgcggcaa gattgagtgg cgctccgcga gcgccggcgg caaagtcgag    780
cgcctggacc cggccaagat gaccgtggct accgagttcg gcgacgagaa aggcggcgtg    840
atcaacgtga taccgcccca gaaagccggc cggatcgcgg tggaaaccgg cctcgccgat    900
accagcggat ggtgccccgt caatccggcc aacttcgaga gcctgcaaca tccgggcatc    960
catgtcatcg gtgacgcggc cttggtgggc acgatgccga agagtggcac cgcagccaac   1020
acccaggcta aggccctggc ggcgtggctc gtggcgagct cggcggggg caatgccggg    1080 gagcacgacc tggcgtccct gtgctactcg ctgctggcgc cgggctacgc catctcggtc   1140
gccggtggct atatccagtc gccggaaggc atcaaagaca acccggacac cgtgcatctc   1200
acgtccatgg aagcgacgac cgcgcagctg gcaggcgagg cagagcaagc gctgcaatgg   1260
taccataaca tctcgcagga cacctggggg                                    1290

<210> SEQ ID NO 46
<211> LENGTH: 330
<212> TYPE: DNA
<213> ORGANISM: Artificial Sequence
<220> FEATURE:
<223> OTHER INFORMATION: Codon optimized Chlorobium tepidum TLS
      cytochrome subunit of sulfide dehydrogenasesequence

<400> SEQUENCE: 46
atgctcgctg ccgcccctct ccttctcgct agtggaaatg gatttgcaac taccggaccc     60
gccgccaaac ccgccgtgaa gcccgtcacc gagtcgcgcg gtgagatctt gagcctgtcg    120
tgcgcgggct gccatggcac cgacggcaat tcgtcctcgg tgatcccgtc catctacggc    180
aagtccccgg agtacatcga aacgcgctg atcgacttca aaaacggctc ccgcaccagc    240
accgtcatgg gtcggcacgc gaagggctat acgggcgaag aaatccacct gattgcggag    300
tatttcggga acctgagcaa aaagaaccat                                     330

<210> SEQ ID NO 47
<211> LENGTH: 1257
<212> TYPE: DNA
<213> ORGANISM: Artificial Sequence
<220> FEATURE:
<223> OTHER INFORMATION: Codon optimized  Thiobacillus denitrificans
      sulfide dehydrogenase (flavocytochrome),
      flavoprotein subunit  sequence

<400> SEQUENCE: 47
atgcatctcg atcgccgcga cttcctgaaa ctttccgctg ccactgccct cgctgcccttt    60 cccggttgtg cctccctgtc cgggaccgcc cggccgcgcg tggtcgtggt gggcgcaggc   120
ttcggtggcg ccacgtgcgc gaagtacctc cgccgctggg gccctgccct cgacgtgacc   180
ctcatcgagc cgaacgaaag gttcgtgagc tgcccgatct cgaactgggt gttgggtggc   240
ctgcggtcca tggatgacat cacgcatggc tatggtggcc tggcgaggca cggaatcacc   300
ctcatccgcg acagcgtcgt cgcgatcgac ccggatacc gcacgctgcg cacggcccag   360
ggcctccaga tcgggtacga gcggctggtg ctggcccctg gggttgagct cctcaccgat   420
agcgtgcgcg gcttcgccga tgcagaggcc gcaggccggg ttgtgcatgc gtggaaggct   480
ggcgcccaaa ccgcgctgct ccggcgccag ttggaagcga tgccggacgg gggcaccttt   540
atcgtcagca ttccggctgc cccataccgc tgcccgccgg acctttatga gcgcgcgtgc   600
ctggtcgccc attacttcaa acagcggaag ccgcggtcga aaatcatcgt cctggacgcg   660
```

| | |
|---|---|
| aatccggaca ttgtgtcgaa gaaacccctg ttcaccgacg cgtggaatac cctctatccg | 720 |
| ggcatgattg actatcgccc caactcgccc gcactggtcg tcgacgccgc caagatgact | 780 |
| gtctcgaccg acttcgagga cgtcaggggc gacgtcctca atatcgtgcc acggcagcgc | 840 |
| gcggccgcgg tctgcgacct cgttggcgca cggaacgacg gcaacaagac ctggtgcacc | 900 |
| gtggatttcg cgaccttcga gtccaccgcg gctcccggcg tccacatcat aggcgactcc | 960 |
| atggcgtccc cgctgccgcg cagcggccac atggcgacca atcaagccaa ggtctgcgcg | 1020 |
| ggagccatcg tggatctgct ggcggaccgc gcaccggatc cggcaccggt gatcgcgaac | 1080 |
| acgtgctact cggcgacgag cgacagtacg gctggctacg tcgcccatgt gtaccggctc | 1140 |
| gtccccggca agggctatgt cgcggccccc gagggtggcg cgaccacgac cggtgacgcg | 1200 |
| cgcaatttcc gctatgccgc ctcctgggcg aagaacatct gggccgagat gctgagt | 1257 |

<210> SEQ ID NO 48
<211> LENGTH: 294
<212> TYPE: DNA
<213> ORGANISM: Artificial Sequence
<220> FEATURE:
<223> OTHER INFORMATION: Codon optimized Thiobacillus denitrificans
      sulfide dehydrogenase (flavocytochrome),
      cytochrome c subunit sequence

<400> SEQUENCE: 48

| | |
|---|---|
| atgaccccca gttccgccgt cgcctcctgc ctcctccttg ccttgtccgg tttcgccgtc | 60 |
| gccgcagatc gccacacgct gaccatcgcg gcgacgtgca tgtcgtgcca tggcccggat | 120 |
| gggcgcagcc tgggcgaaat cccgaggctg acggactgt cgcgcaccga gttcgtgacc | 180 |
| gcgctccggg acttccggag cggcgctcgg cgcgcgacga tcatgcagcg ccaagcgtcg | 240 |
| ggctataccg acgccgagat tgacgcgctc ggcgactact cgcgacccct gaag | 294 |

<210> SEQ ID NO 49
<211> LENGTH: 1290
<212> TYPE: DNA
<213> ORGANISM: Artificial Sequence
<220> FEATURE:
<223> OTHER INFORMATION: Codon optimized Thiocystis violascens
      NAD(FAD)-dependent dehydrogenase sequence

<400> SEQUENCE: 49

| | |
|---|---|
| atgaaactta gtaggaggga ttttgtgaag gttagtgggg cagcaacggc ggtgggattg | 60 |
| ttcggttttc cgtatctggc cctgggcgca acccaaaaag tcgtcgtgat cgggggcggc | 120 |
| accggtggcg ccacggcagc taagtatctg aagctcgccg actccagcat cgacgtgacg | 180 |
| ctcatcgagc cgaacgaagt gtactatacc tgttacctgt ccaacgaagt cattggcggc | 240 |
| gagcggaagc ttgagtcgct ccgccagacg tacgacgggc tgaaagcgca tggcgtcaaa | 300 |
| gtcgtgcatg actccgccac gggaattgat cccgacaaaa agaccgtcaa gaccgcgggt | 360 |
| ggcaccgagt atagctatga ccgctgcatc gttgctccgg catcgagct gctctacgag | 420 |
| aaaatagacg ggtactcgga agcggcggcg gagactctgc cccacgcctg gaaggctggc | 480 |
| gagcagaccc cggattctgc gcaagcaatt gaagatatga agacggcgg caccgtcatc | 540 |
| attgcggccc gcccgcgcc gttccggtgc ccgccaggcc cctatgagcg cgccagccag | 600 |
| atcgcccatt acctgaaggc ccataagccc aagagcaagg tcatcatcct ggacaacagc | 660 |
| caaaagttct cgaaacaagc gcagttcacc aagggtgggg aaaccctcta cggtttcggt | 720 |
| acggacaatg cgctgataga gtggcgcccg ggcccggacg ctgcggtcgt gaaggttgat | 780 |

```
gcgggccaga tgctcgcgga gactaacttc ggcgacgaga tcaaagccga cgtcatcaat    840
gtgatccctc cgcagcgggc cggctcgatc gcgcagaccg caggcctcgc caatgagtcc    900
ggctggtgcc cggtcgacgt gaaaaccttc gagtcgaagc tccacaaggg catccatgtc    960
atcggcgacg cctgcatcgc caccgagatg ccgaagtccg gatactcggc gaactcgcag   1020
ggcaaggtcg ccgcggccgc cgtggtggcc ctgctcaagg gcgaggagcc gggtacgccg   1080
tcgtatctga acacgtgcta cagcatcatc ggtcccgcgt acggcatctc cgtcgcaggg   1140
gtctaccgcc tgtcggaaga tggcgcaacg atcgccagcg tgcccgacag cggtggcgtg   1200
accccggtgg acgcgcccga ttgggctctt gcgcgcgaag tcgagtatgc gtattcctgg   1260
tacaacaata tcgtccacga catcttcggc                                    1290
```

<210> SEQ ID NO 50
<211> LENGTH: 597
<212> TYPE: DNA
<213> ORGANISM: Artificial Sequence
<220> FEATURE:
<223> OTHER INFORMATION: Codon optimized Thiocystis violascens
      cytochrome c553 sequence

<400> SEQUENCE: 50

```
atggcacgca aaattcttca aactactctt ctcaccggcg cattggcact ggcgcatcc     60 tccggagcat gggcagaggc gaccggggcc atgctggcca actcgtgcgc tggctgccat    120
ggcacccacg gtaactccgt cggtccggcc agtcccagca tcgcggccat ggaccccgtc    180
gtgttcgtcg aaaccatgga agagttcaaa aatggcgaaa cgtactcgac catcatgggc    240
cgcatcgcga agggttacag caccggcgag ttcgagaaaa tggcggagta tttccacgcg    300
caaacctacc agccggcgaa gcaaagcttc gacacggccc tcgccgataa gggcgccaag    360
ctgcacgaca agtattgcga agagtgtcat gctgagggcg ggaagccgct cgtggatgaa    420
gaggactata atatcctggc gggccagtgg ctcccgtacc tccagtacgc gatggaggac    480
ttccgggcgg accggcgcga aatggagaag aaaatgcgca ccaagctgaa cgagctgctg    540
aaagccgagg gcgaggatgg catcgccgcc gtgaacgctt ttatgcctc gcagcag       597
```

<210> SEQ ID NO 51
<211> LENGTH: 924
<212> TYPE: DNA
<213> ORGANISM: Artificial Sequence
<220> FEATURE:
<223> OTHER INFORMATION: Codon optimized Acidianus tengchongensis
      sulfur oxygenase/reductase sequence

<400> SEQUENCE: 51

```
atgcccaagc cctatatcgc tatcaacatg gccgacctca aaaatgaacc gaaaacgttc     60
gagatgttct ccgcggtggg ccccaaggtc tgcatggtca cggcgaggca tccgggcttc    120
gtgggcttcc agaatcatgt gcagatcggg tgctcccgt ttggagagcg gttcggtggc    180
gccaagatgg acatgacgaa agaatcgtcg actgtccggg tcctccagta caccatgtgg    240
aaggattgga agaccacga agagatgcat cgccaaaact ggtcctacct cttccgcctg    300
tgctacagct cgccagcca aatggttttgg ggcccatggg agccgattta tgagatcaag    360
tacgcggata tgccgatcaa taccgagatg accgacttca ccgccgtggt gggtaaaaag    420
ttcgccgagg gcaagccgct ggaaattccc gtcatctcgc agccctacgg caagcgcgtc    480
gtcgcgttcg gagagcacac cgtgattccg gcaaggagaa acagttcgaa ggacgcgatc    540
atcaagacgc ttgagatgtt caagcgcgca ccggggtttcc tcggcgcgat gctgttgaag    600
```

```
gagatcggcg tgagcggcat cggctcgttc cagtttgggt ccaagggctt ccatcagctg    660
ctggagagtc cgggctccct ggagccggat ccgaacaatg tcatgtatca agtgcccgag    720
gccaagccca cccctccgca gtacatcgtc catgttgagt gggccaacct ggacgcactc    780
cagttcggta tgggtcgcgt cctcctcagc cggagtatc gcgaagtgca cgacgaagcg    840
ctggacaccc tgatctatgg cccgtatatc cggataatca acccggtcat ggaaggcacc    900
ttctggcgcg agtaccttaa cgag                                           924
```

<210> SEQ ID NO 52
<211> LENGTH: 948
<212> TYPE: DNA
<213> ORGANISM: Artificial Sequence
<220> FEATURE:
<223> OTHER INFORMATION: Codon optimized  Sulfolobus metallicus sulfur
      oxygenase-reductase  sequence

<400> SEQUENCE: 52

```
atgccgaagc cgtatgtcgc gattaaccaa gtcatcgtca aaaatgaacc gaaaacgttc    60
gagatgttcc agagcgtggg ccccaaggtc tgcatgacga ctgcccggca tagggccttt   120
gtgggcttcc agaaccatat cgagattggc gttgtcccga tggggacccg ctacggtgcg   180
gcgaagatgg acatgctgaa agagagctcg accatgggcc tctaccagta caccatgtgg   240
aaagactgga agaccacga agagatgcat aagcaaaatt ggtcgagcct cttccgcctc   300
tgctattcgt gcatgagtca agtcgtgtgg ggtccctggg agccgctgta cgaaatcacg   360
atggccgaca tgcctctcaa caccgagatg accgatttta cggtgatggt cggacaaaag   420
ttcgcgtcgg gtgacgccct ctccttgccg cccatctccc agccgtatgg caagcgcgtc   480
gtgacctacg cgagcatgt cgtgaaggaa ggcatggaga agagttcga ggaaccctc    540 agtcgcctgc tgccgatgtt caagcgcgca cccggtttcc tgggctacat ggtcctgaag   600
gaaatcggcg cgtccccgct gggctcgctg cagctttcgg cgaagtcctg gcatcagctg   660
ctggagtccg ccaacggcat ggacgtgccc gatccaaatg gcaacttcag cccggaacag   720
gcccggaaca gccgcagaa atatgttgtg cacatggagt ggtcgaatac cgatgccgcc   780
cagttcggcc tcggacgcgt gttccttagc ccggagtacc gcgagataca cgaccagatc   840
gtggacacgc tcatctatgg cccctatatc aggatcctca atccggtgat ggagggctcc   900
ttctggcggg agtacctcaa cgaggtcaat ctgcaaaagg ctacctgg              948
```

<210> SEQ ID NO 53
<211> LENGTH: 933
<212> TYPE: DNA
<213> ORGANISM: Artificial Sequence
<220> FEATURE:
<223> OTHER INFORMATION: Codon optimized  Acidithiobacillus caldus
      sulfur oxygenase reductase  sequence

<400> SEQUENCE: 53

```
atggataaga atccgatcgt cgccatcaat cagtccaaag ttgtgaaccg cccagagagt    60
tttgccacca tgatgaaggt cgggcccaag gtctgcataa ccaccgcgtc ccatccgggt   120
ttcctgggat tcgagcaact cctccagacc ggcatgcatc ccatgccgg tcgctacggc   180 ggggcgccg tggacatgcg ggacactatc aacccgatgg cgatgtatca gtatacggtg   240
tggcaagatg tgaagtcgca tgaagagatg catcacgaca acttcaaaga aatctatgaa   300
ctgtgcggca gctgcctgga catggtcatc gaagggccct gggagccgta ctatgagatt   360
```

| | | |
|---|---|---|
| gtgcgctcgg acctcccgcg catcatgggc atgaccgatg ttccggcgca actgggcgca | 420 | |
| gcgttcgcag cccagaagcc cgtgtccaag gtcgcccttg ctagccagcg gtgcatcgcc | 480 | |
| ctgggcgacc attgggtgag cgacggccat gagaaagatt tcgagaaagg cgctgtggcg | 540 | |
| accctgacgt ggatgaaaga aaacatcccg ggtatggtcg gctggatgat cctcaagcaa | 600 | |
| ttcggagtct ccgccattgg ctcgttccag ttggaccccg agggcatgat gaaagcgacg | 660 | |
| ctgggcgcca accgcctgc gtacgcgacc aaccacggca ccgcgatccc cgacaagccg | 720 | |
| cagatcccgg gtcagaggcc gacgcagtac ctcgtgcaca tggagtggga gtcgcccgag | 780 | |
| atggcccaca tgggcatcgg ctacgccatg gtcgactacg agctccgcca gatccacaat | 840 | |
| catggcgtcc ttgcgcatct ggaccggggt ccgtactatc tgttcttcgc gccgatgatg | 900 | |
| gaacagggcc agtggcgccg gaagctcgtc ctg | 933 | |

<210> SEQ ID NO 54
<211> LENGTH: 918
<212> TYPE: DNA
<213> ORGANISM: Artificial Sequence
<220> FEATURE:
<223> OTHER INFORMATION: Codon optimized Sulfobacillus
    thermosulfidooxidans sulfur oxidation protein
    sequence

<400> SEQUENCE: 54

| | | |
|---|---|---|
| atgccacgcc cctacatcgc aatcaatgac gccaaagttg tcaatgccga gtccagcttt | 60 | |
| caagccttcc aacaggtcgg gcccaaggtc tgcatggtga ccgcgaatca tccgggcttc | 120 | |
| gtcggcttcc agaaccatgt gcagatcggc gtgttcccca tgggtggccg ctacggcgga | 180 | |
| gcgaaaatgg atatgcatga ggaacttaac ccgatcggca tccggcagta caccatgtgg | 240 | |
| aagcgctggg aagatcacga ggagatgcat taccaacagt tcgacagcat cttccggctg | 300 | |
| tgctcctcct gcctgggcat ggtcgtggaa ggcccgtggg aagatatgta tgagatcatt | 360 | |
| tcgtcggacc tccccgaagt cattgcgatg accgacgttc cgtcgaagct cggagccgcg | 420 | |
| ttcatggccg gtcagcagcc tgccccggtg gccatgccgt atggccagcg cgtgatcgcg | 480 | |
| gggtcggacc actacataat cccgggcagg gaacaagagt tcgagactgc catcaccgag | 540 | |
| ctgatgaaaa tgttccaaaa ggcaccgggg ttcctgggct acatggtgct caagcaaatt | 600 | |
| ggcgcgagtg cgatcggttc cttccagctg cagcccgagg gcatccatca ggctttgcag | 660 | |
| accctcggcg acaatccccc gaagaataaa gagggcaact ttaagctgat cgaggctaag | 720 | |
| aaaacgccga ccaagtatct ggtccacatg gagtggtcgg acctcaacag cgcgatgttc | 780 | |
| ggcatctccc cgcgtcgtga tcaacggtcgc tatcgggccc agcatgacaa ggtccttgcg | 840 | |
| acggtgctgc agggcccgta tgtgacgctg tggagcccga tgatggagga cacctcgtgg | 900 | |
| cgcgagtatc tcaacgag | 918 | |

<210> SEQ ID NO 55
<211> LENGTH: 570
<212> TYPE: PRT
<213> ORGANISM: Escherichia coli

<400> SEQUENCE: 55

Met Ser Glu Lys His Pro Gly Pro Leu Val Val Glu Gly Lys Leu Thr
 1               5                  10                  15

Asp Ala Glu Arg Met Lys His Glu Ser Asn Tyr Leu Arg Gly Thr Ile
            20                  25                  30

Ala Glu Asp Leu Asn Asp Gly Leu Thr Gly Gly Phe Lys Gly Asp Asn

```
             35                  40                  45
Phe Leu Leu Ile Arg Phe His Gly Met Tyr Gln Gln Asp Arg Asp
 50                  55                  60
Ile Arg Ala Glu Arg Ala Glu Gln Lys Leu Glu Pro Arg His Ala Met
 65                  70                  75                  80
Leu Leu Arg Cys Arg Leu Pro Gly Gly Val Ile Thr Thr Lys Gln Trp
                     85                  90                  95
Gln Ala Ile Asp Lys Phe Ala Gly Glu Asn Thr Ile Tyr Gly Ser Ile
                    100                 105                 110
Arg Leu Thr Asn Arg Gln Thr Phe Gln Phe His Gly Ile Leu Lys Lys
                    115                 120                 125
Asn Val Lys Pro Val His Gln Met Leu His Ser Val Gly Leu Asp Ala
                    130                 135                 140
Leu Ala Thr Ala Asn Asp Met Asn Arg Asn Val Leu Cys Thr Ser Asn
145                 150                 155                 160
Pro Tyr Glu Ser Gln Leu His Ala Glu Ala Tyr Glu Trp Ala Lys Lys
                    165                 170                 175
Ile Ser Glu His Leu Leu Pro Arg Thr Arg Ala Tyr Ala Glu Ile Trp
                    180                 185                 190
Leu Asp Gln Glu Lys Val Ala Thr Thr Asp Glu Pro Ile Leu Gly
                    195                 200                 205
Gln Thr Tyr Leu Pro Arg Lys Phe Lys Thr Thr Val Ile Pro Pro
210                 215                 220
Gln Asn Asp Ile Asp Leu His Ala Asn Asp Met Asn Phe Val Ala Ile
225                 230                 235                 240
Ala Glu Asn Gly Lys Leu Val Gly Phe Asn Leu Leu Val Gly Gly Gly
                    245                 250                 255
Leu Ser Ile Glu His Gly Asn Lys Lys Thr Tyr Ala Arg Thr Ala Ser
                    260                 265                 270
Glu Phe Gly Tyr Leu Pro Leu Glu His Thr Leu Ala Val Ala Glu Ala
                    275                 280                 285
Val Val Thr Thr Gln Arg Asp Trp Gly Asn Arg Thr Asp Arg Lys Asn
                    290                 295                 300
Ala Lys Thr Lys Tyr Thr Leu Glu Arg Val Gly Val Glu Thr Phe Lys
305                 310                 315                 320
Ala Glu Val Glu Arg Arg Ala Gly Ile Lys Phe Glu Pro Ile Arg Pro
                    325                 330                 335
Tyr Glu Phe Thr Gly Arg Gly Asp Arg Ile Gly Trp Val Lys Gly Ile
                    340                 345                 350
Asp Asp Asn Trp His Leu Thr Leu Phe Ile Glu Asn Gly Arg Ile Leu
                    355                 360                 365
Asp Tyr Pro Ala Arg Pro Leu Lys Thr Gly Leu Leu Glu Ile Ala Lys
                    370                 375                 380
Ile His Lys Gly Asp Phe Arg Ile Thr Ala Asn Gln Asn Leu Ile Ile
385                 390                 395                 400
Ala Gly Val Pro Glu Ser Glu Lys Ala Lys Ile Glu Lys Ile Ala Lys
                    405                 410                 415
Glu Ser Gly Leu Met Asn Ala Val Thr Pro Gln Arg Glu Asn Ser Met
                    420                 425                 430
Ala Cys Val Ser Phe Pro Thr Cys Pro Leu Ala Met Ala Glu Ala Glu
                    435                 440                 445
Arg Phe Leu Pro Ser Phe Ile Asp Asn Ile Asp Asn Leu Met Ala Lys
                    450                 455                 460
```

-continued

```
His Gly Val Ser Asp Glu His Ile Val Met Arg Val Thr Gly Cys Pro
465                 470                 475                 480

Asn Gly Cys Gly Arg Ala Met Leu Ala Glu Val Gly Leu Val Gly Lys
            485                 490                 495

Ala Pro Gly Arg Tyr Asn Leu His Leu Gly Gly Asn Arg Ile Gly Thr
        500                 505                 510

Arg Ile Pro Arg Met Tyr Lys Glu Asn Ile Thr Glu Pro Glu Ile Leu
    515                 520                 525

Ala Ser Leu Asp Glu Leu Ile Gly Arg Trp Ala Lys Glu Arg Glu Ala
530                 535                 540

Gly Glu Gly Phe Gly Asp Phe Thr Val Arg Ala Gly Ile Ile Arg Pro
545                 550                 555                 560

Val Leu Asp Pro Ala Arg Asp Leu Trp Asp
                565                 570

<210> SEQ ID NO 56
<211> LENGTH: 599
<212> TYPE: PRT
<213> ORGANISM: Escherichia coli

<400> SEQUENCE: 56

Met Thr Thr Gln Val Pro Pro Ser Ala Leu Leu Pro Leu Asn Pro Glu
1               5                   10                  15

Gln Leu Ala Arg Leu Gln Ala Ala Thr Thr Asp Leu Thr Pro Thr Gln
            20                  25                  30

Leu Ala Trp Val Ser Gly Tyr Phe Trp Gly Val Leu Asn Gln Gln Pro
        35                  40                  45

Ala Ala Leu Ala Ala Thr Pro Ala Pro Ala Ala Glu Met Pro Gly Ile
    50                  55                  60

Thr Ile Ile Ser Ala Ser Gln Thr Gly Asn Ala Arg Arg Val Ala Glu
65                  70                  75                  80

Ala Leu Arg Asp Asp Leu Leu Ala Ala Lys Leu Asn Val Lys Leu Val
                85                  90                  95

Asn Ala Gly Asp Tyr Lys Phe Lys Gln Ile Ala Ser Glu Lys Leu Leu
            100                 105                 110

Ile Val Val Thr Ser Thr Gln Gly Glu Gly Glu Pro Pro Glu Glu Ala
        115                 120                 125

Val Ala Leu His Lys Phe Leu Phe Ser Lys Lys Ala Pro Lys Leu Glu
    130                 135                 140

Asn Thr Ala Phe Ala Val Phe Ser Leu Gly Asp Ser Ser Tyr Glu Phe
145                 150                 155                 160

Phe Cys Gln Ser Gly Lys Asp Phe Asp Ser Lys Leu Ala Glu Leu Gly
                165                 170                 175

Gly Glu Arg Leu Leu Asp Arg Val Asp Ala Asp Val Glu Tyr Gln Ala
            180                 185                 190

Ala Ala Ser Glu Trp Arg Ala Arg Val Val Asp Ala Leu Lys Ser Arg
        195                 200                 205

Ala Pro Val Ala Ala Pro Ser Gln Ser Val Ala Thr Gly Ala Val Asn
    210                 215                 220

Glu Ile His Thr Ser Pro Tyr Ser Lys Asp Ala Pro Leu Val Ala Ser
225                 230                 235                 240

Leu Ser Val Asn Gln Lys Ile Thr Gly Arg Asn Ser Glu Lys Asp Val
                245                 250                 255

Arg His Ile Glu Ile Asp Leu Gly Asp Ser Gly Met Arg Tyr Gln Pro
```

```
              260                 265                 270
Gly Asp Ala Leu Gly Val Trp Tyr Gln Asn Asp Pro Ala Leu Val Lys
                275                 280                 285

Glu Leu Val Glu Leu Leu Trp Leu Lys Gly Asp Glu Pro Val Thr Val
            290                 295                 300

Glu Gly Lys Thr Leu Pro Leu Asn Glu Ala Leu Gln Trp His Phe Glu
305                 310                 315                 320

Leu Thr Val Asn Thr Ala Asn Ile Val Glu Asn Tyr Ala Thr Leu Thr
                325                 330                 335

Arg Ser Glu Thr Leu Leu Pro Leu Val Gly Asp Lys Ala Lys Leu Gln
            340                 345                 350

His Tyr Ala Ala Thr Thr Pro Ile Val Asp Met Val Arg Phe Ser Pro
            355                 360                 365

Ala Gln Leu Asp Ala Glu Ala Leu Ile Asn Leu Arg Pro Leu Thr
            370                 375                 380

Pro Arg Leu Tyr Ser Ile Ala Ser Ser Gln Ala Glu Val Glu Asn Glu
385                 390                 395                 400

Val His Val Thr Val Gly Val Val Arg Tyr Asp Val Glu Gly Arg Ala
                405                 410                 415

Arg Ala Gly Gly Ala Ser Ser Phe Leu Ala Asp Arg Val Glu Glu Glu
            420                 425                 430

Gly Glu Val Arg Val Phe Ile Glu His Asn Asp Asn Phe Arg Leu Pro
            435                 440                 445

Ala Asn Pro Glu Thr Pro Val Ile Met Ile Gly Pro Gly Thr Gly Ile
450                 455                 460

Ala Pro Phe Arg Ala Phe Met Gln Gln Arg Ala Ala Asp Glu Ala Pro
465                 470                 475                 480

Gly Lys Asn Trp Leu Phe Phe Gly Asn Pro His Phe Thr Glu Asp Phe
                485                 490                 495

Leu Tyr Gln Val Glu Trp Gln Arg Tyr Val Lys Asp Gly Val Leu Thr
            500                 505                 510

Arg Ile Asp Leu Ala Trp Ser Arg Asp Gln Lys Glu Lys Val Tyr Val
            515                 520                 525

Gln Asp Lys Leu Arg Glu Gln Gly Ala Glu Leu Trp Arg Trp Ile Asn
            530                 535                 540

Asp Gly Ala His Ile Tyr Val Cys Gly Asp Ala Asn Arg Met Ala Lys
545                 550                 555                 560

Asp Val Glu Gln Ala Leu Leu Glu Val Ile Ala Glu Phe Gly Gly Met
                565                 570                 575

Asp Thr Glu Ala Ala Asp Glu Phe Leu Ser Glu Leu Arg Val Glu Arg
            580                 585                 590

Arg Tyr Gln Arg Asp Val Tyr
            595

<210> SEQ ID NO 57
<211> LENGTH: 553
<212> TYPE: PRT
<213> ORGANISM: Rhodobacter capsulatus

<400> SEQUENCE: 57

Met Tyr Glu Tyr Ser Asp Phe Asp Glu Ala Phe Val Arg Asn Arg Val
1               5                   10                  15

Ala Gln Phe Arg Asp Gln Val Ala Arg Arg Leu Asp Gly Ser Leu Thr
            20                  25                  30
```

-continued

```
Glu Glu Glu Phe Arg Pro Leu Arg Leu Met Asn Gly Leu Tyr Leu Gln
         35                  40                  45
Leu His Ala Tyr Met Leu Arg Val Ala Ile Pro Tyr Gly Thr Leu Ser
 50                  55                  60
Ser Asn Gln Met Arg Ala Leu Ala Asp Val Ala Asp Arg Phe Asp Arg
 65                  70                  75                  80
Gly Tyr Gly His Phe Thr Thr Arg Gln Asn Ile Gln Phe Asn Trp Ile
                 85                  90                  95
Lys Leu Thr Asp Thr Pro Asp Ile Leu Glu Arg Leu Ala Asp Asp Gly
                100                 105                 110
Leu His Ala Ile Gln Thr Ser Gly Asn Cys Ile Arg Asn Val Thr Thr
            115                 120                 125
Asp Ala Phe Ala Gly Ala Ala Asp Glu Ile Glu Asp Pro Arg Pro
        130                 135                 140
Tyr Ala Glu Leu Ile Arg Gln Trp Ser Ser Asp His Ala Glu Phe Gln
145                 150                 155                 160
Phe Leu Pro Arg Lys Phe Lys Ile Ala Ile Thr Gly Ser Pro Glu Asp
                165                 170                 175
Arg Ala Ala Ile Arg Ala His Asp Val Gly Leu Gln Leu Ile Gln Arg
            180                 185                 190
Gly Gly Glu Thr Gly Phe Arg Val Leu Val Gly Gly Leu Gly Arg
        195                 200                 205
Thr Pro Met Leu Ala Pro Glu Leu Arg Asp Phe Leu Pro Lys Ala Asp
    210                 215                 220
Leu Leu Pro Tyr Leu Glu Ala Ile Leu Ala Ala Tyr Asn Leu Ile Gly
225                 230                 235                 240
Arg Arg Asp Asn Lys Tyr Lys Ala Arg Ile Lys Ile Thr Val Phe Glu
                245                 250                 255
Thr Gly Ile Glu Pro Phe Arg Asp Leu Val Glu Gln Glu Phe Glu Arg
            260                 265                 270
Ile Arg Pro Gln Phe Thr Gly Ala Asp Gln Ala Leu Leu Ala Glu Ile
        275                 280                 285
Thr Pro His Phe Ala Leu Pro Asp Leu Val Ala Lys Asp Pro Ala Pro
    290                 295                 300
Phe Ala Ala Gln Val Thr Asp Pro Ala Phe Ala Ala Trp Val Lys
305                 310                 315                 320
His Ser Val Thr Asp His Lys Arg Pro Asp His Ala Val Val Thr Ile
                325                 330                 335
Ser Val Lys Thr Pro Gly Glu Glu Pro Gly Asp Val Ser Ala Ala Gln
            340                 345                 350
Met Arg Ala Val Ala Asp Leu Ala Asp Leu His Gly Tyr Gly Glu Leu
        355                 360                 365
Arg Ile Ser His Met Gln Asn Ile Val Leu Pro His Val Ala Arg Ala
    370                 375                 380
Asp Leu Pro Ala Leu His Ala Leu Arg Lys Val Gly Leu Ala Ala
385                 390                 395                 400
Ala Asn Val Gly Leu Ile Ser Asp Met Ile Ala Cys Pro Gly Met Asp
                405                 410                 415
Tyr Cys Ala Leu Ala Thr Ala Arg Ser Ile Pro Leu Ala Gln Glu Ile
            420                 425                 430
Ala Gln His Phe Glu Thr Leu Gly Leu Val Glu Thr Ile Gly Pro Leu
        435                 440                 445
Pro Leu Lys Ile Ser Gly Cys Ile Asn Ala Cys Gly His His His Leu
```

```
                    450                 455                 460
Gly Ala Ile Gly Ile Leu Gly Leu Asp Arg Ala Gly Ala Glu Asn Tyr
465                 470                 475                 480

Gln Ile Thr Leu Gly Gly Ala Glu Gly Pro Glu Ala Ala Ile Gly Glu
                485                 490                 495

Lys Met Gly Pro Gly Phe Ala Tyr Asp Ala Val Val Pro Ala Ile Glu
                500                 505                 510

Arg Leu Val Arg Ala Tyr Leu Thr Leu Arg Leu Ser Glu Gly Glu Thr
                515                 520                 525

Phe Leu Ala Ala Leu His Arg Leu Gly Arg Glu Pro Phe Arg Ala Ala
                530                 535                 540

Leu Tyr Asp Glu Ala Gln Asp Ala Ala
545                 550
```

<210> SEQ ID NO 58
<211> LENGTH: 735
<212> TYPE: PRT
<213> ORGANISM: Rhodobacter capsulatus

<400> SEQUENCE: 58

```
Met Leu Arg Phe Leu His Arg Trp Pro Gly Leu Leu Ala Ala Leu Leu
 1               5                  10                  15

Val Leu Val Leu Ala Leu Ser Gly Ser Ala Leu Ser Leu Tyr Pro Ala
                20                  25                  30

Leu Glu Arg Leu Ala Val Pro Gln Ala Glu Ser Thr Leu Thr Val Ala
                35                  40                  45

Asp Leu Ala Ala Arg Val Ala Ser Ala His Pro Gly Leu Glu Gln Ile
                50                  55                  60

Arg Arg Ala Pro Ser Gly Arg Val Val Ala Trp Trp Phe Glu Gly Gly
 65              70                  75                  80

Arg Pro Gly Ala Ala Val Ile Asp Pro Ala Thr Gly Ala Asp Leu Gly
                85                  90                  95

Ser Pro Asp Pro Leu Pro Gly Ser Arg Phe Leu Thr Asp Leu His Arg
                100                 105                 110

Glu Leu Phe Ala Gly Asp Thr Gly Arg Leu Val Ala Ala Gly Ala
                115                 120                 125

Ala Leu Met Leu Ala Leu Ala Ile Ser Gly Ala Trp Leu Val Ala Arg
                130                 135                 140

Arg Met Gly Gly Trp Ser Arg Trp Phe Gly Arg Thr Arg Gly Pro Phe
145                 150                 155                 160

Ala Gly Arg Leu His Val Glu Leu Ala Arg Phe Ala Val Gly Gly Leu
                165                 170                 175

Ile Leu Ser Ser Leu Thr Ala Leu Trp Met Thr Ala Ser Met Phe Ser
                180                 185                 190

Leu Leu Pro Asp Gly Ala Ala Glu Pro Ala Pro Ala Leu Ala Thr Ala
                195                 200                 205

Thr Leu Pro Arg Leu Pro Tyr Asp Gln Ile Pro Ala Leu Ala Asn Thr
                210                 215                 220

Pro Ala Ala Ala Leu Arg Glu Leu Ser Leu Pro Ser Pro Asp Asp Pro
225                 230                 235                 240

Thr Asp Thr Phe Lys Leu Val Thr Glu Gly Gly Ala Ala Leu Ile Asp
                245                 250                 255

Pro Gly Thr Gly Ala Met Leu Ser Ser Ala Thr Pro Gly Phe Phe Glu
                260                 265                 270
```

-continued

```
Lys Ala Thr Glu Ile Met Val Met Leu His Thr Gly Gln Gly Ala Ser
            275                 280                 285
Ala Leu Gly Leu Leu Leu Gly Leu Met Ser Leu Ser Val Pro Ala Leu
        290                 295                 300
Ala Leu Thr Gly Ala Gln His Trp Trp Ala Gly Leu Arg Ser Asn Arg
305                 310                 315                 320
Arg Ile Arg Arg Asn Ala Arg Ala Gln Leu Ala Glu Thr Val Val Leu
                325                 330                 335
Val Ala Ser Glu Gly Thr Thr Trp Gly Phe Ala Arg Thr Leu His
            340                 345                 350
Asp Gly Leu Thr Ala Ala Gly Gln Lys Val His Thr Ala Pro Leu Ala
        355                 360                 365
Ser Phe Asp Pro Ala Arg Tyr Ala Arg Ala Arg Phe Leu Ile Leu
370                 375                 380
Ala Ala Thr Tyr Gly Glu Gly Glu Ala Pro Thr Ala Ala Lys Ala Val
385                 390                 395                 400
Leu Asp Arg Ile Ala Ala Leu Thr Ser Ala Pro Ala Ala Pro Leu Ala
                405                 410                 415
Ile Leu Gly Phe Gly Asp Arg Thr Phe Pro Gln Phe Cys Gly Phe Ala
            420                 425                 430
Glu Ser Leu Arg Ala Ala Ala Ala Ile Gly Trp Glu Ser Leu Met
        435                 440                 445
Pro Met Ala Thr Val Asp Arg Gln Ser Ala Gln Asp Phe Ala Arg Trp
        450                 455                 460
Ser Arg Asp Leu Gly Ala Val Leu Gly Leu Pro Leu Asp Leu Thr His
465                 470                 475                 480
Leu Pro Glu Arg Pro Lys Thr Thr Ala Leu Thr Leu Ile Ser Arg Arg
                485                 490                 495
Asp His Gly Ala Glu Val Gln Ala Pro Thr Ser Ile Leu Arg Phe Glu
            500                 505                 510
Val Pro Gln Ala Thr Leu Trp Gln Arg Leu Thr Gly Gln Gly Phe Ala
        515                 520                 525
Arg Phe Glu Ala Gly Asp Leu Ile Gly Ile Leu Pro Lys Gly Ser Asp
530                 535                 540
Leu Pro Arg Phe Tyr Ser Leu Ala Ser Ser Ala Arg Asp Gly Phe Leu
545                 550                 555                 560
Glu Ile Cys Val Arg Arg His Pro Gly Gly Leu Cys Ser Gly Gln Leu
                565                 570                 575
Thr Asp Leu Thr Pro Gly Ala Thr Val Ala Gly Phe Val Arg Arg Asn
            580                 585                 590
Pro Ala Phe Arg Pro Gln Lys Gly Arg Lys Pro Val Ile Leu Ile Gly
        595                 600                 605
Ala Gly Thr Gly Val Gly Pro Leu Ala Gly Phe Leu Arg Ala Asn Arg
        610                 615                 620
Arg His Arg Pro Met His Leu Tyr Phe Gly Ala Arg Ala Pro Gln Ser
625                 630                 635                 640
Asp Leu Leu Tyr Glu Ala Glu Leu Arg Asp Trp Gln Ala Ala Gly Gln
                645                 650                 655
Leu Ser Arg Leu Thr Thr Ala Phe Ser Arg His Gly Pro Lys Thr Tyr
            660                 665                 670
Val Gln Asp Ala Leu Arg Ala Asp Ala Pro Glu Leu Ala Arg Leu Ile
        675                 680                 685
Gly Ala Gly Ala Gln Ile Met Val Cys Gly Gly Arg Asp Met Ala Ala
```

```
            690              695              700
Ala Val Arg Asp Ala Leu Ala Glu Ile Leu Val Pro Ile Gly Gln Thr
705              710              715              720

Pro Ala Ser Leu Lys Ala Glu Gly Arg Tyr Ala Glu Asp Val Tyr
                725              730              735

<210> SEQ ID NO 59
<211> LENGTH: 565
<212> TYPE: PRT
<213> ORGANISM: Shewanella putrefaciens

<400> SEQUENCE: 59

Met Ser Glu Gln Lys Leu Ala Leu Asn Glu Tyr Leu Lys Thr Asp Ser
 1               5                  10                  15

Asp Tyr Leu Arg Gly Thr Ile Lys Glu Gly Leu Asp Ser Ser Val Thr
                20                  25                  30

Gly Ser Phe Ser Asp Gly Asp Gln Gln Leu Ile Lys Phe His Gly Phe
            35                  40                  45

Tyr Gln Gln Asp Asp Arg Asp Leu Arg Asn Glu Arg Lys Glu Gln Lys
        50                  55                  60

Leu Glu Pro Leu Tyr Ser Phe Met Leu Arg Ala Arg Val Pro Gly Gly
65                  70                  75                  80

Ile Cys Ser Pro Gln Gln Trp Leu Gly Val Asp Lys Ile Ala Ser Thr
                85                  90                  95

Leu Thr Ser Ser Asn Ser Ile Arg Leu Thr Thr Arg Gln Thr Phe Gln
            100                 105                 110

Tyr His Gly Ile Pro Lys Arg Asn Leu Lys Thr Ile Ile Gln Asp Leu
        115                 120                 125

Asp Arg Gln Ala Leu Asp Ser Ile Ala Ala Cys Gly Asp Val Asn Arg
130                 135                 140

Asn Val Met Cys Asn Pro Asn Pro Val Glu Ser Lys Leu His Glu Gln
145                 150                 155                 160

Ala Tyr Ala Val Ala Lys Lys Leu Ser Asp His Leu Leu Pro His Thr
                165                 170                 175

Arg Ala Tyr Ala Glu Ile Trp Leu Asp Glu Lys Leu Leu Thr Thr
            180                 185                 190

Glu Asp Glu Thr Val Glu Pro Val Tyr Gly Lys Thr Tyr Leu Pro Arg
        195                 200                 205

Lys Phe Lys Met Ala Val Ala Val Pro Pro Asp Asn Asp Val Asp Val
210                 215                 220

Tyr Thr Asn Asp Leu Gly Phe Ile Ala Val Ala Glu Asn Gly Glu Leu
225                 230                 235                 240

Val Gly Phe Asn Leu Thr Ala Gly Gly Gly Met Gly Ser Thr His Gly
                245                 250                 255

Glu Val Glu Thr Phe Pro Arg Leu Ala Asp Asp Phe Gly Phe Ile Lys
            260                 265                 270

Thr Glu Asp Val Met Lys Phe Ala Glu Ala Val Met Thr Val Gln Arg
        275                 280                 285

Asp Trp Gly Asn Arg Ser Asn Arg Lys Arg Ser Arg Leu Lys Tyr Thr
    290                 295                 300

Ile Val Asp His Gly Tyr Glu Lys Phe Lys Ala Glu Val Glu Ala Arg
305                 310                 315                 320

Ala Gly Val Lys Phe Glu Pro Leu Arg Glu Val Val Ile Gly Asp Arg
                325                 330                 335
```

```
Gly Asp Arg Tyr Gly Trp Val Glu Val Asp Gly Lys Trp His Leu
                340                 345                 350

Thr Leu Phe Ile Glu Ser Gly Arg Ile Lys Asp Leu Pro Gly Gln Thr
        355                 360                 365

Leu Gln Thr Gly Leu Arg Glu Ile Ala Lys Ile His Lys Gly Asp Phe
    370                 375                 380

Arg Met Thr Ser Asn Gln Asn Met Ile Ile Ala Gly Val Ala Ala Glu
385                 390                 395                 400

Asp Lys Ala Thr Ile Glu Gly Leu Ala Arg Lys His Gly Leu Leu Gly
                405                 410                 415

Gln Val Leu Thr Gln Thr Arg Gly His Ser Ile Ala Cys Val Ala Leu
                420                 425                 430

Pro Thr Cys Pro Leu Ala Met Ala Glu Ala Glu Arg Tyr Phe Pro Glu
            435                 440                 445

Phe Ile Asp His Ile Asp Ala Leu Gln Ala Lys His Gly Ile Ser Glu
        450                 455                 460

Gln Ala Ile Val Val Arg Met Thr Gly Cys Pro Asn Gly Cys Ala Arg
465                 470                 475                 480

Pro Phe Ala Ala Glu Ile Gly Leu Val Gly Lys Ala Pro Gly Arg Tyr
                485                 490                 495

Asn Leu Tyr Leu Gly Ala Ser Phe Glu Gly Thr Arg Leu Asn Lys Met
                500                 505                 510

His Arg Glu Asn Ile Gln Glu Ala Asp Ile Leu Ala Glu Leu Asp Thr
            515                 520                 525

Leu Phe Gly Arg Tyr Ala Val Glu Arg Asp Ala Gly Glu Thr Phe Gly
    530                 535                 540

Asn Phe Thr Val Arg Val Gly Val Val Lys Ala Val Ile Asp Ala Ala
545                 550                 555                 560

Lys Asp Phe His Gly
                565

<210> SEQ ID NO 60
<211> LENGTH: 599
<212> TYPE: PRT
<213> ORGANISM: Shewanella putrefaciens

<400> SEQUENCE: 60

Met Leu Leu Lys Glu Leu Ser Ser Leu Ala Ser Pro Leu Ser Gln Gly
1               5                   10                  15

Gln Val Glu Lys Leu Lys Gln Leu Thr Ser Glu Leu Ser Ala Val Gln
            20                  25                  30

Leu Ala Trp Val Ser Gly Tyr Leu Ala Ala Thr Ala Asn Ala Gly Gln
        35                  40                  45

Leu Ala Pro Val Ala Gln Ala Gln Thr Ala Gln Thr Val Thr Ile Leu
    50                  55                  60

Tyr Gly Ser Gln Thr Gly Asn Gly Arg Gly Val Ala Lys Ala Leu Ala
65                  70                  75                  80

Asp Lys Ala Gln Ala Gln Gly Tyr Ala Val Asn Leu Ala Ser Met Gly
                85                  90                  95

Glu Tyr Asn Val Arg Gln Leu Lys Gln Glu Ala Val Leu Leu Leu Val
            100                 105                 110

Val Ser Thr His Gly Glu Gly Glu Ala Pro Asp Asp Ala Ile Glu Leu
        115                 120                 125

His Lys Phe Leu Ala Ser Lys Arg Ala Pro Lys Leu Asp Asn Leu His
    130                 135                 140
```

```
Tyr Ser Val Leu Ala Leu Gly Asp Ser Ser Tyr Glu Phe Phe Cys Gln
145                 150                 155                 160

Thr Gly Lys Asp Phe Asp Thr Arg Leu Ala Leu Gly Ala Lys Ser
            165                 170                 175

Leu Leu Pro Leu Ile Glu Cys Asp Val Asp Tyr Glu Ala Ala Ala Gly
            180                 185                 190

Gln Trp His Ala Asp Val Leu Glu Ala Val Lys Pro Leu Ile Glu Thr
            195                 200                 205

Ser Ser Ala Ser Val Val Ser Ile Gly Thr Ala Lys Ala Ile Gly Glu
210                 215                 220

Ser Glu Phe Thr Lys Gln Asn Pro Tyr Ser Ala Glu Val Leu Val Ser
225                 230                 235                 240

Gln Lys Ile Thr Gly Arg Gly Ser Asp Arg Asp Val Arg His Val Glu
            245                 250                 255

Ile Asp Leu Gly Asp Ser Gly Leu Thr Tyr Gln Ala Gly Asp Ala Leu
            260                 265                 270

Gly Val Trp Phe Ser Asn Asn Glu Ala Leu Val Glu Glu Ile Leu Thr
            275                 280                 285

Ala Leu Ser Leu Ser Gly Asp Glu Gln Val Val Glu Lys Glu Ser
290                 295                 300

Leu Thr Leu Lys Gln Ala Leu Val Asp Lys Lys Glu Leu Thr Gln Leu
305                 310                 315                 320

Tyr Pro Gly Leu Val Lys Ala Trp Ala Glu Leu Ser Gly Ser Ala Glu
            325                 330                 335

Leu Leu Ala Leu Ser Glu Asp Lys Glu Gln Val Arg His Phe Ile Leu
            340                 345                 350

Lys His Gln Phe Ala Asp Leu Val Thr Gln Tyr Pro Leu Ser Asn Asn
            355                 360                 365

Ser Val Thr Leu Asn Ala Ala Lys Leu Leu Glu Leu Leu Arg Pro Leu
370                 375                 380

Thr Pro Arg Leu Tyr Ser Ile Ala Ser Ser Gln Ser Glu Val Glu Thr
385                 390                 395                 400

Glu Val His Leu Thr Val Ala Leu Val Glu Asp Glu Arg His Gly Ala
            405                 410                 415

Ala Arg Phe Gly Gly Ala Ser His Phe Leu Ala Ser Ala Gln Glu Gly
            420                 425                 430

Thr Gln Val Lys Val Tyr Val Glu Pro Asn Lys His Phe Arg Leu Pro
            435                 440                 445

Glu Asn Pro Glu Thr Pro Val Ile Met Ile Gly Pro Gly Thr Gly Val
450                 455                 460

Ala Pro Phe Arg Ala Phe Met Gln Glu Arg Val Ala Gln Gly Ile Gln
465                 470                 475                 480

Gly Asp Ser Trp Leu Phe Phe Gly Asn Pro His Phe Glu Gln Asp Phe
            485                 490                 495

Leu Tyr Gln Thr Glu Trp Gln Gln Tyr Leu Lys Asn Gly Asp Leu Ser
            500                 505                 510

Arg Ile Asp Val Ala Phe Ser Arg Asp Gln Ala His Lys Ile Tyr Val
            515                 520                 525

Gln His Arg Ile Lys Asp Gln Gly Gln Ala Leu Trp Gln Trp Leu Gln
            530                 535                 540

Asn Gly Ala His Ile Tyr Ile Cys Gly Asp Ala Glu Arg Met Ala Lys
545                 550                 555                 560
```

```
Asp Val His Gln Ala Leu Ile Glu Val Ala Val Gly Gly Leu
            565                 570                 575

Asn Thr Glu Ala Ala Glu Ala Tyr Phe Glu Thr Leu Arg Ser Asp Lys
        580                 585                 590

Arg Tyr Gln Lys Asp Val Tyr
        595

<210> SEQ ID NO 61
<211> LENGTH: 605
<212> TYPE: PRT
<213> ORGANISM: Bacillus subtilis

<400> SEQUENCE: 61

Met Gln Leu Gln Val Met Asn Ser Pro Phe Asn Gln Glu Gln Ala Glu
  1               5                  10                  15

Leu Leu Asn Arg Leu Leu Pro Thr Leu Thr Glu Ser Gln Lys Ile Trp
             20                  25                  30

Leu Ser Gly Tyr Leu Ser Ala Gln Ser Val Ser Ala Gln Glu Ala Ala
         35                  40                  45

Gly Thr Pro Ala Ala Ala Val Ser Ala Glu Ala Pro Ala Pro Ala Val
     50                  55                  60

Ser Lys Glu Val Thr Val Leu Tyr Gly Ser Gln Thr Gly Asn Ala Gln
 65                  70                  75                  80

Gly Leu Ala Glu Asn Ala Gly Lys Gln Leu Glu Gln Ser Gly Phe Gln
                 85                  90                  95

Val Thr Val Ser Ser Met Ser Asp Phe Lys Pro Asn Gln Leu Lys Lys
            100                 105                 110

Val Thr Asn Leu Leu Ile Val Val Ser Thr His Gly Glu Gly Glu Pro
        115                 120                 125

Pro Asp Asn Ala Leu Ser Phe His Glu Phe Leu His Gly Arg Arg Ala
    130                 135                 140

Pro Lys Leu Glu Asp Leu Arg Phe Ser Val Leu Ala Leu Gly Asp Ser
145                 150                 155                 160

Ser Tyr Glu Phe Phe Cys Gln Thr Gly Lys Glu Phe Asp Gln Arg Leu
                165                 170                 175

Glu Glu Leu Gly Gly Lys Arg Ile Ser Pro Arg Val Asp Cys Asp Leu
            180                 185                 190

Asp Tyr Asp Glu Pro Ala Ala Glu Trp Leu Glu Gly Val Leu Lys Gly
        195                 200                 205

Leu Asn Glu Ala Gly Gly Gly Ser Ala Ala Pro Ala Pro Ala Ala Ala
    210                 215                 220

Ser Gln Thr Gly Glu Ser Ser Tyr Ser Arg Thr Asn Pro Phe Arg Ala
225                 230                 235                 240

Glu Val Leu Glu Asn Leu Asn Leu Asn Gly Arg Gly Ser Asn Lys Glu
                245                 250                 255

Thr Arg His Val Glu Leu Ser Leu Glu Gly Ser Gly Leu Thr Tyr Glu
            260                 265                 270

Pro Gly Asp Ser Leu Gly Val Tyr Pro Glu Asn Asp Pro Glu Leu Val
        275                 280                 285

Glu Leu Leu Leu Lys Glu Met Asn Trp Asp Pro Glu Glu Ile Val Thr
    290                 295                 300

Leu Asn Lys Gln Gly Asp Val Arg Pro Leu Lys Glu Ala Leu Ile Ser
305                 310                 315                 320

His Tyr Glu Ile Thr Val Leu Thr Lys Pro Leu Leu Glu Gln Ala Ala
                325                 330                 335
```

```
Gln Leu Thr Gly Asn Asp Glu Leu Arg Glu Leu Leu Ala Pro Gly Asn
                340                 345                 350

Glu Glu Asn Val Lys Ala Tyr Ile Glu Gly Arg Asp Leu Leu Asp Leu
            355                 360                 365

Val Arg Asp Tyr Gly Pro Phe Ser Val Ser Ala Gln Glu Phe Val Ser
        370                 375                 380

Ile Leu Arg Lys Met Pro Ala Arg Leu Tyr Ser Ile Ala Ser Ser Leu
385                 390                 395                 400

Ser Ala Asn Pro Asp Glu Val His Leu Thr Ile Gly Ala Val Arg Tyr
                405                 410                 415

Asp Ala His Gly Arg Glu Arg Lys Gly Val Cys Ser Ile Leu Cys Ala
            420                 425                 430

Glu Arg Leu Gln Pro Gly Asp Thr Leu Pro Val Tyr Val Gln His Asn
        435                 440                 445

Gln Asn Phe Lys Leu Pro Lys Asp Pro Glu Thr Pro Ile Ile Met Val
    450                 455                 460

Gly Pro Gly Thr Gly Val Ala Pro Phe Arg Ser Phe Met Gln Glu Arg
465                 470                 475                 480

Glu Glu Thr Gly Ala Glu Gly Lys Ala Trp Met Phe Phe Gly Asp Gln
                485                 490                 495

His Phe Val Thr Asp Phe Leu Tyr Gln Thr Glu Trp Gln Asn Trp Leu
            500                 505                 510

Lys Asp Gly Val Leu Thr Lys Met Asp Val Ala Phe Ser Arg Asp Thr
        515                 520                 525

Glu Glu Lys Val Tyr Val Gln His Arg Met Leu Glu His Ser Ala Glu
    530                 535                 540

Leu Phe Glu Trp Leu Gln Glu Gly Ala Ala Val Tyr Ile Cys Gly Asp
545                 550                 555                 560

Glu Lys His Met Ala His Asp Val His Asn Thr Leu Leu Glu Ile Ile
                565                 570                 575

Glu Lys Glu Gly Asn Met Ser Arg Glu Glu Ala Glu Ala Tyr Leu Ala
            580                 585                 590

Asp Met Gln Gln Gln Lys Arg Tyr Gln Arg Asp Val Tyr
        595                 600                 605

<210> SEQ ID NO 62
<211> LENGTH: 571
<212> TYPE: PRT
<213> ORGANISM: Bacillus subtilis

<400> SEQUENCE: 62

Met Val Thr Lys Ile Leu Lys Ala Pro Asp Gly Ser Pro Ser Asp Val
1               5                   10                  15

Glu Arg Ile Lys Lys Glu Ser Asp Tyr Leu Arg Gly Thr Leu Lys Glu
            20                  25                  30

Val Met Leu Asp Arg Ile Ser Ala Gly Ile Pro Asp Asp Asn Arg
        35                  40                  45

Leu Met Lys His His Gly Ser Tyr Leu Gln Asp Arg Asp Leu Arg
    50                  55                  60

Asn Glu Arg Gln Lys Gln Lys Leu Glu Pro Ala Tyr Gln Phe Met Leu
65                  70                  75                  80

Arg Val Arg Met Pro Gly Gly Val Ser Thr Pro Glu Gln Trp Leu Val
                85                  90                  95

Met Asp Asp Leu Ser Gln Lys Tyr Gly Asn Gly Thr Leu Lys Leu Thr
```

```
                100                 105                 110
Thr Arg Glu Thr Phe Gln Met His Gly Ile Leu Lys Trp Asn Met Lys
            115                 120                 125
Lys Thr Ile Gln Thr Ile His Ser Ala Leu Leu Asp Thr Ile Ala Ala
        130                 135                 140
Cys Gly Asp Val Asn Arg Asn Val Met Cys Ala Ser Asn Pro Tyr Gln
145                 150                 155                 160
Ser Glu Ile His Ser Glu Val Tyr Glu Trp Ser Lys Lys Leu Ser Asp
                165                 170                 175
Asp Leu Leu Pro Arg Thr Arg Ala Tyr His Glu Ile Trp Leu Asp Glu
            180                 185                 190
Glu Arg Val Ala Gly Thr Pro Glu Glu Val Glu Pro Met Tyr Gly
        195                 200                 205
Pro Leu Tyr Leu Pro Arg Lys Phe Lys Ile Gly Ile Ala Val Pro Pro
        210                 215                 220
Ser Asn Asp Ile Asp Val Phe Ser Gln Asp Leu Gly Phe Ile Ala Ile
225                 230                 235                 240
Val Glu Asp Gly Lys Leu Ile Gly Phe Asn Val Ala Ile Gly Gly Gly
                245                 250                 255
Met Gly Met Thr His Gly Asp Thr Ala Thr Tyr Pro Gln Leu Ala Lys
            260                 265                 270
Val Ile Gly Phe Cys Arg Pro Glu Gln Met Tyr Asp Val Ala Glu Lys
            275                 280                 285
Thr Ile Thr Ile Gln Arg Asp Tyr Gly Asn Arg Ser Val Arg Lys Asn
        290                 295                 300
Ala Arg Phe Lys Tyr Thr Val Asp Arg Leu Gly Leu Glu Asn Val Lys
305                 310                 315                 320
Glu Glu Leu Glu Asn Arg Leu Gly Trp Ser Leu Glu Glu Ala Lys Pro
                325                 330                 335
Tyr His Phe Asp His Asn Gly Asp Arg Tyr Gly Trp Val Glu Gly Ile
                340                 345                 350
Glu Asp Lys Trp His Phe Thr Leu Phe Val Glu Gly Gly Arg Ile Thr
            355                 360                 365
Asp Tyr Asp Asp Tyr Lys Leu Met Thr Gly Leu Arg Glu Ile Ala Lys
        370                 375                 380
Val His Thr Gly Glu Phe Arg Leu Thr Ala Asn Gln Asn Leu Met Ile
385                 390                 395                 400
Ala Asn Val Ser Ser Asp Lys Lys Glu Glu Ile Ser Ala Leu Ile Glu
                405                 410                 415
Gln Tyr Gly Leu Thr Asp Gly Lys His Tyr Ser Ala Leu Arg Arg Ser
            420                 425                 430
Ser Met Ala Cys Val Ala Leu Pro Thr Cys Gly Leu Ala Met Ala Glu
            435                 440                 445
Ala Glu Arg Tyr Leu Pro Thr Leu Leu Asp Lys Ile Glu Glu Ile Ile
        450                 455                 460
Asp Glu Asn Gly Leu Arg Asp Gln Glu Ile Thr Ile Arg Met Thr Gly
465                 470                 475                 480
Cys Pro Asn Gly Cys Ala Arg His Ala Leu Gly Glu Ile Gly Phe Ile
                485                 490                 495
Gly Lys Ala Pro Gly Lys Tyr Asn Met Tyr Leu Gly Ala Ala Phe Asp
            500                 505                 510
Gly Ser Arg Leu Ser Lys Met Tyr Arg Glu Asn Ile Gly Glu Ala Asp
            515                 520                 525
```

```
Ile Leu Ser Glu Leu Arg Ile Leu Ser Arg Tyr Ala Lys Glu Arg
    530                 535                 540

Glu Glu Gly Glu His Phe Gly Asp Phe Val Ile Arg Ala Gly Ile Ile
545                 550                 555                 560

Lys Ala Thr Thr Asp Gly Thr Asn Phe His Asp
                565                 570
```

<210> SEQ ID NO 63
<211> LENGTH: 588
<212> TYPE: PRT
<213> ORGANISM: Acidithiobacillus ferrooxidans

<400> SEQUENCE: 63

```
Met Glu Leu Ile Arg Gln Ser Asp Phe Leu Leu Asp Pro Arg Lys Gln
1               5                   10                  15

Glu Asp Leu Arg Arg Phe Ala Glu Gly Met Thr Arg Glu Gln Leu Leu
                20                  25                  30

Trp Ser Ser Gly Tyr Leu Thr Gly Phe Gly Glu Ser Ala Pro Ala Ser
            35                  40                  45

Lys Ile Gln Glu Asp Ile Gly Glu Lys Ile Thr Ile Leu Phe Gly Thr
 50                  55                  60

Glu Thr Gly Asn Ala Lys Arg Leu Ala Glu Leu Leu Ala Ala Arg Ala
65                  70                  75                  80

Gln Ala Met Gly Val Gln Thr Ser Ile Gln Asp Met Leu Thr Tyr Gly
                85                  90                  95

Arg Ala Gln Leu Arg Arg Asp Arg Val Ile Val Leu Ile Val Ser Thr
            100                 105                 110

His Gly Asp Gly Glu Pro Pro Asp Ser Ala Arg Met Leu Leu Ala Ser
        115                 120                 125

Leu Thr Asp Gly Pro Val Pro Asp Leu His Gly Ser Arg Phe Ala Ile
130                 135                 140

Leu Ala Leu Gly Asp Ala Ser Tyr Pro Lys Phe Cys Gln Ala Gly Lys
145                 150                 155                 160

Ala Phe Asp Ile Ala Leu Ala Ser Ala Gly Ala Glu Arg Leu Leu Pro
                165                 170                 175

Arg Val Asp Cys Asp Val Asp Tyr Glu Arg Asp Ala Met Tyr Trp Met
            180                 185                 190

Glu Gln Val Leu Gly Ala Leu Thr Thr Gly Lys Ser Ser Pro Ala Val
        195                 200                 205

Pro Phe Pro Ala Pro Val Pro Lys Gln Gly Tyr Ser Ser His Ala Thr
210                 215                 220

Phe Pro Ala Val Leu Leu Gly Lys Val Asn Leu Ser Gly Arg Gly Ser
225                 230                 235                 240

Asp Arg Glu Val Trp His Leu Glu Leu Asp Leu Asp Gly Ser Gly Leu
                245                 250                 255

His Tyr Ala Pro Gly Asp Ile Val Ser Val Ala Pro Ser Asn Pro Pro
            260                 265                 270

Gln Leu Val Glu Glu Leu Leu Asp Arg Leu Glu Leu Asp His Lys Ala
        275                 280                 285

Ser Val Arg Thr Arg Gln Gly Glu Met Pro Leu Val Glu Ala Leu Ala
290                 295                 300

Ala His Tyr Glu Ile Thr Arg Ile Thr Trp Pro Phe Leu Glu Arg Tyr
305                 310                 315                 320

Ala Arg Leu Ser Asp Ala Lys Ala Leu Gln Ser Ala Ile Ala Gly Arg
```

```
                    325                 330                 335
Asp Val Asn Gly Leu Asp Thr Trp Thr Asp Gly Arg Glu Val Ile Asp
                340                 345                 350

Ile Val Gly Gln Tyr Pro Val Lys Gly Leu Ser Ala Gln Ser Phe Ala
                355                 360                 365

Asp Cys Leu Arg Pro Leu Pro Pro Arg Arg Tyr Ser Ile Ala Ser Ser
            370                 375                 380

Leu Leu Ala Val Pro Gly Glu Val His Leu Thr Val Ala Ala Ile Arg
385                 390                 395                 400

Tyr Ser Ser His Gly Arg Glu Arg Leu Gly Val Ala Ser Thr Phe Leu
                405                 410                 415

Ala Asp Arg Val Ala Ile Gly Arg Pro Val Pro Ile Phe Ile Glu Pro
                420                 425                 430

Asn Ala Glu Phe Arg Leu Pro Glu Asp Ser Gly Gln Ala Met Ile Met
                435                 440                 445

Ile Gly Ala Gly Thr Gly Val Ala Pro Phe Arg Ser Phe Leu Gln Glu
                450                 455                 460

Arg Glu Ala Leu Gly Ala Ala Gly Asn Asn Trp Leu Phe Phe Gly Asp
465                 470                 475                 480

Arg His Phe Ser Thr Asp Phe Leu Tyr Gln Arg Glu Trp Leu Arg Trp
                    485                 490                 495

Leu Arg Asp Gly Arg Leu Thr Arg Leu Asp Val Ala Phe Ser Arg Asp
                500                 505                 510

Gln Glu Arg Lys Ile Tyr Val Gln Asp Arg Leu Arg Glu Arg Ala Gly
                515                 520                 525

Asp Val Phe Ala Trp Leu Glu Glu Gly Ala Ala Val Tyr Val Cys Gly
                530                 535                 540

Ala Glu Ala Met Gly Arg Ala Val His Gln Ser Leu Val Asp Ile Val
545                 550                 555                 560

Gln Ser Ala Gly Arg Thr Gln Val Gln Ala Glu Glu Tyr Ile Leu Glu
                565                 570                 575

Leu Lys Gln Thr Gly Arg Tyr His Arg Asp Val Tyr
                580                 585

<210> SEQ ID NO 64
<211> LENGTH: 563
<212> TYPE: PRT
<213> ORGANISM: Acidithiobacillus ferrooxidans

<400> SEQUENCE: 64

Met Ser Ile Asn Asp Lys Ala Leu Ser Asp Val Glu Arg Ile Lys Ala
1               5                   10                  15

Glu Ser Gln Gly Leu Arg Gly Thr Leu Arg Glu Ser Leu His Asn Pro
                20                  25                  30

Val Thr Gly Ala Leu Ala Glu Asp Val Gln Val Ile Lys Phe His
                35                  40                  45

Gly Ile Tyr Gln Gln Asp Tyr Arg Asp Leu Arg Ala Glu Arg His Gln
            50                  55                  60

Gln Lys Leu Glu Pro Leu Tyr Gln Phe Met Ala Arg Leu Arg Leu Pro
65              70                  75                  80

Gly Gly Val Leu Ser Gly Ala Gln Trp Leu Ala Leu Gly Asp Ile Ala
                85                  90                  95

Arg Thr Tyr Gly Asn Ala Ser Leu Arg Ile Thr Ser Arg Gln Ser Ile
                100                 105                 110
```

```
Gln Phe His Gly Leu Leu Lys Pro His Leu Arg Pro Val Leu Gln Ala
            115                 120                 125

Leu Asp Arg Ala Leu Leu Asp Thr Val Ser Ala Cys Gly Asp Val Asn
130                 135                 140

Arg Asn Val Ile Ala Ser Ser Ala Pro Gln Ile Ser Ala Phe His Ala
145                 150                 155                 160

Glu Ala Tyr Gly Trp Ala Gln Lys Ile Ala Glu His Leu Leu Pro Gln
                165                 170                 175

Ser His Ala Tyr His Glu Ile Trp Leu Gly Gln Gln Ile Thr Ala
            180                 185                 190

Pro Glu Glu Asp Leu Leu Tyr Gly Ser Thr Tyr Leu Pro Arg Lys Phe
            195                 200                 205

Lys Ile Ala Ile Ala Val Pro Pro His Asn Asp Val Asp Val Leu Thr
210                 215                 220

Gln Asp Leu Gly Phe Ile Ala Ile His Glu Glu Gly Arg Leu Ala Gly
225                 230                 235                 240

Phe Asn Val Cys Val Gly Gly Leu Gly Arg Ser His Asn Lys Pro
                245                 250                 255

Asp Thr Tyr Ser Arg Leu Ala Asp Val Cys Gly Phe Cys Ala Pro Gly
            260                 265                 270

Gln Val Leu Ala Ile Ala Glu Ala Val Leu Ile Thr Gln Arg Asp His
        275                 280                 285

Gly Asp Arg Ser Asn Arg Ser His Ala Arg Leu Lys Tyr Thr Val Asp
    290                 295                 300

Arg Met Gly Leu Asp Arg Phe Met Glu Val Gln Gln Arg Thr Gly
305                 310                 315                 320

Phe Ser Leu Ala Pro Pro Arg Pro Phe His Phe Glu Thr Ser Gly Asp
                325                 330                 335

Arg Phe Gly Trp Leu Glu Asn Asp Asp Gly Thr Ala Cys Leu Thr Leu
            340                 345                 350

Phe Ile Pro Gly Gly Arg Val Ala Asp Gly Asp Ile Pro Leu Leu Ser
        355                 360                 365

Gly Leu Asp Ala Leu Ala Arg Leu His His Gly Glu Ile Arg Leu Thr
370                 375                 380

Cys Asn Gln Asn Leu Leu Ile Ala Gly Ile Ser Pro Ala Glu Arg Pro
385                 390                 395                 400

Val Val Glu Thr Val Leu Ala Glu Tyr Gly Leu Asn Arg Leu Leu Asn
                405                 410                 415

Leu Ala Pro Val Arg Ala His Ala Met Ala Cys Val Ala Leu Pro Thr
            420                 425                 430

Cys Pro Leu Ala Met Ala Glu Ala Arg Tyr Leu Pro Val Phe Leu
435                 440                 445

Asp Arg Ile Glu Ala Leu Leu Ala Glu Val Gly Leu Glu Gly Glu Ala
    450                 455                 460

Leu Thr Val Arg Met Thr Gly Cys Pro Asn Gly Cys Ala Arg Pro Tyr
465                 470                 475                 480

Leu Ala Glu Ile Gly Leu Val Gly Lys Ala Pro Gly Leu Tyr Asp Leu
                485                 490                 495

Tyr Leu Gly Gly Asp Arg Thr Gly Met Arg Leu Asn Ala Leu Tyr Arg
            500                 505                 510

Glu Ala Leu Asp Glu Glu Ala Leu Leu Asp Ala Leu Arg Pro Leu Leu
        515                 520                 525

Lys Arg Phe Ala Gly Gln Arg Trp Ala Gly Glu Thr Phe Gly Asp Phe
```

```
                530                 535                 540
Val Arg Arg Gln Asp Leu Leu Pro Pro Asp Pro Gly Leu Pro His Thr
545                 550                 555                 560

Gly Arg Arg

<210> SEQ ID NO 65
<211> LENGTH: 679
<212> TYPE: PRT
<213> ORGANISM: Cyanidioschyzon merolae

<400> SEQUENCE: 65

Met Met Phe Val Thr Tyr Ala Lys Pro Leu Val Gly Ala Arg Arg Gly
 1               5                  10                  15

Leu Ala Pro Thr Gly Ser Ala Ala Pro Gly Val Tyr Pro Leu Thr Glu
             20                  25                  30

Val Leu Leu Arg Asp Arg Leu Arg Gln Arg Gln Cys Arg Thr Ala
             35                  40                  45

Arg Arg Asn Ile Ile Ala Asn Leu Ser Ser Glu Gln Ser Arg Lys Lys
 50                  55                  60

His Thr Val Val Pro Ile Thr Thr Arg Lys His Ile Glu Glu Ala Ile
65                   70                  75                  80

Arg Asp Gly Thr Leu Asp Gln Leu Lys Leu Asn Pro Tyr Glu Leu Pro
                 85                  90                  95

Lys Leu Asn Ser Asp Tyr Leu Arg His Pro Leu Met Glu Glu Leu Gly
            100                 105                 110

Asn Asp Gln Ile Phe Ile Ser Asp Cys Ile Gly Leu Ile Lys Phe
        115                 120                 125

His Gly Gly Tyr Leu Gln Asp Asn Arg Asp Gln Arg Val Arg Gly Glu
130                 135                 140

Leu Lys Lys Tyr Gln Phe Met Leu Arg Leu Lys Met Pro Ala Gly Glu
145                 150                 155                 160

Cys Pro Pro Ser Leu Tyr Thr Thr Leu Asp Asp Ile Ser Glu Thr Tyr
                165                 170                 175

Gly Asn Lys Thr Leu Arg Leu Thr Thr Arg Ser Ser Phe Gln Ile His
            180                 185                 190

Gly Ile His Lys Ser Asn Leu Lys Thr Val Val Gln Ser Ile Val Arg
        195                 200                 205

Ala Gly Gly Leu Tyr Gly Ala Ser Gly Asp Cys Ser Arg Asn Val
    210                 215                 220

Ile Ala Pro Pro Ala Pro Phe Val Asp Ala Ala Tyr Ala Gln Ala Arg
225                 230                 235                 240

His Val Ala Arg Met Val Ala Glu Leu Phe Ala Ile Gln Ser His Ala
                245                 250                 255

Phe Ala Asp Leu Trp Leu Asp Gly Glu Leu Ala Ala Ser Ile Glu Tyr
            260                 265                 270

Trp Lys Lys Glu Leu Asp Met Asp Glu Val Arg Arg Leu Met Thr Glu
        275                 280                 285

Asp Asn Gly Arg Gly Gln Val Leu Gln Asp Ser Val Glu Pro Leu Tyr
    290                 295                 300

Gly Lys Leu Tyr Leu Pro Arg Lys Phe Lys Gly Val Thr Val Pro
305                 310                 315                 320

Gly Asp Asn Ser Ile Asp Ile Tyr Thr His Asp Ile Gly Ile Val Val
                325                 330                 335

Phe Cys Asp Ala Gln Gly Gln Leu Glu Gly Ala Asn Ile Leu Val Gly
```

```
            340                 345                 350
Gly Gly Met Gly Arg Thr His Asn Lys Glu Thr Phe Ala Arg Ala
        355                 360                 365

Ala Asp Pro Leu Gly Tyr Val Pro Ala Ala Leu Tyr Asp Thr Leu
    370                 375                 380

Lys Ala Ile Leu Ala Ala Gln Arg Asp His Gly Asn Arg Ala Val Arg
385                 390                 395                 400

Thr Asn Ala Arg Met Lys Tyr Leu Val His Arg Leu Gly Ile Asp Arg
                405                 410                 415

Phe Arg Glu Leu Val Lys Ser Tyr Met Val Gly Gly Ser Ala Leu
            420                 425                 430

Glu Ser Ile Arg Ser Met Pro Pro Trp Thr Phe Gln Asp Tyr Leu Gly
                435                 440                 445

Trp Arg Glu Gln Gly Asp Gly Arg Trp Phe Phe Gly Leu Tyr Val Gln
        450                 455                 460

Asn Gly Arg Ile Lys Asp Glu Leu Lys Lys Ala Leu Arg Ala Leu Thr
465                 470                 475                 480

Asp Arg Phe Asn Phe Pro Leu Val Cys Thr Pro Gln Gln Asn Leu Leu
                485                 490                 495

Ile Thr Gln Val Pro Ala Thr Ala Arg Pro Asp Val Glu Thr Leu Leu
            500                 505                 510

Ala Ser Phe Gly Val Glu Thr Ala Ala Ser Ala Leu Asp Pro Leu Met
        515                 520                 525

Arg Asp Ala Met Ala Cys Pro Ala Leu Pro Leu Cys Pro Pro Ala Ile
    530                 535                 540

Thr Glu Ala Glu Arg Val Met Pro Arg Tyr Val Gln Arg Val Arg Glu
545                 550                 555                 560

Leu Leu Ser Lys Val Gly Ile Ser Pro His Ala Ser Phe Val Met Arg
                565                 570                 575

Met Thr Gly Cys Pro Asn Gly Cys Thr Arg Pro Tyr Met Ala Glu Leu
            580                 585                 590

Gly Phe Val Gly Ser Gly Pro Asn Cys Thr Tyr Gln Val Trp Leu Gly
        595                 600                 605

Gly Ser Pro Met Gln Thr Arg Leu Ala Trp Pro Tyr Ile Asp Arg Val
    610                 615                 620

Thr Asp Asp Gln Val Glu Arg Val Leu Glu Pro Val Phe Val Phe Trp
625                 630                 635                 640

Lys Ser Ala Arg Glu Pro Asp Glu Ser Phe Gly Asp Phe Cys Asp Arg
                645                 650                 655

Val Gly Lys Ala Gln Leu Glu Ala Tyr Ala Gln Arg Tyr Trp Asp Gly
            660                 665                 670

Val Pro Ala Ala Pro Val Ser
        675

<210> SEQ ID NO 66
<211> LENGTH: 662
<212> TYPE: PRT
<213> ORGANISM: Oscillatoria nigro-viridis

<400> SEQUENCE: 66

Met Ile Thr Ser Ser Thr Ser Thr Pro Val Ala Arg Lys Pro Ser Lys
1               5                   10                  15

Ser Glu Gly Leu Lys Glu Arg Ser Asn Tyr Leu Arg Glu Pro Val Ala
            20                  25                  30
```

```
Thr Glu Leu Leu Gln Glu Thr Thr His Phe Thr Glu Asp Gly Ile Gln
         35                  40                  45

Ile Leu Lys Phe His Gly Ser Tyr Gln Gln Asp Asn Arg Asp Asn Arg
 50                  55                  60

Val Lys Gly Gln Glu Lys Asp Tyr Gln Phe Met Leu Arg Thr Arg Asn
 65                  70                  75                  80

Pro Gly Gly Phe Thr Pro Pro Gln Leu Tyr Leu Ala Leu Asp Lys Leu
                 85                  90                  95

Ser Glu Glu Tyr Gly Asn His Thr Ile Arg Val Thr Thr Arg Gln Gly
                100                 105                 110

Phe Gln Leu His Gly Val Leu Lys Lys Asn Leu Lys Ala Val Phe Ser
             115                 120                 125

Ser Ile Ile Lys Asn Met Gly Ser Thr Leu Gly Ala Cys Gly Asp Leu
 130                 135                 140

Asn Arg Asn Val Met Ala Pro Pro Ala Pro Tyr Lys Asn Arg Pro Glu
 145                 150                 155                 160

Tyr Lys Tyr Ala Leu Gln Tyr Ala Asn Asn Val Ala Asp Leu Leu Thr
                 165                 170                 175

Pro Gln Thr Gly Ala Tyr Tyr Glu Ile Trp Leu Asp Gly Glu Lys Ala
             180                 185                 190

Ile Ser Ala Glu Glu Asp Pro Ala Val Lys Ala Ala Arg Gln Lys Asn
 195                 200                 205

Gly Asn Gly Thr Ile Phe Ser Asp Lys Glu Glu Pro Ile Tyr Gly Ser
 210                 215                 220

His Tyr Met Pro Arg Lys Phe Lys Cys Ser Val Thr Val Pro Gly Asp
225                 230                 235                 240

Asn Ser Ile Asp Leu Tyr Ser Gln Asp Leu Ser Leu Val Val Ile Thr
                 245                 250                 255

Asn Lys Ala Gly Glu Leu Gln Gly Phe Asp Val Phe Ala Gly Gly Gly
                 260                 265                 270

Leu Gly Arg Thr His Asn Lys Glu Glu Thr Phe Ala Arg Val Ala Asp
             275                 280                 285

Glu Ile Cys Tyr Val Ala Lys Asp Asp Val Tyr Asp Leu Val Lys Ala
 290                 295                 300

Ile Val Ala Thr Gln Arg Asp Tyr Gly Asp Arg Thr Asp Arg Arg His
305                 310                 315                 320

Ala Arg Leu Lys Tyr Leu Ile Asn Asp Lys Gly Val Gln Trp Phe Arg
                 325                 330                 335

Glu Lys Val Ala Glu Tyr Phe Gly Lys Pro Leu Glu Ala Phe Lys Pro
             340                 345                 350

Leu Pro Glu Trp Lys Tyr Phe Asp Phe Leu Gly Trp His Asp Gln Gly
             355                 360                 365

Asp Gly Lys Leu Phe Val Gly Ile Ser Val Asp Asn Gly Arg Ile Lys
 370                 375                 380

Asp Glu Gly Ser Phe Gln Leu Lys Thr Ala Leu Arg Glu Ile Val Gln
385                 390                 395                 400

Lys Tyr Asn Leu Pro Val Leu Ala Thr Pro His Gln Asn Val Leu Ile
                 405                 410                 415

Tyr Asp Ile Ser Pro Asp Leu Lys Gln Glu Ile Gln Ile Leu Asp
             420                 425                 430

Arg Cys Gly Ile Gln Arg Glu Thr Ala Ile Asp Pro Leu Val Arg Tyr
             435                 440                 445

Ala Met Ala Cys Pro Ala Met Pro Thr Cys Gly Leu Ala Ile Thr Glu
```

```
                        450                 455                 460
Ser Glu Arg Val Ile Pro Ser Ile Leu Glu Arg Ile Arg Ala Leu Leu
465                 470                 475                 480

Thr Lys Val Gly Leu Glu Asp Glu His Leu Val Val Arg Met Thr Gly
                485                 490                 495

Cys Pro Asn Gly Cys Ala Arg Pro Tyr Met Ala Glu Leu Gly Phe Val
            500                 505                 510

Gly Ser Ser Pro Glu Ser Tyr Gln Ile Trp Leu Gly Gly Ser Pro Asp
        515                 520                 525

Gln Thr Arg Leu Ala Lys Pro Ile Glu Glu Lys Leu His Val Lys Asn
    530                 535                 540

Phe Glu Ala Phe Leu Glu Pro Ile Phe Val Tyr Phe Lys Gln Lys Arg
545                 550                 555                 560

Gln Leu Ser Glu Ser Phe Gly Asn Phe Cys Asp Arg Val Gly Leu Glu
                565                 570                 575

Ser Ile Arg Gln Phe Val Thr Asn Tyr Gln Ser Ala Asp Ser Met Thr
            580                 585                 590

Thr Glu Ile Asn Glu Leu Glu Val Thr Ser Ser Asn Gly Glu Glu Asn
        595                 600                 605

Glu Thr Ala Thr Ala Gly Gly Lys Val Arg Arg Ile Ser Val
    610                 615                 620

Arg Asp Glu Ile Tyr Asn Glu Leu Lys Glu Ala Ala Arg Gln Gly
625                 630                 635                 640

Lys Pro Ile Thr Gln Leu Ala Thr Glu Ala Ile Ser Thr Tyr Leu Lys
                645                 650                 655

Lys Ile Lys Glu Glu Ala
            660

<210> SEQ ID NO 67
<211> LENGTH: 669
<212> TYPE: PRT
<213> ORGANISM: Pseudomonas putida

<400> SEQUENCE: 67

Met Asn Asp Cys His Leu Ile Cys Ala Asn Arg Leu Asp Asp Gly Ala
1               5                   10                  15

Val Val Trp Leu Asp Ala Gly His Glu Trp Val Glu Thr Leu Gln Gln
                20                  25                  30

Ala Gly Thr Phe Asp Ala Gln Ala Leu Val Ser Ala Thr Leu Ala Ala
            35                  40                  45

Glu Ala Ala Val Leu Ala Asn Gln Val Val Ala Pro Thr Pro Cys Glu
50                  55                  60

Ala Trp Leu Val Asp Gly Arg Pro Glu Pro Lys Ser Leu Arg Glu Arg
65                  70                  75                  80

Leu Arg Ala Arg Gly Pro Ser Val Arg Ser Asp Leu Gly Lys Gln Ala
                85                  90                  95

Ala Gly Thr Pro Pro Ser Ser Ile Ala Arg Met Arg Pro Val Leu Pro
            100                 105                 110

Val Glu Ala Gly Gln Ala Gly Val Tyr Arg Tyr Asp Arg Phe Glu Arg
        115                 120                 125

Glu Phe Leu Lys Asp Arg Ala Arg Gln Phe Glu Gln Gln Val Ala Arg
    130                 135                 140

Arg Leu Ser Gly Glu Leu Asp Glu Glu Ala Phe Lys Val Tyr Arg Leu
145                 150                 155                 160
```

```
Met Asn Gly Leu Tyr Leu Gln Leu His Gly Tyr Met Leu Arg Val Ala
            165                 170                 175
Ile Pro Tyr Gly Thr Leu Ser Ala Leu Gln Leu Arg Gln Leu Ala Tyr
            180                 185                 190
Val Ala His Thr Tyr Asp Lys Gly Tyr Gly His Leu Thr Thr Arg Gln
            195                 200                 205
Asn Ile Gln Phe Asn Trp Pro Arg Leu Ala Asp Thr Pro Glu Ile Leu
            210                 215                 220
Ser Val Leu Ala Asp Ala Asp Leu His Cys Ile Gln Thr Ser Gly Asn
225                 230                 235                 240
Cys Ile Arg Asn Val Thr Thr Asp His Phe Ala Gly Ala Ala Glu Asp
            245                 250                 255
Glu Val Leu Asp Pro Arg Val His Ala Glu Ile Leu Arg Gln Trp Ser
            260                 265                 270
Thr Glu His Pro Glu Phe Thr Tyr Leu Pro Arg Lys Phe Lys Ile Ala
            275                 280                 285
Ile Thr Gly Ser Pro Lys Asp Arg Ala Ala Val Arg Phe His Asp Ile
            290                 295                 300
Gly Ile Leu Ala Gln Arg Asn Ala Gln Gly Glu Val Gly Phe Gln Val
305                 310                 315                 320
Tyr Ala Gly Gly Gly Leu Gly Arg Thr Pro Ile Val Gly Thr Arg Val
            325                 330                 335
Arg Glu Trp Leu Pro Glu Arg Glu Leu Leu Arg Tyr Val Glu Ala Ile
            340                 345                 350
Leu Arg Val Tyr Asn Ala Leu Gly Arg Arg Asp Asn Leu Tyr Lys Ala
            355                 360                 365
Arg Ile Lys Ile Leu Val Arg Glu Leu Lys Pro Gly Arg Phe Ile Glu
            370                 375                 380
Met Ile Glu Glu Glu Phe Ala Ser Leu Pro Ala Asp His Gln Tyr Leu
385                 390                 395                 400
Glu Pro Ala Ile Val Gln Gly Ile His Ala Arg Phe Val Gln Pro Ala
            405                 410                 415
Phe Glu Ala Leu Pro Gly Leu Cys Asp Ser Phe Leu Arg Ala Arg Ala
            420                 425                 430
Asp Asp Asn Ala Phe Ala Ser Trp Val Arg Thr Asn Thr His Pro His
            435                 440                 445
Lys Lys Arg Gly Tyr Ile Cys Ala Val Ile Ser Leu Lys Pro Pro Gly
            450                 455                 460
Gly Ile Pro Gly Asp Ile Ser Ala Glu Glu Met Leu Ala Leu Ala Asp
465                 470                 475                 480
Leu Ala Glu Ala Tyr Ser Leu Asn Glu Ile Arg Val Ser His Glu Gln
            485                 490                 495
Asn Val Val Leu Pro His Ile Arg Leu Val Asp Leu Tyr Ser Val Trp
            500                 505                 510
Gln Ala Leu Arg Gln Ala Gly Leu Ala Thr Ser Asn Ile Gly Leu Leu
            515                 520                 525
Ser Asp Thr Ile Ala Cys Pro Gly Met Asp Tyr Cys Ser Leu Ala Thr
            530                 535                 540
Ala Arg Ser Val Pro Val Ala Gln Arg Ile Ala Gln Arg Phe Asp Ala
545                 550                 555                 560
Ala Arg Gln Gln Asp Ile Gly Glu Leu Lys Leu Asn Val Ser Gly Cys
            565                 570                 575
Ile Asn Ala Cys Ala His His Val Ala His Ile Gly Ile Leu Gly
```

```
                    580                 585                 590
Leu Asp Lys Ala Gly His Glu Asn Tyr Gln Ile Thr Leu Gly Gly Ser
                595                 600                 605

Ala Glu Glu Asp Ala Ala Val Gly Thr Ile Leu Gly Arg Ser Val Pro
            610                 615                 620

Phe Glu Glu Val Pro Asp Ile Val Glu Ala Ile Val Ala Ile Tyr Leu
625                 630                 635                 640

Gln Leu Arg Glu Asp Asp Glu Arg Phe Leu Asp Thr Tyr Arg Arg Val
                645                 650                 655

Gly Ile Glu Pro Phe Lys Glu Val Leu Arg Asp Ala Arg
                660                 665

<210> SEQ ID NO 68
<211> LENGTH: 637
<212> TYPE: PRT
<213> ORGANISM: Anabaena cylindrica

<400> SEQUENCE: 68

Met Val Asn Ser Ala Pro Ser Pro Val Ser Asn Arg Lys Pro Ser Lys
1               5                   10                  15

Val Glu Gly Ile Lys Glu Asn Ser Asn Phe Leu Arg Glu Pro Val Ala
            20                  25                  30

Thr Glu Ile Leu Gln Asp Thr Thr His Phe Ser Glu Asp Ala Ile Gln
        35                  40                  45

Ile Leu Lys Phe His Gly Ser Tyr Gln Gln Asp Asn Arg Asp Asn Arg
    50                  55                  60

Ala Lys Gly Gln Glu Lys Asp Tyr Gln Phe Met Leu Arg Thr Lys Asn
65                  70                  75                  80

Pro Gly Gly Leu Val Pro Pro Gln Leu Tyr Leu Ala Leu Asp Lys Leu
                85                  90                  95

Ala Asp Glu Tyr Gly Asn His Thr Leu Arg Ala Thr Thr Arg Gln Gly
            100                 105                 110

Phe Gln Val His Gly Ile Leu Lys Lys Asn Leu Lys Ser Ala Ile Ala
        115                 120                 125

Thr Ile Val Gln Asn Leu Gly Ser Thr Leu Gly Ala Cys Gly Asp Ile
    130                 135                 140

Asn Arg Asn Val Met Ala Pro Ala Pro Leu Lys Asn Arg Pro Glu
145                 150                 155                 160

Tyr Glu Tyr Ala Trp Glu Tyr Ala Gln Asn Ile Ala Asp Leu Leu Ser
                165                 170                 175

Pro Gln Thr Gly Ala Tyr Tyr Glu Ile Trp Leu Asp Gly Glu Lys Ala
            180                 185                 190

Ile Ser Val Glu Glu His Pro Asp Val Lys Ala Ala Arg Gln Ser Asn
        195                 200                 205

Gly Asn Gly Thr Ile Val His Asp Ser Val Glu Pro Ile Tyr Gly Thr
    210                 215                 220

His Tyr Met Pro Arg Lys Phe Lys Ile Cys Val Thr Val Pro Gly Asp
225                 230                 235                 240

Asn Ser Val Asp Leu Tyr Ser Gln Asp Leu Thr Leu Val Ile Thr
                245                 250                 255

Asn Lys Lys Gly Glu Leu Gln Gly Phe Asp Val Phe Ala Gly Gly Gly
            260                 265                 270

Leu Gly Arg Thr His Asn Lys Glu Glu Thr Phe Ala Arg Val Ala Asp
        275                 280                 285
```

```
Pro Ile Cys Tyr Val Gly Lys Asp Asp Val Tyr Asn Phe Val Lys Ala
    290                 295                 300

Val Val Ala Thr Gln Arg Asp Tyr Gly Asp Arg Thr Asp Arg Arg His
305                 310                 315                 320

Ala Arg Leu Lys Tyr Leu Ile Asn Asp Trp Gly Val Asp Lys Phe Arg
                325                 330                 335

Thr Gln Val Glu Glu Tyr Phe Gly Lys Ser Val Glu Pro Phe Lys Pro
            340                 345                 350

Leu Pro Lys Phe Lys Tyr Gln Asp Phe Leu Gly Trp Asn Glu Gln Gly
        355                 360                 365

Asp Gly Lys Leu Phe Leu Gly Ile Ser Ile Glu Asn Gly Arg Val Lys
    370                 375                 380

Asp Glu Gly Ala Phe Gln Leu Lys Thr Ala Leu Arg Glu Ile Val Glu
385                 390                 395                 400

Lys Phe Asn Leu Pro Ile Arg Leu Thr Gly Asn Gln Asn Leu Leu Phe
                405                 410                 415

Tyr Glu Ile Asp Pro Glu Asp Lys Ala Ala Ile Gln Glu Ile Leu Asp
            420                 425                 430

Arg Cys Gly Val Val Ala Asp Pro Ser Gln Ile Ala Ala Leu Thr Arg
        435                 440                 445

Phe Ala Met Ala Cys Pro Ala Leu Pro Thr Cys Gly Leu Ala Ile Thr
    450                 455                 460

Glu Ser Glu Arg Ala Ile Pro Gly Ile Leu Asp Arg Ile Arg Ala Leu
465                 470                 475                 480

Leu Asp Lys Leu Gly Leu Gln Lys Asp His Phe Val Val Arg Met Thr
                485                 490                 495

Gly Cys Pro Asn Gly Cys Ala Arg Pro Tyr Met Ala Glu Leu Gly Phe
            500                 505                 510

Val Gly Ser Ala Pro Glu Ser Tyr Gln Val Trp Leu Gly Gly Ser Pro
        515                 520                 525

Asp Gln Thr Arg Leu Ala Gln Pro Ile Ile Glu Lys Leu His Asp Asn
    530                 535                 540

Asp Ile Glu Ser Phe Leu Glu Pro Ile Phe Ile Tyr Phe Lys Lys Phe
545                 550                 555                 560

Arg Lys Gly Lys Glu Ser Phe Gly Asp Phe Cys Asp Arg Met Gly Phe
                565                 570                 575

Asp Ala Ile Arg Glu Phe Ser Ala Thr Tyr Thr Pro Gly Glu Pro Thr
            580                 585                 590

Ser Ser Gly Lys Ser Arg His Arg Val Ser Leu Arg Asp Asp Val Tyr
        595                 600                 605

Leu His Leu Lys Glu Thr Ala Glu Lys Gln Asn Arg Pro Met Thr Asp
    610                 615                 620

Leu Val His Asp Ala Leu Asp Lys Tyr Phe Gln Asn Leu
625                 630                 635

<210> SEQ ID NO 69
<211> LENGTH: 664
<212> TYPE: PRT
<213> ORGANISM: Halothece sp.

<400> SEQUENCE: 69

Met Met Glu Leu Ile Thr Val Ile Pro Ser Glu Leu Ser Val Ile Gln
1               5                   10                  15

Lys Cys Ala Ala Ile Glu Gln Lys Ala Val Met Val Ala Ser Lys Ala
            20                  25                  30
```

```
Lys Lys Ala Ser Lys Pro Ser Lys Leu Glu Gly Ile Lys Glu Asn Ser
            35                  40                  45
Asn Phe Leu Arg Glu Pro Leu Ala Thr Glu Leu Leu Glu Asp Thr Thr
 50                  55                  60
His Phe Ser Gln Asp Ala Val Gln Ile Leu Lys Phe His Gly Ser Tyr
 65                  70                  75                  80
Gln Gln Asp Asn Arg Asp Asn Arg Gln Lys Gly Gln Glu Lys Asp Tyr
                 85                  90                  95
Gln Phe Met Leu Arg Thr Arg Asn Pro Gly Gly Phe Ile Pro Pro Glu
            100                 105                 110
Leu Tyr Leu Thr Leu Asp Asp Leu Ser Ser Glu Tyr Gly Asn Glu Thr
            115                 120                 125
Leu Arg Val Thr Thr Arg Gln Gly Phe Gln Leu His Gly Ile Leu Lys
            130                 135                 140
Lys Asn Leu Lys Glu Thr Ile Asn Arg Ile Val Arg Asn Leu Gly Ser
145                 150                 155                 160
Thr Leu Gly Ala Cys Gly Asp Leu Asn Arg Asn Val Met Ala Pro Pro
                165                 170                 175
Ala Pro Phe Lys Asp Arg Lys Glu Tyr Gln Tyr Ala Trp Gln Tyr Ala
            180                 185                 190
Asp Asn Ile Ala Asp Leu Leu Arg Pro Gln Thr Glu Ala Tyr Tyr Glu
            195                 200                 205
Ile Trp Leu Asp Gly Glu Lys Phe Leu Ser Val Glu Glu Ala Pro Glu
210                 215                 220
Val Gln Ala Ala Arg Glu Arg Asn Gly Asn Gly Thr Ile Phe His Glu
225                 230                 235                 240
Gly Glu Glu Pro Ile Tyr Gly Lys Tyr Tyr Met Pro Arg Lys Phe Lys
                245                 250                 255
Cys Cys Val Thr Val Pro Gly Asp Asn Ser Ile Asp Val Tyr Thr His
                260                 265                 270
Asp Val Ser Leu Ile Val Ile Thr Asp Asp Gln Gly Glu Leu Lys Gly
            275                 280                 285
Phe Asn Val Leu Ala Gly Gly Met Gly Arg Thr His Asn Lys Glu
            290                 295                 300
Glu Thr Phe Ala Arg Met Ser Asp Pro Ile Cys Tyr Val Asp Lys Ala
305                 310                 315                 320
Asp Val Tyr Asp Leu Leu Lys Ala Ile Val Ala Thr Gln Arg Asp Tyr
                325                 330                 335
Gly Asp Arg Val Gln Arg Arg His Ala Arg Met Lys Tyr Leu Leu Tyr
            340                 345                 350
Asp Trp Gly Val Glu Lys Phe Gln Ser Lys Leu Glu Glu Tyr Tyr Gly
            355                 360                 365
Lys Pro Leu Gln Pro Tyr Gln Asp Leu Pro Pro Phe Glu Tyr Lys Asp
            370                 375                 380
Phe Leu Gly Trp His Glu Gln Gly Asp Gly Lys Leu Phe Phe Gly Leu
385                 390                 395                 400
Ser Val Glu Asn Gly Arg Val Lys Asp Glu Gly Lys Phe Arg Leu Lys
                405                 410                 415
Thr Ala Leu Arg Lys Ile Val Glu Gln Tyr Gln Val Pro Met Arg Leu
            420                 425                 430
Thr Ala Asn His Asp Val Ile Leu Tyr Glu Ile Lys Pro Glu Asp Gln
            435                 440                 445
```

```
Ser Ala Ile Glu Lys Ile Leu Thr Asp His Gly Leu Ile Thr Asp Pro
    450                 455                 460
Asn Asn Leu Asp His Leu Leu Arg Tyr Ser Met Ala Cys Pro Ala Leu
465                 470                 475                 480
Pro Thr Cys Gly Leu Ala Ile Thr Glu Ser Glu Arg Ala Leu Pro Ser
                485                 490                 495
Ile Leu Asp Arg Val Arg Asn Val Leu Lys Lys Leu Gly Met Ala Glu
            500                 505                 510
Gln Asp Leu Val Val Arg Met Thr Gly Cys Pro Asn Gly Cys Ala Arg
        515                 520                 525
Pro Tyr Met Ala Glu Leu Gly Phe Val Gly Ser Ala Pro Lys Ala Tyr
    530                 535                 540
Gln Leu Trp Leu Gly Gly Thr Pro Asn Gln Thr Ala Leu Ala Arg Pro
545                 550                 555                 560
Tyr Met Glu Arg Met Pro Ile Asp Glu Leu Glu Ser Tyr Ile Glu Pro
                565                 570                 575
Met Leu Ala Phe Tyr Lys Glu Lys Arg Gln Lys Asp Glu Ser Phe Gly
            580                 585                 590
Glu Phe Cys Asn Arg Val Gly Phe Glu Ala Ile Glu Thr Tyr Val Lys
        595                 600                 605
Ser Tyr Glu Phe Lys Pro Thr Lys Thr Pro Ser Ala Gly Gly Lys Gly
    610                 615                 620
Arg Arg His Arg Ile Ser Val Tyr Glu Gly Leu His Glu Arg Leu Lys
625                 630                 635                 640
Ala Ala Ala Glu Lys Arg Gly Thr Ser Met Thr Gln Leu Val Ser Glu
                645                 650                 655
Ala Leu Glu Gln Tyr Leu Asp Asp
            660

<210> SEQ ID NO 70
<211> LENGTH: 427
<212> TYPE: PRT
<213> ORGANISM: Rhodobacter capsulatus

<400> SEQUENCE: 70

Met Ala His Ile Val Val Leu Gly Ala Gly Leu Gly Gly Ala Ile Met
1               5                   10                  15
Ala Tyr Glu Leu Arg Glu Gln Val Arg Lys Glu Asp Lys Val Thr Val
            20                  25                  30
Ile Thr Lys Asp Pro Met Tyr His Phe Val Pro Ser Asn Pro Trp Val
        35                  40                  45
Ala Val Gly Trp Arg Asp Arg Lys Glu Ile Thr Val Asp Leu Ala Pro
    50                  55                  60
Thr Met Ala Arg Lys Asn Ile Asp Phe Ile Pro Val Ala Ala Lys Arg
65                  70                  75                  80
Leu His Pro Ala Glu Asn Arg Val Glu Leu Glu Asn Gly Gln Ser Val
                85                  90                  95
Ser Tyr Asp Gln Ile Val Ile Ala Thr Gly Pro Glu Leu Ala Phe Asp
            100                 105                 110
Glu Ile Glu Gly Phe Gly Pro Glu Gly His Thr Gln Ser Ile Cys His
        115                 120                 125
Ile Asp His Ala Glu Glu Ala Arg Leu Ala Phe Asp Arg Phe Cys Glu
    130                 135                 140
Asn Pro Gly Pro Ile Leu Ile Gly Ala Ala Gln Gly Ala Ser Cys Phe
145                 150                 155                 160
```

Gly Pro Ala Tyr Glu Phe Thr Phe Ile Leu Asp Thr Ala Leu Arg Lys
                165                 170                 175

Arg Lys Ile Arg Asp Lys Val Pro Met Thr Phe Val Thr Ser Glu Pro
            180                 185                 190

Tyr Val Gly His Leu Gly Leu Asp Gly Val Gly Asp Thr Lys Gly Leu
        195                 200                 205

Leu Glu Gly Asn Leu Arg Asp Lys His Ile Lys Trp Met Thr Ser Thr
210                 215                 220

Arg Ile Lys Arg Val Glu Lys Gly Lys Met Val Val Glu Glu Val Thr
225                 230                 235                 240

Glu Asp Gly Thr Val Lys Pro Glu Lys Glu Leu Pro Phe Gly Tyr Ala
                245                 250                 255

Met Met Leu Pro Ala Phe Arg Gly Ile Lys Ala Leu Met Gly Ile Glu
                260                 265                 270

Gly Leu Val Asn Pro Arg Gly Phe Val Ile Val Asp Gln His Gln Gln
                275                 280                 285

Asn Pro Thr Phe Lys Asn Val Phe Ala Val Gly Val Cys Val Ala Ile
            290                 295                 300

Pro Pro Ile Gly Pro Thr Pro Val Pro Cys Gly Val Pro Lys Thr Gly
305                 310                 315                 320

Phe Met Ile Glu Ser Met Val Thr Ala Thr Ala His Asn Ile Gly Arg
                325                 330                 335

Ile Val Arg Gly Phe Glu Ala Asp Glu Val Gly Ser Trp Asn Ala Val
                340                 345                 350

Cys Leu Ala Asp Phe Gly Asp Gln Gly Ile Ala Phe Val Ala Gln Pro
                355                 360                 365

Gln Ile Pro Pro Arg Asn Val Asn Trp Ser Ser Gln Gly Lys Trp Val
            370                 375                 380

His Trp Ala Lys Glu Gly Phe Glu Arg Tyr Phe Met His Lys Leu Arg
385                 390                 395                 400

Arg Gly Thr Ser Glu Thr Phe Tyr Glu Lys Ala Ala Met Lys Phe Leu
                405                 410                 415

Gly Ile Asp Lys Leu Lys Ala Val Lys Lys Gly
                420                 425

<210> SEQ ID NO 71
<211> LENGTH: 436
<212> TYPE: PRT
<213> ORGANISM: Oscillatoria limnetica

<400> SEQUENCE: 71

Met Ala His Val Ala Val Ile Gly Ala Gly Leu Ala Gly Leu Pro Thr
1               5                   10                  15

Ala Tyr Glu Leu Arg His Ile Leu Pro Arg Gln His Arg Val Thr Leu
                20                  25                  30

Ile Ser Asp Lys Pro Asn Phe Thr Phe Thr Pro Ser Leu Pro Trp Val
            35                  40                  45

Ala Phe Asp Leu Thr Pro Leu Glu Arg Val Gln Leu Asp Val Gly Lys
50                  55                  60

Leu Leu Lys Gly Arg Asn Ile Asp Trp Ile His Gly Lys Val Asn His
65                  70                  75                  80

Ile Asp Pro Glu Asn Lys Thr Leu Val Ala Gly Glu Gln Thr Leu Glu
                85                  90                  95

Tyr Asp Tyr Val Val Val Ala Thr Gly Pro Glu Leu Ala Thr Asp Ala

```
            100                 105                 110
Ile Ala Gly Leu Gly Pro Glu Asn Gly Tyr Thr Gln Ser Val Cys Asn
            115                 120                 125

Pro His His Ala Leu Met Ala Lys Glu Ala Trp Gln Lys Phe Leu Gln
            130                 135             140

Asp Pro Gly Pro Leu Val Val Gly Ala Val Pro Gly Ala Ser Cys Phe
145                 150                 155                 160

Gly Pro Ala Tyr Glu Phe Ala Leu Leu Ala Asp Tyr Val Leu Arg Arg
                165                 170                 175

Lys Gly Met Arg Asp Arg Val Pro Ile Thr Phe Val Thr Pro Glu Pro
            180                 185                 190

Tyr Val Gly His Leu Gly Ile Gly Gly Met Ala Asn Ser Ala Glu Leu
            195                 200                 205

Val Thr Asp Leu Leu Glu Asn Lys Gly Ile Arg Val Leu Pro Asn Thr
210                 215                 220

Ala Val Lys Glu Ile His Pro Glu His Met Asp Leu Asp Ser Gly Glu
225                 230                 235                 240

Gln Leu Pro Phe Lys Tyr Ala Met Leu Leu Pro Pro Phe Arg Gly Pro
                245                 250                 255

Ala Phe Leu Arg Glu Ala Pro Glu Leu Thr Asn Pro Lys Gly Phe Val
            260                 265                 270

Pro Val Thr Asn Thr Tyr Gln His Pro Lys Tyr Glu Ser Val Tyr Ser
            275                 280                 285

Ala Gly Val Ile Val Glu Ile Asn Pro Pro Glu Lys Thr Pro Leu Pro
            290                 295                 300

Val Gly Val Pro Lys Thr Gly Gln Met Thr Glu Ala Met Gly Met Ala
305                 310                 315                 320

Ala Ala His Asn Ile Ala Ile Lys Leu Gly Val Ser Lys Ala Lys Pro
                325                 330                 335

Val Gln Pro Thr Leu Glu Ala Ile Cys Ile Ala Asp Phe Gly Asp Thr
            340                 345                 350

Gly Ile Val Phe Val Ala Asp Pro Val Leu Pro Asp Pro Lys Thr Gly
            355                 360                 365

Thr Arg Arg Arg Ala Ile Thr Lys Arg Gly Lys Trp Val Ser Trp Ser
370                 375                 380

Lys Thr Ala Phe Glu Thr Phe Leu Ser Lys Met Arg Phe Gly Leu
385                 390                 395                 400

Ala Val Pro Trp Phe Glu Arg Trp Gly Leu Arg Phe Met Gly Leu Ser
            405                 410                 415

Leu Val Glu Pro Leu Asp Thr Thr Arg Glu Thr Gly Asn Gln Ala Phe
            420                 425                 430

Ala Ser Lys Ser
        435

<210> SEQ ID NO 72
<211> LENGTH: 375
<212> TYPE: PRT
<213> ORGANISM: Acidithiobacillus ferrooxidans

<400> SEQUENCE: 72

Met Thr Gln Val Thr Ile Ile Gly Ala Gly Phe Gly Gly Leu Thr Ala
1               5                   10                  15

Val Arg His Leu Arg Arg Arg Met Pro Asp Ala Glu Ile Thr Val Ile
            20                  25                  30
```

-continued

```
Ala Pro Arg Ala Glu Phe Val Tyr Pro Ser Leu Ile Trp Ile Pro
         35                  40                  45

Thr Gly Leu Arg Gln Gly Glu Asn Leu Arg Ile Pro Leu Asp Arg Phe
 50                  55                  60

Phe Gln Arg Arg Val Gln Phe His Gln Gly Arg Val Thr Gly Leu
 65                  70                  75                  80

Arg Asp Gly Gly Arg Thr Val Ile Thr Asp Gln Gly Glu Val Arg Asn
                 85                  90                  95

Asp Ala Leu Ile Ile Ala Ser Gly Gly Arg Gly Ile Arg Lys Leu Pro
                100                 105                 110

Gly Ile Glu His Ser Phe Ala Ile Cys Asp Gly Ile Asp Ala Ala Glu
                115                 120                 125

Asn Ile Arg Asp Arg Leu Ala Leu Met Asp Lys Gly Thr Ile Ala Phe
130                 135                 140

Gly Phe Ala Gly Asn Pro Leu Glu Pro Thr Ala Val Arg Gly Gly Pro
145                 150                 155                 160

Val Phe Glu Leu Leu Phe Gly Ile Asp Thr Tyr Leu Arg Gln Ile Asp
                165                 170                 175

Lys Arg Gly Gln Ile Glu Leu Val Phe Phe Asn Pro Met Thr Glu Pro
                180                 185                 190

Gly Asn Arg Leu Gly Pro Lys Ala Val Glu Gly Leu Leu Ala Glu Met
                195                 200                 205

Gln Arg Arg Asp Ile Arg Thr His Leu Gly His Lys Ile Ser Gly Phe
210                 215                 220

Ser Val Asn Lys Val Met Thr Glu Gly Gly Asp Ile Ala Ala Asp Leu
225                 230                 235                 240

Ile Leu Phe Met Pro Gly Met Thr Gly Pro Asp Trp Ala Ala Asp Ser
                245                 250                 255

Gly Leu Pro Leu Ser Ala Gly Gly Phe Phe Gln Ser Asp Leu His Cys
                260                 265                 270

Thr Val Pro Asp His Pro Gly Val Phe Val Ile Gly Asp Gly Gly Ser
                275                 280                 285

Tyr Ala Gly Ser Pro Asp Trp Leu Pro Lys Gln Gly His Met Ala Asp
290                 295                 300

Leu Gln Ala Gly Thr Ala Val His Asn Leu Leu His Leu Gln Gly
305                 310                 315                 320

Lys Ala Ala Asp Asn Thr Phe Arg Ser Glu Leu Ile Cys Ile Val Asp
                325                 330                 335

Thr Leu Asp Ser Gly Ile Met Val Tyr Arg Ser Pro Asn His Ala Ser
                340                 345                 350

Ile Leu Pro Asn Ser Leu Trp His Ala Ala Lys Val Ala Phe Glu Trp
                355                 360                 365

Arg Tyr Leu Leu His Tyr Arg
370                 375

<210> SEQ ID NO 73
<211> LENGTH: 430
<212> TYPE: PRT
<213> ORGANISM: Aquifex aeolicus

<400> SEQUENCE: 73

Met Ala Lys His Val Val Ile Gly Gly Val Gly Gly Ile Ala
 1               5                  10                  15

Thr Ala Tyr Asn Leu Arg Asn Leu Met Pro Asp Leu Lys Ile Thr Leu
                 20                  25                  30
```

Ile Ser Asp Arg Pro Tyr Phe Gly Phe Thr Pro Ala Phe Pro His Leu
            35                  40                  45

Ala Met Gly Trp Arg Lys Phe Glu Asp Ile Ser Val Pro Leu Ala Pro
 50                  55                  60

Leu Leu Pro Lys Phe Asn Ile Glu Phe Ile Asn Glu Lys Ala Glu Ser
 65                  70                  75                  80

Ile Asp Pro Asp Ala Asn Thr Val Thr Gln Ser Gly Lys Lys Ile
                85                  90                  95

Glu Tyr Asp Tyr Leu Val Ile Ala Thr Gly Pro Lys Leu Val Phe Gly
                100                 105                 110

Ala Glu Gly Gln Glu Asn Ser Thr Ser Ile Cys Thr Ala Glu His
                115                 120                 125

Ala Leu Glu Thr Gln Lys Lys Leu Gln Glu Leu Tyr Ala Asn Pro Gly
 130                 135                 140

Pro Val Val Ile Gly Ala Ile Pro Gly Val Ser Cys Phe Gly Pro Ala
145                  150                 155                 160

Tyr Glu Phe Ala Leu Met Leu His Tyr Glu Leu Lys Lys Arg Gly Ile
                165                 170                 175

Arg Tyr Lys Val Pro Met Thr Phe Ile Thr Ser Glu Pro Tyr Leu Gly
                180                 185                 190

His Phe Gly Val Gly Gly Ile Gly Ala Ser Lys Arg Leu Val Glu Asp
                195                 200                 205

Leu Phe Ala Glu Arg Asn Ile Asp Trp Ile Ala Asn Val Ala Val Lys
                210                 215                 220

Ala Ile Glu Pro Asp Lys Val Ile Tyr Glu Asp Leu Asn Gly Asn Thr
225                 230                 235                 240

His Glu Val Pro Ala Lys Phe Thr Met Phe Met Pro Ser Phe Gln Gly
                245                 250                 255

Pro Glu Val Val Ala Ser Ala Gly Asp Lys Val Ala Asn Pro Ala Asn
                260                 265                 270

Lys Met Val Ile Val Asn Arg Cys Phe Gln Asn Pro Thr Tyr Lys Asn
                275                 280                 285

Ile Phe Gly Val Gly Val Val Thr Ala Ile Pro Ile Glu Lys Thr
                290                 295                 300

Pro Ile Pro Thr Gly Val Pro Lys Thr Gly Met Met Ile Glu Gln Met
305                 310                 315                 320

Ala Met Ala Val Ala His Asn Ile Val Asn Asp Ile Arg Asn Asn Pro
                325                 330                 335

Asp Lys Tyr Ala Pro Arg Leu Ser Ala Ile Cys Ile Ala Asp Phe Gly
                340                 345                 350

Glu Asp Ala Gly Phe Phe Phe Asp Pro Val Ile Pro Pro Arg Glu
                355                 360                 365

Arg Val Ile Thr Lys Met Gly Lys Trp Ala His Tyr Phe Lys Thr Ala
                370                 375                 380

Phe Glu Lys Tyr Phe Leu Trp Lys Val Arg Asn Gly Asn Ile Ala Pro
385                 390                 395                 400

Ser Phe Glu Glu Lys Val Leu Glu Ile Phe Leu Lys Val His Pro Ile
                405                 410                 415

Glu Leu Cys Lys Asp Cys Glu Gly Ala Pro Gly Ser Arg Cys
                420                 425                 430

<210> SEQ ID NO 74
<211> LENGTH: 437

<212> TYPE: PRT
<213> ORGANISM: Halothece sp.

<400> SEQUENCE: 74

```
Met Ala His Ile Val Ile Val Gly Gly Gly Phe Gly Gly Leu Ser Ala
1               5                   10                  15

Ala Tyr Glu Leu Lys His Leu Leu His Gly Lys His Lys Ile Thr Leu
            20                  25                  30

Ile Ser Asp Glu Thr Thr Phe Thr Phe Ile Pro Ser Leu Pro Trp Val
        35                  40                  45

Ala Phe Asn Leu Arg Arg Leu Glu Asp Val Gln Leu Pro Leu Ala Pro
    50                  55                  60

Leu Leu Ala Arg Gln Gly Ile Asn Trp Gln His Gly Arg Val Thr Gly
65                  70                  75                  80

Leu Asp Pro Asn Gln Lys Arg Val Ser Val Gly Glu Asp Ile Thr Phe
                85                  90                  95

Asp Tyr Asp Tyr Leu Val Ile Thr Thr Gly Ala Ser Leu Ala Tyr His
            100                 105                 110

Leu Met Ser Gly Leu Gly Pro Glu Glu Gly Tyr Thr Gln Ser Val Cys
        115                 120                 125

Asn Ala His His Ala Glu Met Ala Arg Asp Ala Trp Asp Glu Phe Leu
    130                 135                 140

Glu Asn Pro Gly Pro Leu Leu Val Gly Ala Val Pro Gly Ala Ser Cys
145                 150                 155                 160

Met Gly Pro Ala Tyr Glu Phe Ala Leu Leu Ala Asp Tyr Ala Leu Arg
                165                 170                 175

Gln Glu Gly Lys Arg Asp Gln Val Pro Ile Thr Phe Ile Ser Pro Glu
            180                 185                 190

Pro Tyr Leu Gly His Leu Gly Ile Gly Gly Met Ala Asn Ser Gly Lys
        195                 200                 205

Leu Val Thr Glu Leu Met Lys Gln Arg Asn Ile Asp Trp Val Glu Asn
    210                 215                 220

Ala Glu Ile Ala Glu Ile Lys Glu Asp His Val Lys Leu Thr Asp Gly
225                 230                 235                 240

Arg Glu Phe Pro Phe Asn Tyr Ser Met Phe Leu Pro Pro Phe Arg Gly
                245                 250                 255

Ala Gln Phe Leu Lys Glu Val Pro Gly Leu Thr Asp Glu Lys Gly Phe
            260                 265                 270

Leu Pro Val Leu Asp Thr Tyr Gln His Pro Asp Tyr Pro Ser Ile Tyr
        275                 280                 285

Ser Ala Gly Val Ile Thr Gln Leu Ala Ala Pro Glu Glu Thr Glu Val
    290                 295                 300

Pro Leu Gly Ala Pro Lys Thr Gly Gln Met Thr Glu Ser Met Ala Met
305                 310                 315                 320

Ala Val Ala His Asn Ile Ala Arg Glu Leu Gly Glu Ile Asn Ala Arg
                325                 330                 335

Pro Val Lys Pro Ser Leu Glu Ala Ile Cys Met Ala Asp Phe Gly Asp
            340                 345                 350

Thr Gly Ile Ile Phe Ile Ala Ala Pro Val Val Pro Asp Pro Ser Val
        355                 360                 365

Gly His Arg Arg His Ala Thr Ala Leu Arg Gly Leu Trp Val Asn Trp
    370                 375                 380

Ala Lys Asn Ala Phe Glu Trp Tyr Phe Leu Ala Lys Met Arg Trp Gly
385                 390                 395                 400
```

```
Thr Ala Val Pro Trp Phe Glu Lys Leu Gly Leu Tyr Leu Leu Arg Leu
            405                 410                 415

Thr Leu Val Thr Pro Ile Ser Glu Thr Pro Thr Gln Gln Lys Asp Leu
            420                 425                 430

Thr Ser Ile Lys Gly
            435

<210> SEQ ID NO 75
<211> LENGTH: 431
<212> TYPE: PRT
<213> ORGANISM: Allochromatium vinosum

<400> SEQUENCE: 75

Met Thr Leu Asn Arg Arg Asp Phe Ile Lys Thr Ser Gly Ala Ala Val
 1                5                  10                  15

Ala Ala Val Gly Ile Leu Gly Phe Pro His Leu Ala Phe Gly Ala Gly
                20                  25                  30

Arg Lys Val Val Val Gly Gly Thr Gly Gly Ala Thr Ala Ala
            35                  40                  45

Lys Tyr Ile Lys Leu Ala Asp Pro Ser Ile Glu Val Thr Leu Ile Glu
        50                  55                  60

Pro Asn Thr Asp Tyr Tyr Thr Cys Tyr Leu Ser Asn Glu Val Ile Gly
 65                 70                  75                  80

Gly Asp Arg Lys Leu Glu Ser Ile Lys His Gly Tyr Asp Gly Leu Arg
                85                  90                  95

Ala His Gly Ile Gln Val Val His Asp Ser Ala Thr Gly Ile Asp Pro
            100                 105                 110

Asp Lys Lys Leu Val Lys Thr Ala Gly Gly Ala Glu Phe Gly Tyr Asp
        115                 120                 125

Arg Cys Val Val Ala Pro Gly Ile Glu Leu Ile Tyr Asp Lys Ile Glu
130                 135                 140

Gly Tyr Ser Glu Glu Ala Ala Lys Leu Pro His Ala Trp Lys Ala
145                 150                 155                 160

Gly Glu Gln Thr Ala Ile Leu Arg Lys Gln Leu Glu Asp Met Ala Asp
                165                 170                 175

Gly Gly Thr Val Val Ile Ala Pro Pro Ala Ala Pro Phe Arg Cys Pro
            180                 185                 190

Pro Gly Pro Tyr Glu Arg Ala Ser Gln Val Ala Tyr Tyr Leu Lys Ala
        195                 200                 205

His Lys Pro Lys Ser Lys Val Ile Ile Leu Asp Ser Ser Gln Thr Phe
210                 215                 220

Ser Lys Gln Ser Gln Phe Ser Lys Gly Trp Glu Arg Leu Tyr Gly Phe
225                 230                 235                 240

Gly Thr Glu Asn Ala Met Ile Glu Trp His Pro Gly Pro Asp Ser Ala
                245                 250                 255

Val Val Lys Val Asp Gly Gly Glu Met Met Val Glu Thr Ala Phe Gly
            260                 265                 270

Asp Glu Phe Lys Ala Asp Val Ile Asn Leu Ile Pro Pro Gln Arg Ala
        275                 280                 285

Gly Lys Ile Ala Gln Ile Ala Gly Leu Thr Asn Asp Ala Gly Trp Cys
290                 295                 300

Pro Val Asp Ile Lys Thr Phe Glu Ser Ser Ile His Lys Gly Ile His
305                 310                 315                 320

Val Ile Gly Asp Ala Cys Ile Ala Asn Pro Met Pro Lys Ser Gly Tyr
```

```
                    325                 330                 335
Ser Ala Asn Ser Gln Gly Lys Val Ala Ala Ala Val Val Ala Leu
                340                 345                 350

Leu Lys Gly Glu Glu Pro Gly Thr Pro Ser Tyr Leu Asn Thr Cys Tyr
        355                 360                 365

Ser Ile Leu Ala Pro Ala Tyr Gly Ile Ser Val Ala Ala Ile Tyr Arg
370                 375                 380

Pro Asn Ala Asp Gly Ser Ala Ile Glu Ser Val Pro Asp Ser Gly Gly
385                 390                 395                 400

Val Thr Pro Val Asp Ala Pro Asp Trp Val Leu Glu Arg Glu Val Gln
                405                 410                 415

Tyr Ala Tyr Ser Trp Tyr Asn Asn Ile Val His Asp Thr Phe Gly
                420                 425                 430

<210> SEQ ID NO 76
<211> LENGTH: 199
<212> TYPE: PRT
<213> ORGANISM: Allochromatium vinosum

<400> SEQUENCE: 76

Met Thr Gln Ser Thr Pro Arg Leu Met Leu Ala Ala Ser Val Leu Ala
1               5                   10                  15

Leu Gly Leu Ala Ser Asn Ala Gly Ala Glu Pro Thr Ala Glu Met Leu
            20                  25                  30

Thr Asn Asn Cys Ala Gly Cys His Gly Thr His Gly Asn Ser Val Gly
        35                  40                  45

Pro Ala Ser Pro Ser Ile Ala Gln Met Asp Pro Met Val Phe Val Glu
    50                  55                  60

Val Met Glu Gly Phe Lys Ser Gly Glu Ile Ala Ser Thr Ile Met Gly
65              70                  75                  80

Arg Ile Ala Lys Gly Tyr Ser Thr Ala Asp Phe Glu Lys Met Ala Gly
                85                  90                  95

Tyr Phe Lys Gln Gln Thr Tyr Gln Pro Ala Lys Gln Ser Phe Asp Thr
            100                 105                 110

Ala Leu Ala Asp Thr Gly Ala Lys Leu His Asp Lys Tyr Cys Glu Lys
        115                 120                 125

Cys His Val Glu Gly Gly Lys Pro Leu Ala Asp Glu Asp Tyr His
    130                 135                 140

Ile Leu Ala Gly Gln Trp Thr Pro Tyr Leu Gln Tyr Ala Met Ser Asp
145                 150                 155                 160

Phe Arg Glu Glu Arg Arg Pro Met Glu Lys Met Ala Ser Lys Leu
                165                 170                 175

Arg Glu Leu Leu Lys Ala Glu Gly Asp Ala Gly Leu Asp Ala Leu Phe
            180                 185                 190

Ala Phe Tyr Ala Ser Gln Gln
        195

<210> SEQ ID NO 77
<211> LENGTH: 430
<212> TYPE: PRT
<213> ORGANISM: Chlorobium limicola

<400> SEQUENCE: 77

Met Ser Gln Lys Phe Ser Arg Arg Asp Phe Asn Lys Leu Leu Val Ser
1               5                   10                  15

Gly Val Ala Gly Ser Ala Phe Gly Ile Phe Gly Ala Val Arg Pro Ala
```

-continued

```
                20                  25                  30
Tyr Ala Ala Gln Asn Arg Ile Val Val Ile Gly Gly Phe Gly Gly
             35                  40                  45
Ala Ser Ala Ala Lys Tyr Leu Arg Lys Leu Asp Pro Ser Leu Ser Val
 50                  55                  60
Thr Leu Val Glu Pro Lys Ala Thr Phe Tyr Thr Cys Pro Phe Ser Asn
 65                  70                  75                  80
Trp Val Leu Gly Gly Leu Lys Asn Met Glu Asp Ile Ala Gln Thr Tyr
                 85                  90                  95
Thr Val Leu Lys Asn Lys Tyr Gly Val Asn Val Ile Ala Asp Tyr Ala
                100                 105                 110
Ser Ser Ile Asp Ala Ala Lys Gly Thr Val Thr Leu Lys Ser Gly Lys
                115                 120                 125
Val Leu Asn Tyr Asp Arg Leu Ile Val Ser Pro Gly Ile Asp Phe Lys
                130                 135                 140
Trp Asn Thr Ile Glu Gly Tyr Ser Glu Ser Val Ser Asn Thr Lys Met
145                 150                 155                 160
Pro His Ala Tyr Glu Ala Gly Pro Gln Thr Val Leu Leu His Lys Gln
                165                 170                 175
Leu Leu Ala Met Asn Asp Gly Gly Thr Val Leu Ile Cys Pro Pro Ala
                180                 185                 190
Asn Pro Phe Arg Cys Pro Pro Gly Pro Tyr Glu Arg Ala Ser Leu Val
                195                 200                 205
Ala His Tyr Leu Lys Glu Lys Pro Lys Ser Lys Ile Ile Ile Leu
                210                 215                 220
Asp Pro Lys Asp Lys Phe Ser Lys Gln Gly Leu Phe Lys Lys Gly Trp
225                 230                 235                 240
Glu Lys Leu Tyr Pro Gly Met Ile Glu Trp Arg Ser Val Ala Thr Gly
                245                 250                 255
Gly Lys Ile Ser Lys Val Asp Ala Ala Thr Met Thr Val Thr Thr Asp
                260                 265                 270
Phe Gly Val Glu Lys Gly Asp Val Ile Asn Ile Ile Pro Pro Gln Gln
                275                 280                 285
Ala Gly Lys Ile Ala Val Asp Ala Gly Leu Thr Asp Ala Ser Gly Trp
                290                 295                 300
Cys Pro Val Asn Pro Ile Thr Phe Glu Ser Thr Ile His Pro Gly Ile
305                 310                 315                 320
His Val Ile Gly Asp Ala Cys Ile Ala Gly Ala Met Pro Lys Ser Gly
                325                 330                 335
Phe Ala Ala Ser Ser Gln Gly Lys Val Val Ala Ala Ser Ile Ile Arg
                340                 345                 350
Leu Cys Gln Gly Lys Val Pro Ala Pro Pro Ser Leu Val Asn Thr Cys
                355                 360                 365
Tyr Ser Leu Ile Gly Pro Gly Tyr Gly Val Ser Val Ala Gly Val Tyr
                370                 375                 380
Lys Leu Thr Ser Ala Gly Ile Val Glu Ile Pro Gly Ser Gly Gly Leu
385                 390                 395                 400
Thr Pro Met Asp Ala Asp Asp His Leu Asn Glu Glu Ala Thr Phe
                405                 410                 415
Ala Arg Gly Trp Tyr Asn Asn Ile Val Gln Asp Ile Trp Gly
                420                 425                 430

<210> SEQ ID NO 78
```

```
<211> LENGTH: 123
<212> TYPE: PRT
<213> ORGANISM: Chlorobium limicola

<400> SEQUENCE: 78

Met Leu Gly Leu Val Phe Thr Val Pro Leu Phe His Ala Gly Ser
 1               5                  10                  15

Thr Val Met Ala Ala Asp Ala Pro Ala Thr Val Ala Ala Pro
             20                  25                  30

Ala Pro Thr Pro Ala Met Asp Pro Ala Lys Met Arg Glu Arg Gly Gln
             35                  40                  45

Ile Leu Ala Leu Ser Cys Ser Gly Cys His Gly Thr Asp Gly Lys Ser
 50                  55                  60

Ser Ser Ile Met Pro Ser Ile Tyr Gly Lys Thr Thr Gly Tyr Ile Glu
65                   70                  75                  80

Ser Ala Leu Leu Asp Phe Lys Ser Gly Ala Arg Met Ser Thr Val Met
                 85                  90                  95

Gly Arg His Ala Lys Gly Tyr Thr Pro Glu Glu Ile His Leu Ile Ala
             100                 105                 110

Glu Tyr Phe Gly Asn Leu Ser Lys Lys Lys Asn
             115                 120

<210> SEQ ID NO 79
<211> LENGTH: 430
<212> TYPE: PRT
<213> ORGANISM: Chlorobium tepidum

<400> SEQUENCE: 79

Met Gly Asn Thr Ile Ser Arg Arg Thr Phe Asn Arg Leu Leu Ile Ser
 1               5                  10                  15

Gly Leu Ala Gly Ser Ser Leu Leu Met Ser Gly Gly Pro Leu Met Ala
             20                  25                  30

Ser Ala Pro Lys Ala His Val Val Ile Gly Gly Gly Phe Gly Gly
             35                  40                  45

Ala Thr Val Ala Arg Tyr Leu Arg Gln Leu Asp Pro Ser Ile Ser Val
 50                  55                  60

Thr Leu Val Glu Pro Lys Lys Val Phe His Thr Cys Pro Met Ser Asn
65                   70                  75                  80

Trp Val Ile Gly Gly Leu Phe Ser Met Gln Asn Thr Ala His Thr Tyr
                 85                  90                  95

His Ala Leu Arg Ser Arg Tyr Gly Val Glu Val Gln Glu Met Ala
             100                 105                 110

Thr Gly Ile Asp Pro Val Lys Lys Thr Val Lys Leu Lys Gly Gly Arg
             115                 120                 125

Met Leu Ser Tyr Asp Arg Leu Val Val Ser Pro Gly Val Asp Phe Ile
             130                 135                 140

Trp Asp Ala Ile Glu Gly Tyr Ser Arg Asp Val Ala Glu Ser Ser Met
145                 150                 155                 160

Pro Tyr Ala Trp Glu Ala Gly Pro Gln Thr Leu Leu Arg Arg Gln
                 165                 170                 175

Leu Leu Gly Met Lys Asp Gly Glu Asn Val Ile Ile Cys Ala Pro Lys
             180                 185                 190

Asn Pro Phe Arg Cys Pro Ala Ala Pro Tyr Glu Arg Ala Ser Leu Ile
             195                 200                 205

Ala Tyr Tyr Leu Lys Lys Ser Lys Pro Lys Ser Lys Val Ile Ile Leu
             210                 215                 220
```

```
Asp Asp Lys Glu Val Phe Thr Lys Gln Asp Leu Phe Met Leu Gly Trp
225                 230                 235                 240

Asp Arg Leu Tyr Arg Gly Lys Ile Glu Trp Arg Ser Ala Ser Ala Gly
            245                 250                 255

Gly Lys Val Glu Arg Leu Asp Pro Ala Lys Met Thr Val Ala Thr Glu
        260                 265                 270

Phe Gly Asp Glu Lys Gly Gly Val Ile Asn Val Ile Pro Pro Gln Lys
    275                 280                 285

Ala Gly Arg Ile Ala Val Glu Thr Gly Leu Ala Asp Thr Ser Gly Trp
290                 295                 300

Cys Pro Val Asn Pro Ala Asn Phe Glu Ser Leu Gln His Pro Gly Ile
305                 310                 315                 320

His Val Ile Gly Asp Ala Ala Leu Val Gly Thr Met Pro Lys Ser Gly
            325                 330                 335

Thr Ala Ala Asn Thr Gln Ala Lys Ala Leu Ala Trp Leu Val Ala
        340                 345                 350

Ser Phe Gly Gly Gly Asn Ala Gly Glu His Asp Leu Ala Ser Leu Cys
    355                 360                 365

Tyr Ser Leu Leu Ala Pro Gly Tyr Ala Ile Ser Val Ala Gly Gly Tyr
370                 375                 380

Ile Gln Ser Pro Glu Gly Ile Lys Asp Asn Pro Asp Thr Val His Leu
385                 390                 395                 400

Thr Ser Met Glu Ala Thr Thr Ala Gln Leu Ala Gly Glu Ala Glu Gln
            405                 410                 415

Ala Leu Gln Trp Tyr His Asn Ile Ser Gln Asp Thr Trp Gly
        420                 425                 430

<210> SEQ ID NO 80
<211> LENGTH: 110
<212> TYPE: PRT
<213> ORGANISM: Chlorobium tepidum

<400> SEQUENCE: 80

Met Leu Ala Ala Ala Pro Leu Leu Ala Ser Gly Asn Gly Phe Ala
1               5                   10                  15

Thr Thr Gly Pro Ala Ala Lys Pro Ala Val Lys Pro Val Thr Glu Ser
            20                  25                  30

Arg Gly Glu Ile Leu Ser Leu Ser Cys Ala Gly Cys His Gly Thr Asp
        35                  40                  45

Gly Asn Ser Ser Ser Val Ile Pro Ser Ile Tyr Gly Lys Ser Pro Glu
    50                  55                  60

Tyr Ile Glu Thr Ala Leu Ile Asp Phe Lys Asn Gly Ser Arg Thr Ser
65                  70                  75                  80

Thr Val Met Gly Arg His Ala Lys Gly Tyr Thr Gly Glu Glu Ile His
            85                  90                  95

Leu Ile Ala Glu Tyr Phe Gly Asn Leu Ser Lys Lys Asn His
        100                 105                 110

<210> SEQ ID NO 81
<211> LENGTH: 419
<212> TYPE: PRT
<213> ORGANISM: Thiobacillus denitrificans

<400> SEQUENCE: 81

Met His Leu Asp Arg Arg Asp Phe Leu Lys Leu Ser Ala Ala Thr Ala
1               5                   10                  15
```

```
Leu Ala Ala Leu Pro Gly Cys Ala Ser Leu Ser Gly Thr Ala Arg Pro
            20                  25                  30

Arg Val Val Val Gly Ala Gly Phe Gly Gly Ala Thr Cys Ala Lys
    35                  40                  45

Tyr Leu Arg Arg Trp Gly Pro Ala Leu Asp Val Thr Leu Ile Glu Pro
50                  55                  60

Asn Glu Arg Phe Val Ser Cys Pro Ile Ser Asn Trp Val Leu Gly Gly
65                  70                  75                  80

Leu Arg Ser Met Asp Asp Ile Thr His Gly Tyr Gly Leu Ala Arg
                85                  90                  95

His Gly Ile Thr Leu Ile Arg Asp Ser Val Val Ala Ile Asp Pro Asp
            100                 105                 110

Thr Arg Thr Leu Arg Thr Ala Gln Gly Leu Gln Ile Gly Tyr Glu Arg
            115                 120                 125

Leu Val Leu Ala Pro Gly Val Glu Leu Leu Thr Asp Ser Val Arg Gly
130                 135                 140

Phe Ala Asp Ala Glu Ala Ala Gly Arg Val Val His Ala Trp Lys Ala
145                 150                 155                 160

Gly Ala Gln Thr Ala Leu Leu Arg Arg Gln Leu Glu Ala Met Pro Asp
                165                 170                 175

Gly Gly Thr Phe Ile Val Ser Ile Pro Ala Ala Pro Tyr Arg Cys Pro
            180                 185                 190

Pro Gly Pro Tyr Glu Arg Ala Cys Leu Val Ala His Tyr Phe Lys Gln
            195                 200                 205

Arg Lys Pro Arg Ser Lys Ile Ile Val Leu Asp Ala Asn Pro Asp Ile
    210                 215                 220

Val Ser Lys Lys Pro Leu Phe Thr Asp Ala Trp Asn Thr Leu Tyr Pro
225                 230                 235                 240

Gly Met Ile Asp Tyr Arg Pro Asn Ser Pro Ala Leu Val Val Asp Ala
                245                 250                 255

Ala Lys Met Thr Val Ser Thr Asp Phe Glu Asp Val Arg Gly Asp Val
            260                 265                 270

Leu Asn Ile Val Pro Arg Gln Arg Ala Ala Val Cys Asp Leu Val
    275                 280                 285

Gly Ala Arg Asn Asp Gly Asn Lys Thr Trp Cys Thr Val Asp Phe Ala
290                 295                 300

Thr Phe Glu Ser Thr Ala Ala Pro Gly Val His Ile Ile Gly Asp Ser
305                 310                 315                 320

Met Ala Ser Pro Leu Pro Arg Ser Gly His Met Ala Thr Asn Gln Ala
                325                 330                 335

Lys Val Cys Ala Gly Ala Ile Val Asp Leu Leu Ala Arg Ala Pro
            340                 345                 350

Asp Pro Ala Pro Val Ile Ala Asn Thr Cys Tyr Ser Ala Thr Ser Asp
            355                 360                 365

Ser Thr Ala Gly Tyr Val Ala His Val Tyr Arg Leu Val Pro Gly Lys
    370                 375                 380

Gly Tyr Val Ala Ala Pro Glu Gly Gly Ala Thr Thr Thr Gly Asp Ala
385                 390                 395                 400

Arg Asn Phe Arg Tyr Ala Ala Ser Trp Ala Lys Asn Ile Trp Ala Glu
                405                 410                 415

Met Leu Ser
```

<210> SEQ ID NO 82
<211> LENGTH: 98
<212> TYPE: PRT
<213> ORGANISM: Thiobacillus denitrificans

<400> SEQUENCE: 82

Met Thr Pro Ser Ser Ala Val Ala Ser Cys Leu Leu Ala Leu Ser
1               5                   10                  15

Gly Phe Ala Val Ala Ala Asp Arg His Thr Leu Thr Ile Ala Ala Thr
            20                  25                  30

Cys Met Ser Cys His Gly Pro Asp Gly Arg Ser Leu Gly Glu Ile Pro
            35                  40                  45

Arg Leu Asp Gly Leu Ser Arg Thr Glu Phe Val Thr Ala Leu Arg Asp
50                  55                  60

Phe Arg Ser Gly Ala Arg Arg Ala Thr Ile Met Gln Arg Gln Ala Ser
65                  70                  75                  80

Gly Tyr Thr Asp Ala Glu Ile Asp Ala Leu Gly Asp Tyr Phe Ala Thr
                85                  90                  95

Leu Lys

<210> SEQ ID NO 83
<211> LENGTH: 430
<212> TYPE: PRT
<213> ORGANISM: Thiocystis violascens

<400> SEQUENCE: 83

Met Lys Leu Ser Arg Arg Asp Phe Val Lys Val Ser Gly Ala Ala Thr
1               5                   10                  15

Ala Val Gly Leu Phe Gly Phe Pro Tyr Leu Ala Leu Gly Ala Thr Gln
            20                  25                  30

Lys Val Val Ile Gly Gly Thr Gly Ala Thr Ala Ala Lys
            35                  40                  45

Tyr Leu Lys Leu Ala Asp Ser Ser Ile Asp Val Thr Leu Ile Glu Pro
50                  55                  60

Asn Glu Val Tyr Tyr Thr Cys Tyr Leu Ser Asn Glu Val Ile Gly Gly
65                  70                  75                  80

Glu Arg Lys Leu Glu Ser Leu Arg Gln Thr Tyr Asp Gly Leu Lys Ala
                85                  90                  95

His Gly Val Lys Val Val His Asp Ser Ala Thr Gly Ile Asp Pro Asp
            100                 105                 110

Lys Lys Thr Val Lys Thr Ala Gly Gly Thr Glu Tyr Ser Tyr Asp Arg
            115                 120                 125

Cys Ile Val Ala Pro Gly Ile Glu Leu Leu Tyr Glu Lys Ile Asp Gly
130                 135                 140

Tyr Ser Glu Ala Ala Ala Glu Thr Leu Pro His Ala Trp Lys Ala Gly
145                 150                 155                 160

Glu Gln Thr Arg Ile Leu Arg Lys Gln Leu Glu Asp Met Lys Asp Gly
                165                 170                 175

Gly Thr Val Ile Ile Ala Ala Pro Ala Pro Phe Arg Cys Pro Pro
            180                 185                 190

Gly Pro Tyr Glu Arg Ala Ser Gln Ile Ala His Tyr Leu Lys Ala His
            195                 200                 205

Lys Pro Lys Ser Lys Val Ile Ile Leu Asp Asn Ser Gln Lys Phe Ser
210                 215                 220

Lys Gln Ala Gln Phe Thr Lys Gly Trp Glu Thr Leu Tyr Gly Phe Gly
225                 230                 235                 240

```
Thr Asp Asn Ala Leu Ile Glu Trp Arg Pro Gly Pro Asp Ala Ala Val
            245                 250                 255

Val Lys Val Asp Ala Gly Gln Met Leu Ala Glu Thr Asn Phe Gly Asp
            260                 265                 270

Glu Ile Lys Ala Asp Val Ile Asn Val Ile Pro Pro Gln Arg Ala Gly
            275                 280                 285

Ser Ile Ala Gln Thr Ala Gly Leu Ala Asn Glu Ser Gly Trp Cys Pro
            290                 295                 300

Val Asp Val Lys Thr Phe Glu Ser Lys Leu His Lys Gly Ile His Val
305                 310                 315                 320

Ile Gly Asp Ala Cys Ile Ala Thr Glu Met Pro Lys Ser Gly Tyr Ser
                325                 330                 335

Ala Asn Ser Gln Gly Lys Val Ala Ala Ala Val Val Ala Leu Leu
                340                 345                 350

Lys Gly Glu Glu Pro Gly Thr Pro Ser Tyr Leu Asn Thr Cys Tyr Ser
            355                 360                 365

Ile Ile Gly Pro Ala Tyr Gly Ile Ser Val Ala Gly Val Tyr Arg Leu
            370                 375                 380

Ser Glu Asp Gly Ala Thr Ile Ala Ser Val Pro Asp Ser Gly Gly Val
385                 390                 395                 400

Thr Pro Val Asp Ala Pro Asp Trp Ala Leu Ala Arg Glu Val Glu Tyr
            405                 410                 415

Ala Tyr Ser Trp Tyr Asn Asn Ile Val His Asp Ile Phe Gly
            420                 425                 430

<210> SEQ ID NO 84
<211> LENGTH: 199
<212> TYPE: PRT
<213> ORGANISM: Thiocystis violascens

<400> SEQUENCE: 84

Met Ala Arg Lys Ile Leu Gln Thr Thr Leu Leu Thr Gly Ala Leu Ala
1               5                   10                  15

Leu Gly Ala Ser Ser Gly Ala Trp Ala Glu Ala Thr Gly Ala Met Leu
            20                  25                  30

Ala Asn Ser Cys Ala Gly Cys His Gly Thr His Gly Asn Ser Val Gly
        35                  40                  45

Pro Ala Ser Pro Ser Ile Ala Ala Met Asp Pro Val Val Phe Val Glu
    50                  55                  60

Thr Met Glu Glu Phe Lys Asn Gly Glu Thr Tyr Ser Thr Ile Met Gly
65                  70                  75                  80

Arg Ile Ala Lys Gly Tyr Ser Thr Gly Glu Phe Glu Lys Met Ala Glu
                85                  90                  95

Tyr Phe His Ala Gln Thr Tyr Gln Pro Ala Lys Gln Ser Phe Asp Thr
            100                 105                 110

Ala Leu Ala Asp Lys Gly Ala Lys Leu His Asp Lys Tyr Cys Glu Lys
        115                 120                 125

Cys His Ala Glu Gly Gly Lys Pro Leu Val Asp Glu Asp Tyr Asn
    130                 135                 140

Ile Leu Ala Gly Gln Trp Leu Pro Tyr Leu Gln Tyr Ala Met Glu Asp
145                 150                 155                 160

Phe Arg Ala Asp Arg Arg Glu Met Glu Lys Lys Met Arg Thr Lys Leu
                165                 170                 175

Asn Glu Leu Leu Lys Ala Glu Gly Glu Asp Gly Ile Ala Ala Val Asn
```

Ala Phe Tyr Ala Ser Gln Gln
              195

<210> SEQ ID NO 85
<211> LENGTH: 308
<212> TYPE: PRT
<213> ORGANISM: Acidianus tengchongensis

<400> SEQUENCE: 85

Met Pro Lys Pro Tyr Ile Ala Ile Asn Met Ala Asp Leu Lys Asn Glu
 1               5                  10                  15

Pro Lys Thr Phe Glu Met Phe Ser Ala Val Gly Pro Lys Val Cys Met
                20                  25                  30

Val Thr Ala Arg His Pro Gly Phe Val Gly Phe Gln Asn His Val Gln
            35                  40                  45

Ile Gly Val Leu Pro Phe Gly Glu Arg Phe Gly Gly Ala Lys Met Asp
        50                  55                  60

Met Thr Lys Glu Ser Ser Thr Val Arg Val Leu Gln Tyr Thr Met Trp
65                  70                  75                  80

Lys Asp Trp Lys Asp His Glu Glu Met His Arg Gln Asn Trp Ser Tyr
                85                  90                  95

Leu Phe Arg Leu Cys Tyr Ser Cys Ala Ser Gln Met Val Trp Gly Pro
            100                 105                 110

Trp Glu Pro Ile Tyr Glu Ile Lys Tyr Ala Asp Met Pro Ile Asn Thr
        115                 120                 125

Glu Met Thr Asp Phe Thr Ala Val Val Gly Lys Lys Phe Ala Glu Gly
130                 135                 140

Lys Pro Leu Glu Ile Pro Val Ile Ser Gln Pro Tyr Gly Lys Arg Val
145                 150                 155                 160

Val Ala Phe Gly Glu His Thr Val Ile Pro Gly Lys Glu Lys Gln Phe
                165                 170                 175

Glu Asp Ala Ile Ile Lys Thr Leu Glu Met Phe Lys Arg Ala Pro Gly
            180                 185                 190

Phe Leu Gly Ala Met Leu Leu Lys Glu Ile Gly Val Ser Gly Ile Gly
        195                 200                 205

Ser Phe Gln Phe Gly Ser Lys Gly Phe His Gln Leu Leu Glu Ser Pro
    210                 215                 220

Gly Ser Leu Glu Pro Asp Pro Asn Asn Val Met Tyr Gln Val Pro Glu
225                 230                 235                 240

Ala Lys Pro Thr Pro Gln Tyr Ile Val His Val Glu Trp Ala Asn
                245                 250                 255

Leu Asp Ala Leu Gln Phe Gly Met Gly Arg Val Leu Leu Ser Pro Glu
            260                 265                 270

Tyr Arg Glu Val His Asp Glu Ala Leu Asp Thr Leu Ile Tyr Gly Pro
        275                 280                 285

Tyr Ile Arg Ile Ile Asn Pro Val Met Glu Gly Thr Phe Trp Arg Glu
    290                 295                 300

Tyr Leu Asn Glu
305

<210> SEQ ID NO 86
<211> LENGTH: 316
<212> TYPE: PRT
<213> ORGANISM: Sulfolobus metallicus

<400> SEQUENCE: 86

Met Pro Lys Pro Tyr Val Ala Ile Asn Gln Val Ile Val Lys Asn Glu
1               5                   10                  15

Pro Lys Thr Phe Glu Met Phe Gln Ser Val Gly Pro Lys Val Cys Met
            20                  25                  30

Thr Thr Ala Arg His Lys Gly Phe Val Gly Phe Gln Asn His Ile Glu
            35                  40                  45

Ile Gly Val Val Pro Met Gly Thr Arg Tyr Ala Ala Lys Met Asp
    50                  55                  60

Met Leu Lys Glu Ser Ser Thr Met Gly Leu Tyr Gln Tyr Thr Met Trp
65              70                  75                  80

Lys Asp Trp Lys Asp His Glu Met His Lys Gln Asn Trp Ser Ser
                85                  90                  95

Leu Phe Arg Leu Cys Tyr Ser Cys Met Ser Gln Val Val Trp Gly Pro
            100                 105                 110

Trp Glu Pro Leu Tyr Glu Ile Thr Met Ala Asp Met Pro Leu Asn Thr
            115                 120                 125

Glu Met Thr Asp Phe Thr Val Met Val Gly Gln Lys Phe Ala Ser Gly
            130                 135                 140

Asp Ala Leu Ser Leu Pro Pro Ile Ser Gln Pro Tyr Gly Lys Arg Val
145             150                 155                 160

Val Thr Tyr Gly Glu His Val Val Lys Glu Gly Met Glu Lys Glu Phe
            165                 170                 175

Glu Glu Thr Leu Ser Arg Leu Leu Pro Met Phe Lys Arg Ala Pro Gly
            180                 185                 190

Phe Leu Gly Tyr Met Val Leu Lys Glu Ile Gly Ala Ser Pro Leu Gly
            195                 200                 205

Ser Leu Gln Leu Ser Ala Lys Ser Trp His Gln Leu Leu Glu Ser Ala
            210                 215                 220

Asn Gly Met Asp Val Pro Asp Pro Asn Gly Asn Phe Ser Pro Glu Gln
225             230                 235                 240

Ala Arg Asn Lys Pro Gln Lys Tyr Val Val His Met Glu Trp Ser Asn
                245                 250                 255

Thr Asp Ala Ala Gln Phe Gly Leu Gly Arg Val Phe Leu Ser Pro Glu
            260                 265                 270

Tyr Arg Glu Ile His Asp Gln Ile Val Asp Thr Leu Ile Tyr Gly Pro
            275                 280                 285

Tyr Ile Arg Ile Leu Asn Pro Val Met Glu Gly Ser Phe Trp Arg Glu
            290                 295                 300

Tyr Leu Asn Glu Val Asn Leu Gln Lys Ala Thr Trp
305                 310                 315

<210> SEQ ID NO 87
<211> LENGTH: 311
<212> TYPE: PRT
<213> ORGANISM: Acidithiobacillus caldus

<400> SEQUENCE: 87

Met Asp Lys Asn Pro Ile Val Ala Ile Asn Gln Ser Lys Val Val Asn
1               5                   10                  15

Arg Pro Glu Ser Phe Ala Thr Met Met Lys Val Gly Pro Lys Val Cys
            20                  25                  30

Ile Thr Thr Ala Ser His Pro Gly Phe Leu Gly Phe Glu Gln Leu Leu
            35                  40                  45

-continued

Gln Thr Gly Met His Pro Met Ala Gly Arg Tyr Gly Gly Ala Val
    50              55                  60

Asp Met Arg Asp Thr Ile Asn Pro Met Ala Met Tyr Gln Tyr Thr Val
65              70                  75                  80

Trp Gln Asp Val Lys Ser His Glu Glu Met His His Asp Asn Phe Lys
                85                  90                  95

Glu Ile Tyr Glu Leu Cys Gly Ser Cys Leu Asp Met Val Ile Glu Gly
            100                 105                 110

Pro Trp Glu Pro Tyr Tyr Glu Ile Val Arg Ser Asp Leu Pro Arg Ile
        115                 120                 125

Met Gly Met Thr Asp Val Pro Ala Gln Leu Gly Ala Ala Phe Ala Ala
    130                 135                 140

Gln Lys Pro Val Ser Lys Val Ala Leu Ala Ser Gln Arg Cys Ile Ala
145                 150                 155                 160

Leu Gly Asp His Trp Val Ser Asp Gly His Glu Lys Asp Phe Glu Lys
                165                 170                 175

Gly Ala Val Ala Thr Leu Thr Trp Met Lys Glu Asn Ile Pro Gly Met
            180                 185                 190

Val Gly Trp Met Ile Leu Lys Gln Phe Gly Val Ser Ala Ile Gly Ser
        195                 200                 205

Phe Gln Leu Asp Pro Glu Gly Met Met Lys Ala Thr Leu Gly Ala Asn
    210                 215                 220

Pro Pro Ala Tyr Ala Thr Asn His Gly Thr Ala Ile Pro Asp Lys Pro
225                 230                 235                 240

Gln Ile Pro Gly Gln Arg Pro Thr Gln Tyr Leu Val His Met Glu Trp
                245                 250                 255

Glu Ser Pro Glu Met Ala His Met Gly Ile Gly Tyr Ala Met Val Asp
            260                 265                 270

Tyr Glu Leu Arg Gln Ile His Asn His Gly Val Leu Ala His Leu Asp
        275                 280                 285

Arg Gly Pro Tyr Tyr Leu Phe Phe Ala Pro Met Met Glu Gln Gly Gln
    290                 295                 300

Trp Arg Arg Lys Leu Val Leu
305                 310

<210> SEQ ID NO 88
<211> LENGTH: 306
<212> TYPE: PRT
<213> ORGANISM: Sulfobacillus thermosulfidooxidans

<400> SEQUENCE: 88

Met Pro Arg Pro Tyr Ile Ala Ile Asn Asp Ala Lys Val Val Asn Ala
1               5                   10                  15

Glu Ser Ser Phe Gln Ala Phe Gln Gln Val Gly Pro Lys Val Cys Met
                20                  25                  30

Val Thr Ala Asn His Pro Gly Phe Val Gly Phe Gln Asn His Val Gln
            35                  40                  45

Ile Gly Val Phe Pro Met Gly Gly Arg Tyr Gly Gly Ala Lys Met Asp
        50                  55                  60

Met His Glu Glu Leu Asn Pro Ile Gly Ile Arg Gln Tyr Thr Met Trp
65                  70                  75                  80

Lys Arg Trp Glu Asp His Glu Glu Met His Tyr Gln Gln Phe Asp Ser
                85                  90                  95

Ile Phe Arg Leu Cys Ser Ser Cys Leu Gly Met Val Val Glu Gly Pro
            100                 105                 110

```
Trp Glu Asp Met Tyr Glu Ile Ile Ser Ser Asp Leu Pro Glu Val Ile
        115                 120                 125

Ala Met Thr Asp Val Pro Ser Lys Leu Gly Ala Ala Phe Met Ala Gly
        130                 135                 140

Gln Gln Pro Ala Pro Val Ala Met Pro Tyr Gly Gln Arg Val Ile Ala
145                 150                 155                 160

Gly Ser Asp His Tyr Ile Ile Pro Gly Arg Glu Gln Glu Phe Glu Thr
                165                 170                 175

Ala Ile Thr Glu Leu Met Lys Met Phe Gln Lys Ala Pro Gly Phe Leu
                180                 185                 190

Gly Tyr Met Val Leu Lys Gln Ile Gly Ala Ser Ala Ile Gly Ser Phe
                195                 200                 205

Gln Leu Gln Pro Glu Gly Ile His Gln Ala Leu Gln Thr Leu Gly Asp
        210                 215                 220

Asn Pro Pro Lys Asn Lys Glu Gly Asn Phe Lys Leu Ile Glu Ala Lys
225                 230                 235                 240

Lys Thr Pro Thr Lys Tyr Leu Val His Met Glu Trp Ser Asp Leu Asn
                245                 250                 255

Ser Ala Met Phe Gly Ile Ser Arg Val Val Ile Asn Gly Arg Tyr Arg
        260                 265                 270

Ala Gln His Asp Lys Val Leu Ala Thr Val Leu Gln Gly Pro Tyr Val
        275                 280                 285

Thr Leu Trp Ser Pro Met Met Glu Asp Thr Ser Trp Arg Glu Tyr Leu
        290                 295                 300

Asn Glu
305

<210> SEQ ID NO 89
<211> LENGTH: 545
<212> TYPE: PRT
<213> ORGANISM: Gordonia sp.

<400> SEQUENCE: 89

Met Ser Arg Gln Ser Leu Thr Lys Ala His Ala Lys Ile Thr Glu Leu
1               5                   10                  15

Ser Trp Glu Pro Thr Phe Ala Thr Pro Ala Thr Arg Phe Gly Thr Asp
                20                  25                  30

Tyr Thr Phe Glu Lys Ala Pro Lys Lys Asp Pro Leu Lys Gln Ile Met
        35                  40                  45

Arg Ser Tyr Phe Pro Met Glu Glu Lys Asp Asn Arg Val Tyr Gly
50                  55                  60

Ala Met Asp Gly Ala Ile Arg Gly Asn Met Phe Arg Gln Val Gln Glu
65                  70                  75                  80

Arg Trp Leu Glu Trp Gln Lys Leu Phe Leu Ser Ile Ile Pro Phe Pro
                85                  90                  95

Glu Ile Ser Ala Ala Arg Ala Met Pro Met Ala Ile Asp Ala Val Pro
            100                 105                 110

Asn Pro Glu Ile His Asn Gly Leu Ala Val Gln Met Ile Asp Glu Val
        115                 120                 125

Arg His Ser Thr Ile Gln Met Asn Leu Lys Lys Leu Tyr Met Asn Asn
        130                 135                 140

Tyr Ile Asp Pro Ala Gly Phe Asp Ile Thr Glu Lys Ala Phe Ala Asn
145                 150                 155                 160

Asn Tyr Ala Gly Thr Ile Gly Arg Gln Phe Gly Glu Gly Phe Ile Thr
```

```
                   165                 170                 175
Gly Asp Ala Ile Thr Ala Ala Asn Ile Tyr Leu Thr Val Val Ala Glu
            180                 185                 190

Thr Ala Phe Thr Asn Thr Leu Phe Val Ala Met Pro Asp Glu Ala Ala
        195                 200                 205

Ala Asn Gly Asp Tyr Leu Leu Pro Thr Val Phe His Ser Val Gln Ser
    210                 215                 220

Asp Glu Ser Arg His Ile Ser Asn Gly Tyr Ser Ile Leu Leu Met Ala
225                 230                 235                 240

Leu Ala Asp Glu Arg Asn Arg Pro Leu Leu Glu Arg Asp Leu Arg Tyr
                245                 250                 255

Ala Trp Trp Asn Asn His Cys Val Val Asp Ala Ala Ile Gly Thr Phe
            260                 265                 270

Ile Glu Tyr Gly Thr Lys Asp Arg Arg Lys Asp Arg Glu Ser Tyr Ala
        275                 280                 285

Glu Met Trp Arg Arg Trp Ile Tyr Asp Asp Tyr Tyr Arg Ser Tyr Leu
    290                 295                 300

Leu Pro Leu Glu Lys Tyr Gly Leu Thr Ile Pro His Asp Leu Val Glu
305                 310                 315                 320

Glu Ala Trp Asn Arg Ile Val Asp Lys His Tyr Val His Glu Val Ala
                325                 330                 335

Arg Phe Phe Ala Thr Gly Trp Pro Val Asn Tyr Trp Arg Ile Asp Ala
            340                 345                 350

Met Thr Asp Thr Asp Phe Glu Trp Phe Glu Glu Lys Tyr Pro Gly Trp
        355                 360                 365

Tyr Asn Lys Phe Gly Lys Trp Trp Glu Asn Tyr Asn Arg Leu Ala Tyr
    370                 375                 380

Pro Gly Lys Asn Lys Pro Ile Ala Phe Glu Asp Val Asp Tyr Glu Tyr
385                 390                 395                 400

Pro His Arg Cys Trp Thr Cys Met Val Pro Cys Leu Ile Arg Glu Asp
                405                 410                 415

Met Val Thr Asp Lys Val Asp Gly Gln Trp Arg Thr Tyr Cys Ser Glu
            420                 425                 430

Thr Cys Ala Trp Thr Asp Lys Val Ala Phe Arg Pro Glu Tyr Glu Gly
        435                 440                 445

Arg Pro Thr Pro Asn Met Gly Arg Leu Thr Gly Phe Arg Glu Trp Glu
    450                 455                 460

Thr Leu His His Gly Lys Asp Leu Ala Asp Ile Ile Thr Asp Leu Gly
465                 470                 475                 480

Tyr Val Arg Asp Asp Gly Lys Thr Leu Ile Pro Gln Pro His Leu Asp
                485                 490                 495

Leu Asp Pro Lys Lys Met Trp Thr Leu Asp Asp Val Arg Gly Ile Pro
            500                 505                 510

Phe Gly Ser Pro Asn Val Ala Leu Asn Glu Met Ser Asp Asp Glu Arg
        515                 520                 525

Glu Ala His Ile Ala Ala Tyr Met Ala Asn Lys Asn Gly Ala Val Thr
    530                 535                 540

Val
545

<210> SEQ ID NO 90
<211> LENGTH: 368
<212> TYPE: PRT
<213> ORGANISM: Gordonia sp.
```

<400> SEQUENCE: 90

| Met | Ser | Ala | Pro | Ala | Gln | Pro | Arg | Glu | Arg | Ser | Phe | Pro | Ser | Ile | Glu |
|---|---|---|---|---|---|---|---|---|---|---|---|---|---|---|---|
| 1 | | | | 5 | | | | | 10 | | | | | 15 | |

| Phe | Thr | Asp | Ala | Glu | Ala | Asp | Ala | Arg | Glu | Phe | Pro | Ser | Ser | Arg | Ser |
|---|---|---|---|---|---|---|---|---|---|---|---|---|---|---|---|
| | | | 20 | | | | | 25 | | | | | 30 | | |

| Arg | Lys | Tyr | Asn | Tyr | Tyr | Gln | Pro | Ser | Lys | Lys | Arg | Ala | Thr | Ile | Tyr |
|---|---|---|---|---|---|---|---|---|---|---|---|---|---|---|---|
| | | | 35 | | | | | 40 | | | | | 45 | | |

| Glu | Asp | Val | Thr | Val | Asp | Val | Gln | Pro | Asp | Pro | Glu | Arg | His | Leu | Thr |
|---|---|---|---|---|---|---|---|---|---|---|---|---|---|---|---|
| 50 | | | | | 55 | | | | | 60 | | | | | |

| Gln | Gly | Trp | Ile | Tyr | Gly | Phe | Gly | Asp | Gly | Pro | Gly | Gly | Tyr | Pro | Lys |
|---|---|---|---|---|---|---|---|---|---|---|---|---|---|---|---|
| 65 | | | | 70 | | | | | 75 | | | | | 80 | |

| Glu | Trp | Thr | Ser | Ala | Gln | Ser | Ser | Asn | Trp | His | Gln | Phe | Leu | Asp | Pro |
|---|---|---|---|---|---|---|---|---|---|---|---|---|---|---|---|
| | | | | 85 | | | | | 90 | | | | | 95 | |

| Asn | Glu | Glu | Trp | Glu | Gln | Ser | Ile | Tyr | Arg | Asn | Asn | Ser | Ala | Val | Val |
|---|---|---|---|---|---|---|---|---|---|---|---|---|---|---|---|
| | | | 100 | | | | | 105 | | | | | 110 | | |

| His | Gln | Val | Asp | Leu | Cys | Leu | Gln | Asn | Ala | Lys | Arg | Ala | Arg | Ala | Tyr |
|---|---|---|---|---|---|---|---|---|---|---|---|---|---|---|---|
| | | | 115 | | | | | 120 | | | | | 125 | | |

| Asp | Gly | Trp | Asn | Ser | Ala | Trp | Leu | Lys | Phe | Ile | Glu | Arg | Asn | Leu | Gly |
|---|---|---|---|---|---|---|---|---|---|---|---|---|---|---|---|
| | 130 | | | | | 135 | | | | | 140 | | | | |

| Ala | Trp | Met | His | Ala | Glu | Ser | Gly | Met | Gly | Leu | His | Val | Phe | Thr | Ser |
|---|---|---|---|---|---|---|---|---|---|---|---|---|---|---|---|
| 145 | | | | | 150 | | | | | 155 | | | | | 160 |

| Ile | Gln | Arg | Ser | Ala | Pro | Thr | Asn | Met | Ile | Asn | Asn | Ala | Val | Cys | Val |
|---|---|---|---|---|---|---|---|---|---|---|---|---|---|---|---|
| | | | | 165 | | | | | 170 | | | | | 175 | |

| Asn | Ala | Ala | His | Lys | Leu | Arg | Phe | Ala | Gln | Asp | Leu | Ala | Leu | Phe | Asn |
|---|---|---|---|---|---|---|---|---|---|---|---|---|---|---|---|
| | | | 180 | | | | | 185 | | | | | 190 | | |

| Leu | Asp | Leu | Ser | Glu | Ala | Glu | Glu | Ala | Phe | Asp | Gly | Ser | Ala | His | Lys |
|---|---|---|---|---|---|---|---|---|---|---|---|---|---|---|---|
| | | | 195 | | | | | 200 | | | | | 205 | | |

| Glu | Val | Trp | Gln | Ser | Ala | Pro | Glu | Trp | Gln | Pro | Thr | Arg | Glu | Ala | Val |
|---|---|---|---|---|---|---|---|---|---|---|---|---|---|---|---|
| | 210 | | | | | 215 | | | | | 220 | | | | |

| Glu | Arg | Leu | Thr | Ala | Ile | Gly | Asp | Trp | Ala | Leu | Leu | Phe | Cys | Ser |
|---|---|---|---|---|---|---|---|---|---|---|---|---|---|---|
| 225 | | | | | 230 | | | | | 235 | | | | | 240 |

| Asn | Ile | Val | Phe | Glu | Gln | Leu | Val | Gly | Ser | Leu | Phe | Arg | Ser | Glu | Leu |
|---|---|---|---|---|---|---|---|---|---|---|---|---|---|---|---|
| | | | | 245 | | | | | 250 | | | | | 255 | |

| Val | Met | Gln | Val | Ala | Ala | Arg | Asn | Gly | Asp | Tyr | Ile | Thr | Pro | Thr | Ile |
|---|---|---|---|---|---|---|---|---|---|---|---|---|---|---|---|
| | | | 260 | | | | | 265 | | | | | 270 | | |

| Val | Gly | Thr | Gly | Glu | Tyr | Asp | Tyr | Asp | Arg | Asp | Leu | Asn | Tyr | Ser | Arg |
|---|---|---|---|---|---|---|---|---|---|---|---|---|---|---|---|
| | | | 275 | | | | | 280 | | | | | 285 | | |

| Ala | Leu | Phe | Gln | Met | Leu | Ala | Arg | Asp | Glu | Lys | His | Gly | Ile | Asp | Asn |
|---|---|---|---|---|---|---|---|---|---|---|---|---|---|---|---|
| | 290 | | | | | 295 | | | | | 300 | | | | |

| Arg | Lys | Leu | Phe | Ser | Arg | Trp | Met | Ser | Glu | Trp | Phe | Pro | Gly | Ala | Ser |
|---|---|---|---|---|---|---|---|---|---|---|---|---|---|---|---|
| 305 | | | | | 310 | | | | | 315 | | | | | 320 |

| Thr | Arg | Ala | Arg | Gly | Leu | Gln | Pro | Ile | Trp | Ser | Gln | Pro | Ala | Asp | Lys |
|---|---|---|---|---|---|---|---|---|---|---|---|---|---|---|---|
| | | | | 325 | | | | | 330 | | | | | 335 | |

| Ser | Val | Thr | Phe | Ser | Ser | Ser | Leu | Glu | His | Ala | Lys | Thr | Lys | Phe | Ala |
|---|---|---|---|---|---|---|---|---|---|---|---|---|---|---|---|
| | | | 340 | | | | | 345 | | | | | 350 | | |

| Asp | Val | Leu | Ala | Ala | Ile | Asp | Val | Asp | Ile | Pro | Glu | Glu | Leu | Asn | Lys |
|---|---|---|---|---|---|---|---|---|---|---|---|---|---|---|---|
| | | | 355 | | | | | 360 | | | | | 365 | | |

<210> SEQ ID NO 91
<211> LENGTH: 346
<212> TYPE: PRT
<213> ORGANISM: Gordonia sp.

<400> SEQUENCE: 91

Met Ala Asp Thr His Lys Ile Ser Phe Glu Pro Val Asp Ile Glu Met
1               5                   10                  15

Glu Val Gly Glu Asp Glu Thr Ile Leu Asp Ala Ala Phe Arg Gln Glu
            20                  25                  30

Ser Thr Ser Cys Thr Ala Ala Arg Pro Leu Phe Gly Cys Lys Ser
        35                  40                  45

Tyr Met Leu Glu Gly Asp Val Gln Met Asp Asp Tyr Ser Thr Phe Ala
    50                  55                  60

Cys Asn Asp Ala Glu Glu Ala Glu Gly Tyr Val Leu Leu Cys Arg Thr
65                  70                  75                  80

Tyr Ala Tyr Ser Asp Cys Glu Ile Glu Leu Leu Asn Phe Asp Glu Asp
                85                  90                  95

Glu Leu Leu Gly Gly Ala Pro Ile Gln Asp Val Thr Thr Lys Val Ala
                100                 105                 110

Ala Ile Glu Pro Met Thr Pro Asp Ile Val Ser Leu Lys Leu Asp Val
        115                 120                 125

Val Glu Pro Glu Ser Val Glu Phe Lys Ser Gly Gln Tyr Phe Asp Leu
    130                 135                 140

Phe Ile Pro Gly Thr Glu Asp Lys Arg Ser Phe Ser Ile Ala Thr Thr
145                 150                 155                 160

Pro Ala Thr Pro Asp Arg Leu Glu Phe Leu Ile Lys Lys Tyr Pro Gly
                165                 170                 175

Gly Leu Phe Ala Gly Met Leu Thr Asp Gly Leu Ser Val Gly Gln Glu
                180                 185                 190

Ile Lys Leu Asn Gly Pro Tyr Gly Ser Cys Thr Leu Arg Asn Gly His
        195                 200                 205

Val Leu Pro Ile Val Ala Ile Gly Gly Ala Gly Met Ala Pro Leu
    210                 215                 220

Leu Ser Leu Leu Arg His Ile Ser Glu Thr Gly Leu Asn Arg Pro Val
225                 230                 235                 240

Arg Phe Tyr Tyr Gly Ala Arg Thr Ala Ala Asp Leu Phe Leu Leu Asp
                245                 250                 255

Glu Ile Ala Thr Leu Gly Glu Lys Ile Asp Asp Phe Ser Phe Thr Ala
                260                 265                 270

Cys Leu Ser Glu Ser Thr Asp Asn Ala Pro Glu Gly Val Thr Val Ile
        275                 280                 285

Gly Gly Asn Val Thr Asp Ile Val Asn Asp Asn Glu Ala Asp Leu Ala
        290                 295                 300

Arg Thr Glu Val Tyr Phe Cys Ala Pro Pro Met Val Asp Ala Ala
305                 310                 315                 320

Leu Ala Leu Ala Glu Gln His Ser Val Pro His Asp Gln Ile Phe Tyr
                325                 330                 335

Asp Lys Phe Thr Ser Pro Ala Phe Asp Ser
                340                 345

<210> SEQ ID NO 92
<211> LENGTH: 111
<212> TYPE: PRT
<213> ORGANISM: Gordonia sp.

<400> SEQUENCE: 92

Met Gln Phe Gly Ala Asp Thr Glu Phe Ser Asn Met Cys Gly Val Thr
1               5                   10                  15

Leu Met Asn Thr Pro Ile Gly Arg Val Val Ala Asp Val Met Gly Ala

```
            20                  25                  30
Lys Asp Gly Val Glu Leu Thr Glu Tyr Pro Ser Met Ile Arg Val Asp
        35                  40                  45

Gly Val Asn Arg Leu Asp Phe Asp Tyr Asp Glu Leu Thr Asp Ala Leu
    50                  55                  60

Gly Gln Asp Phe Asp Gly Ser Ile Phe Glu Ile Ser Ser Thr His
65                  70                  75                  80

Tyr Gly Arg Met Val His Leu Asp Asp Lys Thr Ile Leu Phe Ala Ser
                85                  90                  95

Pro Glu Asp Ala Ala Glu Phe Ile Gly Phe Asp Leu Thr Ala Ser
            100                 105                 110

<210> SEQ ID NO 93
<211> LENGTH: 568
<212> TYPE: PRT
<213> ORGANISM: Thauera butanivorans

<400> SEQUENCE: 93

Met Ile Ser Leu Asn Cys Lys Lys Thr Thr Thr Gly Leu Thr Ala His
1               5                   10                  15

Leu Ala Leu Val Arg Gly Met Lys Ala Leu Ala Glu Leu Val Gly Thr
            20                  25                  30

Thr Leu Gly Pro Gln Gly Arg His Val Met Leu Ala His Arg Ala Gly
        35                  40                  45

Leu Ala Pro His Val Ser Lys Asp Gly Val Glu Val Ala Arg His Leu
    50                  55                  60

Ser Leu Pro Asp Ser Glu Glu Leu Gly Val Arg Leu Leu Arg Asn
65                  70                  75                  80

Ala Ala Val Ala Val Ser Glu Ser Phe Gly Asp Gly Thr Ser Thr Ala
                85                  90                  95

Thr Val Phe Thr Ala Asp Leu Ala Val Arg Ala Leu Lys Leu Ile Gly
            100                 105                 110

Ala Gly Ala Asp Thr Leu Glu Val Arg Arg Gly Leu Gly Leu Ala Ala
        115                 120                 125

Tyr Ala Ala Leu Val Ala Leu Asn Asp Met Ala Arg Arg Ala Asp Arg
    130                 135                 140

Gly Met Leu Thr Ala Val Ala Gln Thr Ala Ala Asn Gly Asp Arg Arg
145                 150                 155                 160

Val Ala Asp Leu Leu Val Glu Ala Phe Glu Arg Val Gly Ala Glu Gly
                165                 170                 175

Thr Ile Glu Val Glu Met Gly Asn Ser Val Glu Asp Val Leu Glu Val
            180                 185                 190

Ala Gln Gly Ser Tyr Phe Asp Thr Val Pro Leu Val Thr Ala Leu Leu
        195                 200                 205

Pro Pro Thr Gly Gln Val Glu Phe Ala Arg Pro Leu Ile Leu Phe His
    210                 215                 220

Cys Asp Ala Ile Glu Thr Ala Asp Glu Ile Leu Pro Ala Leu Glu Leu
225                 230                 235                 240

Ala Arg Ser Ser Arg Arg Pro Leu Leu Ile Leu Ala Asp Ser Val Gly
                245                 250                 255

Ile Asp Val Glu Thr Leu Leu Val Arg Asn Gln Asn Glu Gly Thr Leu
            260                 265                 270

Ala Val Ala Val Val Arg Ala Pro Met Tyr Gly Asp Thr Arg Arg Glu
        275                 280                 285
```

```
Ala Leu Leu Asp Leu Thr Ser Lys Phe Gly Thr Ala Phe Gly Arg
        290                 295                 300

Glu Gly Phe Val Glu Phe Ala Leu Arg Ser Leu Gly Ser Leu Glu
305                 310                 315                 320

Gly Asp Leu Gly Gln Ala Asp Glu Ala Ile Leu Glu Ala Asp Gly Val
                325                 330                 335

Thr Leu Arg Gly Ala Gly Asn Asn Pro Ser Ala Leu Glu Asp Arg Ile
            340                 345                 350

Ala Leu Val Arg Ala Glu Leu Asp Arg Gly Asp Val Ser Val Gly Asp
                355                 360                 365

Ser Pro Ser Ala Lys Leu Asp Tyr Ile Glu Lys Arg Lys Glu Arg Leu
370                 375                 380

Lys Leu Ala Ala Gly Ser Ala Lys Leu His Ile Gly Gly Pro Thr
385                 390                 395                 400

Asp Val Glu Ile Lys Thr Arg Leu Pro Leu Ala Glu Asn Ala His Arg
                405                 410                 415

Ala Leu Leu Ala Ala Lys Ser Gly Val Leu Pro Gly Gly Gly Val
                420                 425                 430

Ala Met Ile Arg Ala Ala Glu Lys Val Gln Gln Glu Met Gly Arg Leu
                435                 440                 445

Glu Gly Asp Val Ala Ser Gly Ala Ser Ile Phe Leu Gln Ser Leu Asp
450                 455                 460

Thr Pro Ile Arg Trp Ile Ala Arg Asn Ala Gly Leu Arg Pro Asp Glu
465                 470                 475                 480

Val Leu Ala Arg Thr Leu Ala Asn Glu Ser Asp Phe Tyr Gly Leu Asn
                485                 490                 495

Ala Met Thr Gly Arg Tyr Gly Asp Leu Ala Glu Asp Gly Val Leu Asp
                500                 505                 510

Ala Leu Asp Met Val Thr Asp Val Ile Arg Val Ala Val Ser Val Val
                515                 520                 525

Gly Ser Met Leu Gly Val Gly Ala Leu Val Thr Arg Ala Ser Pro Lys
                530                 535                 540

Pro Ala Pro Glu Arg Phe Lys Gly Thr Glu Arg Val His Asp Lys Leu
545                 550                 555                 560

Met Arg Glu Gly Gly Phe Asp Glu
                565

<210> SEQ ID NO 94
<211> LENGTH: 364
<212> TYPE: PRT
<213> ORGANISM: Thauera butanivorans

<400> SEQUENCE: 94

Met Leu Met Gln Gln Tyr Lys Ile Val Ala Arg Phe Glu Asp Gly Val
 1               5                  10                  15

Thr Tyr Glu Tyr Asp Cys Gly Glu Asp Glu Asn Leu Leu Ala Ala Ala
            20                  25                  30

Leu Arg Gln Asn Val Arg Leu Leu Cys Gln Cys Arg Lys Ala Phe Cys
        35                  40                  45

Gly Ser Cys Lys Ala Leu Cys Ser Glu Gly Asp Tyr Glu Leu Gly Asp
    50                  55                  60

His Ile Asn Val Gln Val Leu Pro Pro Asp Glu Glu Asp Gly Val
65                  70                  75                  80

Val Val Thr Cys Asp Thr Phe Pro Arg Ser Asp Leu Val Leu Glu Phe
                85                  90                  95
```

Pro Tyr Thr Ser Asp Arg Leu Gly Thr Val Thr Ala Thr Glu Ala Lys
            100                 105                 110

Thr Ser Val Val Ser Val Glu Arg Leu Ser Ser Thr Val Tyr Arg Leu
        115                 120                 125

Val Leu Gln Ala Leu Asp Ala Glu Gly Met Pro Ala Arg Phe Asp Phe
    130                 135                 140

Val Pro Gly Gln Tyr Val Glu Ile Ser Thr Ala Asp Ser Leu Glu Thr
145                 150                 155                 160

Arg Ala Phe Ser Leu Ala Asn Leu Pro Asn Asp Ala Gly Leu Leu Glu
                165                 170                 175

Phe Leu Ile Arg Leu Val Pro Gly Gly Tyr Tyr Ala Ala Tyr Leu Glu
            180                 185                 190

Gln Arg Ala Ala Gly Gln Thr Ile Asn Val Lys Gly Pro Phe Gly
        195                 200                 205

Glu Phe Val Leu Arg Glu His Glu Leu Val Glu Asp Phe Thr Leu Pro
    210                 215                 220

Ala Asp Ser Pro Ala Arg Gly Gly Thr Ile Ala Phe Leu Ala Gly Ser
225                 230                 235                 240

Thr Gly Leu Ala Pro Leu Ala Ser Met Leu Arg Glu Leu Gly Arg Arg
                245                 250                 255

Gly Phe Asn Gly Glu Cys His Leu Phe Phe Gly Met Gln Asp Thr Ala
            260                 265                 270

Thr Met Phe Tyr Glu Lys Glu Leu Arg Asp Ile Lys Arg Thr Leu Pro
        275                 280                 285

Gly Leu Thr Leu His Leu Ala Leu Met Val Pro Ser Ala Glu Trp Glu
    290                 295                 300

Gly Tyr Arg Gly Asn Ala Val Ala Ala Phe Lys Glu His Phe Ala Ala
305                 310                 315                 320

Ser Ser Gln Ile Pro Glu Asn Val Tyr Leu Cys Gly Pro Gly Pro Met
                325                 330                 335

Ile Ala Ala Ala Leu Gly Ala Cys Arg Glu Leu Gly Ile Pro Asp Asn
            340                 345                 350

Arg Val His Arg Glu Glu Phe Val Ala Ser Gly Gly
        355                 360

<210> SEQ ID NO 95
<211> LENGTH: 168
<212> TYPE: PRT
<213> ORGANISM: Thauera butanivorans

<400> SEQUENCE: 95

Met Ser Lys Gln Val Trp Tyr Asn Thr Pro Val Arg Asp Glu Trp Ile
1               5                   10                  15

Glu Lys Ile Thr Ala Ile Arg Thr Ala Arg Glu Gly Thr Asp Met Leu
            20                  25                  30

Ala Arg Phe Arg Ala Glu His Thr Gly Pro Asp Arg Thr Thr Tyr Asp
        35                  40                  45

Leu Lys Lys Glu Tyr Asn Trp Ile Glu Ser Arg Ile Glu Met Arg Val
    50                  55                  60

Ser Gln Leu His Ala Glu Ala Thr Ala Ser Asp Glu Asp Leu Leu Thr
65                  70                  75                  80

Lys Thr Ile Asp Gly Arg Cys Ala Lys Glu Val Ala Ala Glu Trp Leu
                85                  90                  95

Lys Lys Ala Ala Asp Ile Asp Cys His Tyr Glu Met Glu Arg Leu Cys

```
                100             105             110
Val Ala Phe Arg Lys Ala Cys Lys Pro Pro Met Met Pro Ile Asn Phe
            115                 120                 125

Phe Ala Pro Ala Glu Lys Glu Leu Val Ala Lys Leu Met Lys Leu Arg
    130                 135                 140

Ala Pro Thr Tyr Leu Thr Thr Ser Leu Asp Glu Leu Arg Glu Ala Arg
145                 150                 155                 160

Gly Val Thr Met Ile Ser Val Gln
                165
```

<210> SEQ ID NO 96
<211> LENGTH: 87
<212> TYPE: PRT
<213> ORGANISM: Thauera butanivorans

<400> SEQUENCE: 96

```
Met Lys Glu Ala Pro Ala Ile Pro Asp Leu Pro Gly Leu Pro Glu Thr
1               5                   10                  15

Val Gly Glu Pro Thr Leu Val Leu Glu Asp Gly Phe Arg Val Phe
                20                  25                  30

Ala Thr Glu Leu Thr Ile Met Trp Arg Trp Asp Ile Tyr Asn Gly Asp
            35                  40                  45

Ala His Val His Thr Gly Cys Ala Gln His Pro Glu Ser Cys Val Val
        50                  55                  60

Ala Ala Arg Ser Lys Ile Arg Phe Leu Arg Arg Pro Thr Val Ala Met
65                  70                  75                  80

Leu Leu Gly Gly Glu Gly Gln
                85
```

<210> SEQ ID NO 97
<211> LENGTH: 137
<212> TYPE: PRT
<213> ORGANISM: Thauera butanivorans

<400> SEQUENCE: 97

```
Met Ser Asn Val Asn Ala Tyr His Ala Gly Thr Asn Gly Lys Glu Gly
1               5                   10                  15

Gln Asp Phe Ile Asp Asp Phe Leu Ser Glu Glu Asn Ser Ala Leu Pro
                20                  25                  30

Thr Ser Glu Ala Val Val Leu Ala Leu Met Lys Thr Glu Glu Ile Asp
            35                  40                  45

Ala Val Val Asp Glu Met Ile Lys Pro Gln Met Glu Asp Asn Pro Thr
        50                  55                  60

Ile Ala Val Glu Asp Arg Gly Gly Tyr Trp Trp Ile Lys Ala Asn Gly
65                  70                  75                  80

Lys Ile Val Ile Asp Cys Asp Glu Ala Thr Glu Leu Leu Gly Lys Lys
                85                  90                  95

Tyr Thr Val Tyr Asp Leu Leu Val Asn Val Ser Thr Thr Val Gly Arg
                100                 105                 110

Ala Met Thr Leu Gly Asn Gln Phe Ile Ile Thr Asn Glu Leu Leu Gly
            115                 120                 125

Leu Glu Thr Lys Val Glu Ser Val Tyr
            130                 135
```

<210> SEQ ID NO 98
<211> LENGTH: 391
<212> TYPE: PRT

<213> ORGANISM: Thauera butanivorans

<400> SEQUENCE: 98

```
Met Ser Thr Asn Ile Phe Thr Arg Gly Met Val Asp Pro Glu Arg Gln
  1               5                  10                  15

Ala Cys Ile Gln Glu Val Val Pro Lys Ala Pro Leu Glu Thr Lys Arg
             20                  25                  30

Asp His Ile Pro Phe Ala Lys Arg Gly Trp Arg Arg Leu Thr Glu Tyr
         35                  40                  45

Glu Ala Val Met Leu His Ala Gln Asn Ser Leu Asp Ala Val Pro Gly
     50                  55                  60

Ser Gln Glu Val Gly Val Val Gln Lys Trp Pro Gly Gly Arg Pro
 65                  70                  75                  80

Asn Tyr Gly Val Glu Ser Thr Ala Ala Leu Ser Ser Asn Trp Phe His
                 85                  90                  95

Phe Arg Asp Pro Ser Lys Arg Trp Phe Met Pro Tyr Val Lys Gln Lys
            100                 105                 110

Asn Glu Glu Gly Gln Thr Ala Glu Arg Ala Met Lys Ser Trp Ala Glu
        115                 120                 125

Gly Gly Asp Ala Glu Met Met Asn Ala Ala Trp Arg Glu His Ile Leu
130                 135                 140

Ala Arg His Tyr Gly Ala Phe Val Tyr Asn Glu Tyr Gly Leu Phe Ser
145                 150                 155                 160

Ala His Ser Thr Thr Val Tyr Gly Gly Leu Ser Asp Leu Ile Lys Thr
                165                 170                 175

Trp Ile Ala Glu Ala Ala Phe Asp Lys Asn Asp Ala Gly Gln Met Ile
            180                 185                 190

Gln Met Gln Arg Val Leu Leu Ser Lys Val Phe Pro Gly Phe Asp Ala
        195                 200                 205

Asp Leu Ala Glu Ala Lys Gln Ala Trp Thr Glu Asp Lys Ser Trp Lys
210                 215                 220

Pro Ala Arg Glu Phe Val Glu His Ile Trp Ala Glu Thr Tyr Asp Trp
225                 230                 235                 240

Val Glu Gln Leu Trp Ala Ile His Ala Val Tyr Asp His Ile Phe Gly
                245                 250                 255

Gln Phe Val Arg Arg Glu Phe Phe Gln Arg Leu Gly Gly Ile His Gly
            260                 265                 270

Asp Thr Leu Thr Pro Phe Ile Gln Asn Gln Ala Leu Thr Tyr His Leu
        275                 280                 285

Gln Ala Arg Asp Gly Val Thr Ala Leu Cys Phe Lys Phe Leu Ile Glu
290                 295                 300

Asp Glu Pro Val Tyr Ala Gln His Asn Arg Arg Tyr Leu Arg Ala Trp
305                 310                 315                 320

Thr Gly Arg Tyr Leu Pro Gln Val Gly Arg Ala Leu Lys Ala Phe Leu
                325                 330                 335

Ala Ile Tyr Lys Glu Val Pro Val Lys Ile Asp Gly Val Thr Cys Arg
            340                 345                 350

Glu Gly Val Arg Ala Ser Val Glu Arg Val Val Asp Asp Trp Ala Ala
        355                 360                 365

Arg Phe Ala Glu Pro Ile Asn Phe Lys Phe Asn Arg Ala Ala Phe Ile
370                 375                 380

Asp Asp Val Leu Ser Gly Tyr
385                 390
```

<210> SEQ ID NO 99
<211> LENGTH: 530
<212> TYPE: PRT
<213> ORGANISM: Thauera butanivorans

<400> SEQUENCE: 99

```
Met Ser Ala Asn Met Ala Val Lys Gln Ala Leu Lys Ala Asn Pro Val
1               5                   10                  15

Pro Ser Ser Val Asp Pro Gln Glu Val His Lys Trp Leu Gln Asp Phe
            20                  25                  30

Thr Trp Asp Phe Lys Gly Lys Thr Ala Lys Tyr Pro Thr Lys Tyr Glu
        35                  40                  45

Met Asp Val Asn Thr Arg Glu Gln Phe Lys Leu Thr Ala Lys Glu Tyr
    50                  55                  60

Ala Arg Met Glu Ser Ile Lys Glu Glu Arg Gln Tyr Gly Thr Leu Leu
65                  70                  75                  80

Asp Gly Leu Asp Arg Leu Asp Ala Gly Asn Lys Val His Pro Lys Trp
                85                  90                  95

Gly Glu Val Met Lys Leu Val Ser Asn Phe Leu Glu Thr Gly Glu Tyr
            100                 105                 110

Gly Ala Ile Ala Gly Ser Ala Leu Leu Trp Asp Thr Ala Gln Ser Pro
        115                 120                 125

Glu Gln Arg Asn Gly Tyr Leu Ala Gln Val Ile Asp Glu Ile Arg His
    130                 135                 140

Val Asn Gln Thr Ala Tyr Val Asn Tyr Tyr Gly Lys His Tyr Tyr
145                 150                 155                 160

Asp Pro Ala Gly His Thr Asn Met Arg Gln Leu Arg Ala Ile Asn Pro
                165                 170                 175

Leu Tyr Pro Gly Val Lys Arg Ala Phe Gly Glu Gly Phe Leu Ala Gly
            180                 185                 190

Asp Ala Val Glu Ser Ser Ile Asn Leu Gln Leu Val Gly Glu Ala Cys
        195                 200                 205

Phe Thr Asn Pro Leu Ile Val Ser Leu Thr Glu Trp Ala Ala Ala Asn
    210                 215                 220

Gly Asp Glu Ile Thr Pro Thr Val Phe Leu Ser Ile Glu Thr Asp Glu
225                 230                 235                 240

Leu Arg His Met Ala Asn Gly Tyr Gln Thr Ile Val Ser Ile Met Asn
                245                 250                 255

Asn Pro Glu Thr Met Lys Tyr Leu Gln Thr Asp Leu Asp Asn Ala Phe
            260                 265                 270

Trp Thr Gln His Lys Phe Leu Thr Pro Phe Val Gly Val Ala Leu Glu
        275                 280                 285

Tyr Gly Ser Lys Tyr Lys Val Glu Pro Trp Ala Lys Ser Trp Asn Arg
    290                 295                 300

Trp Val Tyr Glu Asp Trp Ala Gly Ile Trp Leu Gly Arg Leu Gln Gln
305                 310                 315                 320

Phe Gly Val Lys Thr Pro Lys Cys Leu Pro Asp Ala Lys Lys Asp Ala
                325                 330                 335

Val Trp Ala His His Asp Leu Ala Leu Leu Ala Leu Ala Leu Trp Pro
            340                 345                 350

Leu Thr Gly Ile Arg Met Glu Leu Pro Asp Ser Leu Ala Met Glu Trp
        355                 360                 365

Phe Glu Ala Asn Tyr Pro Gly Trp Tyr Asn His Tyr Gly Lys Ile Tyr
    370                 375                 380
```

Glu Glu Trp Arg Ala Ala Gly Phe Glu Asp Pro Lys Ser Gly Phe Cys
385                 390                 395                 400

Gly Ala Leu Trp Leu Met Glu Arg Gly His Gly Ile Phe Val Asp His
            405                 410                 415

Ala Ser Gly Leu Pro Phe Cys Pro Ser Leu Ala Lys Ser Ser Ile Lys
        420                 425                 430

Pro Arg Phe Thr Glu Tyr Asn Gly Lys Arg Tyr Ala Phe Ala Glu Pro
    435                 440                 445

Tyr Gly Glu Arg Gln Trp Leu Leu Glu Pro Glu Arg Tyr Glu Phe Gln
450                 455                 460

Asn Phe Phe Glu Gln Phe Glu Gly Trp Glu Leu Ser Asp Leu Val Lys
465                 470                 475                 480

Ala Ala Gly Gly Val Arg Ser Asp Gly Lys Thr Leu Ile Ala Gln Pro
                485                 490                 495

His Leu Arg Asp Thr Asp Met Trp Thr Leu Asp Asp Leu Lys Arg Ile
            500                 505                 510

Asn Leu Thr Ile Pro Asp Pro Met Lys Ile Leu Asn Trp Gln Pro Val
        515                 520                 525

Ala Gln
    530

<210> SEQ ID NO 100
<211> LENGTH: 255
<212> TYPE: PRT
<213> ORGANISM: Nocardioides sp.

<400> SEQUENCE: 100

Met Thr Val Ala Thr Glu Ser Val Glu Thr Pro Gln His Pro Pro Pro
1               5                   10                  15

Thr Arg Met Ile Gly Arg Arg Trp Asp Ile Leu Leu Val Ala Ser Ala
            20                  25                  30

Leu Leu Leu Val Ala Gly Ala Ala His Leu Asn Asn Met Leu Phe Val
        35                  40                  45

Gly Asp Trp Ser Phe Trp Val Asp Trp Lys Asp Arg Gln Trp Trp Pro
50                  55                  60

Leu Leu Thr Pro Ala Leu Ser Ile Ile Val Pro Ala Ala Leu Gln Tyr
65                  70                  75                  80

Ile Thr Trp Thr Gln Leu Arg Leu Pro Phe Gly Ala Thr Leu Gly Ala
                85                  90                  95

Val Ala Leu Val Leu Ala Glu Trp Val Ser Arg Tyr Phe Ser Phe Glu
            100                 105                 110

Trp Trp Ala Asn Ile Pro Leu Asn Phe Thr Trp Pro Glu Thr Leu Val
        115                 120                 125

Leu Ala Ala Val Val Leu Asp Val Ile Leu Leu Ile Thr Arg Ser Phe
130                 135                 140

Phe Leu Thr Ser Leu Phe Gly Gly Leu Met Trp Gly Phe Val Phe Trp
145                 150                 155                 160

Phe Phe Asn Trp Pro Ala Leu Ala Pro Phe Met Gln Pro Val Glu Phe
                165                 170                 175

His Gly Tyr Ile Val Thr Val Ala Asp Val Met Ser Phe Asn Ile Val
            180                 185                 190

Arg Thr Gln Thr Pro Glu Tyr Leu Arg Ile Ile Glu Glu Gly Arg Leu
        195                 200                 205

Arg Ala Leu Val Glu Asn Ile Thr Met Val Val Ser Phe Phe Ala Gly

```
                210                 215                 220
Met Leu Ser Ala Ala Val Tyr Trp Phe Gly Leu Ala Ile Gly Lys Phe
225                 230                 235                 240

Leu Ala Val Ala Pro Ala Gly Arg Phe Phe Arg Leu Gly Ser Asp
                245                 250                 255

<210> SEQ ID NO 101
<211> LENGTH: 418
<212> TYPE: PRT
<213> ORGANISM: Nocardioides sp.

<400> SEQUENCE: 101

Met Arg Leu Met Arg Ile Ser Met Asn Pro Glu Ser Thr Gly His Leu
1               5                   10                  15

Leu Arg Arg Leu Phe Arg Leu Ala Val Gly Val Leu Ala Leu Leu Val
                20                  25                  30

Leu Pro Val Ser Pro Ala Ser Ala His Gly Glu Glu Ser Gln Gln Ala
                35                  40                  45

Phe Gln Arg Thr Ser Thr Val Val Phe Tyr Asp Val Lys Phe Ser Asp
    50                  55                  60

Asp Thr Val Asp Val Gly Glu Ser Val Thr Ile Thr Gly Met Val Arg
65                  70                  75                  80

Val Met Lys Ser Trp Pro Asp His Thr Leu Glu Pro Pro Glu Met Gly
                85                  90                  95

Tyr Leu Thr Val Ser Thr Pro Gly Pro Val Phe Tyr Val Gln Glu Arg
                100                 105                 110

Glu Met Ser Gly Glu Phe Thr Pro Gln Ser Val Arg Ile Glu Lys Gly
                115                 120                 125

Ala Thr Tyr Pro Phe Lys Leu Val Ile Lys Ala Arg Gln Pro Gly Thr
130                 135                 140

Trp His Val His Pro Gly Phe Gly Val Glu Gly Ala Gly Thr Leu Val
145                 150                 155                 160

Gly Ala Gly Lys Asp Ile Thr Val Asn Asp Thr Gly Val Phe Glu Asn
                165                 170                 175

Thr Val Thr Leu Ala Asn Gly Thr Thr Val Asp Leu Glu Thr Phe Gly
                180                 185                 190

Leu Gly Arg Val Val Thr Trp His Leu Ile Ser Leu Val Val Gly Leu
                195                 200                 205

Ala Trp Leu Leu Phe Trp Leu Arg Arg Pro Ile Leu Asp Arg Ala Met
210                 215                 220

Ala Ile Ser Glu Gly Arg Gly Ala Thr Leu Ile Thr Arg Ser Asp Arg
225                 230                 235                 240

Arg Ile Gly Ile Gly Phe Ala Val Val Ala Leu Val Val Gly Thr Gly
                245                 250                 255

Gly Tyr Ala Tyr Ala Glu Met Thr Gln Ser Ser Val Pro Leu Gln
                260                 265                 270

Val Val Arg Thr Thr Pro Val Pro Leu Ala Glu Glu Val Ser Gly
                275                 280                 285

Ala Val Ala Pro Glu Ile Glu Ser Ile Arg Phe Asn Ala Glu Ala Asp
290                 295                 300

Thr Leu Thr Met Lys Leu Arg Val Glu Asn Thr Gly Ala Ala Ala Val
305                 310                 315                 320

Arg Leu Gln Arg Val Gln Phe Gly Asp Val Glu Phe Val Ser Pro Ser
                325                 330                 335
```

```
Phe Ala Ser Ala Ala Asp Pro Asp Ala Gln Ala Met Thr Val Thr Pro
                340                 345                 350

Asp Gln Ala Ile Glu Pro Gly Gly Ser Ala Thr Phe Thr Val Glu Ile
            355                 360                 365

Gln Ser Glu Asp Leu Ile Val Arg Ser Leu Val Pro Val Asn Glu Ala
        370                 375                 380

Glu Leu Arg Val Thr Gly Leu Leu Phe Phe Glu Asp Glu Thr Gly Glu
385                 390                 395                 400

Gln Val Val Ser Glu Val Asn Glu Leu Thr Ser Ala Ile Leu Gln Asp
                405                 410                 415

Phe His
```

<210> SEQ ID NO 102
<211> LENGTH: 247
<212> TYPE: PRT
<213> ORGANISM: Nocardioides sp.

<400> SEQUENCE: 102

```
Met Leu Leu Trp Arg Trp Tyr Gln Gln Ala Phe Ala Phe Thr Lys Gly
1               5                   10                  15

Leu Asp Arg Thr Leu Pro Glu Phe Asn Gln Phe Trp Gly Thr Met Phe
            20                  25                  30

Leu Val Asn Met Thr Val Leu Pro Leu Leu Ala Gly Ala Trp Tyr Val
        35                  40                  45

Tyr Leu Trp Ser Ser Ser Arg Lys Leu Ala Pro Pro Ala Asn Gly Ala
    50                  55                  60

Glu Glu Ala Gly Arg Ile Trp Arg Leu Trp Leu Val Ala Gly Phe
65                  70                  75                  80

Thr Ala Ala Val Tyr Trp Gly Gly Ser Tyr Phe Ala Glu Gln Asp Ala
                85                  90                  95

Ser Trp His Gln Val Thr Met Arg Asp Ser Ala Phe Thr Pro Ser His
            100                 105                 110

Ala Ile Leu Phe Tyr Gly Val Phe Pro Leu Met Ile Tyr Met Ala Thr
        115                 120                 125

Gly Thr Tyr Leu Tyr Ala Arg Thr Arg Leu Pro His Leu Tyr Gly Gly
    130                 135                 140

Lys Ala Ile Pro Val Ser Phe Ala Leu Met Ile Gly Gly Ser Ser Leu
145                 150                 155                 160

Leu Val Phe Gln Val Ala Met Asn Glu Phe Gly His Ser Phe Trp Glu
                165                 170                 175

Ala Glu Glu Leu Phe Ser Ala Ser Leu His Trp Pro Phe Val Ile Phe
            180                 185                 190

Gly Tyr Leu Leu Ala Ala Thr Phe Ser Val Trp Phe Glu Thr Thr Pro
        195                 200                 205

Arg Leu Phe Ala Ile Ala Arg Gln Glu Arg Asp Ala Leu Val Ala Ala
    210                 215                 220

Glu Gln Gln Met Thr Pro Ala Ala Pro Ala Gly Glu Ser Asn Thr Ala
225                 230                 235                 240

Thr Thr Gln Pro Thr Ser Ile
                245
```

<210> SEQ ID NO 103
<211> LENGTH: 497
<212> TYPE: PRT
<213> ORGANISM: Xanthobacter autotrophicus

<400> SEQUENCE: 103

```
Met Ala Leu Leu Asn Arg Asp Asp Trp Tyr Asp Ile Ala Arg Asp Val
 1               5                  10                  15

Asp Trp Thr Leu Ser Tyr Val Asp Arg Ala Val Ala Phe Pro Glu Glu
            20                  25                  30

Trp Lys Gly Glu Lys Asp Ile Cys Gly Thr Ala Trp Asp Asp Trp Asp
        35                  40                  45

Glu Pro Phe Arg Val Ser Phe Arg Glu Tyr Val Met Val Gln Arg Asp
    50                  55                  60

Lys Glu Ala Ser Val Gly Ala Ile Arg Glu Ala Met Val Arg Ala Lys
65                  70                  75                  80

Ala Tyr Glu Lys Leu Asp Asp Gly His Lys Ala Thr Ser His Leu His
                85                  90                  95

Met Gly Thr Ile Thr Met Val Glu His Met Ala Val Thr Met Gln Ser
            100                 105                 110

Arg Phe Val Arg Phe Ala Pro Ser Ala Arg Trp Arg Ser Leu Gly Ala
        115                 120                 125

Phe Gly Met Leu Asp Glu Thr Arg His Thr Gln Leu Asp Leu Arg Phe
    130                 135                 140

Ser His Asp Leu Leu Asn Asp Ser Pro Ser Phe Asp Trp Ser Gln Arg
145                 150                 155                 160

Ala Phe His Thr Asp Glu Trp Ala Val Leu Ala Thr Arg Asn Leu Phe
                165                 170                 175

Asp Asp Ile Met Leu Asn Ala Asp Cys Val Glu Ala Ala Leu Ala Thr
            180                 185                 190

Ser Leu Thr Leu Glu His Gly Phe Thr Asn Ile Gln Phe Val Ala Leu
        195                 200                 205

Ala Ser Asp Ala Met Glu Ala Gly Asp Val Asn Phe Ser Asn Leu Leu
    210                 215                 220

Ser Ser Ile Gln Thr Asp Glu Ala Arg His Ala Gln Leu Gly Phe Pro
225                 230                 235                 240

Thr Leu Asp Val Met Met Lys His Asp Pro Lys Arg Ala Gln Gln Ile
                245                 250                 255

Leu Asp Val Ala Phe Trp Arg Ser Tyr Arg Ile Phe Gln Ala Val Thr
            260                 265                 270

Gly Val Ser Met Asp Tyr Tyr Thr Pro Val Ala Lys Arg Gln Met Ser
        275                 280                 285

Phe Lys Glu Phe Met Leu Glu Trp Ile Val Lys His Glu Arg Ile
    290                 295                 300

Leu Arg Asp Tyr Gly Leu Gln Lys Pro Trp Tyr Trp Asp Thr Phe Glu
305                 310                 315                 320

Lys Thr Leu Asp His Gly His His Ala Leu His Ile Gly Thr Trp Phe
                325                 330                 335

Trp Arg Pro Thr Leu Phe Trp Asp Pro Asn Gly Gly Val Ser Arg Glu
            340                 345                 350

Glu Arg Arg Trp Leu Asn Gln Lys Tyr Pro Asn Trp Glu Glu Ser Trp
        355                 360                 365

Gly Val Leu Trp Asp Glu Ile Ile Ser Asn Ile Asn Ala Gly Asn Ile
    370                 375                 380

Glu Lys Thr Leu Pro Glu Thr Leu Pro Met Leu Cys Asn Val Thr Asn
385                 390                 395                 400

Leu Pro Ile Gly Ser His Trp Asp Arg Phe His Leu Lys Pro Glu Gln
                405                 410                 415
```

```
Leu Val Tyr Lys Gly Arg Leu Tyr Thr Phe Asp Ser Asp Val Ser Lys
                420                 425                 430

Trp Ile Phe Glu Leu Asp Pro Glu Arg Tyr Ala Gly His Thr Asn Val
            435                 440                 445

Val Asp Arg Phe Ile Gly Gly Gln Ile Gln Pro Met Thr Ile Glu Gly
450                 455                 460

Val Leu Asn Trp Met Gly Leu Thr Pro Glu Val Met Gly Lys Asp Val
465                 470                 475                 480

Phe Asn Tyr Arg Trp Ala Gly Asp Tyr Ala Glu Asn Arg Ile Ala Ala
                485                 490                 495

Glu

<210> SEQ ID NO 104
<211> LENGTH: 88
<212> TYPE: PRT
<213> ORGANISM: Xanthobacter autotrophicus

<400> SEQUENCE: 104

Met Ser Leu Phe Pro Ile Val Gly Arg Phe Val Gly Asp Phe Val Pro
1               5                   10                  15

His Leu Val Ala Val Asp Thr Ser Asp Thr Ile Asp Gln Ile Ala Glu
            20                  25                  30

Lys Val Ala Val His Thr Val Gly Arg Arg Leu Pro Pro Asp Pro Thr
        35                  40                  45

Ala Thr Gly Tyr Glu Val Leu Leu Asp Gly Glu Thr Leu Asp Gly Gly
    50                  55                  60

Ala Thr Leu Glu Ala Ile Met Thr Lys Arg Glu Met Leu Pro Leu Gln
65                  70                  75                  80

Trp Phe Asp Val Arg Phe Lys Lys
                85

<210> SEQ ID NO 105
<211> LENGTH: 122
<212> TYPE: PRT
<213> ORGANISM: Xanthobacter autotrophicus

<400> SEQUENCE: 105

Met Asn Leu His Ala Pro Asn Ala Glu Gln Asp Asp Ile Glu Tyr Val
1               5                   10                  15

Asp Val Cys Ala Val Asp Asp Leu Trp Asp Gly Glu Met Asp Val Phe
            20                  25                  30

Asp Val Gly Glu His Glu Val Leu Leu Val Lys His Glu Gly Arg Phe
        35                  40                  45

His Ala Tyr Asp Gly Ile Cys Pro His Gln Ser Val Ser Leu Val Glu
    50                  55                  60

Gly His Leu Thr Glu Asp Gly Val Leu Ile Cys Lys Ala His Glu Trp
65                  70                  75                  80

Gln Phe Ser Val Glu Gly Gly Gln Gly Ile Asn Pro Ala Asn Val Cys
                85                  90                  95

Leu Gln Ser Phe Pro Leu Lys Val Glu Gly Gly Arg Val Leu Ile Gly
            100                 105                 110

Thr Glu Pro Leu Pro Lys Glu Gly Glu Ala
        115                 120

<210> SEQ ID NO 106
<211> LENGTH: 101
```

```
<212> TYPE: PRT
<213> ORGANISM: Xanthobacter autotrophicus

<400> SEQUENCE: 106

Met Ser Asn Ala Thr Val Asp Met Asp Glu Asn Leu Val Gly Pro
1               5                   10                  15

Val Ile Arg Ala Gly Asp Leu Ala Asp Ala Val Ile Asp Ala Val Ile
                20                  25                  30

Ala Asp Asn Pro Gly Lys Glu Val His Val Ile Glu Arg Gly Asp Tyr
            35                  40                  45

Val Arg Ile His Thr Asp Arg Asp Cys Arg Leu Thr Arg Ala Ser Ile
50                  55                  60

Glu Gln Ala Leu Gly Arg Ser Phe Val Leu Ala Ala Ile Glu Ala Glu
65                  70                  75                  80

Met Ser Ser Phe Lys Gly Arg Met Ser Ser Asp Ser Glu Met Arg
                85                  90                  95

Trp Tyr Tyr Lys Ser
            100

<210> SEQ ID NO 107
<211> LENGTH: 341
<212> TYPE: PRT
<213> ORGANISM: Xanthobacter autotrophicus

<400> SEQUENCE: 107

Met Thr Gln Gln Arg Pro Thr Arg Thr Arg Glu Arg Lys Lys Thr Trp
1               5                   10                  15

Thr Ala Phe Gly Asn Leu Gly Arg Lys Pro Thr Asp Tyr Glu Val Val
                20                  25                  30

Thr His Asn Met Asn His Thr Met Arg Gly Thr Pro Leu Glu Leu Ser
            35                  40                  45

Pro Thr Val His Ala Asn Val Trp Leu Lys Lys Asn Arg Asp Glu Ile
50                  55                  60

Ala Leu Lys Val Asp Ser Trp Asp Leu Phe Arg Asp Pro Asp Arg Thr
65                  70                  75                  80

Thr Tyr Asp Thr Tyr Val Lys Met Gln Asp Asp Gln Glu Thr Tyr Val
                85                  90                  95

Asp Asn Leu Leu Leu Ser Tyr Thr Gly Glu Gly Arg Tyr Asp Glu Glu
            100                 105                 110

Leu Ser Ser Arg Ser Leu Asp Leu Leu Ser Ala Gly Leu Thr Pro Thr
        115                 120                 125

Arg Tyr Leu Gly His Gly Leu Gln Met Leu Ala Ala Tyr Ile Gln Gln
130                 135                 140

Leu Ala Pro Ser Ala Tyr Val Gly Asn Cys Ala Val Phe Gln Thr Ser
145                 150                 155                 160

Asp Ala Leu Arg Arg Val Gln Arg Val Ala Tyr Arg Thr Arg Gln Leu
                165                 170                 175

Ala Asp Ala His Pro Ala Arg Gly Phe Gly Ser Gly Asp Arg Ala Val
            180                 185                 190

Trp Glu Lys Ser Pro Asp Trp Gln Pro Ile Arg Lys Ala Ile Glu Glu
        195                 200                 205

Leu Leu Val Thr Phe Glu Trp Asp Lys Ala Leu Ala Gly Thr Asn Phe
210                 215                 220

Val Val Lys Pro Ile Leu Asp Glu Leu Phe Leu Asn His Leu Ala Arg
225                 230                 235                 240
```

```
Leu Leu His Val Glu Gly Asp Glu Leu Asp Ser Leu Val Leu Arg Asn
                245                 250                 255

Leu His Gly Asp Ala Gln Arg His Ala Arg Trp Thr Ala Ala Leu Gly
            260                 265                 270

Arg Phe Ala Val Glu Gln Asn Val Asn Asn Arg Thr Val Leu Arg Asp
        275                 280                 285

Ala Ile Ala Gly Trp His Glu Thr Gly Glu Ala Val Leu Ala Ala Gly
    290                 295                 300

Ala Gly Met Leu Ala Ser Arg Ala Pro Ser Ala Asp Ala Ala Lys Ile
305                 310                 315                 320

Ala Asp Glu Val Arg Ala Thr Leu Ala Gln Leu His Ala Asn Ala Gly
                325                 330                 335

Leu Gly His Asp Ala
            340

<210> SEQ ID NO 108
<211> LENGTH: 327
<212> TYPE: PRT
<213> ORGANISM: Xanthobacter autotrophicus

<400> SEQUENCE: 108

Met Arg Leu Asn Asp Gly Arg Ser Phe Ser Cys Arg Ser Asp Gln Thr
1               5                   10                  15

Val Leu His Ala Ala Leu Ala Ala Gly Ile Asp Met Pro Tyr Glu Cys
                20                  25                  30

Ala Ser Gly Ser Cys Gly Ser Cys Arg Cys Arg Leu Ser His Gly Ser
            35                  40                  45

Val Ser Leu Leu Trp Pro Glu Ala Pro Gly Leu Ser Ala Arg Asp Arg
    50                  55                  60

Gln Lys Gly Asp Arg Ile Leu Ala Cys Gln Ser Thr Pro Ser Ser Asp
65                  70                  75                  80

Leu Glu Ile Asn Val Arg Ala Gly Asp Ala Leu Leu Glu Pro Pro
                85                  90                  95

Arg Arg His Ala Ala Arg Val Thr Val Lys Glu Thr Leu Cys Ala Ser
                100                 105                 110

Val Ile Arg Leu Val Leu Asn Val Gly Gly Pro Ile His Phe Leu Pro
            115                 120                 125

Gly Gln Phe Phe Ile Leu Asp Leu Pro Gly Ala Gly Arg Arg Ala Tyr
    130                 135                 140

Ser Val Ala Asn Leu Glu Asn Ala Ala Gly Ile Glu Leu Leu Ile
145                 150                 155                 160

Lys Arg Lys Ile Gly Gly Ala Gly Thr Ala Ala Leu Phe Asp Gln Cys
                165                 170                 175

Ala Pro Gly Met Gly Leu Val Ile Glu Gly Pro Tyr Gly Arg Ala Tyr
            180                 185                 190

Leu Arg Ala Asp Ser Ala Arg Gly Ile Val Ala Val Ala Gly Gly Ser
        195                 200                 205

Gly Leu Ala Pro Met Leu Ser Ile Leu Arg Gly Ala Leu Ala Arg Gly
    210                 215                 220

Phe Gly Gly Pro Met Asp Leu Tyr Phe Gly Val Asn Thr Ala Glu Glu
225                 230                 235                 240

Leu Phe Cys Val Pro Glu Leu Ser Ala Leu Gln Ala Ala Gly Ala Arg
                245                 250                 255

Val His Leu Ala Leu Arg Asp Gly Gly Pro Gly Pro Ala Gly Leu His
            260                 265                 270
```

```
Arg Gln Ala Gly Leu Ile Gly Asp Ala Leu Val Ala Gly Glu Pro Asp
        275                 280                 285

Leu Lys Ala Lys Asp Leu Tyr Val Ala Gly Pro Ala Pro Met Thr Asp
        290                 295                 300

Asp Ile Leu Ala Arg Thr Val Arg Gln Glu Ala Ile Pro Ala Asp Arg
305                 310                 315                 320

Val Phe Phe Asp Arg Phe Val
                325
```

COMPOSITIONS AND METHODS FOR RECOVERY OF STRANDED GAS AND OIL

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_412USPC_SEQUENCE LISTING. The text file is 254 KB, was created on Jul. 7, 2016, and is being submitted electronically via EFS-Web.

BACKGROUND

Oil deposits are associated, in many cases, with natural gas, which can often be tainted with significant levels of sulfur (referred to as 'sour gas') and other contaminants (like $CO_2$). Natural gas is highly flammable and potentially explosive, hence the gas must be dealt with to allow access to an associated oil deposit. Historically, gas was transferred to a pipeline for sale (requiring scrubbing to remove contaminants as well as additional costs to pressurize the gas for introduction into the pipeline), flared (e.g., as waste gas or smokeless), incinerated, and sometimes simply vented to the atmosphere. However, current environmental regulations prevent the flaring and venting of gas in many locations, especially due to the highly polluting effects of sulfur and other contaminants. Further, the current low price of natural gas means that introducing the gas into a pipeline is often unprofitable because more money will be required to make the gas suitable for the pipeline than can be recovered from its sale. An additional complication is that as new oil drilling and recovery technologies have come online, the majority of new oil deposits are located far from existing gas pipelines. Thus, even if a well operator was willing to spend money to remove the gas, the infrastructure does not exist to enable the operation.

For these and other reasons, there currently exist a number of known oil deposits which cannot be accessed due to the difficulties in mitigating the associated gas deposits. Given the high price of oil, there is a need in the art for alternative methods for converting gas (and associated contaminants) into safe and non-polluting forms in a cost-effective manner. The present disclosure meets such needs, and further provides other related advantages.

BRIEF SUMMARY

In brief, the present disclosure provides a recombinant $C_1$ metabolizing microorganism having a first exogenous nucleic acid molecule encoding a polypeptide capable of metabolizing an S substrate, wherein the recombinant microorganism is capable of assimilating and/or oxidizing the S substrate, a $C_1$ substrate, or both.

In some aspects, the present disclosure provides a method for treating gas comprising culturing a first recombinant $C_1$ metabolizing microorganism with a tainted gas feedstock comprised of a $C_1$ substrate and an S substrate; wherein the recombinant microorganism includes a first exogenous nucleic acid molecule encoding a polypeptide capable of metabolizing the S substrate and the recombinant $C_1$ metabolizing microorganism assimilates and/or oxidizes each substrate.

In some aspects, the present disclosure provides a system for treating gas comprising a source of gas comprising a $C_1$ substrate and an S substrate; a bioreactor comprising a recombinant $C_1$ metabolizing microorganism comprising a first exogenous nucleic acid molecule encoding a polypeptide capable of metabolizing the S substrate; and a connector disposed between the gas source and the bioreactor to allow flow of the gas into the bioreactor; wherein the recombinant $C_1$ metabolizing microorganism assimilates and/or oxidizes each substrate.

In another aspect, the present disclosure provides a system for recovering stranded gas and/or oil, comprising a mechanism for recovering gas from an underground formation, wherein the gas comprises a $C_1$ substrate and an S substrate, and the mechanism for recovering comprises a well; a mechanism for assimilating and/or oxidizing at least a portion of each substrate from the recovered gas, the mechanism for assimilating and/or oxidizing comprising a bioreactor, wherein the bioreactor comprises a recombinant $C_1$ metabolizing microorganism comprising a first exogenous nucleic acid molecule encoding a polypeptide capable of metabolizing the S substrate; and a mechanism for recovering the bioremediated stranded oil from the underground formation, wherein the mechanism for recovering comprises a well.

In some embodiments, a polypeptide capable of metabolizing an S substrate is a hydrogen sulfide:$NADP^+$ oxidoreductase, hydrogen sulfide:ferredoxin oxidoreductase, sulfide:flavocytochrome-c oxidoreductase, sulfide:quinone oxidoreductase, sulfur dioxygenase, sulfite oxidase, or any combination thereof. For example, the polypeptide capable of metabolizing the S substrate is (1) hydrogen sulfide:$NADP^+$ oxidoreductase, sulfite oxidase, or both; (2) hydrogen sulfide:ferredoxin oxidoreductase, sulfite oxidase, or both; (3) sulfide:flavocytochrome-c oxidoreductase, sulfite oxidase, or both; (4) sulfide:quinone oxidoreductase, sulfite oxidase, or both; (5) a hydrogen sulfide:$NADP^+$ oxidoreductase, hydrogen sulfide:ferredoxin oxidoreductase, sulfide:flavocytochrome-c oxidoreductase, or sulfide:quinone oxidoreductase, and wherein the endogenous sulfite oxidase activity is increased; or (6) a sulfur oxygenase.

In some embodiments, the polypeptide capable of metabolizing the S substrate is encoded by a nucleic acid wherein the nucleic acid comprises a sequence as set forth in any one of SEQ ID NOS.:21-54. In some embodiments, the polypeptide capable of metabolizing the S substrate comprises an amino acid sequence as set forth in any one of SEQ ID NOS.:55-88.

In some embodiments, the $C_1$ substrate, the S substrate, or both are converted into a biological material, such as an animal feed, a fertilizer or an oil composition. In other embodiments, the S substrate is oxidized to a sulfate or a sulfide.

In some embodiments, a tainted gas feedstock is a light alkane gas, natural gas, unconventional natural gas, syngas, casinghead gas, wellhead condensate, or any combination thereof. In some embodiments, a tainted gas feedstock is an acid gas or a sour gas.

In any of the aforementioned embodiments, a recombinant $C_1$ metabolizing microorganism may further comprise a second exogenous nucleic acid molecule encoding a fatty acid producing enzyme, a formaldehyde assimilation enzyme, or a combination thereof and wherein the recombinant $C_1$ metabolizing microorganism converts the $C_1$ substrate into an oil composition. For example, the oil composition produced may be substantially located in the cell membrane of the $C_1$ metabolizing microorganism.

In certain embodiments, the present disclosure further provides the step of obtaining the oil composition by extraction. In further embodiments, the extracted oil composition is further refined into a fuel, such as jet fuel, diesel fuel, paraffinic kerosene, gasoline, or any combination thereof.

In any of the aforementioned embodiments, the present disclosure further provides a second recombinant $C_1$ metabolizing microorganism or cell lysate thereof, wherein the second recombinant $C_1$ metabolizing microorganism comprises an exogenous nucleic acid molecule encoding a polypeptide capable of oxidizing light alkanes; and wherein the second recombinant $C_1$ metabolizing microorganism or cell lysate thereof oxidizes the $C_1$ substrate into an alcohol composition. In some embodiments, the first recombinant $C_1$ metabolizing microorganism further comprises a second exogenous nucleic acid molecule encoding a polypeptide capable of oxidizing light alkanes such that the recombinant microorganism or cell lysate thereof oxidizes the $C_1$ substrate into an alcohol composition. In any of these embodiments, a polypeptide capable of oxidizing light alkanes may be a monooxygenase selected from a MMO, AMO, BMO, PMO or P450.

In certain embodiments, the exogenous nucleic acid molecule encoding a polypeptide capable of oxidizing light alkanes comprises a sequence as set forth in any one of SEQ ID NOS.:1-20. In some embodiments, the polypeptide capable of oxidizing light alkanes comprises a sequence as set forth in any one of SEQ ID NOS.:89-108.

In some embodiments, the recombinant $C_1$ metabolizing microorganism further comprises a second exogenous nucleic acid molecule encoding a fatty acid converting enzyme; and wherein the recombinant $C_1$ metabolizing microorganism converts the $C_1$ substrate into a $C_8$-$C_{24}$ fatty acid derivative comprising a fatty aldehyde, a fatty alcohol, a hydroxy fatty acid, a dicarboxylic acid, or any combination thereof. In certain embodiments, the fatty acid converting enzyme is a fatty acyl-CoA reductase capable of forming a fatty alcohol. In some embodiments, the fatty acyl-CoA reductase capable of forming a fatty alcohol is FAR, CER4, or Maqu_2220. In certain embodiments, the fatty acid converting enzyme is a fatty acyl-CoA reductase capable of forming a fatty aldehyde. In certain embodiments, the fatty acyl-CoA reductase capable of forming a fatty aldehyde is acr1. In some embodiments, the fatty acid converting enzyme is a carboxylic acid reductase.

In some embodiments, the recombinant $C_1$ metabolizing microorganism further comprises an exogenous nucleic acid molecule encoding a thioesterase. In certain embodiments, the thioesterase is a tesA lacking a signal peptide, UcFatB or BTE. In certain embodiments, endogenous thioesterase activity is reduced, minimal or abolished as compared to unaltered endogenous thioesterase activity.

In some embodiments, the recombinant $C_1$ metabolizing microorganism further comprises an exogenous nucleic acid molecule encoding an acyl-CoA synthetase. In certain embodiments, the acyl-CoA synthetase is FadD, yng1, or FAA2. In certain embodiments, endogenous acyl-CoA synthetase activity is reduced, minimal or abolished as compared to unaltered endogenous acyl-CoA synthetase activity.

In some embodiments, the present disclosure further provides a recombinant nucleic acid molecule encoding a monooxygenase to produce ω-hydroxy fatty acid. In certain embodiments, endogenous alcohol dehydrogenase activity is reduced, minimal or abolished as compared to unaltered endogenous alcohol dehydrogenase activity.

In some embodiments, endogenous alcohol dehydrogenase activity is increased or elevated as compared to unaltered endogenous alcohol dehydrogenase activity to produce dicarboxylic acid.

In some embodiments, the $C_1$ metabolizing microorganism is selected from the group consisting of *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* and *Pseudomonas*. In other embodiments, the $C_1$ metabolizing microorganism is selected from the group consisting of *Candida, Yarrowia, Hansenula, Pichia, Torulopsis,* and *Rhodotorula*.

In some embodiments, the $C_1$ metabolizing microorganism is a bacterium. In certain aspects, the $C_1$ metabolizing bacterium is a methanotroph or methylotroph. In certain aspects, the $C_1$ metabolizing bacterium is a methanotroph. In certain embodiments, the methanotroph is a *Methylomonas, Methylobacter, Methylococcus, Methylosinus, Methylocystis, Methylomicrobium, Methanomonas,* or a combination thereof. In some aspects, the methanotroph is a *Methylococcus capsulatus* Bath strain, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11, 200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis daltona* strain SB2, *Methylocystis bryophila, Methylocapsa aurea* KYG, *Methylacidiphilum infernorum, Methylibium petroleiphilum, Methylomicrobium alcaliphilum,* or a combination thereof. In some aspects, the methanotroph is *Methylosinus trichosporium* OB3b, *Methylococcus capsulatus* Bath, *Methylomonas* sp. 16a, *Methylomicrobium alcaliphilum,* or a high growth variant thereof.

In some embodiments, the $C_1$ metabolizing bacterium is a methylotroph. In certain embodiments, the methylotroph is *Methylobacterium extorquens, Methylobacterium radiotolerans, Methylobacterium populi, Methylobacterium chloromethanicum, Methylobacterium nodulans,* or a combination thereof.

In some embodiments, the $C_1$ metabolizing bacterium is a natural gas, unconventional natural gas, or syngas metabolizing bacterium. In certain embodiments, the syngas metabolizing bacterium is *Clostridium, Moorella, Pyrococcus, Eubacterium, Desulfobacterium, Carboxydothermus, Acetogenium, Acetobacterium, Acetoanaerobium, Butyribacterium, Peptostreptococcus,* or a combination thereof. In certain aspects, the syngas metabolizing bacterium is *Clostridium autoethanogenum, Clostridium ljungdahli, Clostridium ragsdalei, Clostridium carboxydivorans, Butyribacterium methylotrophicum, Clostridium woodii, Clostridium neopropanologen,* or a combination thereof. In some aspects, the $C_1$ metabolizing microorganism is an obligate $C_1$ metabolizing microorganism.

In certain embodiments, the culture further comprises a heterologous bacterium.

DETAILED DESCRIPTION

The instant disclosure provides compositions and methods for biologically converting gas, along with any unwanted impurities or contaminants, into useful compositions, such as high-value molecules (e.g., alcohols, fatty acid derivatives, oil composition), biological material (e.g., animal feed), or a combination thereof. For example, oil may be stranded because it is associated with gas, such as tainted gas (e.g., acidic, sour gas). Such oil associated gas can be fed to recombinant $C_1$ metabolizing microorganisms comprising a nucleic acid molecule encoding a sulfur utilizing (e.g., sulfide converting) enzyme, to generate one or more different compounds and allow recovery of the previously stranded oil. This new approach allows for the use of methylotroph or methanotroph bacteria as a new host system to bioremediate stranded oil.

By way of background, natural gas from a well may contain a number of undesirable compounds that must be removed or reduced prior to distribution and sale, or the natural gas and any associated contaminants must be removed to access stranded oil. Hydrogen sulfide is one of the most common problems in the gas industry because it is a toxic gas that is very corrosive in the presence of water. Current regulations require that natural gas destined for the fuel market contain no more than 0.25 grains per 100 standard cubic feet or 4 parts per million (ppm) on a volume basis. The most common process to remove hydrogen sulfide involves a two-step treatment: (1) an amine process (also known as the Girdler process, usually using alkanolamines (e.g., monoethanolamine, diethanolamine) to remove hydrogen sulfide from natural gas; Maddox, Gas and Liquid Sweetening, $2^{nd}$ Edition, Norman, Okla.: Campbell Petroleum Series, 1974) followed by (2) the Claus process (for elemental sulfur recovery) (Canjur and Manning, Thermodynamic Properties and Reduced Correlations for Gases, Gulf Publishing Co., 1967). But, the hydrophobic elemental sulfur produced by the Claus process requires the use of surfactants since sulfur tends to float and aggregate, which leads to foaming and plugging. Moreover, when the sulfur content is not at sufficient levels or when the $CO_2$ content is greater than the $H_2S$ content, the Claus process is not economical. The instant disclosure provides compositions and methods for biologically consuming gas associated with oil (or removing other sources of gas), along with any contaminants contained in a gas, to simplify the process for mitigating a major barrier to stranded oil and to eliminate much of the processing equipment needed to scrub tainted gas.

In one aspect, the present disclosure provides compositions, methods, and systems for treating gas (e.g., deacidifying, desulfurizing), comprising use of a recombinant $C_1$ metabolizing microorganism in the presence of an acid gas feedstock, wherein the recombinant $C_1$ metabolizing microorganism comprises an exogenous nucleic acid molecule encoding a polypeptide capable of oxidizing or assimilating sulfur. In certain embodiments, the recombinant $C_1$ metabolizing microorganism may further comprise another exogenous nucleic acid molecule that encodes a biocatalytic enzyme capable of oxidizing light alkanes into various compounds of interest, as described herein.

In another aspect, this disclosure provides a system for treating gas comprising a source of tainted gas comprising an S substrate, a bioreactor comprising a recombinant $C_1$ metabolizing microorganism (e.g., methanotroph) that includes a first exogenous nucleic acid molecule encoding a polypeptide capable of oxidizing or assimilating sulfur, and optionally includes a second exogenous nucleic acid molecule that encodes a biocatalytic enzyme capable of oxidizing light alkanes, and a connector disposed between the gas source and bioreactor to allow flow of the tainted gas into the bioreactor; wherein the recombinant microorganism utilizes the sulfur and light alkanes to produce one or more high-value molecules (e.g., alcohols, fatty acid derivatives), biological material (e.g., animal feed, oil composition), or a combination thereof.

In still a further aspect, the present disclosure provides a system for bioremediation of stranded oil, comprising a well for recovering oil associated gas from an underground formation, wherein the gas comprises at least one acidic compound; a bioreactor comprising a recombinant $C_1$ metabolizing microorganism having a first exogenous nucleic acid molecule encoding a polypeptide capable of oxidizing or assimilating sulfur, wherein the $C_1$ metabolizing microorganism uses the gas as a carbon and energy source and substantially converts the acidic compounds from the recovered oil associated gas into, for example, compounds of interest; whereby the bioremediation process substantially removes the oil associated gas and allows recovery of previously stranded oil from the underground formation.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "$C_1$ substrate" or "$C_1$ compound" refers to any carbon containing molecule or composition that lacks a carbon-carbon bond. $C_1$ substrates include natural gas, unconventional natural gas, syngas, methane, methanol, formaldehyde, formic acid (formate), carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), cyanide, or any combination thereof.

As used herein, "$C_1$ metabolizing microorganism" or "$C_1$ metabolizing microorganism" refers to any microorganism having the ability to use a $C_1$ substrate as a source of energy or as its primary source of energy or as its sole source of energy and biomass, and may or may not use other carbon substrates (such as sugars and complex carbohydrates) for energy and biomass. For example, a $C_1$ metabolizing microorganism may oxidize a $C_1$ substrate, such as methane, natural gas, or methanol. $C_1$ metabolizing microorganisms include bacteria (such as methanotrophs and methylotrophs) and yeast. In certain embodiments, a $C_1$ metabolizing microorganism does not include a photosynthetic microorganism, such as algae. In certain embodiments, a $C_1$ metabolizing microorganism will be an "obligate $C_1$ metabolizing microorganism," meaning its primary source of energy are $C_1$ substrates. In further embodiments, a $C_1$ metabolizing microorganism (e.g., methanotroph) will be cultured in the presence of a $C_1$ substrate feedstock (i.e., using the $C_1$ substrate as a source of energy).

As used herein, the term "methanotroph," "methanotrophic bacterium" or "methanotrophic bacteria" refers to a methylotrophic bacteria capable of utilizing $C_1$ substrates, such as methane or unconventional natural gas, as its primary or sole carbon and energy source. As used herein, "methanotrophic bacteria" include "obligate methanotrophic bacteria" that can only utilize $C_1$ substrates for carbon and energy sources and "facultative methanotrophic bacteria" that are naturally able to use multi-carbon substrates, such as acetate, pyruvate, succinate, malate, or ethanol, in addition to $C_1$ substrates as their carbon and energy source.

As used herein, the term "methylotroph" or "methylotrophic bacteria" refers to any bacteria capable of oxidizing organic compounds that do not contain carbon-carbon bonds. In certain embodiments, a methylotrophic bacterium may be a methanotroph. For example, "methanotrophic bacteria" refers to any methylotrophic bacteria that have the ability to oxidize methane as it primary source of carbon and energy. Exemplary methanotrophic bacteria include *Methylomonas, Methylobacter, Methylococcus, Methylosinus, Methylocystis, Methylomicrobium,* or *Methanomonas*. In certain other embodiments, the methylotrophic bacterium is an "obligate methylotrophic bacterium," which refers to bacteria that are limited to the use of $C_1$ substrates for the generation of energy.

As used herein, "gas" refers to one or mixture of light alkane gases (light alkane refers to saturated or unsaturated $C_1$-$C_6$ alkanes optionally substituted), such as methane, ethane, propane, butane, pentane; natural gas; unconventional natural gas; synthesis gas (syngas); casinghead gas; wellhead condensate; or other hydrocarbon gas taken from the earth or water, whether produced by conventional or unconventional methods, or whether produced from a gas well or a well also producing oil, distillate or condensate or both, or other products. "Casinghead gas" means gas or vapor indigenous to an oil stratum and produced from the stratum with oil. "Condensate" means liquid hydrocarbon that is or can be recovered from gas by a separator, or may be liquid hydrocarbon recovered from gas by refrigeration or absorption and separated by a fractionating process.

As used herein, "tainted gas" refers to gas having unwanted contaminant(s), such as $CO_2$ or $H_2S$ or both as may be found in acid gas, $H_2S$ as found in sour gas, or the like. "Sour gas" means gas having at least one "S substrate," wherein an S substrate may be any sulfur-containing compound associated with or mixed in gas, such as hydrogen sulfide ($H_2S$), thiosulfate, sulfite, carbon disulfide, elemental sulfur, other organosulfur compounds (e.g., mercaptans such as thiols (R—SH, where R is a hydrocarbon), thiol carboxylic acids (RCO—SH), dithio acids (RCS—SH), or the like. In a certain embodiments, more than 50% of sulfur-containing compounds of an "S substrate" will be comprised of $H_2S$. In a certain embodiments, sour gas comprises more than 0.25 grains (gr) of $H_2S$ per 100 standard cubic feet (scf) or 6 parts per million (ppm) on a volume basis, or 10 gr of sulfur per 100 scf, or about 0.1% to about 25% sulfur content. A "standard cubic foot" is a measure of quantity (not volume) at 70° F. and one atmosphere (atm=14.7 pounds per square inch (psi) absolute). "Sweet gas" means gas other than acid gas, sour gas, or casinghead gas (e.g., gas treated to remove unwanted contaminants). In certain embodiments, sweet gas will contain 0.25 gr or less (4 ppm or less) of $H_2S$ or other organosulfur compounds, or have a heating value of at least 920 to 1,000 Btu/scf.

As used herein, "methane" refers to the simplest ($C_1$) alkane compound with the chemical formula $CH_4$, which is a colorless and odorless gas at room temperature and pressure. Sources of methane include natural sources (such as natural gas fields), "unconventional natural gas" sources (such as shale gas or coal bed methane, wherein methane content will vary from about 75% to about 97%, depending on the source), and biological sources where it is synthesized by, for example, methanogenic microorganisms (biogenic natural gas), and industrial or laboratory synthesis. Methane includes pure methane, substantially purified compositions, such as "pipeline quality natural gas" or "dry natural gas", which is 95-98% percent methane, and unpurified compositions, such as "wet natural gas", wherein other hydrocarbons have not yet been removed and methane comprises more than 60% of the composition.

As used herein, "natural gas" refers to naturally occurring gas mixtures that have formed in porous reservoirs and can be accessed by conventional processes (e.g., drilling, waterflooding) and are primarily made up of methane, but may also have other light alkane gases (e.g., ethane, propane, butane, pentane), carbon dioxide, nitrogen, hydrogen sulfide, or the like, or any combination thereof.

As used herein, "unconventional natural gas" refers to a naturally occurring gas mixtures created in formations with low permeability that must be accessed by unconventional methods, such as hydraulic fracturing, horizontal drilling or directional drilling. Exemplary unconventional natural gas deposits include tight gas sands formed in sandstone or carbonate, coal bed methane formed in coal deposits and adsorbed in coal particles, shale gas formed in fine-grained shale rock and adsorbed in clay particles or held within small pores or microfractures, methane hydrates that are a crystalline combination of natural gas and water formed at low temperature and high pressure in places such as under the oceans and permafrost. Unconventional natural gas tends to have a more variable composition, including having potentially higher levels of ethane, propane, butane, $CO_2$, or any combination thereof, as compared to natural gas.

As used herein, "synthesis gas" or "syngas" refers to a mixture of carbon monoxide (CO) and hydrogen ($H_2$), which may be produced, for example, by steam reforming of natural gas or liquid hydrocarbons, or by gasification of coal, biomass or waste. Syngas may also include methane, $CO_2$, $H_2S$, and other gases in smaller quantities relative to CO and $H_2$.

As used herein, "nucleic acid molecule," also known as a polynucleotide, refers to a polymeric compound comprised of covalently linked subunits called nucleotides. Nucleic acid molecules include polyribonucleic acid (RNA), polydeoxyribonucleic acid (DNA), both of which may be single or double stranded. DNA includes cDNA, genomic DNA, synthetic DNA, semi-synthetic DNA, or the like.

As used herein, "biological material" refers to organic material having a biological origin, which may include whole cells, lysed cells, extracellular material, or the like. For example, the material harvested from a cultured microorganism (e.g., bacterial or yeast culture) is considered the biological material, which can include secreted products. Such a culture may be considered a renewable resource.

As used herein, "oil composition" refers to the lipid content of a biological material, including fatty acids, triglycerides, phospholipids, polyhyroxyakanoates, isoprenes, terpenes, or the like. An oil composition contained in biological material may be extracted from the rest of the biological material by methods known in the art, such as by hexane extraction. In addition, an "oil composition" may be found in any one or more areas of a culture, including the cell membrane, cell cytoplasm, inclusion bodies, secreted or excreted in the culture medium, or any combination thereof. In certain embodiments, an oil composition functions as a fuel precursor since it can be refined into a fuel, such as jet fuel, diesel fuel, paraffinic kerosene, gasoline, or any combination thereof.

As used herein, the term "host" refers to a cell or microorganism (e.g., methanotroph) that may be genetically modified with an exogenous nucleic acid molecule to produce a polypeptide of interest (e.g., sulfide oxidoreductase, monooxygenase, cysteine synthase). In certain embodiments, a host cell may optionally already possess other genetic modifications that confer desired properties related or unrelated to the exogenous polypeptide being expressed (e.g., sulfur oxidation as disclosed herein). For example, a host cell may possess genetic modifications conferring additional or enhanced sulfite oxidase activity, additional or enhanced light alkane oxidation activity, high growth, tolerance of contaminants or particular culture conditions (e.g., $H_2S$ tolerance, biocide resistance), ability to metabolize additional carbon substrates, or ability to synthesize desirable products or intermediates.

For example, an exogenous nucleic acid molecule may encode a polypeptide capable of oxidizing or assimilating sulfur. Exemplary polypeptides capable of oxidizing or assimilating sulfur include hydrogen sulfide:$NADP^+$ oxidoreductase (also known as sulfite reductase (NADPH) or cysJ/cysI), hydrogen sulfide:ferredoxin oxidoreductase (also known as sulfite reductase (ferredoxin) or SIR), sulfide:flavocytochrome-c oxidoreductase (also known as sulfide-cytochrome-c reductase (flavocytochrome c) or flavocytochrome c sulfide dehydrogenase or FCC), sulfide:quinone oxidoreductase (also known as sulfide quinone reductase or SQR), sulfur dioxygenase, sulfur oxygenase (also known as sulfur oxygenase/reductase or SOR), or the like, which may be useful in converting, for example, hydrogen sulfide into elemental sulfur, sulfite, sulfate, or any combination thereof.

As used herein, the term "recombinant" or "non-natural" refers to an organism, microorganism, cell, nucleic acid molecule, or vector that includes at least one genetic alternation or has been modified by introduction of an exogenous nucleic acid molecule, or refers to a cell that has been altered such that the expression of an endogenous nucleic acid molecule or gene can be controlled, where such alterations or modifications are introduced by genetic engineering. Genetic alterations include, for example, modifications introducing expressible nucleic acid molecules encoding proteins or enzymes, or other nucleic acid molecule additions, deletions, substitutions or other functional disruption of the cell's genetic material. Such modifications include, for example, coding regions and functional fragments thereof for heterologous or homologous polypeptides for the referenced species. Additional modifications include, for example, non-coding regulatory regions in which the modifications alter expression of a gene or operon.

Recombinant methods for expression of exogenous or heterologous nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Exemplary exogenous proteins or enzymes to be expressed include those involved in sulfur oxidation (e.g., hydrogen sulfide:$NADP^+$ oxidoreductase, hydrogen sulfide:ferredoxin oxidoreductase, sulfide:flavocytochrome-c oxidoreductase, sulfide:quinone oxidoreductase, sulfur dioxygenase, sulfur oxygenase, sulfite oxidase, or any combination thereof) or in sulfur assimilation (e.g., sulfate adenylyltransferase, sulfite reductase). Genetic modifications to nucleic acid molecules encoding enzymes, or functional fragments thereof, can confer a biochemical or metabolic capability to a recombinant cell that is altered from its naturally occurring state.

As used herein, "transformation" refers to the introduction of a nucleic acid molecule (e.g., exogenous or heterologous nucleic acid molecule) into a host cell. The transformed host cell may carry the exogenous or heterologous nucleic acid molecule extra-chromosomally or integrated in the chromosome. Integration into a host cell genome and self-replicating vectors generally result in genetically stable inheritance of the transformed nucleic acid molecule. Host cells containing the transformed nucleic acids are referred to as "recombinant" or "non-naturally occurring" or "genetically engineered" or "transformed" or "transgenic" cells (e.g., bacteria).

As used herein, the term "endogenous" or "native" refers to a gene, protein, compound or activity that is normally present in a host cell.

As used herein, "heterologous" or "exogenous" nucleic acid molecule, construct or sequence refers to a nucleic acid molecule or portion of a nucleic acid molecule that is not native to a host cell, a nucleic acid molecule or portion of a nucleic acid molecule native to a host cell that has been altered or mutated, or a nucleic acid molecule with an altered expression as compared to the native expression levels under similar conditions. For example, a heterologous control sequence (e.g., promoter, enhancer) may be used to regulate expression of a native gene or nucleic acid molecule in a way that is different from the way a native gene or nucleic acid molecule is normally expressed in nature or culture. In certain embodiments, heterologous or exogenous nucleic acid molecules may not be endogenous to a host cell or host genome, but instead may have been added to a host cell by conjugation, transformation, transfection, electroporation, or the like, wherein the added molecule may integrate into the host genome or can exist as extra-chromosomal genetic material (e.g., as a plasmid or other self replicating vector). In addition, "heterologous" can refer to an enzyme, protein or other activity that is different or altered from that found endogenous to a host cell, or is not native to a host cell but instead is encoded by a nucleic acid molecule introduced into the host cell. The term "homologous" or "homolog" refers to a molecule or activity found in or derived from a host cell, species or strain. For example, a heterologous or exogenous nucleic acid molecule may be homologous to a native host cell gene, but may have an altered expression level or have a different sequence or both.

In certain embodiments, more than one heterologous or exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one heterologous or exogenous nucleic acid. For example, as disclosed herein, a $C_1$ metabolizing microorganism can be modified to express two or more heterologous or exogenous nucleic acid molecules encoding desired sulfur and light alkane oxidizing components (e.g., hydrogen sulfide:$NADP^+$ oxidoreductase or hydrogen sulfide:ferredoxin oxidoreductase, optionally a sulfite oxidase, optionally a monooxygenase, optionally a fatty acid converting enzyme). When two or more exogenous nucleic acid molecules are introduced into a host $C_1$ metabolizing microorganism, it is understood that the two more exogenous nucleic acid molecules can be introduced as a single nucleic acid molecule (e.g., on a single vector), on separate vectors, integrated into the host chromosome at a single site or multiple sites, and each of these embodiments is still to be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

The term "chimeric" refers to any nucleic acid molecule or protein that is not endogenous and comprises sequences joined or linked together that are not normally found joined or linked together in nature. For example, a chimeric nucleic acid molecule may comprise regulatory sequences and coding sequences that are derived from different sources, or regulatory sequences and coding sequences that are derived from the same source but arranged in a manner different than that found in nature.

The "percent identity" between two or more nucleic acid sequences is a function of the number of identical positions shared by the sequences (i.e., % identity=number of identical positions/total number of positions ×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8).

"Inhibit" or "inhibited," as used herein, refers to an alteration, reduction, down regulation or abrogation, directly or indirectly, in the expression of a target gene or in the activity of a target molecule (e.g., alcohol dehydrogenase) relative to a control, endogenous or reference molecule, wherein the alteration, reduction, down regulation or abrogation is statistically, biologically, industrially, or clinically significant.

As used herein, the term "derivative" refers to a modification of a compound by chemical or biological means, with or without an enzyme, which modified compound is structurally similar to a parent compound and (actually or theoretically) derivable from that parent compound. A derivative may have different chemical, biological or physical properties from the parent compound, such as being more hydrophilic or having altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). Other exemplary derivatizations include glycosylation, alkylation, acylation, acetylation, ubiqutination, esterification, and amidation.

The term "derivative" also refers to all solvates, for example, hydrates or adducts (e.g., adducts with alcohols), active metabolites, and salts of a parent compound. The type of salt depends on the nature of the moieties within the compound. For example, acidic groups, such as carboxylic acid groups, can form alkali metal salts or alkaline earth metal salts (e.g., sodium salts, potassium salts, magnesium salts, calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts with, for example, inorganic acids such as hydrochloric acid, sulfuric acid or phosphoric acid, or with organic carboxylic acids or sulfonic acids such as acetic acid, citric acid, lactic acid, benzoic acid, maleic acid, fumaric acid, tartaric acid, methanesulfonic acid or p-toluenesulfonic acid. Compounds that simultaneously contain a basic group and an acidic group, for example, a carboxyl group in addition to basic nitrogen atoms, can be present as zwitterions. Salts can be obtained by customary methods known to those skilled in the art, for example, by combining a compound with an inorganic or organic acid or base in a solvent or diluent, or from other salts by cation exchange or anion exchange.

$C_1$ Metabolizing Microorganisms—Host Cells

The $C_1$ metabolizing microorganisms of the instant disclosure may be a natural strain, strain adapted (e.g., performing fermentation to select for strains with improved sulfite oxidase activity, improved growth rates, or increased total biomass yield compared to the parent strain), or recombinantly modified to treat gas (e.g., desulfurize), convert alkanes or alkenes to their corresponding alcohol or epoxide, to have increased sulfite oxidase activity, to have increased growth rates, or any combination thereof. In certain preferred embodiments, the $C_1$ metabolizing microorganisms are not photosynthetic microorganisms, such as algae or plants.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas.*

In further embodiments, the $C_1$ metabolizing bacteria are a methanotroph or a methylotroph. Exemplary methanotrophs include *Methylomonas, Methylobacter, Methylococcus, Methylosinus, Methylocystis, Methylomicrobium, Methanomonas, Methylocella,* or a combination thereof. Exemplary methylotrophs include *Methylobacterium extorquens, Methylobacterium radiotolerans, Methylobacterium populi, Methylobacterium chloromethanicum, Methylobacterium nodulans,* or a combination thereof.

In certain embodiments, methanotrophic bacteria are genetically engineered with the capability to sweeten gas or convert $C_1$ substrate feedstock into, for example, alcohols or biomass. Methanotrophic bacteria have the ability to oxidize methane as a carbon and energy source. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway.

Methanotrophic bacteria include obligate methanotrophs, which can only utilize $C_1$ substrates for carbon and energy sources, and facultative methanotrophs, which naturally have the ability to utilize some multi-carbon substrates as a sole carbon and energy source. Exemplary facultative methanotrophs include some species of *Methylocella, Methylocystis*, and *Methylocapsa* (e.g., *Methylocella silvestris, Methylocella palustris, Methylocella tundrae, Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. Exemplary obligate methanotrophic bacteria include *Methylococcus capsulatus* Bath, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas Flagellata* sp AJ-3670 (FERM P-2400), *Methylacidiphilum infernorum, Methylacidiphilum fumariolicum, Methylomicrobium alcaliphilum*, or high growth variants thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus*, Acetogenium, Acetobacterium, Acetoanaerobium, Butyribaceterium, *Peptostreptococcus*, or a combination thereof. Exemplary syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

In certain other embodiments, $C_1$ metabolizing microorganisms are eukaryotes such as yeast, including *Candida, Yarrowia, Hansenula, Pichia, Torulopsis*, or *Rhodotorula*.

In certain other embodiments, the $C_1$ metabolizing microorganism is an obligate $C_1$ metabolizing microorganism, such as an obligate methanotroph or methylotroph.

In certain embodiments, a non-natural $C_1$ metabolizing microorganism is a recombinant methanotroph comprising a heterologous polynucleotide encoding a hydrogen sulfide: $NADP^+$ oxidoreductase, hydrogen sulfide:ferredoxin oxidoreductase, sulfide:quinone oxidoreductase, sulfide:flavocytochrome-c oxidoreductase, or sulfur dioxygenase. In certain embodiments, a non-natural $C_1$ metabolizing microorganism is a recombinant methanotroph comprising a heterologous polynucleotide encoding a sulfur oxygenase (e.g., SOR).

In certain embodiments, a non-natural $C_1$ metabolizing microorganism is a recombinant methanotroph comprising a first heterologous polynucleotide encoding a hydrogen sulfide:$NADP^+$ oxidoreductase (e.g., cysJ/cysI), and optionally a second heterologous nucleic acid molecule that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof; or optionally a second heterologous nucleic acid molecule that encodes a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof; or optionally a second heterologous nucleic acid molecule encoding a fatty acid producing enzyme, a formaldehyde assimilation enzyme, or a combination thereof, capable of converting a gas (e.g., natural gas) into an oil composition; or any combination thereof.

In certain embodiments, a non-natural $C_1$ metabolizing microorganism is a recombinant methanotroph comprising a first heterologous polynucleotide encoding a hydrogen sulfide:ferredoxin oxidoreductase (SIR), and optionally a second heterologous nucleic acid molecule that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof; or optionally a second heterologous nucleic acid molecule that encodes a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof; or optionally a second heterologous nucleic acid molecule encoding a fatty acid producing enzyme, a formaldehyde assimilation enzyme, or a combination thereof, capable of converting a gas (e.g., natural gas) into an oil composition; or any combination thereof.

In certain embodiments, a non-natural $C_1$ metabolizing microorganism is a recombinant methanotroph comprising a first heterologous polynucleotide encoding a sulfide:quinone oxidoreductase (SQR), and optionally a second heterologous nucleic acid molecule that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof; or optionally a second heterologous nucleic acid molecule that encodes a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof; or optionally a second heterologous nucleic acid molecule encoding a fatty acid producing enzyme, a formaldehyde assimilation enzyme, or a combination thereof, capable of converting a gas (e.g., natural gas) into an oil composition; or any combination thereof.

In certain embodiments, a non-natural $C_1$ metabolizing microorganism is a recombinant methanotroph comprising a first heterologous polynucleotide encoding a sulfide:flavocytochrome-c oxidoreductase (FCC), and optionally a second heterologous nucleic acid molecule that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof; or optionally a second heterologous nucleic acid molecule that encodes a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof; or optionally a second heterologous nucleic acid molecule encoding a fatty acid producing enzyme, a formaldehyde assimilation enzyme, or a combination thereof, capable of converting a gas (e.g., natural gas) into an oil composition; or any combination thereof.

In certain embodiments, a non-natural $C_1$ metabolizing microorganism is a recombinant methanotroph comprising a first heterologous polynucleotide encoding a sulfur dioxygenase, and optionally a second heterologous nucleic acid molecule that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof; or optionally a second heterologous nucleic acid molecule that encodes a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof; or optionally a second heterologous nucleic acid molecule encoding a fatty acid producing enzyme, a formaldehyde assimilation enzyme, or a combination thereof, capable of converting a gas (e.g., natural gas) into an oil composition; or any combination thereof.

In certain embodiments, a non-natural $C_1$ metabolizing microorganism is a recombinant methanotroph comprising a first heterologous polynucleotide encoding a sulfur oxygenase, and optionally a second heterologous nucleic acid molecule that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof; or optionally a second heterologous nucleic acid molecule that encodes a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof; or optionally a second heterologous nucleic acid molecule encoding a fatty acid producing enzyme, a formaldehyde assimilation enzyme, or a combination thereof, capable of converting a gas (e.g., natural gas) into an oil composition; or any combination thereof.

In any of the aforementioned embodiments, a non-natural $C_1$ metabolizing microorganism is a recombinant methanotroph that encodes a biocatalytic enzyme capable of oxidizing light alkanes, such as an alkane monooxygenase (e.g., AMO, BMO, PMO, MMO), alkene monooxygenase or alkane hydroxylase, or a cell lysate thereof, further comprises a genetic modification to attenuate, inhibit, substantially reduce or functionally delete an alcohol dehydrogenase activity when the compound or composition to be produced comprises alcohol.

In any of the aforementioned embodiments, the $C_1$ metabolizing microorganism may be a $C_1$ metabolizing non-photosynthetic microorganism.

Codon Optimization

Expression of recombinant proteins may be difficult outside their original host. For example, variation in codon usage bias has been observed across different species of bacteria (Sharp et al., *Nucl. Acids. Res.* 33:1141, 2005). Over-expression of recombinant proteins even within their native host may also be difficult. In certain embodiments, nucleic acid molecules (e.g., nucleic acids encoding sulfur or alkane oxidizing enzymes) to be introduced into a host as described herein may be subjected to codon optimization prior to introduction into the host to ensure protein expression is enhanced. Codon optimization refers to alteration of codons in genes or coding regions of nucleic acids before transformation to reflect the typical codon usage of the host without altering the polypeptide encoded by the DNA molecule. Codon optimization methods for optimum gene expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Publication Nos. 2011/0111413 and 2008/0292918; disclosure of which are incorporated herein by reference, in their entirety).

In some embodiments, exogenous nucleic acid molecules of this disclosure are codon optimized for $C_1$ metabolizing microorganisms, such as bacteria. In certain embodiments, exogenous nucleic acid molecules of this disclosure are codon optimized for methanotrophs and methylotrophs as described herein. In particular embodiments, exogenous nucleic acid molecules of this disclosure are codon optimized for *Methylococcus capsulatus* Bath. Exemplary codon optimized nucleic acid molecules for expression in a $C_1$ metabolizing microorganism are provided in SEQ ID NOS.:1-54.

Similarly, exogenous nucleic acid molecules of this disclosure encoding polypeptide variants may be designed using the phylogenetic-based methods described in the references noted above (U.S. Pat. No. 8,005,620; Gustafsson; Welch et al.; Villalobos et al.; Minshull et al.). Each variant polypeptide generated by these methods will retain at least 50% activity (preferably 100% or more activity) and have a polypeptide sequence that is at least 90%, at least 91%, at least 92%, at least 93%, at least 94%, at least 95%, at least 96%, at least 97%, at least 98%, at least 99% identical, or 100% identical to a reference or parental wild-type polypeptide sequence. In certain embodiments, variant polypeptides will include at least one amino acid substitution (e.g., 1, 2, 3, 5, 6, 7, 8, 9 or 10 or more or up to 20, 25, or 30 substitutions) at a pre-determined position relative to a reference or parental wild-type enzyme, provided that a variant retains an activity of interest (e.g., sulfur oxidation or assimilation, light alkane oxidation, fatty acid production, fatty acid conversion, formaldehyde assimilation).

Transformation Methods

Any of the recombinant $C_1$ metabolizing microorganisms or methanotrophic bacteria described herein may be transformed to comprise at least one exogenous nucleic acid to provide the host with a new or enhanced activity (e.g., enzymatic activity) or may be genetically modified to remove or substantially reduce an endogenous gene function using any of a variety of methods known in the art.

Transformation refers to the transfer of a nucleic acid molecule (e.g., exogenous nucleic acid) into the genome of a host cell, resulting in genetically stable inheritance. Host cells containing the transformed nucleic acid molecules are referred to as "non-naturally occurring" or "recombinant" or "transformed" or "transgenic" cells.

Expression systems and expression vectors useful for the expression of heterologous nucleic acids in $C_1$ metabolizing microorganisms or methanotrophic bacteria are known.

Electroporation of $C_1$ metabolizing bacteria has been previously described in, for example, Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Patent Appl. Pub. No. 2008/0026005.

Bacterial conjugation, which refers to a particular type of transformation involving direct contact of donor and recipient cells, is more frequently used for the transfer of nucleic acids into $C_1$ metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Publication No. WO 02/18617; and Ali et al., *Microbiol.* 152:2931, 2006.

Expression of heterologous nucleic acids in $C_1$ metabolizing bacteria is known in the art (see, e.g., U.S. Pat. No. 6,818,424, U.S. Patent Appl. Pub. No. 2003/0003528). Mu transposon based transformation of methylotrophic bacteria has been described (Akhverdyan et al., *Appl. Microbiol. Biotechnol.* 91:857, 2011). A mini-Tn7 transposon system for single and multicopy expression of heterologous genes without insertional inactivation of host genes in *Methylobacterium* has been described (U.S. Patent Appl. Pub. No. 2008/0026005).

Various methods for inactivating, knocking-out, or deleting endogenous gene function in $C_1$ metabolizing bacteria may be used. Allelic exchange using suicide vectors to construct deletion/insertional mutants in slow growing C1 metabolizing bacteria have also been described in, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003.

Suitable homologous or heterologous promoters for high expression of exogenous nucleic acids may be utilized. For example, U.S. Pat. No. 7,098,005 describes the use of promoters that are highly expressed in the presence of methane or methanol for heterologous gene expression in C1 metabolizing bacteria. Additional promoters that may be used include deoxy-xylulose phosphate synthase methanol dehydrogenase operon promoter (Springer et al., *FEMS Microbiol. Lett.* 160:119, 1998); the promoter for PHA synthesis (Foellner et al., *Appl. Microbiol. Biotechnol.* 40:284, 1993); or promoters identified from native plasmid in methylotrophs (EP 296484). Non-native promoters include the lac operon Plac promoter (Toyama et al., *Microbiol.* 143:595, 1997) or a hybrid promoter such as Ptrc (Brosius et al., *Gene* 27:161, 1984). In certain embodiments, promoters or codon optimization are used for high constitutive expression of exogenous nucleic acids encoding sulfur utilization pathway enzymes in host methanotrophic bacteria. Regulated expression of an exogenous nucleic acid in a host methanotrophic bacterium may also be utilized. In certain embodiments, regulated expression of exogenous nucleic acids encoding sulfur utilization enzymes may be desirable to optimize growth rate of the non-naturally occurring methanotrophic bacteria. Controlled expression of nucleic acid molecules encoding sulfur utilization enzymes for response to the presence of an S substrate may improve bacterial growth in a variety of carbon source conditions. For example, an inducible/regulatable system of recombinant protein expression in methylotrophic and methanotrophic bacteria as described in, for example, U.S. Patent Appl. No. US 2010/0221813 may be used.

$C_1$ Metabolizing Microorganisms—Recombinant

The $C_1$ metabolizing microorganisms of this disclosure can be recombinantly modified to include nucleic acid molecules that express or over-express polypeptides of interest, which results in recombinant microorganisms useful for converting (e.g., assimilating, oxidizing) various components of gas or tainted gas (e.g., acid or sour natural gas) into other useful compounds.

For example, a $C_1$ metabolizing microorganism (such as a methanotroph or methylotroph) can be recombinantly transformed to produce a polypeptide capable of metabolizing an S substrate (e.g., sulfide oxidoreductase), recombinantly transformed to produce an alcohol composition (e.g., alkyl monooxygenase or hydroxylase), recombinantly transformed to produce fatty acid derivatives from light alkanes (e.g., fatty acyl-CoA reductase, carboxylic acid reductase, and optionally a thioesterase, acyl-CoA synthetase, monooxygenase), recombinantly transformed to produce an oil composition (e.g., a fatty acid producing enzyme, a formaldehyde assimilation enzyme, or a combination thereof), recombinantly transformed or genetically modified to optionally increase production of native sulfite oxidase, or any combination thereof. Exemplary amino acid sequences suitable for production by a $C_1$-metabolizing microorganism are provided in SEQ ID NOS.:55-108.

In certain embodiments, any of the recombinant polypeptides produced by $C_1$ metabolizing microorganisms as described herein may be stable in the presence of a chemical or environmental stress. The modifications to $C_1$ metabolizing microorganisms described herein can be through genomic alterations, addition of extrachromosomal recombinant expression systems, or a combination thereof.

By way of background, several biological pathways exist for the oxidation or assimilation of sulfur. Different steps in the pathway are catalyzed by various enzymes and, therefore, each of these may be over-expressed to increase the amount of enzyme and thus drive the oxidation or assimilation of sulfur. Nucleic acid molecules encoding enzymes required for the pathway may also be recombinantly added to a $C_1$ metabolizing microorganism lacking such enzymes. Finally, steps that would compete with the pathway leading to oxidation or assimilation of sulfur can be attenuated or blocked in order to maximize the removal of sulfur from, for example, sour gas. Elemental sulfur can be produced by partial oxidation of sulfide (Equation 1), which can then be removed by sedimentation. Complete oxidation of sulfide results in the production of sulfate (Equation 2), which is innocuous and water soluble.

$$2HS^- + O_2 \rightarrow 2S^0 + 2OH^- \quad (1)$$

$$2HS^- + 4O_2 \rightarrow 2SO_4^- + 2H^+ \quad (2)$$

Inorganic reduced sulfur compounds serve as electron donors in many phototrophic and chemotrophic bacteria (Friedrich, *Adv. Microb. Physiol.* 39:235, 1998). Hydrogen sulfide, the most reduced form of inorganic sulfur, occurs in hydrothermal vents and in sediments, where it is generated by sulfate reducing bacteria (Jannasch, Autotrophic Bacteria, Schlegel and Bowien (eds.) Springer Verlag, Berlin Heidelberg, pages 147-167, 1989; Trudinger, Early Organic Evolution, Schidlowski (ed.) Springer Verlag, Berlin Heidelberg, pages 367-377, 1992). Although hydrogen sulfide is toxic for most organisms, mainly because of the inhibition of aerobic respiration (Gosselin et al., Hydrogen sulfide In: *Clinical toxicology of commercial products*, 5th ed. Baltimore, Md., Williams and Wilkins, pages III-198-III-202, 1984), it serves as an electron donor for the energy generating systems of photo- and chemolithotrophic bacteria (Kelly et al., *Antonie Van Leeuwenhoek* 71:95, 1997; Stetter, *FEMS Microbiol. Rev.* 18:149, 1996).

In bacteria, the transport of electrons from sulfide to $NAD^+$ is mediated by membrane bound electron transport. The electrons from sulfide enter the chain either at the level of quinone via a sulfide:quinone oxidoreductase (SQR; EC 1.8.5.4), or at the level of c type cytochromes via a sulfide: cytochrome c oxidoreductase (flavocytochrome c, FCC; EC 1.8.2.3). In contrast, to assimilate sulfur into biosynthetic pathways (e.g., cysteine synthesis), hydrogen sulfide is required and therefore is produced by reduction of sulfate. Sulfate is first reduced to sulfite (see, e.g., Kopriva et al., *J. Biol. Chem.* 277:21786, 2002), which in turn can be further reduced to sulfide by sulfite reductases (Lillig, *Arch. Biochem. Biophys.* 392:303, 2001). Two types of sulfite reductase enzymes are known—hydrogen sulfide:$NADP^+$ oxidoreductase (also known as sulfite reductase (NADPH); EC 1.8.1.2) and hydrogen sulfide:ferredoxin oxidoreductase (also known as sulfite reductase (ferredoxin) or SIR, EC 1.8.7.1). But, the reduction of sulfite to sulfide is a reversible reaction and, therefore, can instead be an oxidation reaction of sulfide to sulfite, which in turn can be further oxidized to sulfate.

Any sulfide that is produced or is present for use by a $C_1$ metabolizing microorganism can enter the cysteine biosynthesis pathway, wherein cysteine synthase incorporates $H_2S$ into O-acetyl-serine to produce cysteine. Alternatively, sulfide can enter the homocysteine biosynthesis pathway wherein O-acetylhomoserine sulfhydrylase incorporates $H_2S$ into O-acetylhomoserine to produce homocysteine, which can be further converted into methionine by methionine synthase (cobalamin dependent or independent) or homocysteine methyltransferase.

An alternate pathway for inorganic sulfur (including elemental sulfur) oxidation is through a pathway found in several sulfur-oxidizing organisms, including the facultative chemolithotroph *Starkeya novella*, thermoacidophilic *Sulfobacillus sibiricus*, and acidophilic Thiobacilli, such as *Thiobacillus thioparus* or *Thiobacillus denitrificans*. Another group is Acidithiobacilii, which are bacteria capable of catalyzing the oxidation of inorganic sulfur compounds under acidic conditions and ambient temperatures. Several members of *Acidithiobacillus* (e.g., *Acidithiobacillus ferrooxidans*, *Acidithiobacillus thiooxidans*) and *Acidiphilium* (e.g., *Acidiphilium acidophilum*) can grow chemolithoautotrophically with sulfide, elemental sulfur, thiosulfate or polythionates (Hiraishi et al., *Int. J. Syst. Bacteriol.* 48:1389, 1998; Kelly and Wood, *Int. J. Syst. Evol. Microbiol.* 50:511, 2000). Another exemplary group having this pathway are the *Acidianus* spp. (e.g., *Acidianus ambivalens*, *Acidianus brierleyi*), which are obligately chemolithotrophic, facultatively aerobic archaea isolated from acidothermal springs. This alternate pathway comprises the use of sulfur dioxygenase or glutathione-dependent sulfur dioxygenase (EC 1.13.11.18) to oxidize sulfide via S-sulfanylglutathione (GSSH), a product of the non-enzymatic reaction of glutathione disulfide (GSSG) with $H_2S$.

Another pathway for inorganic sulfur oxidation involves sulfur oxygenase reductase (SOR, EC 1.13.11.55), which is found in thermophilic microorganisms. SOR simultaneously catalyzes oxidation and reduction of elemental sulfur to produce sulfite, thiosulfate, and sulfide in the presence of molecular oxygen. Exemplary organisms that produce this enzyme include *Acidianus ambivalens*, *Acidianus tengchongensis*, *Aquifex aeolicus*, *Acidithiobacillus caldus*, *Halothiobacillus neopolitanus*, *Sulfolobus metallicus*, *Sulfolobus tokodaii*, *Sulfobacillus acidophillus*, and *Sulfobacillus thermosulfidooxidans*

In certain embodiments, $C_1$ metabolizing microorganisms and $C_1$ metabolizing non-photosynthetic microorganisms of this disclosure may be engineered to express or overproduce hydrogen sulfide:$NADP^+$ oxidoreductase (also known as sulfite reductase (NADPH) or cysJ/cysI; EC 1.8.1.2), including both subunits (a and 13). One advantage of using this enzyme is that the sulfide to sulfate reaction will generate reducing equivalents that can provide energy for the cells to grow faster and for carbon fixation.

For example, to express or overproduce sulfide:$NADP^+$ oxidoreductase, one or more genes from *Bacillus subtilis* (cysJ and cysI), *Escherichia coli* (cysJ and cysI), or *Saccharomyces cerevisiae* (met10 and met5) can be introduced into and expressed or overexpressed in a $C_1$ metabolizing microorganism or a $C_1$ metabolizing non-photosynthetic microorganism (e.g., non-natural methanotroph bacteria), thereby producing or overproducing exogenous sulfite reductase (NADPH) alpha and beta subunit polypeptides or functional fragments thereof. Other sources of sulfite reductase (NADPH) alpha and beta subunit polypeptides or functional fragments thereof can be from *Rhodobacter capsulatus*, *Shewanella putrefaciens*, or *Acidithiobacillus ferrooxidans*. In certain embodiments, sulfite reductase (NADPH) alpha and beta subunit polypeptides for use in the compositions and methods disclosed herein are from *Rhodobacter capsulatus* SB 1003 (Genbank Accession Nos. YP_003579141.1 [α] and YP_003577746.1 [β]), *Escherichia coli* K-12 substrain MG1655 (Genbank Accession No. AAA69273.1 [α] and AAA69274.1 [β]), *Shewanella putrefaciens* CN-32 (Genbank Accession No. ABP76777.1 [α] and ABP76776.1 [β]), *Bacillus subtilis* MB73/2 (Genbank Accession No. EME08247.1 [α] and EME08683.1 [β]), or *Acidithiobacillus ferrooxidans* ATCC 23270 (Genbank Accession No. YP 002427483.1[α] and YP 002427484.1 [β]).

In certain embodiments, sulfite reductase (NADPH) alpha and beta subunit polypeptides or functional fragments thereof are derived or obtained from *Rhodobacter capsulatus* SB 1003 or *Escherichia coli* K-12 substrain MG1655 and have an amino acid sequence that is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession Nos. YP_003579141.1 [α] and YP_003577746.1 [β] or AAA69273.1 [α] and AAA69274.1 [β], respectively, or a functional fragments thereof. In another embodiment, the recombinant encoded sulfite reductase (NADPH) alpha and beta subunit polypeptides have amino acid sequences that are identical to the sequences set forth in Genbank Accession Nos. YP_003579141.1 [α] and YP_003577746.1 [β] or AAA69273.1 [α] and AAA69274.1 [β] or comprises a consensus sequence of known sulfite reductase (NADPH) α-subunits and a consensus sequence of known sulfite reductase (NADPH) β-subunits.

In certain embodiments, the sulfite reductase (NADPH) alpha and beta subunit polypeptides or functional fragments thereof are encoded by a nucleic acid sequence that has been codon optimized. The codon optimized sulfite reductase (NADPH) alpha and beta subunit polypeptides or functional fragments thereof may be encoded by nucleic acids comprising any one of SEQ ID NOS.:21-35. In certain embodiment, the recombinant encoded sulfite reductase (NADPH) alpha and beta subunit polypeptides have amino acid sequences that are identical to the sequences set forth in any one of SEQ ID NOS.:55-69. In some embodiments, the recombinant encoded sulfite reductase (NADPH) alpha and beta subunit polypeptides have amino acid sequences that are at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in any one of SEQ ID NOS.:55-69.

In certain embodiments, $C_1$ metabolizing microorganisms and $C_1$ metabolizing non-photosynthetic microorganisms as described herein may be engineered to express or overproduce hydrogen sulfide:ferredoxin oxidoreductase (SIR, EC 1.8.7.1). One advantage of using this enzyme is that the sulfide to sulfate reaction will generate reducing equivalents that can provide energy for the cells to grow faster and for carbon fixation.

For example, a nucleic acid molecule from *Cyanidioschyzon merolae* encoding a SIR enzyme can be introduced into and expressed or overexpressed in a $C_1$ metabolizing microorganism or a $C_1$ metabolizing non-photosynthetic microorganism (e.g., non-natural methanotroph bacteria), thereby producing or overproducing exogenous SIR polypeptides or functional fragments thereof. Other sources of exogenous SIR polypeptides or functional fragments thereof can be from *Cyanidioschyzon merolae*, *Aphonathece halophytica*, *Oscillatoria nigro-viridis*, *Pseudomonas putida*, or *Anabaena cylindrica*. In certain embodiments, an SIR enzyme for use in the compositions and methods disclosed herein is from *Cyanidioschyzon merolae* 10D (Genbank Accession No. BAM79554.1), *Oscillatoria nigro-viridis* PCC 7112 (Genbank Accession No. YP_007113209.1), *Pseudomonas putida* GB-1 (Genbank Accession No. YP_001669502.1), *Anabaena cylindrica* PCC 7220 (Genbank Accession No. YP_007159823.1), or *Aphonathece halophytica* 7418 (Genbank Accession No. YP_007168206.1).

In certain embodiments, a SIR polypeptide or functional fragment thereof is derived or obtained from *Cyanidioschyzon merolae* 10D or *Oscillatoria nigro-viridis* PCC 7112 and has an amino acid sequence that is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. BAM79554.1 or YP_007113209.1, respectively, or a functional fragment thereof. In another embodiment, the recombinant encoded SIR polypeptide has an amino acid sequence that is identical to the sequence set forth in Genbank Accession No. BAM79554.1 or YP_007113209.1 or comprises a consensus sequence of known SIR polypeptide sequences.

In certain embodiments, $C_1$ metabolizing microorganisms and $C_1$ metabolizing non-photosynthetic microorganisms as described herein may be engineered to express or overproduce sulfide:quinone oxidoreductase (SQR; EC 1.8.5.4). The SQR polypeptide appears to transfer electrons from sulfide directly into the quinone pool. One advantage of using this enzyme is that the sulfide can be oxidized to elemental sulfate and will likely precipitate, which may be in the form of intracellular globules or granules as observed in native sulfur metabolizing microorganisms. Also, the native cofactor (quinone) can be used to provide the reducing power to the cells.

Exemplary SQR polypeptides (encoded by sqr gene) or functional fragments thereof can be found in *Rhodobacter capsulatus*, *Shewanella putrefaciens*, *Paracoccus denitrificans*, *Acidithiobacillus ferrooxidans*, *Thiobacillus ferrooxidans*, *Aquifex aeolicus*, *Oscillatoria limnetica*, *Chlorobaculum tepidum*, *Chlorobium limicola*, *Anabaena* ATCC 7120, and *Aphonathece halophytica*. SQR polypeptide sequences are publicly available and exemplary sequences are provided in FIG. 3 of Griesbeck et al., Recent Res. Dev. Microbiol. 4:179, 2000, which figure and sequences therein are hereby incorporated by reference in their entirety. In certain embodiments, an SQR enzyme for use in the compositions and methods disclosed herein is from *Rhodobacter capsulatus* SB 1003 (Genbank Accession No. YP_003576957.1), *Oscillatoria limnetica* 'Solar Lake' (Genbank Accession No. AAF72962.1), *Acidithiobacillus ferrooxidans* ATCC 23270 (Genbank Accession No. YP_002424774.1), *Aquifex aeolicus* VF5 (Genbank Accession No. AAC07903.1), *Aphonathece halophytica* 7418 (Genbank Accession No. YP_007167227.1).

In certain embodiments, an SQR polypeptide or functional fragment thereof is derived or obtained from *Rhodobacter capsulatus* SB 1003 or *Oscillatoria limnetica* 'Solar Lake' and has an amino acid sequence that is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession No. YP_003576957.1 or AAF72962.1, respectively, or a functional fragment thereof. In another embodiment, the recombinant encoded SQR enzyme has an amino acid sequence that is identical to the sequence set forth in Genbank Accession No. YP_003576957.1 or AAF72962.1, or comprises a consensus sequence of known SQR polypeptide sequences.

In certain embodiments, the SQR polypeptide or functional fragments thereof is encoded by a nucleic acid sequence that has been codon optimized. The codon optimized SQR polypeptide or functional fragments thereof may be encoded by nucleic acids comprising any one of SEQ ID NOS.:36-40. In certain embodiment, the recombinant encoded SQR polypeptide has an amino acid sequence that is identical to the sequence set forth any one of SEQ ID NOS.:70-74. In some embodiments, the recombinant encoded SQR polypeptide has an amino acid sequences that is at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in any one of SEQ ID NOS.:70-74.

In certain embodiments, $C_1$ metabolizing microorganisms and $C_1$ metabolizing non-photosynthetic microorganisms as described herein may be engineered to express or overproduce sulfide:cytochrome c oxidoreductase (flavocytochrome c sulfide dehydrogenase, FCC; EC 1.8.2.3). The sulfide dehydrogenases are generally either soluble periplasmic heterodimeric enzymes having a flavoprotein subunit and a heme subunit, or are monomeric membrane-bound enzymes having a single heme $c_{554}$ subunit. The FCC polypeptide appears to shuttle electrons from sulfide to a cytochrome c. One advantage of using this enzyme is that the sulfide can be oxidized to elemental sulfate and will likely precipitate, which may be in the form of intracellular globules or granules as observed in native sulfur metabolizing microorganisms. Also, the native cofactors (cytochromes) can be used to provide the reducing power to the cells.

Exemplary polypeptides (encoded by fcc gene) can be found in *Allochromatium vinosum*, *Thiobacillus* spp. W5, *Chlorobium limicola*, *Ectothiorhodospira shaposhnikovii*, *Chlorobaculum tepidum*, *Thiobacillus denitrificans*, or *Thiocystis violascens*. Representative FCC polypeptide sequences are publicly available, and an exemplary polypeptide sequence from *Allochromatium vinosum* is provided in FIG. 3 of Griesbeck et al., Recent Res. Dev. Microbiol. 4:179, 2000, which figure and sequence therein are hereby incorporated by reference in their entirety. In certain embodiments, FCC flavoprotein and heme subunit polypeptides for use in the compositions and methods disclosed herein are from *Allochromatium vinosum* DSM 180 (Genbank Accession No. AAB86576.1 [flavo] and AAA23316.1 [heme]), *Chlorobium limicola* (Genbank Accession No. ACD89119.1 [flavo] and AAL68891.1 [heme]), *Chlorobaculum tepidum* TLS (Genbank Accession No. AAM72249.1 [flavo] and Q8KAS5.1 [heme]), *Thiobacillus denitrificans* ATCC 25259 (Genbank Accession No. YP_315793.1 [flavo] and YP_315792.1 [heme]), or *Thiocystis violascens* DSM 198 (Genbank Accession No. YP_006416402.1 [flavo] and YP_006416403.1 [heme]).

In certain embodiments, FCC flavoprotein and heme subunit polypeptides or functional fragment thereof are derived or obtained from *Allochromatium vinosum* DSM 180 or *Thiocystis violascens* DSM 198 and have an amino acid sequence that is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession Nos. AAB86576.1 [flavo] and AAA23316.1 [heme] or YP_006416402.1 [flavo] and YP_006416403.1 [heme], respectively, or a functional fragment thereof. In another embodiment, the recombinant encoded FCC flavoprotein and heme subunit polypeptides have amino acid sequences that are identical to the sequence set forth in Genbank Accession Nos. AAB86576.1 [flavo] and AAA23316.1 [heme] or YP_006416402.1 [flavo] and YP_006416403.1 [heme], or comprise a consensus sequence of known FCC flavo subunits and a consensus sequence of known FCC heme subunits, respectively.

In certain embodiments, the FCC flavoprotein and heme subunit polypeptides or functional fragments thereof are encoded by a nucleic acid sequence that has been codon optimized. The codon optimized FCC flavoprotein and heme subunit polypeptides or functional fragments thereof may be encoded by nucleic acids comprising any one of SEQ ID NOS.:41-48. In certain embodiment, the recombinant encoded FCC flavoprotein and heme subunit polypeptides have amino acid sequences that are identical to the sequences set forth in any one of SEQ ID NOS.:75-84. In some embodiments, the recombinant encoded FCC flavoprotein and heme subunit polypeptides have amino acid sequences that are at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in any one of SEQ ID NOS.:75-84.

In certain embodiments, $C_1$ metabolizing microorganisms and $C_1$ metabolizing non-photosynthetic microorganisms as described herein may be engineered to express or overproduce sulfur oxygenase (sulfur oxygenase/reductase, SOR). Exemplary SOR polypeptides for use in the microorganisms, compositions and methods disclosed herein include those from *Acidianus tegchongensis* (Genbank Accession No. AAK58572.1), *Sulfolobus metallicus* (Genbank Accession No. ABN04222.1), *Acidithiobacillus caldus* ATCC 51756 (Genbank Accession No. AIA55075.1), *Sulfobacillus thermosulfidooxidans* (Genbank Accession No. WP 028963476.1), or any combination thereof.

In certain embodiments, SOR polypeptides or functional fragment thereof are derived or obtained from *Acidianus tegchongensis* or *Sulfolobus metallicus* and have an amino acid sequence that is at least at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in Genbank Accession Nos. AAK58572.1 or ABN04222.1, respectively, or a functional fragment thereof. In another embodiment, the recombinant encoded SOR polypeptides have amino acid sequences that are identical to the sequence set forth in Genbank Accession Nos. AAK58572.1 or ABN04222.1 or comprise a consensus sequence of known SOR polypeptides, respectively.

In certain embodiments, the SOR polypeptides or functional fragments thereof are encoded by a nucleic acid sequence that has been codon optimized. The codon optimized SOR polypeptides or functional fragments thereof may be encoded by nucleic acids comprising any one of SEQ ID NOS.:51-54. In certain embodiment, the recombinant encoded SOR polypeptides have amino acid sequences that are identical to the sequences set forth in any one of SEQ ID NOS.:85-88. In some embodiments, the SOR polypeptides have amino acid sequences that are at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the sequence set forth in any one of SEQ ID NOS.:85-88.

In some embodiments, the recombinant $C_1$ metabolizing microorganism is expressing a polypeptide capable of metabolizing an S substrate that is a hydrogen sulfide:$NADP^+$ oxidoreductase, hydrogen sulfide:ferredoxin oxidoreductase, sulfide:flavocytochrome-c oxidoreductase, sulfide:quinone oxidoreductase, sulfur dioxygenase, or any combination thereof, and optionally expresses an exogenous sulfite oxidase or has increased endogenous sulfite oxidase activity.

In certain embodiments, the recombinant $C_1$ metabolizing microorganism is expressing a polypeptide capable of metabolizing an S substrate that is a sulfide:flavocytochrome-c oxidoreductase, sulfide:quinone oxidoreductase, and sulfur dioxygenase, and optionally expresses an exogenous sulfite oxidase or has increased endogenous sulfite oxidase activity.

In some embodiments, the recombinant $C_1$ metabolizing microorganism is expressing a polypeptide capable of metabolizing an S substrate that is a sulfur oxygenase, and optionally expresses an exogenous sulfite oxidase or has increased endogenous sulfite oxidase activity.

In some embodiments, the recombinant microorganism is expressing a polypeptide capable of metabolizing an S substrate that is hydrogen-sulfide:$NADP^+$ oxidoreductase, and optionally expresses an exogenous sulfite oxidase or has increased endogenous sulfite oxidase activity.

In some embodiments, the recombinant microorganism is expressing a polypeptide capable of metabolizing an S substrate that is hydrogen sulfide:ferredoxin oxidoreductase, and optionally expresses an exogenous sulfite oxidase or has increased endogenous sulfite oxidase activity.

In some embodiments, the recombinant microorganism is expressing a polypeptide capable of metabolizing an S substrate that is sulfide:flavocytochrome-c oxidoreductase, and optionally expresses an exogenous sulfite oxidase or has increased endogenous sulfite oxidase activity.

In some embodiments, the recombinant microorganism is expressing a polypeptide capable of metabolizing an S substrate that is sulfide:quinone oxidoreductase, and optionally expresses an exogenous sulfite oxidase, has increased endogenous sulfite oxidase activity, or is expressing a sulfide:flavocytochrome-c oxidoreductase encoded by an exogenous nucleic acid molecule.

In some embodiments, the recombinant microorganism is expressing a polypeptide capable of metabolizing an S substrate that is sulfur dioxygenase, and optionally expresses an exogenous sulfite oxidase, has increased endogenous sulfite oxidase activity, is expressing a sulfide:flavocytochrome-c oxidoreductase encoded by an exogenous nucleic acid molecule, or is expressing a sulfide:quinone oxidoreductase encoded by an exogenous nucleic acid molecule.

In any of the aforementioned embodiments, a polypeptide capable of metabolizing an S substrate is stable in the presence of a chemical or environmental stress.

In further aspects, several additional different modifications can be made to a recombinant $C_1$ metabolizing microorganism or a recombinant $C_1$ metabolizing non-photosynthetic microorganism as described herein, either in combination with the sulfur oxidizing or assimilation activity or individually, to utilize the $C_1$ substrate feedstock to obtain, for example, light alkane conversion to alcohol; light alkane conversion to a $C_8$-$C_{24}$ fatty aldehyde, fatty alcohol, fatty ester wax, hydroxy fatty acid, dicarboxylic acid, or any combination thereof; light alkane conversion to biological material (including oil composition); or any combination thereof.

For example, a recombinant $C_1$ metabolizing microorganism of the present disclosure may further comprise an exogenous nucleic acid molecule encoding a polypeptide capable of oxidizing light alkanes, such as a biocatalytic enzyme with monooxygenase or hydroxylase activity, to convert $C_1$ substrates contained in gas into high-value molecules (e.g., alcohol, fatty acid derivatives, fuel precursor). In certain embodiments, the polypeptide capable of oxidizing light alkanes is stable in the presence of a chemical or environmental stress. In further embodiments, a recombinant $C_1$ metabolizing microorganism of the present disclosure may be engineered to have at least one inactivated alcohol dehydrogenase or at least one alcohol dehydrogenase with reduced activity to facilitate specific oxidation of light hydrocarbons, including mixed gas substrates, into an alcohol composition or a mixed alcohol composition.

Monooxygenases, expressed by methanotrophic bacteria, utilize an enzyme-associated metal center to split the O—O bond of dioxygen ($O_2$), wherein one oxygen atom is reduced to form $H_2O$, while the other oxygen atom attacks a C—H bond of a light alkane (e.g., methane) and is incorporated into the light alkane to form the corresponding alcohol (e.g., methanol will be produced from methane). A reducing agent, such as formate, duroquinol, and hydrogen gas ($H_2$) (see, e.g., Shiemke et al., Arch. Biochem. Biophys. 321:421, 1995; U.S. Patent Publication No. 2003/0203456), can help complete this oxidation reaction and regenerate the monooxygenase.

Exemplary monooxygenases include methane monooxygenases (MMOs, which may be soluble, sMMO, or membrane-bound, pMMO), ammonia monooxygenases (AMO), butane monooxygenases (BMOs, which may be soluble, sBMO, or membrane-bound, pBMO, and optionally associate with a hydroxylase, reductase or chaperonin-like protein), propane monooxygenase (PMO, which may be soluble, sPMO or associated with P450, referred to as PMO:P450), alkene monooxygenases, alkane hydroxylases, or P450 (also known as cytochrome P450 or CYP). Moreover, monooxygenases can utilize a broad range of substrates beyond methane, including ethane, propane, butane or pentane, into their corresponding alcohols (see, e.g., Jiang et al., Biochem. Engineering J. 49:277, 2010; Colby et al., Biochem. J. 165:395, 1977; Hyman et al., Applied Environ. Microbiol. 54:3187, 1988; Chen et al., Protein Eng. Design Selection 25:171, 2012; Chen, 2011, Directed evolution of cytochrome P450 for small alkane hydroxylation. Dissertation (Ph.D.), California Institute of Technology). Additionally, monooxygenases can oxidize propene into propene oxide, but-1-ene into 1,2-epoxybutane, 1,3-butadiene into 1,2-epoxybut-3-ene, cis-but-2-ene into cis-2,3-epoxybutane and crotonaldehyde, and trans-but-2-ene into trans-2,3-epoxybutane, crotonyl alcohol and crotonaldehyde. sMMO can oxidize ethane, propane, butane, hexane, octane, and 2-methylpropane into their associated alcohols, as well as oxide ethene into epoxyethane, propene into epoxypropane, but-1-ene into 1,2-epoxybutane, cis-but-2-ene into cis-2,3-epoxybutane and cis-2-buten-1-ol, and trans-but-2-ene into trans-2,3-epoxybutane and trans-2-buten-1-ol. Also, alkene monooxygenases can catalyze aromatic monohydroxylation of benzene, toluene, and phenol (see, e.g., Zhou et al. Applied Environ. Microbiol. 65:1589-95, 1999).

Numerous monooxygenases and P450 genes have been sequenced and characterized (see, e.g., Stainthorpe et al., Arch. Microbiol. 152:154, 1989; Stainthorpe et al., Gene 91:27, 1990; Coufal et al., Eur. J. Biochem. 267:2174, 2000; Cardy et al., Mol. Microbiol. 5:335, 1991; Cardy et al., Arch. Microbiol. 156:477, 1991; Semrau et al., J. Bacteriol. 177:3071, 1995; Stolyar et al., Microbiol. 145:1235, 1999; Gilbert et al., Appl. Environ. Microbiol. 66:966, 2000; Bodrossy et al., Applied Environ. Microbiol. 61:3549, 1995; Bodrossy et al., FEMS Microbiol. Lett. 170:335, 1999; Lin et al., Appl. Environ. Microbiol. 71:6458, 2005; Hou et al., Biol. Direct. 3:26, 2008; McTavish et al., J. Bacteriol. 175:2436, 1993; Norton et al., Arch. Microbiol. 177:139, 2002; Nelson et al., Pharmacogenetics 6:1, 1996; Funhoff et al., J. Bacteriol. 188:5220, 2006; Kubota et al., Biosci. Biotechnol. Biochem. 69:2421, 2005). Exemplary pMMO amino acid sequences and AMO amino acid sequences are provided in International Patent Publication No. WO 2014/062703, which sequences are incorporated herein in their entirety.

In certain embodiments, MMO, BMO, PMO, AMO, alkene monooxygenase, alkane hydroxylase, or P450 polypeptides or functional fragments thereof are encoded by a nucleic acid sequence that has been codon optimized. A codon optimized MMO, BMO, PMO, AMO, alkene monooxygenase, alkane hydroxylase, or P450 polypeptide, or functional fragment thereof, may be encoded by nucleic acids as set forth in any one of SEQ ID NOS.:1-20. In certain embodiments, a MMO, BMO, PMO, AMO, alkene monooxygenase, alkane hydroxylase, or P450 polypeptide as used herein has an amino acid sequence that is identical to the corresponding sequence set forth in any one of SEQ ID NOS.:89-108. In some embodiments, a MMO, BMO, PMO, AMO, alkene monooxygenase, alkane hydroxylase, or P450 polypeptide has an amino acid sequence that is at least 75%, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the corresponding sequence set forth in any one of SEQ ID NOS.:89-108.

As provided herein, methods for oxidizing hydrocarbons, including converting alkanes into their corresponding alcohols or alkenes into their corresponding epoxides, comprises providing a genetically engineered $C_1$ microorganism or cell lysate thereof in the presence of air or oxygen and a reducing agent. In certain embodiments, a gas substrate comprising a light alkane (e.g., methane, ethane, propane, butane) is converted into a corresponding alcohol, a light alkene (e.g., ethylene, propylene, butylene, butadiene) is converted into a corresponding epoxide, or a mixed gas composition comprising light alkanes, alkenes, or both are converted into their corresponding alcohol(s), their corresponding epoxide(s), or mixture of alcohols and epoxides, respectively.

In certain embodiments, there are provided recombinant $C_1$ metabolizing microorganisms or $C_1$ metabolizing non-photosynthetic microorganisms, or a cell lysate thereof, comprising an exogenous nucleic acid molecule that encodes a polypeptide capable of oxidizing light alkanes, such as a methane monooxygenase (MMO), an ammonia monooxygenases (AMO), or P450 enzyme.

In further embodiments, any one of the aforementioned $C_1$ metabolizing microorganisms or $C_1$ metabolizing non-photosynthetic microorganisms, or a cell lysate thereof, comprising an exogenous hydrogen sulfide:$NADP^+$ oxidoreductase, hydrogen sulfide:ferredoxin oxidoreductase, sulfide:quinone oxidoreductase, sulfide:flavocytochrome-c oxidoreductase, sulfur dioxygenase, or any combination thereof, may further comprise a second exogenous nucleic acid molecule that encodes a polypeptide capable of oxidizing light alkanes, such as a methane monooxygenase (MMO), a butane monooxygenase (BMO), a propane monooxygenase (PMO), an ammonia monooxygenase (AMO), an alkane hydroxylase, or a P450 enzyme.

In further embodiments, any one of the aforementioned $C_1$ metabolizing microorganisms or $C_1$ metabolizing non-photosynthetic microorganisms, or a cell lysate thereof, comprising an exogenous sulfur oxygenase, may further comprise a second exogenous nucleic acid molecule that encodes a polypeptide capable of oxidizing light alkanes, such as a methane monooxygenase (MMO), a butane monooxygenase (BMO), a propane monooxygenase (PMO), an ammonia monooxygenase (AMO), an alkane hydroxylase, or a P450 enzyme.

An enzyme with monooxygenase activity may comprise multiple components. In certain embodiments, a nucleic acid molecule encoding a polypeptide with monooxygenase activity (capable of oxidizing light alkanes) may comprise polynucleotides encoding a gene cluster or operon for an enzyme with methane monooxygenase activity, or for a single subunit that constitutes the active site for the enzyme. By way of example, where an enzyme with methane monooxygenase activity is pMMO, a nucleic acid may comprise polynucleotides comprising a pmoCAB gene cluster or a pmoA gene ((3 subunit). In another example, where an enzyme with methane monooxygenase activity is sMMO, a nucleic acid may comprise polynucleotides comprising a mmoXYZ gene cluster or a mmoX gene (a subunit).

The introduction of an exogenous nucleic acid encoding a polypeptide capable of oxidizing light alkanes, such as a monooxygenase, can confer upon non-naturally occurring microorganisms provided herein the capability of converting light alkanes into their corresponding alcohols (e.g., converting ethane, propane, and butane into their corresponding alcohols, ethanol, propanol, and butanol, respectively), or converting alkenes into their corresponding epoxides (e.g., converting ethylene, propylene, butene, and butadiene into their corresponding epoxides ethylene oxide, propylene oxide, butene oxide, and butadiene 1,2 oxide respectively).

In certain embodiments, methane is converted into methanol, ethane is converted into ethanol, propane is converted into propanol, butane is converted into butanol, pentane is converted into pentanol, or any combination thereof. In further embodiments, butane is converted into butanol and the butanol is comprised substantially of n-butanol (i.e., n-butanol comprises at least 50% or more of the butanol product). In still further embodiments, propane is converted into propanol and the propanol is comprised substantially of n-propanol (i.e., n-propanol comprises at least 50% or more of the propanol product).

In certain embodiments, recombinant $C_1$ metabolizing microorganisms or $C_1$ metabolizing non-photosynthetic microorganisms, or a cell lysate thereof, of this disclosure may be capable of converting ethylene, propylene, butene, butadiene into their corresponding epoxides, ethylene oxide, propylene oxide, butene oxide, and butadiene 1,2 oxide respectively.

In certain embodiments, provided are recombinant $C_1$ metabolizing microorganisms or $C_1$ metabolizing non-photosynthetic microorganisms, or a cell lysate thereof, of this disclosure capable of converting a mixed alkane gas into a mixed alcohol composition. A mixed alkane gas may be wet (unprocessed) natural gas or a partially separated derivative thereof (e.g., natural gas liquids separated from wet natural gas during processing). Natural gas liquids may include ethane, propane, butane, or a combination thereof. In certain embodiments, provided are non-naturally occurring $C_1$ metabolizing microorganisms or $C_1$ metabolizing non-photosynthetic microorganisms capable of converting light alkanes (i.e., any combination of two or more alkanes selected from methane, ethane, propane, butane, pentane, or any combination thereof) into their corresponding alcohols, which produces a mixed alcohol composition.

In certain embodiments, provided are recombinant $C_1$ metabolizing microorganisms or $C_1$ metabolizing non-photosynthetic microorganisms, or a cell lysate thereof, of this disclosure capable of converting a mixed alkene gas into a mixed epoxide product. A mixed alkene gas may be a gas stream from a petroleum cracker or a partially separated derivative thereof. In certain embodiments, provided are recombinant microorganisms of this disclosure capable of converting light alkenes (i.e., any combination of two or more alkenes selected from ethylene, propylene, butene, butadiene, or any combination thereof) into their corresponding epoxides.

By way of background, alcohol or epoxide products, including methanol, produced by enzymes with monooxygenase or hyrdroxylase activity may be oxidized further into unwanted products by endogenous alcohol dehydrogenases (see, e.g., Anthony and Zatman, *Biochem. J.* 96:808, 1965; Lu et al., *J. Am. Chem. Soc.* 132:15451, 2010). Recombinant microorganisms provided herein may exhibit poor yields due to downstream metabolism of methanol, other alcohol products (e.g., ethanol, propanol, and butanol), or epoxides. By inactivating at least one alcohol dehydrogenase (e.g., methanol dehydrogenase), reduction of alcohol or epoxide product loss and improvement of product yield may be achieved.

In certain embodiments, a recombinant microorganism or cell lysate thereof of this disclosure is capable of using a reducing agent to convert the light alkane gas to an alcohol composition. In one embodiment, the reducing agent is hydrogen ($H_2$) gas. For example, an alkane monooxygenase, alkene monooxygenase, alkane hydroxylases, or combination thereof expressed in the recombinant microorganism or cell lysate thereof is capable of directly using $H_2$ as a reducing agent to convert light alkane gas to an alcohol composition. In certain embodiments, an alkane monooxygenase is pMMO, sMMO, AMO, pBMO, sBMO, sPMO, PMO:P450, P450, or any combination thereof. In certain embodiments, the alkane monooxygenase is a methane monooxygenase, such as a pMMO, sMMO, or P450. In certain embodiments, the chemical or environmental stress is a temperature at least 60° C., a pH of at least 9, or a pH of no more than 5. In certain embodiments, the alcohol dehydrogenase is inactivated by the chemical or environmental stress, such as a temperature at least 60° C., a pH of at least 9, or a pH of no more than 5, or the alcohol dehydrogenase is inactivated by genetic modification. In certain embodiments, the at least one inactivated alcohol dehydrogenase comprises a methanol dehydrogenase.

Any one of the aforementioned $C_1$ metabolizing microorganisms or $C_1$ metabolizing non-photosynthetic microorganisms comprising an exogenous hydrogen sulfide:$NADP^+$ oxidoreductase, hydrogen sulfide:ferredoxin oxidoreductase, sulfide:quinone oxidoreductase, sulfide:flavocytochrome-c oxidoreductase, sulfur dioxygenase, sulfur oxygenase, cysteine synthase, O-acetylhomoserine sulfhydrylase, methionine synthase (cobalamin dependent or independent), or homocysteine methyltransferase; an exogenous nucleic acid molecule that encodes a polypeptide capable of oxidizing light alkanes (e.g., monooxygenase or hydroxylase) or a cell lysate thereof, or both; may further comprise at least one endogenous protein function that is attenuated, inhibited, substantially reduced or functionally deleted, such as alcohol dehydrogenase (e.g., methanol dehydrogenase activity).

In certain embodiments, at least one alcohol dehydrogenase that is deactivated or reduced in activity comprises a methanol dehydrogenase (MDH). In certain embodiments, alcohol dehydrogenase activity is reduced, inhibited or knocked-out by genetic modification or by a chemical or environmental stress (e.g., a temperature of at least 60° C., a pH of at least 9, or a pH no more than 5).

As used herein, an alcohol dehydrogenase refers to any enzyme that catalyzes the reversible conversion of alcohols into their corresponding aldehydes or ketones with the reduction of $NAD^+$ to NADH. An alcohol dehydrogenase is inactivated if it possesses less than 25% activity as compared to a wild type or reference enzyme or possesses less than 25% activity during or after exposure to a chemical or environmental stress as compared to normal conditions. For example, an inactivated ADH (e.g., genetically inactivated) may possess 24%, 20%, 15%, 14%, 13%, 12%, 11%, 10%, 9%, 8%, 7%, 6%, 5%, 4%, 3%, 2%, 1%, or less activity as compared to a wild type ADH. In another example, an inactivated ADH may possess 24%, 20%, 15%, 14%, 13%, 12%, 11%, 10%, 9%, 8%, 7%, 6%, 5%, 4%, 3%, 2%, 1%, or less activity during exposure to a chemical or environmental stress (e.g., heat of at least 60° C.) as compared to in the absence of a chemical or environmental stress (e.g., at normal temperature).

In certain embodiments, provided are $C_1$ metabolizing microorganisms or $C_1$ metabolizing non-photosynthetic microorganisms or a cell lysate thereof in which two, three, four, or more alcohol dehydrogenases are attenuated, inhibited, inactivated, or functionally deleted. As an example, ADH sequences that may be inactivated in *Methylosinus trichosporium* OB3b, *Methylococcus capsulatus* str. Bath, and *Methylomicrobium alcaliphilum* are provided in FIG. 5 of U.S. Provisional Patent Application No. 61/714,123, which sequences are incorporated herein in their entirety.

In certain embodiments, a nucleic acid molecule encoding a polypeptide capable of metabolizing sulfur, a nucleic acid molecule encoding a polypeptide capable of oxidizing light alkanes, or both, may encode polypeptides that naturally possess a desired "stability" or "stable activity" in the presence of a chemical or environmental stress, which may be used to generate a recombinant $C_1$ metabolizing microorganism, a recombinant $C_1$ metabolizing non-photosynthetic microorganism, or a cell lysate thereof of this disclosure. In further embodiments, an enzyme may inherently have chemical or environmental stress stability, e.g., thermophilic, alkaliphilic, or acidophilic polypeptides may be used. In some embodiments, a substantial amount or most of the endogenous enzymes of the $C_1$ metabolizing microorganism are inactivated by a chemical or environmental stress, except for the exogenous polypeptides with sulfur oxidizing activity, alkane oxidizing activity, or both.

An environmental or chemical stress refers to a condition that can affect the ability of a microorganism to metabolize normally, survive, or affect the ability of a protein or enzyme to function. Environmental stress conditions include temperature extremes (heat or cold), light availability, water availability, or oxygen concentration. Chemical stress conditions include increased metal concentration, pH stress (high acidity or alkalinity), increased salt concentration, exposure to chemicals, and low nutrient availability. By way of example, an environment stress may be a temperature of at least 40° C., at least 45° C., at least 50° C., at least 55° C., at least 60° C., at least 65° C., at least 70° C., at least 75° C., at least 80° C., at least 85° C., at least 90° C., or at least 95° C. In another example a chemical stress may be a pH of at least 8, at least 8.5, at least 9, at least 9.2, at least 9.4, at least 9.6, at least 9.8, at least 10 or a pH no more than 6, no more than 5.5, no more than 5, no more than 4.8, no more than 4.6, no more than 4.4, no more than 4.2, no more than 4. In certain embodiments, a chemical or environmental stress is a temperature of at least 60° C., a pH of at least 9, or a pH of no more than 5.

A polypeptide with enzyme activity that is stable in the presence of a chemical or environmental stress refers to a polypeptide that retains substantial activity (e.g., ability to oxidize sulfur, alkanes, or both) during exposure to a chemical or environmental stress (i.e., retains at least 25% catalytic activity under the stress condition as compared to in the absence of the stress condition), which stability may be inherent or may be genetically engineered. A polypeptide with enzyme activity that is stable in the presence of a chemical or environmental stress may retain at least 25%, 30%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% activity under the stress condition as compared to in the absence of the stress condition, or for genetically modified, as compared to a wild-type or reference enzyme exposed to the same stress condition (i.e., wild type or reference enzyme retains less than 25% catalytic activity during exposure to a stress condition than in the absence of the stress condition).

Exemplary pMMO amino acid sequences from thermostable methanotrophic bacteria that may be used are provided in FIG. 3 of U.S. Provisional Patent Application No. 61/714,123, which sequences are incorporated herein in their entirety. Exemplary AMO amino acid sequences from halotolerant bacteria and from highly stress resistant bacteria are provided in FIG. 4 of U.S. Provisional Patent Application No. 61/714,123, which sequences are incorporated herein in their entirety. Exemplary reference pMMO and AMO amino acid sequences that may be genetically engineered are provided in FIGS. 2 and 4 of U.S. Provisional Patent Application No. 61/714,123, which sequences are incorporated herein in their entirety.

In certain further aspects, for example, in addition to converting contaminants in tainted gas into non-toxic and non-polluting molecules or utilizing gas and contaminant molecules as a source of carbon and energy, a recombinant $C_1$ metabolizing microorganism of the present disclosure may further comprise an exogenous nucleic acid molecule encoding a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or any combination thereof.

In certain embodiments, any one of the aforementioned $C_1$ metabolizing microorganisms or $C_1$ metabolizing non-photosynthetic microorganisms comprising an exogenous nucleic acid encoding hydrogen sulfide:$NADP^+$ oxidoreductase, hydrogen sulfide:ferredoxin oxidoreductase, sulfide:quinone oxidoreductase, sulfide:flavocytochrome-c oxidoreductase, sulfur dioxygenase, or any combination thereof, may further comprise a second exogenous nucleic acid molecule encoding a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof. In some embodiments, the recombinant fatty acid converting enzyme of a $C_1$ metabolizing microorganism (e.g., non-natural methanotroph bacteria) is a fatty acyl-CoA reductase (FAR) for converting a gas feedstock (e.g., natural gas) into $C_8$ to $C_{24}$ fatty acid derivatives, such as fatty alcohol. In various embodiments, a recombinant $C_1$ metabolizing microorganism expresses or over expresses a nucleic acid molecule that encodes a FAR enzyme. In certain embodiments, a FAR enzyme may be endogenous to the $C_1$ metabolizing microorganism or a FAR enzyme may be heterologous to the $C_1$ metabolizing microorganism.

In certain embodiments, any one of the aforementioned $C_1$ metabolizing microorganisms or $C_1$ metabolizing non-photosynthetic microorganisms comprising an exogenous nucleic acid encoding sulfur oxygenase, may further comprise a second exogenous nucleic acid molecule encoding a fatty acid converting enzyme capable of converting a gas (e.g., natural gas) into a $C_8$-$C_{24}$ fatty acid derivative comprising a fatty aldehyde, a fatty alcohol, a fatty ester wax, a hydroxy fatty acid, a dicarboxylic acid, or a combination thereof. In some embodiments, the recombinant fatty acid converting enzyme of a $C_1$ metabolizing microorganism (e.g., non-natural methanotroph bacteria) is a fatty acyl-CoA reductase (FAR) for converting a gas feedstock (e.g., natural gas) into $C_8$ to $C_{24}$ fatty acid derivatives, such as fatty alcohol. In various embodiments, a recombinant $C_1$ metabolizing microorganism expresses or over expresses a nucleic acid molecule that encodes a FAR enzyme. In certain embodiments, a FAR enzyme may be endogenous to the $C_1$ metabolizing microorganism or a FAR enzyme may be heterologous to the $C_1$ metabolizing microorganism.

In further embodiments, the present disclosure provides a non-natural methanotroph contains a fatty acid converting enzyme that is an acyl-CoA dependent fatty acyl-CoA reductase, such as acr1, FAR, CER4 (Genbank Accession No. JN315781.1), or Maqu_2220, capable of forming a fatty alcohol. In certain embodiments, the non-natural methanotroph contains a fatty acid converting enzyme that is an acyl-CoA dependent fatty acyl-CoA reductase capable of forming a fatty aldehyde, such as acr1. In some embodiments, the process will result in the production of fatty alcohols comprising $C_8$, $C_{10}$, $C_{12}$, $C_{14}$, $C_{16}$, $C_{18}$, $C_{20}$, $C_{22}$ or $C_{24}$ carbons in length.

In any of the aforementioned recombinant $C_1$ metabolizing microorganisms capable of producing fatty acid derivatives (e.g., fatty alcohols), a $C_1$ metabolizing microorganism (e.g., non-natural methanotroph bacteria) further comprises a recombinant nucleic acid molecule encoding a thioesterase, such as a tesA lacking a leader sequence, UcFatB, or BTE. In certain embodiments, the endogenous thioesterase activity is reduced, minimal or abolished as compared to unaltered endogenous thioesterase activity.

In any of the aforementioned recombinant $C_1$ metabolizing microorganisms capable of producing fatty acid derivatives (e.g., fatty alcohols), a $C_1$ metabolizing microorganism (e.g., non-natural methanotroph bacteria) further comprises a recombinant nucleic acid molecule encoding an acyl-CoA synthetase, such as FadD, yng1, or FAA2. In certain embodiments, the endogenous acyl-CoA synthetase activity is reduced, minimal or abolished as compared to unaltered endogenous acyl-CoA synthetase activity.

In still further embodiments, the present disclosure provides a $C_1$ metabolizing microorganism (e.g., non-natural methanotroph bacteria) having a recombinant nucleic acid encoding hydrogen sulfide:$NADP^+$ oxidoreductase, hydrogen sulfide:ferredoxin oxidoreductase, sulfide:quinone oxidoreductase, sulfide:flavocytochrome-c oxidoreductase, sulfur dioxygenase, or any combination thereof; a recombinant nucleic acid molecule encoding a heterologous acyl-CoA dependent fatty acyl-CoA reductase, a recombinant nucleic acid molecule encoding a heterologous thioesterase, and a recombinant nucleic acid molecule encoding a heterologous acyl-CoA synthetase, wherein the $C_1$ metabolizing microorganism is capable of oxidizing sulfur and converting a gas (e.g., natural gas) into a $C_8$-$C_{24}$ fatty alcohol. In certain embodiments, a fatty acyl-CoA reductase is over-expressed as compared to the expression level of the native fatty acyl-CoA reductase. In certain embodiments, an acyl-CoA dependent fatty acyl-CoA reductase capable of forming a fatty aldehyde, fatty alcohol, or both is acr1, or the acyl-CoA independent fatty acyl-CoA reductase capable of forming a fatty alcohol is FAR, CER4, or Maqu_2220. In certain embodiments, the acyl-CoA synthetase is FadD, yng1, or FAA2.

In still further embodiments, the present disclosure provides a $C_1$ metabolizing microorganism (e.g., non-natural methanotroph bacteria) having a recombinant nucleic acid encoding sulfur oxygenase; a recombinant nucleic acid molecule encoding a heterologous acyl-CoA dependent fatty acyl-CoA reductase, a recombinant nucleic acid molecule encoding a heterologous thioesterase, and a recombinant nucleic acid molecule encoding a heterologous acyl-CoA synthetase, wherein the $C_1$ metabolizing microorganism is capable of oxidizing sulfur and converting a gas (e.g., natural gas) into a $C_8$-$C_{24}$ fatty alcohol. In certain embodiments, a fatty acyl-CoA reductase is over-expressed as compared to the expression level of the native fatty acyl-CoA reductase. In certain embodiments, an acyl-CoA dependent fatty acyl-CoA reductase capable of forming a fatty aldehyde, fatty alcohol, or both is acr1, or the acyl-CoA independent fatty acyl-CoA reductase capable of forming a fatty alcohol is FAR, CER4, or Maqu_2220. In certain embodiments, the acyl-CoA synthetase is FadD, yng1, or FAA2.

In yet further embodiments, there is provided a $C_1$ metabolizing microorganism (e.g., non-natural methanotroph bacteria) having a recombinant nucleic acid molecule encoding a heterologous acyl-CoA independent fatty acyl-CoA reductase, and a recombinant nucleic acid molecule encoding a heterologous thioesterase, wherein the methanotroph is capable of converting a gas (e.g., natural gas) into a $C_8$-$C_{24}$ fatty alcohol. In certain embodiments, the fatty acyl-CoA reductase is over-expressed in the non-natural methanotroph as compared to the expression level of the native fatty acyl-CoA reductase.

In certain embodiments, recombinant $C_1$ metabolizing microorganisms capable of producing fatty acid derivatives (e.g., fatty alcohols) will comprise a heterologous nucleic acid molecule encoding a carboxylic acid reductase (CAR). In some embodiments, recombinant microorganisms will additionally comprise one or more heterologous nucleic acid molecules selected from an acyl-ACP thioesterase (TE), ketoreductase/alcohol dehydrogenase (ADH), or phosphopantetheinyl transferase (PPTase), as further described herein.

Intracellular expression of a carboxylic acid reductase of this disclosure will lead to production not only of fatty aldehyde but also the corresponding fatty alcohol, which is due to alcohol dehydrogenase activity within a recombinant host cell. In some embodiments, the process will result in the production of fatty alcohols comprising $C_8$, $C_{10}$, $C_{12}$, $C_{14}$, $C_{16}$, $C_{18}$, $C_{20}$, $C_{22}$ or $C_{24}$ carbons in length.

In even further embodiments, there is provided a $C_1$ metabolizing microorganism or non-natural methanotroph having a recombinant nucleic acid encoding hydrogen sulfide:NADP$^+$ oxidoreductase, hydrogen sulfide:ferredoxin oxidoreductase, sulfide:quinone oxidoreductase, sulfide:flavocytochrome-c oxidoreductase, sulfur dioxygenase, or any combination thereof; a recombinant nucleic acid molecule encoding a carboxylic acid reductase; a recombinant nucleic acid molecule encoding a phosphopantetheinyl transferase; and a recombinant nucleic acid molecule encoding an alcohol dehydrogenase; wherein the $C_1$ metabolizing microorganism or methanotroph is capable of oxidizing sulfur and converting a gas (e.g., natural gas) into a $C_8$-$C_{24}$ fatty alcohol.

In even further embodiments, there is provided a $C_1$ metabolizing microorganism or non-natural methanotroph having a recombinant nucleic acid encoding sulfur oxygenase; a recombinant nucleic acid molecule encoding a carboxylic acid reductase; a recombinant nucleic acid molecule encoding a phosphopantetheinyl transferase; and a recombinant nucleic acid molecule encoding an alcohol dehydrogenase; wherein the $C_1$ metabolizing microorganism or methanotroph is capable of oxidizing sulfur and converting a gas (e.g., natural gas) into a $C_8$-$C_{24}$ fatty alcohol.

In other aspects, this disclosure provides any of the aforementioned $C_1$ metabolizing microorganisms or non-natural methanotrophs that further comprise a recombinant nucleic acid molecule encoding a P450 enzyme, monooxygenase, or hydroxylase enzyme to produce an ω-hydroxy fatty acid. In certain embodiments, the endogenous alcohol dehydrogenase activity is inhibited as compared to unaltered endogenous alcohol dehydrogenase activity. In other embodiments, the endogenous alcohol dehydrogenase activity is increased or elevated as compared to unaltered endogenous alcohol dehydrogenase activity to produce dicarboxylic acid.

In still further embodiments, there is provided a $C_1$ metabolizing microorganism or non-natural methanotroph having a recombinant nucleic acid molecule encoding a heterologous fatty acyl-CoA reductase; a recombinant nucleic acid molecule encoding a heterologous thioesterase; and a recombinant nucleic acid molecule encoding a heterologous P450, monooxygenase or hydroxylase, wherein the native alcohol dehydrogenase is inhibited, and wherein the $C_1$ metabolizing microorganism or methanotroph is capable of converting a $C_1$ substrate into a $C_8$-$C_{24}$ ω-hydroxy fatty acid.

In still further embodiments, there is provided a $C_1$ metabolizing microorganism or non-natural methanotroph having a recombinant nucleic acid encoding hydrogen sulfide:NADP$^+$ oxidoreductase, hydrogen sulfide:ferredoxin oxidoreductase, sulfide:quinone oxidoreductase, sulfide:flavocytochrome-c oxidoreductase, sulfur dioxygenase, or any combination thereof; a recombinant nucleic acid molecule encoding a heterologous fatty acyl-CoA reductase, and a recombinant nucleic acid molecule encoding a heterologous thioesterase, wherein the $C_1$ metabolizing microorganism or methanotroph is over-expressing native alcohol dehydrogenase as compared to the normal expression level of native alcohol dehydrogenase, transformed with a recombinant nucleic acid molecule encoding a heterologous alcohol dehydrogenase, or both, and wherein the $C_1$ metabolizing microorganism or methanotroph is capable of oxidizing sulfur and converting a gas (e.g., natural gas) into a $C_8$-$C_{24}$ dicarboxylic acid alcohol.

In still further embodiments, there is provided a $C_1$ metabolizing microorganism or non-natural methanotroph having a recombinant nucleic acid encoding sulfur oxygenase; a recombinant nucleic acid molecule encoding a heterologous fatty acyl-CoA reductase, and a recombinant nucleic acid molecule encoding a heterologous thioesterase, wherein the $C_1$ metabolizing microorganism or methanotroph is over-expressing native alcohol dehydrogenase as compared to the normal expression level of native alcohol dehydrogenase, transformed with a recombinant nucleic acid molecule encoding a heterologous alcohol dehydrogenase, or both, and wherein the $C_1$ metabolizing microorganism or methanotroph is capable of oxidizing sulfur and converting a gas (e.g., natural gas) into a $C_8$-$C_{24}$ dicarboxylic acid alcohol.

In any of the aforementioned $C_1$ metabolizing microorganisms or non-natural methanotrophs, a fatty alcohol is produced comprising one or more of $C_8$-$C_{14}$ or $C_{10}$-$C_{16}$ or $C_{12}$-$C_{14}$ or $C_{14}$-$C_{18}$ or $C_{14}$-$C_{24}$ fatty alcohols. In certain embodiments, the $C_1$ metabolizing microorganism or non-natural methanotroph produces fatty alcohol comprising $C_{10}$ to $C_{18}$ fatty alcohol and the $C_{10}$ to $C_{18}$ fatty alcohols comprise at least 70% of the total fatty alcohol. In further embodiments, the $C_1$ metabolizing microorganism or non-natural methanotroph produces fatty alcohol comprising a branched chain fatty alcohol.

In further embodiments, a fatty acid derivative is a saturated or unsaturated surfactant product having a carbon chain length of about 8 to about 24 carbon atoms, about 8 to about 18 carbon atoms, about 8 to about 14 carbon atoms, about 10 to about 18 carbon atoms, or about 12 to about 16 carbon atoms. In another example, the surfactant product has a carbon chain length of about 10 to about 14 carbon atoms, or about 12 to about 14 carbon atoms.

In yet other embodiments, a fatty acid derivative contains a carbon chain of about 8 to 24 carbon atoms, about 8 to 18 carbon atoms, about 10 to 18 carbon atoms, about 10 to 16 carbon atoms, about 12 to 16 carbon atoms, about 12 to 14 carbon atoms, about 14 to 24 carbon atoms, about 14 to 18 carbon atoms, about 8 to 16 carbon atoms, or about 8 to 14 carbon atoms. In alternative embodiments, a fatty acid derivative contains a carbon chain less than about 20 carbon atoms, less than about 18 carbon atoms, less than about 16 carbon atoms, less than about 14 carbon atoms, or less than about 12 carbon atoms. In more embodiments, a fatty ester product is a saturated or unsaturated fatty ester product having a carbon atom content between 8 and 24 carbon atoms. In further embodiments, a fatty ester product has a carbon atom content between 8 and 14 carbon atoms. In other embodiments, a fatty ester product has a carbon content of 14 and 20 carbons. In yet other embodiments, a fatty ester is the methyl ester of $C_{18:1}$. In still further embodiments, a fatty ester is the ethyl ester of $C_{16:1}$. In further embodiments, a fatty ester is a methyl ester of $C_{16:1}$. In yet other embodiments, a fatty ester is octadecyl ester of octanol.

In certain other aspects, a recombinant $C_1$ metabolizing microorganism or a non-natural methanotroph of the present disclosure is capable of converting gas (e.g., light alkanes such as methane, ethane, propane, butane) and associated contaminants (e.g., $H_2S$, $CO_2$) into biological material, wherein an oil composition can be extracted from the biological material, or the biological material can be used as animal feed or fertilizer. In certain embodiments, for example, in addition to converting contaminants in tainted gas into non-toxic and non-polluting molecules or utilizing gas and contaminant molecules as a source of carbon and energy, a recombinant $C_1$ metabolizing microorganism or a non-natural methanotroph of the present disclosure may further comprise an exogenous nucleic acid molecule encoding a fatty acid producing enzyme, a formaldehyde assimilation enzyme, or a combination thereof, capable of converting a gas (e.g., natural gas) into an oil composition.

In further embodiments, there is provided a $C_1$ metabolizing microorganism or non-natural methanotroph having a recombinant nucleic acid molecule encoding hydrogen sulfide:NADP$^+$ oxidoreductase, hydrogen sulfide:ferredoxin oxidoreductase, sulfide:quinone oxidoreductase, sulfide:flavocytochrome-c oxidoreductase, sulfur dioxygenase, or any combination thereof; and a recombinant nucleic acid molecule encoding a fatty acid producing enzyme, a recombinant nucleic acid molecule encoding a formaldehyde assimilation enzyme, or a combination thereof; wherein the $C_1$ metabolizing microorganism or methanotroph is capable of oxidizing sulfur and converting a gas (e.g., natural gas) into an oil composition.

In further embodiments, there is provided a $C_1$ metabolizing microorganism or non-natural methanotroph having a recombinant nucleic acid molecule encoding sulfur oxygenase; and a recombinant nucleic acid molecule encoding a fatty acid producing enzyme, a recombinant nucleic acid molecule encoding a formaldehyde assimilation enzyme, or a combination thereof; wherein the $C_1$ metabolizing microorganism or methanotroph is capable of oxidizing sulfur and converting a gas (e.g., natural gas) into an oil composition.

In still further embodiments, a recombinant $C_1$ metabolizing microorganism or a non-natural methanotroph of the present disclosure may have one or more improved properties (e.g., higher growth rate, ability to grow in high pH, improved utilization of nutrients, temperature stability, increased biomaterial yield). In related embodiments, a product such as an oil composition (e.g., fatty acids, triglycerides, phospholipids, isoprenes, terpenes, PHA) is recovered from the recombinant $C_1$ metabolizing microorganism or non-natural methanotroph, and optionally an oil composition is refined to produce plastic prescursors or one or more fuels, such as jet fuel, diesel fuel, gasoline, or a combination thereof. In still further embodiments, a recombinant $C_1$ metabolizing microorganism or a non-natural methanotroph of the present disclosure may produce an oil composition and an alcohol (such as methanol, ethanol, propanol, or longer chain fatty alcohols), wherein the oil composition is reacted with an alcohol (e.g., in an esterification plant) to generate biodiesel.

In yet further embodiments, an oil composition is derived or extracted from cell membrane of the $C_1$ metabolizing non-photosynthetic microorganism (e.g., methylotroph, methanotroph) or may be recovered from a culture supernatant if secreted or excreted, or a combination thereof. Extraction of an oil composition may be accomplished using various different solvents (e.g., a polar solvent, a non-polar solvent, a neutral solvent, an acidic solvent, a basic solvent, hexane, or a combination thereof), such as hexane or acidic methanol or chloroform/methanol mix, in extraction methods known in the art.

In certain embodiments, the present disclosure provides a recombinant $C_1$ metabolizing microorganism comprising a first exogenous nucleic acid molecule encoding a polypeptide capable of metabolizing an S substrate, wherein the recombinant microorganism is capable of scrubbing sulfur containing compounds from sour gas to produce sweet gas when all the light alkanes are not fully consumed or converted.

In any of the aforementioned embodiments, a plasmid containing one or more of the aforementioned genes, all under the control of a constitutive or otherwise controllable promoter, can be used. Several additional different modifications can be made as described herein, either in combination or individually, to a $C_1$ metabolizing microorganism or a $C_1$ metabolizing non-photosynthetic microorganism or to any of the exogenous nucleic acid molecules introduced into the microorganism or any combination changes to microorganism and recombinant nucleic acid molecules to produce high-value molecules (e.g., alcohols, fatty acid derivatives, amino acids), biological materials (e.g., animal feed, fertilizer, oil composition), sweetened gas, or any combination thereof.

In any of the aforementioned recombinant $C_1$ metabolizing microorganisms (e.g., non-natural methanotroph bacteria), the recombinant microorganism is converting natural gas, unconventional natural gas, casinghead gas, or vapor above a confined sour hydrocarbon, and is capable of producing an alcohol composition, such as methanol, ethanol, propanol, butanol, or a combination thereof.

In some embodiments, a variant sulfide:NADP$^+$ oxidoreductase, hydrogen sulfide:ferredoxin oxidoreductase, sulfide:flavocytochrome-c oxidoreductase, sulfide:quinone oxidoreductase, cysteine synthase, O-acetylhomoserine sulfhydrylase, methionine synthase (cobalamin dependent or independent), homocysteine methyltransferase, sulfur dioxygenase, sulfur oxygenase, or sulfite oxidase may encompass one or more amino acid substitutions, including variants having one or more conservative substitutions. In certain embodiments, conservatively substituted variants of a sulfide:NADP$^+$ oxidoreductase, hydrogen sulfide:ferredoxin oxidoreductase, sulfide:flavocytochrome-c oxidoreductase, sulfide:quinone oxidoreductase, hydrogen sulfide S-acetyltransferase, cysteine synthase, sulfur dioxygenase, sulfur oxygenase, or sulfite oxidase will include substitutions of a small percentage, such as less than 5%, less than 4%, less than 3%, less than 2%, or less than 1% of the amino acids of a sulfide:NADP$^+$ oxidoreductase, hydrogen sulfide:ferredoxin oxidoreductase, sulfide:flavocytochrome-c oxidoreductase, sulfide:quinone oxidoreductase, hydrogen sulfide S-acetyltransferase, sulfur dioxygenase, sulfur oxygenase, or sulfite oxidase polypeptide sequence, respectively.

In any of the aforementioned recombinant $C_1$ metabolizing microorganisms (e.g., non-natural methanotroph bacteria) capable of metabolizing an S substrate as encompassed by the present disclosure, the amount of alcohol produced ranges from about 1 mg/L to about 0.5 g/L to about 1 g/L to about 2 g/L to about 5 g/L to about 10 g/L to about 50 g/L to about 100 g/L to about 500 g/L. In certain other embodiments, a $C_1$ substrate feedstock for a $C_1$ metabolizing microorganism or non-natural methanotroph as described herein is a light alkane gas mixture, natural gas, unconventional natural gas, syngas, casinghead gas, wellhead condensate, refinery gas, pyrolysis gas, ventilation (air) stream, or vapor above a confined sour hydrocarbon. In certain embodiments, a $C_1$ metabolizing microorganism or non-natural methanotroph is capable of converting alkane gas mixture, natural gas, unconventional natural gas, syngas, casinghead gas, wellhead condensate, refinery gas, pyrolysis gas, ventilation (air) stream, or vapor above a confined sour hydrocarbon into their corresponding alcohols or other compositions.

For example, the recombinant microorganisms of this disclosure are capable of converting a mixture of light alkanes (i.e., any combination of two or more alkanes selected from methane, ethane, propane, butane, pentane, or any combination thereof) into their corresponding alcohols. In further embodiments, ethane, propane, and butane are converted into their corresponding alcohols, ethanol, propanol, and butanol, respectively, or converting ethylene, propylene, butene, and butadiene into their corresponding epoxides. In yet further embodiments, butanol comprises substantially of n-butanol (i.e., n-butanol comprises at least 50% or more of the butanol product). In still further embodiments, propanol comprises substantially of n-propanol (i.e., n-propanol comprises at least 50% or more of the propanol product). In further embodiments, recombinant microorganisms of this disclosure may be capable of converting ethylene, propylene, butene, butadiene into their corresponding epoxides, ethylene oxide, propylene oxide, butene oxide, and butadiene 1,2 oxide respectively. In certain embodiments, provided are recombinant microorganisms of this disclosure capable of converting a mixed alkene gas from, for example, a petroleum cracker or a partially separated derivative thereof, into a mixed epoxide product.

Any of the aforementioned $C_1$ metabolizing microorganisms or non-natural methanotroph bacteria may also have undergone strain adaptation under selective conditions to produce variants with improved properties for metabolizing a gas and any associated contaminants, before or after introduction of the recombinant nucleic acid molecules. Improved properties may include increased growth rate, yield of desired products (e.g., increased sulfite oxidase activity or production, desulfurized gas, light alkanes oxidized to alcohols), or tolerance to process or culture contaminants. In particular embodiments, a high growth variant $C_1$ metabolizing microorganism or methanotroph comprises a host bacteria capable of growing on a light alkane gas or methane feedstock as a primary carbon and energy source and that possesses a faster exponential phase growth rate (i.e., shorter doubling time) than its parent, reference, or wild-type bacteria (see, e.g., U.S. Pat. No. 6,689,601).

Each of the recombinant microorganisms of this disclosure may be grown as an isolated culture, with a heterologous organism that may aid with growth, or one or more of these bacteria may be combined to generate a mixed culture. In still further embodiments, $C_1$ metabolizing microorganisms of this disclosure are obligate $C_1$ metabolizing microorganisms capable of utilizing (e.g., oxidizing or assimilating) an S substrate.

Culture Methods

In certain embodiments, methods described herein use recombinant microorganisms or cell lysates thereof immobilized on, within, or behind a solid matrix. In further embodiments, the non-naturally occurring microorganisms, cell lysates or cell-free extracts thereof are in a substantially non-aqueous state (e.g., lyophilized). Recombinant microorganisms, cell lysates or cell-free fractions thereof are temporarily or permanently attached on, within, or behind a solid matrix within a bioreactor. Nutrients, substrates, and other required factors are supplied to the solid matrices so that the cells may catalyze desired reactions. Recombinant microorganisms may grow on the surface of a solid matrix (e.g., as a biofilm). Recombinant microorganisms, cell lysates or cell-free fractions derived thereof may be attached on the surface or within a solid matrix without cellular growth or in a non-living state. Exemplary solid matrix supports for microorganisms include polypropylene rings, ceramic bio-rings, ceramic saddles, fibrous supports (e.g., membrane), porous glass beads, polymer beads, charcoal, activated carbon, dried silica gel, particulate alumina, Ottawa sand, clay, polyurethane cell support sheets, and fluidized bed particle carrier (e.g., sand, granular-activated carbon, diatomaceous earth, calcium alginate gel beads).

A variety of culture methodologies may be used for recombinant methanotrophic bacteria described herein. For example, methanotrophic bacteria may be grown by batch culture or continuous culture methodologies. In certain embodiments, the cultures are grown in a controlled culture unit, such as a fermenter, bioreactor, hollow fiber membrane bioreactor, or the like.

A classical batch culturing method is a closed system where the composition of the media is set at the beginning of the culture and not subject to external alterations during the culture process. Thus, at the beginning of the culturing process, the media is inoculated with the desired $C_1$ metabolizing microorganism (e.g., methanotroph) and growth or metabolic activity is permitted to occur without adding anything to the system. Typically, however, a "batch" culture is batch with respect to the addition of carbon source and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, *Appl. Biochem. Biotechnol.* 36:227, 1992).

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where carbon and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the carbon source or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art, and a variety of methods are detailed by Brock, supra.

Liquid phase bioreactors (e.g., stirred tank, packed bed, one liquid phase, two liquid phase, hollow fiber membrane) are well known in the art and may be used for growth of non-naturally occurring microorganisms and biocatalysis.

By using gas phase bioreactors, substrates for biocatalysis or bioremediation are absorbed from a gas by non-naturally occurring microorganisms, cell lysates or cell-free fractions thereof, rather than from a liquid. Use of gas phase bioreactors with microorganisms is known in the art (e.g., U.S. Pat. Nos. 2,793,096; 4,999,302; 5,585,266; 5,079,168; and 6,143,556; U.S. Statutory Invention Registration H1430; U.S. Patent Application Publication No. 2003/0032170; *Emerging Technologies in Hazardous Waste Management III*, 1993, eds. Tedder and Pohland, pp 411-428). Exemplary gas phase bioreactors include single pass system, closed loop pumping system, and fluidized bed reactor. By utilizing gas phase bioreactors, methane or other gaseous substrates is readily available for biocatalysis by polypeptides with monooxygenase or hydroxylase activity. Furthermore, distillation of an alcohol product from aqueous solution, which represents a significant cost in liquid phase bioreactors, may be bypassed in gas phase bioreactors. In preferred embodiments, methods for desulfurizing a gas or converting a gas into an alcohol composition are performed in gas phase bioreactors. In further embodiments, methods for desulfurizing a gas or converting a gas into an alcohol composition are performed in fluidized bed reactors. In a fluidized bed reactor, a fluid (i.e., gas or liquid) is passed upward through particle bed carriers, usually sand, granular-activated carbon, or diatomaceous earth, on which microorganisms can attach and grow. The fluid velocity is such that particle bed carriers and attached microorganisms are suspended (i.e., bed fluidization). The microorganisms attached to the particle bed carriers freely circulate in the fluid, allowing for effective mass transfer of substrates in the fluid to the microorganisms and increased microbial growth. Exemplary fluidized bed reactors include plug-flow reactors and completely mixed reactors. Uses of fluidized bed reactors with microbial biofilms are known in the art (e.g., Pfluger et al., *Bioresource Technol.* 102:9919, 2011; Fennell et al., *Biotechnol, Bioengin.* 40:1218, 1992; Ruggeri et al., *Water Sci. Technol.* 29:347, 1994; U.S. Pat. Nos. 4,032,407; 4,009,098; 4,009,105; and 3,846,289).

Methanotrophic bacteria described in the present disclosure may be grown as an isolated pure culture, with a heterologous non-methanotrophic microorganism(s) that may aid with growth, or with one or more different strains or species of methanotrophic bacteria may be combined to generate a mixed culture.

Methods for Treating and Converting Gas

In other aspects, as described herein, there are provided methods for treating a gas by culturing a recombinant $C_1$ metabolizing microorganism with a tainted gas feedstock for a time sufficient for the recombinant microorganism to metabolize unwanted contaminants from the tainted gas and convert the gas into compounds of interest, wherein the tainted feedstock comprises a $C_1$ substrate and an S substrate and the recombinant $C_1$ metabolizing microorganism comprises an exogenous nucleic acid molecule encoding a polypeptide capable of metabolizing the S substrate. In certain embodiments, the recombinant $C_1$ metabolizing microorganism assimilates or oxidizes each substrate. The assimilation or oxidation can be partial, substantial, or complete.

In further aspects, as described herein, there are provided methods for treating a gas by culturing a recombinant $C_1$ metabolizing microorganism with a sulfur-containing gas feedstock for a time sufficient to metabolize an S substrate, wherein the recombinant $C_1$ metabolizing microorganism comprises an exogenous nucleic acid molecule encoding a sulfide converting enzyme.

In yet further aspects, as described herein, there are provided methods for treating a gas by culturing a recombinant $C_1$ metabolizing microorganism with an acid or sour gas feedstock for a time sufficient to recover sweetened gas, wherein the recombinant $C_1$ metabolizing microorganism comprises an exogenous nucleic acid molecule encoding a polypeptide capable of oxidizing sulfide.

In still further aspects, as described herein, there are provided methods for treating a gas by culturing a recombinant $C_1$ metabolizing microorganism with a tainted gas feedstock for a time sufficient for the recombinant microorganism to in part decontaminate the gas and in part convert the gas to biomass, wherein the recombinant $C_1$ metabolizing microorganism comprises an exogenous nucleic acid molecule encoding a polypeptide capable of oxidizing sulfide.

In any of the aforementioned methods for using recombinant $C_1$ metabolizing microorganisms (e.g., non-natural methanotroph bacteria) to produce compounds of interest (or even some treated gas) as disclosed in the present disclosure, the polypeptide capable of oxidizing sulfur is a hydrogen sulfide:$NADP^+$ oxidoreductase, hydrogen sulfide:ferredoxin oxidoreductase, sulfide:flavocytochrome-c oxidoreductase, sulfide:quinone oxidoreductase, sulfur dioxygenase, or any combination thereof, and optionally expresses an exogenous sulfite oxidase or has increased endogenous sulfite oxidase activity and that are optionally stable in the presence of chemical or environmental stress. In certain embodiments, the S substrate is oxidized to a sulfate.

In any of the aforementioned methods for using recombinant $C_1$ metabolizing microorganisms (e.g., non-natural methanotroph bacteria) to produce compounds of interest (or even some treated gas) as disclosed in the present disclosure, the polypeptide capable of oxidizing sulfur is a sulfur oxygenase, and optionally expresses an exogenous sulfite oxidase or has increased endogenous sulfite oxidase activity and that are optionally stable in the presence of chemical or environmental stress. In certain embodiments, the S substrate is oxidized to a sulfide or a sulfate.

In certain embodiments, the polypeptide capable of oxidizing an S substrate is a sulfide:flavocytochrome-c oxidoreductase, sulfide:quinone oxidoreductase, and sulfur dioxygenase, and optionally expresses an exogenous sulfite oxidase or has increased endogenous sulfite oxidase activity or has increased endogenous sulfide:quinone oxidoreductase. In further embodiments, the polypeptide capable of oxidizing an S substrate is hydrogen sulfide:$NADP^+$ oxidoreductase, and optionally expresses an exogenous sulfite oxidase or has increased endogenous sulfite oxidase activity or has increased endogenous sulfide:quinone oxidoreductase. In further embodiments, the polypeptide capable of oxidizing an S substrate is hydrogen sulfide:ferredoxin oxidoreductase, and optionally expresses an exogenous sulfite oxidase or has increased endogenous sulfite oxidase activity or has increased endogenous sulfide:quinone oxidoreductase. In further embodiments, the polypeptide capable of oxidizing an S substrate is sulfide:flavocytochrome-c oxidoreductase, and optionally expresses an exogenous sulfite oxidase or has increased endogenous sulfite oxidase activity or has increased endogenous sulfide:quinone oxidoreductase. In further embodiments, the polypeptide capable of oxidizing an S substrate is sulfide:quinone oxidoreductase, and optionally expresses an exogenous sulfite oxidase, has increased endogenous sulfite oxidase activity or has increased endogenous sulfide:quinone oxidoreductase, or is expressing a sulfide:flavocytochrome-c oxidoreductase encoded by an exogenous nucleic acid molecule. In further embodiments, the polypeptide capable of oxidizing an S substrate is sulfur dioxygenase, and optionally expresses an exogenous sulfite oxidase, has increased endogenous sulfite oxidase activity or has increased endogenous sulfide:quinone oxidoreductase, or is expressing a sulfide:flavocytochrome-c oxidoreductase encoded by an exogenous nucleic acid molecule, or is expressing a sulfide:quinone oxidoreductase encoded by an exogenous nucleic acid molecule.

In certain embodiments, the polypeptide capable of oxidizing an S substrate is a sulfur oxygenase, and optionally expresses an exogenous sulfite oxidase or has increased endogenous sulfite oxidase activity or has increased endogenous sulfide:quinone oxidoreductase.

In any of the aforementioned methods, the $C_1$ substrate, the S substrate, or both are converted into a biological material, such as animal feed, a fertilizer or an oil composition.

In any of the aforementioned methods, a $C_1$ metabolizing microorganisms (e.g., non-natural methanotroph bacteria) having a first exogenous nucleic acid molecule encoding a polypeptide capable of metabolizing the S substrate further comprises a second exogenous nucleic acid molecule encoding a fatty acid producing enzyme, a formaldehyde assimilation enzyme, or a combination thereof, wherein the recombinant $C_1$ metabolizing microorganism converts the $C_1$ substrate into an oil composition. In certain embodiments, the oil composition is substantially located in the cell membrane of the $C_1$ metabolizing microorganism. In some embodiments, the method further comprises the step of obtaining the oil composition by extraction. In certain embodiments, the method further comprises the step of refining the extracted oil composition into a fuel, wherein the fuel comprises jet fuel, diesel fuel, paraffinic kerosene, gasoline, or a combination thereof.

In any of the aforementioned methods for using recombinant $C_1$ metabolizing microorganisms (e.g., non-natural methanotroph bacteria) to produce treated gas or convert light alkanes to other products (e.g., alcohol, oil, biomass) as disclosed in the present disclosure, the method further comprises a second recombinant $C_1$ metabolizing microorganism or cell lysate thereof, wherein the second recombinant microorganism or cell lysate thereof (e.g., methanotrophic bacterium) comprises an exogenous nucleic acid molecule encoding a polypeptide capable of oxidizing light alkanes, wherein the second recombinant microorganism or cell lysate thereof (e.g., methanotrophic bacterium) oxidizes the $C_1$ substrate into an alcohol composition. In certain embodiments, the culturing is performed in the presence of a reducing agent, such as hydrogen gas ($H_2$) or formate, and optionally air or oxygen.

Alternatively, in any of the aforementioned methods for using recombinant $C_1$ metabolizing microorganisms (e.g., non-natural methanotroph bacteria) to decontaminate gas or to partially, substantially, or fully convert the gas to a mixed alcohol composition as disclosed in the present disclosure, the method comprises a recombinant $C_1$ metabolizing microorganism further comprising a second exogenous nucleic acid molecule encoding a polypeptide capable of oxidizing light alkanes, wherein the recombinant $C_1$ metabolizing microorganism or cell lysate thereof oxidizes the $C_1$ substrate into an alcohol composition. In certain embodiments, the polypeptide capable of oxidizing light alkanes, such as an alkane monooxygenase, alkene monooxygenase or alkane hydroxylase, is capable of directly using $H_2$ as a reducing agent to convert light alkane gas to an alcohol composition. In further embodiments, the polypeptide capable of oxidizing light alkanes is a monooxygenase, such as pMMO, sMMO, AMO, pBMO, sBMO, sPMO, PMO:P450, P450, or any combination thereof. In further embodiments, the method is performed under a chemical or environmental stress, such as a temperature at least 60° C., a pH of at least 9, or a pH of no more than 5. In further embodiments, the alcohol dehydrogenase is inactivated by the chemical or environmental stress, such as a temperature at least 60° C., a pH of at least 9, or a pH of no more than 5.

In other embodiments, at least one alcohol dehydrogenase is inactivated, such as by genetic modification. In certain embodiments, the at least one alcohol dehydrogenase comprises methanol dehydrogenase. In further embodiments, the recombinant $C_1$ metabolizing microorganism or cell lysate thereof is immobilized on a solid matrix in a substantially non-aqueous state.

In any of the aforementioned methods, a $C_1$ metabolizing microorganisms (e.g., non-natural methanotroph bacteria) having a first exogenous nucleic acid molecule encoding a polypeptide capable of metabolizing the S substrate further comprises a second exogenous nucleic acid molecule encoding a fatty acid converting enzyme capable of converting a $C_1$ substrate into a $C_8$-$C_{24}$ fatty acid derivative comprising a fatty aldehyde, a fatty alcohol, a hydroxy fatty acid, a dicarboxylic acid, or any combination thereof. In certain embodiments, the fatty acid converting enzyme is a fatty acyl-CoA reductase, such as FAR, CER4, or Maqu_2220, capable of forming a fatty alcohol. In some embodiments, the fatty acid converting enzyme is a fatty acyl-CoA reductase, such as acr1, capable of forming a fatty aldehyde. In some embodiments, the fatty acid converting enzyme is a carboxylic acid reductase.

In any of the aforementioned embodiments comprising a fatty acid converting enzyme, the recombinant $C_1$ metabolizing microorganism further comprises an exogenous nucleic acid molecule encoding a thioesterase, such as a tesA lacking a signal peptide, UcFatB or BTE. In some embodiments, endogenous thioesterase activity is reduced, minimal or abolished as compared to unaltered endogenous thioesterase activity. In any of these embodiments, the recombinant $C_1$ metabolizing microorganism further comprises an exogenous nucleic acid molecule encoding an acyl-CoA synthetase, such as FadD, yng1, or FAA2. In some embodiments, endogenous acyl-CoA synthetase activity is reduced, minimal or abolished as compared to unaltered endogenous acyl-CoA synthetase activity.

In any of the aforementioned embodiments comprising a fatty acid converting enzyme and another exogenous nucleic acid molecule encoding a thioesterase or acyl-CoA synthetase, the recombinant $C_1$ metabolizing microorganism further comprises a recombinant nucleic acid molecule encoding a monooxygenase or hydroxylase to produce ω-hydroxy fatty acid. In certain embodiments, endogenous alcohol dehydrogenase activity is reduced, minimal or abolished as compared to unaltered endogenous alcohol dehydrogenase activity.

In any of the aforementioned embodiments comprising a fatty acid converting enzyme and one or more other exogenous nucleic acid molecules, endogenous alcohol dehydrogenase activity is increased or elevated as compared to unaltered endogenous alcohol dehydrogenase activity to produce dicarboxylic acid.

In any of the aforementioned methods, the $C_1$ metabolizing microorganisms can be cultured in a controlled culturing unit, such as a fermenter or bioreactor. In further embodiments, the bioreactor is a gas phase bioreactor or a fluidized bed reactor.

In any of the aforementioned methods for using recombinant $C_1$ metabolizing microorganisms (e.g., non-natural methanotroph bacteria) to produce treated gas or convert light alkanes to other products (e.g., alcohol, oil, biomass) as disclosed in the present disclosure, the gas feedstock is a light alkane gas, natural gas, unconventional natural gas, syngas, casinghead gas, wellhead condensate, refinery gas, pyrolysis gas, ventilation (air) stream, or any combination thereof. In certain embodiments, the tainted gas feedstock is an acid gas or a sour gas.

In any of the aforementioned methods for using recombinant $C_1$ metabolizing microorganisms (e.g., non-natural methanotroph bacteria) to produce treated gas or convert light alkanes to other products (e.g., alcohol, epoxide, biomass) as disclosed in the present disclosure, the $C_1$ metabolizing microorganism being cultured is *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Pseudomonas, Candida, Yarrowia, Hansenula, Pichia, Torulopsis,* or *Rhodotorula*. In further embodiments, $C_1$ metabolizing microorganism being cultured is bacteria, such as a methanotroph or methylotroph.

The recombinant microorganism may be a *Methylococcus capsulatus* Bath strain, *Methylomonas* 16a (ATCC PTA 2402), *Methylosinus trichosporium* OB3b (NRRL B-11, 196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis daltona* strain SB2, *Methylocystis bryophila, Methylocapsa aurea* KYG, *Methylacidiphilum infernorum, Methylibium petroleiphilum, Methylomicrobium alcaliphilum*, or a combination thereof. In certain related embodiments, the recombinant microorganism is a *Methylococcus capsulatus* Bath strain, *Methylomonas* 16a (ATCC PTA 2402), or *Methylomicrobium alcaliphilum*.

In further embodiments, the $C_1$ metabolizing microorganism or bacteria can metabolize natural gas, unconventional natural gas, or syngas. In certain embodiments, the syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

In certain other embodiments, the metabolizing microorganism is an obligate $C_1$ metabolizing microorganism. In certain other embodiments, the metabolizing microorganism is a facultative $C_1$ metabolizing microorganism. In certain embodiments, the culture comprises a $C_1$ metabolizing microorganism that is a methanotroph and the culture further comprises one or more heterologous bacteria.

In certain embodiments, methods for converting light alkane gas into a composition of interest as provided herein produce at least about or up to 1 liter (L), at least about or up to 10 L, at least about or up to 100 L, at least about or up to 1000 L, at least about or up to 10000 L, or at least about or up to 50000 L compound(s) of interest/day.

In any of the aforementioned methods, the $C_1$ metabolizing microorganism is an obligate $C_1$ metabolizing microorganism.

Systems for Treating and Converting Gas

Substantial amounts of natural gas containing undesirable components (such as acid and sour gas) can be produced at natural gas wells, oil wells (e.g., as associated gas), and from natural gas storage reservoirs, for example, infected with hydrogen sulfide producing bacteria. Hydrogen sulfide and other sulfhydryl compounds can be found in natural gas, in refinery gases, pyrolysis gas, ventilation (air) streams, or in vapor spaces above confined hydrogen sulfide containing hydrocarbons (such as storage tanks or barges). The compositions, methods and systems of this disclosure can be used to treat and convert gas in any of these settings.

Natural gas has a wide range of acid gas concentrations, ranging from parts per million to 50 volume percent or higher, depending on the source. Acid gases are corrosive in the presence of water ($H_2S$ and $CO_2$), toxic ($H_2S$), or lack heating value ($CO_2$), so salable gas must be sweetened to contain no more than, depending on regulations or agreements, a quarter grain $H_2S$ per 100 standard cubic feet (4 parts per million) and to have a heating value of no less than 920 to 980 Btu/SCF. The most widely used processes to sweeten natural gas entail the use of alkanolamines; the two most common are monoethanolamine (MEA) and diethanolamine (DEA). As simple gas sweetening system involve introducing acid or sour gas into the bottom of an absorber where the gas flows up the tower countercurrent of an aqueous (lean) amine stream, which fed through the top of the tower. Within the tower, the acid or sour gas is absorbed by the amine (referred to as rich amine). From the absorber, the rich amine is directed to the top of a stripping tower where a drop in pressure and application of heat strips the solvent of the sour or acid gas. The once again lean amine is circulated back to the absorber for sweetening. But, amine gas sweetening plants can experience operating difficulties including foaming, failure to meet sweet gas specification, high solvent losses, corrosion, fouling of equipment, and contamination of the amine solution. Often one operating difficulty is the cause of another, although not all plants experience the same problems or to the same degree.

The compositions, methods and systems of the instant disclosure solve many of these problems, although the compositions, methods and systems of the instant disclosure can be used with the amine systems currently in operation.

In certain aspects, there is provided a system for treating a gas comprising a source of gas comprising a $C_1$ substrate and an S substrate and a bioreactor comprising a recombinant $C_1$ metabolizing microorganism, wherein the recombinant microorganism comprises an exogenous nucleic acid molecule encoding a polypeptide capable of metabolizing the S substrate, wherein a connector disposed between the gas source and the bioreactor is present to allow flow of gas into the bioreactor and the recombinant microorganism oxidizes or assimilates each substrate. In certain embodiments, the source of gas is first treated through an amine system, and the $H_2S$, $CO_2$, or both released from the rich amine are fed into the bioreactor. In further embodiments, the bioreactor is a gas bioreactor, such as a fluidized bed reactor, and the recombinant $C_1$ metabolizing microorganism in contact with a solid matrix in the bioreactor. In further embodiments, the solid matrix comprises a polypropylene, ceramic, glass, charcoal, sand, activated carbon, or diatomaceous earth support. In further embodiments, the recombinant microorganism is a whole cell or a cell lysate thereof that is immobilized on the solid matrix and in a substantially non-aqueous state.

In other aspects, there is provided a system for recovering stranded gas or oil, comprising a mechanism for recovering oil or gas from an underground formation, wherein the gas comprises a $C_1$ substrate and an S substrate and the mechanism for recovering comprises a well, a mechanism for oxidizing or assimilating at least a portion of each substrate from the recovered gas, the mechanism for oxidizing or assimilating comprising a bioreactor, wherein the bioreactor comprises a recombinant $C_1$ metabolizing microorganism comprising an exogenous nucleic acid molecule encoding a polypeptide capable of metabolizing the S substrate, and a mechanism for recovering the bioremediated stranded oil from the underground formation, wherein the mechanism for recovering comprises a well. In certain embodiments, the source of gas is first treated through an amine system, and the $H_2S$, $CO_2$, or both released from the rich amine are fed into the bioreactor. In further embodiments, the bioreactor is a gas bioreactor, such as a fluidized bed reactor, and the recombinant $C_1$ metabolizing microorganism in contact with a solid matrix in the bioreactor. In further embodiments, the solid matrix comprises a polypropylene, ceramic, glass, charcoal, sand, activated carbon, or diatomaceous earth support. In further embodiments, the recombinant microorganism is a whole cell or a cell lysate thereof that is immobilized on the solid matrix and in a substantially non-aqueous state.

The recovery of oil or gas with a sulfur compound from an underground formation may be accomplished by any known method. Suitable methods include subsea production, surface production, fracking, primary, secondary, or tertiary production. The selection of the method used to recover the oil or gas from an underground formation is not critical. For example, oil or gas with a sulfur compound may be recovered from a formation into a well, and flow through the well and flowline to a facility. In other instances, enhanced oil recovery, with the use of an agent such as steam, water, a surfactant, a polymer flood, or a miscible agent, may be used to increase the flow of oil or gas from the formation.

In any of the aforementioned systems, the $C_1$ substrate, the S substrate, or both are converted into a biological material, such as animal feed, a fertilizer or an oil composition.

In any of the aforementioned systems, a $C_1$ metabolizing microorganisms (e.g., non-natural methanotroph bacteria) having a first exogenous nucleic acid molecule encoding a polypeptide capable of metabolizing the S substrate further comprises a second exogenous nucleic acid molecule encoding a fatty acid producing enzyme, a formaldehyde assimilation enzyme, or a combination thereof, wherein the recombinant $C_1$ metabolizing microorganism converts the $C_1$ substrate into an oil composition. In certain embodiments, the oil composition is substantially located in the cell membrane of the $C_1$ metabolizing microorganism. In some embodiments, the method further comprises the step of obtaining the oil composition by extraction. In certain embodiments, the method further comprises the step of refining the extracted oil composition into a fuel, wherein the fuel comprises jet fuel, diesel fuel, paraffinic kerosene, gasoline, or a combination thereof.

In any of the aforementioned systems for treating gas or converting gas to other products (e.g., alcohol, oil, biomass) as disclosed in the present disclosure, the polypeptide capable of capable of metabolizing the S substrate is a hydrogen sulfide:$NADP^+$ oxidoreductase, hydrogen sulfide:ferredoxin oxidoreductase, sulfide:flavocytochrome-c oxidoreductase, sulfide:quinone oxidoreductase, sulfur dioxygenase, or any combination thereof, and optionally expresses an exogenous sulfite oxidase or has increased endogenous sulfite oxidase activity. In certain embodiments, the polypeptide capable of metabolizing an S substrate is a sulfide:flavocytochrome-c oxidoreductase, sulfide:quinone oxidoreductase, and sulfur dioxygenase, and optionally expresses an exogenous sulfite oxidase or has increased endogenous sulfite oxidase activity or has increased endogenous sulfide:quinone oxidoreductase. In further embodiments, the polypeptide capable of metabolizing an S substrate is hydrogen sulfide:$NADP^+$ oxidoreductase, and optionally expresses an exogenous sulfite oxidase or has increased endogenous sulfite oxidase activity or has increased endogenous sulfide:quinone oxidoreductase. In further embodiments, the polypeptide capable of metabolizing an S substrate is hydrogen sulfide:ferredoxin oxidoreductase, and optionally expresses an exogenous sulfite oxidase or has increased endogenous sulfite oxidase activity or has increased endogenous sulfide:quinone oxidoreductase. In further embodiments, the polypeptide capable of metabolizing an S substrate is sulfide:flavocytochrome-c oxidoreductase, and optionally expresses an exogenous sulfite oxidase or has increased endogenous sulfite oxidase activity or has increased endogenous sulfide:quinone oxidoreductase. In further embodiments, the polypeptide capable of metabolizing an S substrate is sulfide:quinone oxidoreductase, and optionally expresses an exogenous sulfite oxidase, has increased endogenous sulfite oxidase activity or has increased endogenous sulfide:quinone oxidoreductase, or is expressing a sulfide:flavocytochrome-c oxidoreductase encoded by an exogenous nucleic acid molecule. In further embodiments, the polypeptide capable of metabolizing an S substrate is sulfur dioxygenase, and optionally expresses an exogenous sulfite oxidase, has increased endogenous sulfite oxidase activity or has increased endogenous sulfide:quinone oxidoreductase, or is expressing a sulfide:flavocytochrome-c oxidoreductase encoded by an exogenous nucleic acid molecule, or is expressing a sulfide:quinone oxidoreductase encoded by an exogenous nucleic acid molecule.

In any of the aforementioned systems for treating gas or converting gas to other products (e.g., alcohol, oil, biomass) as disclosed in the present disclosure, the polypeptide capable of capable of metabolizing the S substrate is a sulfur oxygenase, and optionally expresses an exogenous sulfite oxidase or has increased endogenous sulfite oxidase activity.

In any of the aforementioned systems for treating gas or converting gas to other products (e.g., alcohol, oil, biomass) as disclosed in the present disclosure, the recombinant $C_1$ metabolizing microorganism further comprises a second exogenous nucleic acid molecule encoding a polypeptide oxidizing light alkanes (e.g., alkyl monooxygenase or hydroxylase) that is optionally stable in the presence of chemical or environmental stress.

Alternatively, any of the aforementioned systems for treating gas or converting gas to other products (e.g., alcohol, oil, biomass) as disclosed in the present disclosure, the bioreactor further comprises a second recombinant $C_1$ metabolizing microorganism comprising a second exogenous nucleic acid molecule encoding a polypeptide capable of oxidizing light alkanes that is optionally stable in the presence of chemical or environmental stress. In certain embodiments, the recombinant microorganism or a cell lysate thereof partially converts the gas into a mixed alcohol composition. In further embodiments, the system further comprises a chemical or environmental control unit capable of maintaining a chemical or environmental stress condition in the bioreactor, such as a temperature at least 60° C., a pH of at least 9, or a pH of no more than 5.

In any of the aforementioned systems, a $C_1$ metabolizing microorganisms (e.g., non-natural methanotroph bacteria) having a first exogenous nucleic acid molecule encoding a polypeptide capable of metabolizing the S substrate further comprises a second exogenous nucleic acid molecule encoding a fatty acid converting enzyme capable of converting a $C_1$ substrate into a $C_8$-$C_{24}$ fatty acid derivative comprising a fatty aldehyde, a fatty alcohol, a hydroxy fatty acid, a dicarboxylic acid, or any combination thereof. In certain embodiments, the fatty acid converting enzyme is a fatty acyl-CoA reductase, such as FAR, CER4, or Maqu_2220, capable of forming a fatty alcohol. In some embodiments, the fatty acid converting enzyme is a fatty acyl-CoA reductase, such as acr1, capable of forming a fatty aldehyde. In some embodiments, the fatty acid converting enzyme is a carboxylic acid reductase.

In any of the aforementioned embodiments comprising a fatty acid converting enzyme, the recombinant $C_1$ metabolizing microorganism further comprises an exogenous nucleic acid molecule encoding a thioesterase, such as a tesA lacking a signal peptide, UcFatB or BTE. In some embodiments, endogenous thioesterase activity is reduced, minimal or abolished as compared to unaltered endogenous thioesterase activity. In any of these embodiments, the recombinant $C_1$ metabolizing microorganism further comprises an exogenous nucleic acid molecule encoding an acyl-CoA synthetase, such as FadD, yng1, or FAA2. In some embodiments, endogenous acyl-CoA synthetase activity is reduced, minimal or abolished as compared to unaltered endogenous acyl-CoA synthetase activity.

In any of the aforementioned embodiments comprising a fatty acid converting enzyme and another exogenous nucleic acid molecule encoding a thioesterase or acyl-CoA synthetase, the recombinant $C_1$ metabolizing microorganism further comprises a recombinant nucleic acid molecule encoding a monooxygenase or hydroxylase to produce ω-hydroxy fatty acid. In certain embodiments, endogenous alcohol dehydrogenase activity is reduced, minimal or abolished as compared to unaltered endogenous alcohol dehydrogenase activity.

In any of the aforementioned embodiments comprising a fatty acid converting enzyme and one or more other exogenous nucleic acid molecules, endogenous alcohol dehydrogenase activity is increased or elevated as compared to unaltered endogenous alcohol dehydrogenase activity to produce dicarboxylic acid.

In any of the aforementioned systems for treating gas or converting gas to other products (e.g., alcohol, oil, biomass) as disclosed in the present disclosure, the recombinant $C_1$ metabolizing microorganism or cell lysate thereof is capable of using $H_2$ as a reducing agent to convert light alkane gas to an alcohol composition. In certain embodiments, the system further comprises a reducing agent source connected to the bioreactor, such as hydrogen gas ($H_2$) gas. In further embodiments, the polypeptide having monooxygenase activity, such as an alkane monooxygenase, alkene monooxygenases or alkane hydroxylase, is capable of directly using $H_2$ as a reducing agent to convert light alkane gas to an alcohol composition. In further embodiments, the polypeptide having monooxygenase activity is an alkane monooxygenase, such as pMMO, sMMO, AMO, pBMO, sBMO, sPMO, PMO:P450, P450, or any combination thereof. In certain embodiments, the polypeptide having monooxygenase activity is a methane monooxygenase, such as pMMO, sMMO, P450, or any combination thereof. In further embodiments, the system further comprises a source of air or oxygen connected to the bioreactor. In further embodiments, the alcohol dehydrogenase is inactivated by the chemical or environmental stress, such as a temperature at least 60° C., a pH of at least 9, or a pH of no more than 5. In other embodiments, the alcohol dehydrogenase is inactivated by genetic modification. In certain embodiments, the at least one alcohol dehydrogenase comprises methanol dehydrogenase. In further embodiments, the recombinant $C_1$ metabolizing microorganism or cell lysate thereof is immobilized on a solid matrix in a substantially non-aqueous state.

In any of the aforementioned systems for treating gas or converting gas to other products (e.g., alcohol, oil, biomass) as disclosed in the present disclosure, the gas source is a light alkane gas mixture, natural gas, unconventional natural gas, syngas, casinghead gas, wellhead condensate, refinery gas, pyrolysis gas, ventilation (air) stream, or vapor above a confined sour hydrocarbon or a combination thereof. In certain embodiments, the source of gas is from an oil refinery, oil well, or natural gas well. In further embodiments, the gas comprises methane and the corresponding alcohol composition comprises methanol. In further embodiments, the gas comprises ethane and the corresponding alcohol composition comprises ethanol. In further embodiments, the gas comprises propane and the corresponding alcohol composition comprises propanol, n-propanol, or a combination thereof. In further embodiments, the gas comprises butane and the corresponding alcohol composition comprises butanol, n-butanol, or a combination thereof.

In any of the aforementioned systems for treating gas or converting gas to other products (e.g., alcohol, oil, biomass) as disclosed in the present disclosure, the system further comprises a collection unit for collecting the alcohol composition, such as a condenser. In further embodiments, the system further comprises a distillation unit for separating the alcohol composition from water byproduct. In further embodiments, the system further comprises a recycling unit for recycling unconverted gas back into the bioreactor. In further embodiments, the system further comprises a pipeline for transporting the sweet gas. In further embodiments, the system further comprises a refrigeration unit for liquefying the sweet gas.

In any of the aforementioned systems for treating gas or converting gas to other products (e.g., alcohol, epoxide, biomass) as disclosed in the present disclosure, the $C_1$ metabolizing microorganism being cultured is *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Pseudomonas, Candida, Yarrowia, Hansenula, Pichia, Torulopsis,* or *Rhodotorula*. In further embodiments, $C_1$ metabolizing microorganism being cultured is bacteria, such as a methanotroph or methylotroph.

The recombinant microorganism may be a *Methylococcus capsulatus* Bath strain, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis daltona* strain SB2, *Methylocystis bryophila, Methylocapsa aurea* KYG, *Methylacidiphilum infernorum, Methylibium petroleiphilum, Methylomicrobium alcaliphilum,* or a combination thereof. In certain related embodiments, the recombinant microorganism is a *Methylococcus capsulatus* Bath strain, *Methylomonas* 16a (ATCC PTA 2402), or *Methylomicrobium alcaliphilum*.

In further embodiments, the $C_1$ metabolizing microorganism or bacteria can metabolize natural gas, unconventional natural gas, or syngas. In certain embodiments, the syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen,* or a combination thereof.

In certain other embodiments, the metabolizing microorganism is an obligate $C_1$ metabolizing microorganism. In certain other embodiments, the metabolizing microorganism is a facultative $C_1$ metabolizing microorganism. In certain embodiments, the culture comprises a $C_1$ metabolizing microorganism that is a methanotroph and the culture further comprises one or more heterologous bacteria.

The various embodiments described above can be combined to provide further embodiments. All of the patent and non-patent publications referred to in this specification or listed in the Application Data Sheet, including the disclosure of U.S. provisional application No. 61/928,349, filed Jan. 16, 2014, are incorporated herein by reference, in their entirety. Aspects of the embodiments can be modified, if necessary to employ concepts of the various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

Conversion of Contaminated Gas into Animal Feed Using a Methylotroph

Host cells (*Methylococcus capsulatus* Bath) are engineered to possess an exogenous hydrogen sulfide:ferredoxin oxidoreductase (sir) gene to enable conversion of contaminated gas into biomass. A nucleic acid sequence encoding the SIR protein from *Cyanidioschyzon merolae* 10D (SEQ ID NO.:31) is codon optimized for introduction into *M. capsulatus* Bath. The sir nucleic acid molecule is cloned into an expression vector (encoding kanamycin resistance) for conjugation into *M. capsulatus* Bath based on the methods reported by Ali and Murrell (*Microbiology* 155:761, 2009).

Briefly, a mobilizable plasmid containing a gene of interest (e.g., sir) operatively linked to a methanol dehydrogenase promoter (for constitutive expression), and encoding kanamycin resistance is first transformed into *E. coli* S17-1 using standard electroporation methods. Transformation is confirmed by selection of kanamycin-resistant colonies on Luria-Bertani (LB)-agar containing 30 µg/mL kanamycin. Transformed colonies are inoculated into LB media containing 30 µg/mL kanamycin and shaken overnight at 37° C. A 10 mL aliquot of the overnight culture is then collected on a sterile 47 mm nitrocellulose filter (0.2 mm pore size). The *E. coli* donor cells are washed on the filter with 50 mL sterile Higgins minimal nitrate salts medium (NSM; Cornish et al., *J. Gen. Microbiol.* 130:2565, 1984; Park et al., *Biotechnol. Bioeng.* 38:423, 1991) to remove residual media and antibiotic.

In parallel, a sample of the *M. capsulatus* Bath (NCIMB 11132) recipient strain is inoculated into 100 mL serum bottles containing 20-50 mL NSM media. The headspace of the bottles is then flushed with a 1:1 mixture of oxygen and methane, and the bottles are sealed with butyl rubber septa and crimped. The bottles are shaken continuously in a 45° C. incubator until reaching an $OD_{600}$ of approximately 0.3. The *M. capsulatus* Bath cells are then collected on the same filter as the *E. coli* donor strain. The filter is again washed with 50 mL of sterile NSM media. The filter is placed cell-side up on an NSM agar plate containing 0.2% yeast extract and incubated for 24 h at 37° C. in the presence of a 1:1 mixture of methane and air. After 24 h, cells are re-suspended in 10 mL sterile NSM medium before being concentrated by centrifugation. The harvested cells are re-suspended in 1 mL sterile NSM media. 100 µL aliquots of the re-suspended cells are spread onto NSM agar plates containing 10 µg/mL kanamycin.

The plates are incubated at 45° C. in sealed chambers containing a 1:1 mixture of methane and air. The gas mixture is replenished every 2 days until colonies form, typically after 7-14 days. Colonies are streaked onto NSM plates containing kanamycin to confirm kanamycin resistance and to further isolate transformed methanotroph cells from residual *E. coli* donor cells.

The presence of sir expression or SIR function is verified by one or more of (1) PCR and sequencing, (2) Western blot analysis, or (3) assaying for SIR activity. For example, to verify transfer, plasmid DNA is isolated and subjected to PCR using the Illustra PuReTaq Ready-To-Go™ PCR Beads (GE Healthcare) under standard conditions (95° C. for 5 min; 32 cycles of 95° C. for 30 s, 50° C. for 30 s, and 72° C. for 1 min; 72° C. for 10 min). As a further control, 1 µl of each of the isolated plasmids is transformed into *E. coli* XL 1-Blue MRF' Kan (Stratagene, La Jolla, Calif.), and plasmids are isolated to verify the presence of the sir insert by restriction endonuclease digests.

The recombinant *M. capsulatus* Bath are cultured at 42° C. in serum bottles containing NSM or MM-W1 medium (0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4*2H_2O$, 1 µM $CuSO_4*5H_2O$, 10 µM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA)). The headspace composition is adjusted to a 1:1 volume of pure methane:air, or a 1:1 volume of contaminated natural gas:air. The bottles are shaken at a rate of 200-250 rpm. The growth of the non-recombinant control strains are compared to the SIR expressing strains.

What is claimed is:

1. A method for treating gas, comprising culturing a first recombinant methanotrophic bacterium or methylotrophic bacterium with a tainted gas feedstock,
wherein the tainted gas feedstock comprises a methane and an S substrate;
wherein the first recombinant methanotrophic bacterium or methylotrophic bacterium comprises a first heterologous nucleic acid molecule encoding a polypeptide capable of metabolizing the S substrate selected from:
(a) a hydrogen sulfide:NADP$^+$ oxidoreductase, hydrogen sulfide:ferredoxin oxidoreductase, sulfide:flavocytochrome-c oxidoreductase, sulfide:quinone oxidoreductase, sulfur dioxygenase, sulfite oxidase, or any combination thereof;
(b) a hydrogen sulfide:NADP$^+$ oxidoreductase, sulfite oxidase, or both;
(c) a hydrogen sulfide:ferredoxin oxidoreductase, sulfite oxidase, or both;
(d) a sulfide:flavocytochrome-c oxidoreductase, sulfite oxidase, or both;
(e) a sulfide:quinone oxidoreductase, sulfite oxidase, or both; or
(f) a hydrogen sulfide:NADP$^+$ oxidoreductase, hydrogen sulfide:ferredoxin oxidoreductase, sulfide:flavocytochrome-c oxidoreductase, or sulfide:quinone oxidoreductase, and wherein endogenous sulfite oxidase activity is increased; and
wherein the first methanotrophic bacterium or methylotrophic bacterium assimilates and/or oxidizes the methane and the S substrate.

2. The method according to claim 1, wherein the methane and the S substrate are converted into a biological material.

3. The method according to claim 2, wherein the biological material comprises an animal feed, a fertilizer or an oil composition.

4. The method according to claim 1, wherein the S substrate is oxidized to a sulfate.

5. The method according to claim 1, wherein the tainted gas feedstock is:
(a) a light alkane gas, natural gas, unconventional natural gas, casinghead gas, wellhead condensate, or any combination thereof; or
(b) an acid gas or a sour gas.

6. The method according to claim 1, wherein the recombinant methanotrophic bacterium or methylotrophic bacterium further comprises a second heterologous nucleic acid molecule encoding a fatty acid producing enzyme, a formaldehyde assimilation enzyme, or a combination thereof; and wherein the recombinant methanotrophic bacterium or methylotrophic bacterium converts the methane into an oil composition.

7. The method according to claim 6, wherein the oil composition is substantially located in the cell membrane of the methanotrophic bacterium or methylotrophic bacterium.

8. The method according to claim 6, wherein the method further comprises the step of obtaining the oil composition by extraction.

9. The method according to claim 1, wherein the method further comprises the step of refining the extracted oil composition into a fuel, wherein the fuel comprises jet fuel, diesel fuel, paraffinic kerosene, gasoline, or a combination thereof.

10. The method according to claim 1, wherein the method further comprises a second recombinant methanotrophic bacterium or methylotrophic bacterium or cell lysate thereof,
wherein the second recombinant methanotrophic bacterium or methylotrophic bacterium comprises a heterologous nucleic acid molecule encoding an alkane monooxygenase or an alkene monooxygenase; and
wherein the second recombinant methanotrophic bacterium or methylotrophic bacterium or cell lysate thereof oxidizes the methane into an alcohol composition.

11. The method according to claim 1, wherein the first recombinant methanotrophic bacterium or methylotrophic bacterium further comprises a second heterologous nucleic acid molecule encoding an alkane or an alkene monooxygenase; and
wherein the first recombinant methanotrophic bacterium or methylotrophic bacterium or cell lysate thereof oxidizes the methane into an alcohol composition.

12. The method according to claim 10, wherein the alkane monooxygenase is selected from a membrane-bound methane monooxygenase (pMMO), soluble methane monooxygenase (sMMO), an ammonia monooxygenase (AMO), a membrane-bound butane monooxygenases (pBMO), a soluble butane monooxygenase (sBMO), an alkane hydroxylase, a soluble propane monooxygenase (sPMO), PMO:P450, P450, or any combination thereof.

13. The method according to claim 1, wherein the first recombinant methanotrophic bacterium or methylotrophic bacterium further comprises a second heterologous nucleic acid molecule encoding a fatty acid converting enzyme selected from:
(a) a fatty acyl-CoA reductase capable of forming a fatty alcohol;
(b) a fatty acyl-CoA reductase capable of forming a fatty aldehyde; and/or
(c) a carboxylic acid reductase; and
wherein the first recombinant methanotrophic bacterium or methylotrophic bacterium converts the methane into a $C_8$-$C_{24}$ fatty acid derivative comprising a fatty aldehyde, a fatty alcohol, a hydroxy fatty acid, a dicarboxylic acid, or any combination thereof.

14. The method according to claim 13, wherein:
(a) the fatty acyl-CoA reductase capable of forming a fatty alcohol is FAR, CER4, or Maqu_2220; and/or
(b) the fatty acyl-CoA reductase capable of forming a fatty aldehyde is acr1.

15. The method according to claim 13, wherein the first recombinant methanotrophic bacterium or methylotrophic bacterium further comprises an heterologous nucleic acid molecule encoding:
(a) a thioesterase; or
(b) a thioesterase, wherein the thioesterase is a tesA lacking a signal peptide, UcFatB or BTE; and/or
(c) an acyl-CoA synthetase; or
(d) an acyl-CoA synthetase, wherein the acyl-CoA synthetase is a FadD, yng1, or FAA2.

16. The method according to claim 15, wherein endogenous:
(a) thioesterase activity is reduced, minimal or abolished as compared to unaltered endogenous thioesterase activity; and/or
(b) acyl-CoA synthetase activity is reduced, minimal or abolished as compared to unaltered endogenous acyl-CoA synthetase activity.

17. The method according to claim 13, wherein the first recombinant methanotrophic bacterium or methylotrophic bacterium further comprises a recombinant nucleic acid molecule encoding a monooxygenase to produce ω-hydroxy fatty acid.

18. The method according to claim 17, wherein endogenous alcohol dehydrogenase activity is reduced, minimal or abolished as compared to unaltered endogenous alcohol dehydrogenase activity.

19. The method according to claim 13, wherein endogenous alcohol dehydrogenase activity is increased or elevated as compared to unaltered endogenous alcohol dehydrogenase activity to produce dicarboxylic acid.

20. The method according to claim 1, wherein the first recombinant methanotrophic bacterium or methylotrophic bacterium is:
(a) a methanotrophic bacterium
(b) a methanotrophic bacterium selected from a *Methylococcus capsulatus* Bath strain, *Methylomonas* 16a, *Methylosinus trichosporium* OB3b, *Methylosinus sporium*, *Methylocystis parvus*, *Methylomonas methanica*, *Methylomonas albus*, *Methylobacter capsulatus*, *Methylobacterium organophilum*, *Methylomonas* sp AJ-3670, *Methylocella silvestris*, *Methylocella palustris*, *Methylocella tundrae*, *Methylocystis daltona* strain SB2, *Methylocystis bryophila*, *Methylocapsa aurea* KYG, *Methylacidiphilum infernorum*, *Methylomicrobium alcaliphilum*, or any combination thereof;
(c) the methanotrophic bacterium of (a) or (b), wherein the culture further comprises a heterologous bacterium;
(d) a methylotrophic bacterium; or
(e) a methylotrophic bacterium selected from *Methylobacterium extorquens*, *Methylobacterium radiotolerans*, *Methylobacterium populi*, *Methylobacterium chloromethanicum*, *Methylobacterium nodulans*, or any combination thereof.

21. A system for treating gas, comprising:
a source of gas comprising a methane and an S substrate;
a bioreactor comprising a recombinant methanotrophic bacterium or methylotrophic bacterium comprising a first heterologous nucleic acid molecule encoding a polypeptide capable of metabolizing the S substrate selected from:
(a) a hydrogen sulfide:NADP$^+$ oxidoreductase, hydrogen sulfide:ferredoxin oxidoreductase, sulfide:flavocytochrome-c oxidoreductase, sulfide:quinone oxidoreductase, sulfur dioxygenase, sulfite oxidase, or any combination thereof;
(b) a hydrogen sulfide:NADP$^+$ oxidoreductase, sulfite oxidase, or both;
(c) a hydrogen sulfide:ferredoxin oxidoreductase, sulfite oxidase, or both;
(d) a sulfide:flavocytochrome-c oxidoreductase, sulfite oxidase, or both;
(e) a sulfide:quinone oxidoreductase, sulfite oxidase, or both; and
(f) a hydrogen sulfide:NADP$^+$ oxidoreductase, hydrogen sulfide:ferredoxin oxidoreductase, sulfide:flavocytochrome-c oxidoreductase, or sulfide:quinone oxidoreductase, wherein endogenous sulfite oxidase activity of the bacterium is increased; and
a connector disposed between the gas source and the bioreactor to allow flow of the gas into the bioreactor; and
wherein the recombinant methanotrophic bacterium or methylotrophic bacterium assimilates and/or oxidizes the methane and the S substrate.

22. The system according to claim 21, wherein the recombinant methanotrophic bacterium or methylotrophic bacterium further comprises a second heterologous nucleic acid molecule encoding a fatty acid producing enzyme, a formaldehyde assimilation enzyme, or a combination thereof, and wherein the recombinant methanotrophic bacterium or methylotrophic bacterium converts the methane into an oil composition.

23. The system according to claim 21, wherein the recombinant methanotrophic bacterium or methylotrophic bacterium further comprises a second heterologous nucleic acid molecule encoding an alkanes monooxygenase or an alkene monooxygenase; and
wherein the recombinant methanotrophic bacterium or methylotrophic bacterium or cell lysate thereof oxidizes the methane into an alcohol composition.

24. The system according to claim 21, wherein the recombinant methanotrophic bacterium or methylotrophic bacterium further comprises a second heterologous nucleic acid molecule encoding a fatty acid converting enzyme selected from:
(a) a fatty acyl-CoA reductase capable of forming a fatty alcohol;
(b) a fatty acyl-CoA reductase capable of forming a fatty aldehyde; and/or
(c) a carboxylic acid reductase; and
wherein the recombinant methanotrophic bacterium or methylotrophic bacterium converts the $C_1$ substrate into a $C_8$-$C_{24}$ fatty acid derivative comprising a fatty aldehyde, a fatty alcohol, a hydroxy fatty acid, a dicarboxylic acid, or any combination thereof.

25. A recombinant methanotrophic bacterium or methylotrophic bacterium, comprising a first heterologous nucleic acid molecule encoding a polypeptide capable of metabolizing an S substrate selected from:
(a) a hydrogen sulfide:NADP$^+$ oxidoreductase, hydrogen sulfide:ferredoxin oxidoreductase, sulfide:flavocytochrome-c oxidoreductase, sulfide:quinone oxidoreductase, sulfur dioxygenase, sulfite oxidase, or any combination thereof;
(b) a hydrogen sulfide:NADP$^+$ oxidoreductase, sulfite oxidase, or both;

(c) a hydrogen sulfide:ferredoxin oxidoreductase, sulfite oxidase, or both;
(d) a sulfide:flavocytochrome-c oxidoreductase, sulfite oxidase, or both;
(e) a sulfide:quinone oxidoreductase, sulfite oxidase, or both; and
(f) a hydrogen sulfide:NADP⁺ oxidoreductase, hydrogen sulfide:ferredoxin oxidoreductase, sulfide:flavocytochrome-c oxidoreductase, or sulfide:quinone oxidoreductase, wherein endogenous sulfite oxidase activity of the bacterium is increased; and
wherein the recombinant methanotrophic bacterium or methylotrophic bacterium is capable of assimilating and/or oxidizing the S substrate and a $C_1$ substrate comprising methane.

26. The recombinant methanotrophic bacterium or methylotrophic bacterium according to claim 25, wherein the methanotrophic bacterium or methylotrophic bacterium is:
(a) a methanotrophic bacterium
(b) a methanotrophic bacterium selected from a *Methylococcus capsulatus* Bath strain, *Methylomonas* 16a, *Methylosinus trichosporium* OB3b, *Methylosinus sporium*, *Methylocystis parvus*, *Methylomonas methanica*, *Methylomonas albus*, *Methylobacter capsulatus*, *Methylobacterium organophilum*, *Methylomonas* sp AJ-3670, *Methylocella silvestris*, *Methylocella palustris*, *Methylocella tundrae*, *Methylocystis daltona* strain SB2, *Methylocystis bryophila*, *Methylocapsa aurea* KYG, *Methylacidiphilum infernorum*, *Methylomicrobium alcaliphilum*, or any combination thereof;
(c) a methylotrophic bacterium; or
(d) a methylotrophic bacterium selected from *Methylobacterium extorquens*, *Methylobacterium radiotolerans*, *Methylobacterium populi*, *Methylobacterium chloromethanicum*, *Methylobacterium nodulans*, or any combination thereof.

27. The recombinant $C_1$ bacterium according to claim 25, wherein the polypeptide capable of metabolizing the S substrate:
(a) is encoded by a nucleic acid comprising the polynucleotide sequence as set forth in any one of SEQ ID NOS.:21-54;
(b) comprises the amino acid sequence as set forth in any one of SEQ ID NOS.:55-88;
(c) is a sulfur oxygenase; or
(d) is a sulfur oxygenase having an amino acid sequence that is at least 75% identical to the sequence set forth in Genbank Accession No. AAK58572.1 or ABN04222.1, or a functional fragment thereof.

28. The method according to claim 11, wherein the alkane monooxygenase is selected from a membrane-bound methane monooxygenase (pMMO), soluble methane monooxygenase (sMMO), an ammonia monooxygenase (AMO), a membrane-bound butane monooxygenases (pBMO), a soluble butane monooxygenase (sBMO), an alkane hydroxylase, a soluble propane monooxygenase (sPMO), PMO:P450, P450, or any combination thereof.

* * * * *